(12) United States Patent
Suga et al.

(10) Patent No.: US 12,359,237 B2
(45) Date of Patent: Jul. 15, 2025

(54) COMPOUND LIBRARY AND METHOD FOR PRODUCING COMPOUND LIBRARY

(71) Applicant: The University of Tokyo, Tokyo (JP)

(72) Inventors: Hiroaki Suga, Tokyo (JP); Yuki Goto, Tokyo (JP); Hiroyasu Onaka, Tokyo (JP); Alexander Vinogradov, Tokyo (JP)

(73) Assignee: The University of Tokyo, Tokyo (JP)

( * ) Notice: Subject to any disclaimer, the term of this patent is extended or adjusted under 35 U.S.C. 154(b) by 1077 days.

(21) Appl. No.: 17/279,634

(22) PCT Filed: Sep. 27, 2019

(86) PCT No.: PCT/JP2019/038431
§ 371 (c)(1),
(2) Date: Jul. 26, 2021

(87) PCT Pub. No.: WO2020/067550
PCT Pub. Date: Apr. 2, 2020

(65) Prior Publication Data
US 2023/0074955 A1    Mar. 9, 2023

(30) Foreign Application Priority Data
Sep. 28, 2018 (JP) .................... 2018-185481

(51) Int. Cl.
C40B 50/06 (2006.01)
C12P 21/02 (2006.01)
C40B 40/10 (2006.01)

(52) U.S. Cl.
CPC .............. *C12P 21/02* (2013.01); *C40B 40/10* (2013.01)

(58) Field of Classification Search
None
See application file for complete search history.

(56) References Cited

U.S. PATENT DOCUMENTS

| 2016/0083719 A1 | 3/2016 | Suga |
| 2017/0159046 A1 | 6/2017 | Suga |

FOREIGN PATENT DOCUMENTS

| WO | 2014136971 | 9/2014 |
| WO | 2015115661 | 8/2015 |
| WO | 2018165159 | 9/2018 |

OTHER PUBLICATIONS

International Search Report received in PCT/JP2019/038431, mailed Dec. 10, 2019.
(Continued)

*Primary Examiner* — Christian C Boesen
(74) *Attorney, Agent, or Firm* — Suzannah K. Sundby, Esq.; Canady + Lortz LLP

(57) ABSTRACT

The present invention provides a method for producing a compound library comprising two or more cyclic compounds represented by the formula (I), comprising a step of allowing a macrocyclase in vitro to act on two or more peptides represented by the formula (II): LP-X-(Xa)$_m$-Y-Z (II) wherein X represents a group represented by the formula (1), Y is a peptide residue consisting of four amino acids and/or analogs thereof and contains a group represented by the formula (2) (wherein R$^1$ and B$^1$ are as defined above, and R$^3$ represents a hydrogen or a hydrocarbon group), and LP is present or absent and, when present, represents a peptide residue consisting of 1 to 100 amino acids and/or analogs thereof, and forming the nitrogen-containing 6-membered ring A while eliminating LP, if present, to form the two or more cyclic compounds represented by the formula (I).

20 Claims, 51 Drawing Sheets
Specification includes a Sequence Listing.

(56) References Cited

OTHER PUBLICATIONS

Written Opinion received in PCT/JP2019/038431, mailed Dec. 10, 2019.
Arnison et al., "Ribosomally synthesized and post-translationally modified peptide natural products: overview and recommendations for a universal nomenclature", 2013, pp. 108-160, vol. 30, No. 1, Publisher: Nat Prod Rep.
Bowers et al., "Generation of thiocillin ring size variants by prepeptide gene replacement and in vivo processing by Bacillus cereus", Jun. 27, 2012, pp. 10313-10316, vol. 134, No. 25, Publisher: J Am Chem Soc.
Goto et al., "Flexizymes for genetic code reprogramming", May 12, 2011, pp. 779-790, vol. 6, Publisher: Nat Protoc.
Hayashi et al., "Genome mining reveals a minimum gene set for the biosynthesis of 32-membered macrocyclic thiopeptides lactazoles", 2014, pp. 679-688, vol. 21, No. 5, Publisher: Chem Biol.
Hayashi et al., "Genome mining reveals six genes, a minimum gene set for the biosynthesis of 32-membered macrocyclic thiopeptides, Structure and biosynthesis of lactaz", 2014, pp. 61-66, vol. 56, Publisher: Symposium on the Chemistry of Natural Products, symposium papers (partial translation).
Ozaki, et al., "Dissection of goadsporin biosynthesis by in vitro reconstitution leading to designer analogues expressed in vivo", Feb. 6, 2017, vol. 8, No. 14207, Publisher: Nat Commun.
Shimizu et al., "Cell-free translation reconstituted with purified components", Aug. 2001, pp. 751-755, vol. 19, No. 8, Publisher: Nat Biotechnol.
Young et al., "Codon randomization for rapid exploration of chemical space in thiopeptide antibiotic variants", Dec. 21, 2012, pp. 1600-1610, vol. 19, No. 12, Publisher: Chem Biol.
Bennallack & Griffitts, Elucidating and engineering thiopeptide biosynthesis, Jun. 1, 2017, p. 119, vol. 33, No. 6, Publisher: World J Microbiol Biotechnol.

[Fig.1]

LazA

```
    -38        -30       -20       -10     -1 1     5      10     15   19
    MSDITASRVESLDLQDLDLSELTVTSLRDTVALPENGASWGSCSCQASSSCAQPQDM
                    Leader peptide                  Core peptide
```

LazA*

```
    -38        -30       -20       -10     -1 1     5      10     15
    MSDITASRVESLDLQDLDLSELTVTSLRDTVALPENGASWGSCSCQASSSCAQP
                    Leader peptide                  Core peptide
```

[Fig.2]

| T7 promoter | Translation enhancer sequence | SD sequence | Start codon | lazA* sequence | End codon |
|---|---|---|---|---|---|
| TAA···ATA | TTAACTTTA | AAGGAGAA | ATGTCT | ··· | XXXTAAGCTTCG |

[Fig.3]

| ATG | TCT | GAC | ATT | ACC | GCG | TCA | CGT | GTT | GAA |
|---|---|---|---|---|---|---|---|---|---|
| M | S | D | I | T | A | S | R | V | E |

| TCT | TTA | GAT | CTT | CAA | GAC | CTT | GAT | CTG | TCT |
|---|---|---|---|---|---|---|---|---|---|
| S | L | D | L | Q | D | L | D | L | S |

| GAG | CTG | ACT | GTT | ACG | TCA | CTG | CGC | GAC | ACC |
|---|---|---|---|---|---|---|---|---|---|
| E | L | T | V | T | S | L | R | D | T |

| GTG | GCA | TTG | CCG | GAA | AAT | GGG | GCA | AGC | TGG |
|---|---|---|---|---|---|---|---|---|---|
| V | A | L | P | E | N | G | A | S | W |

Core peptide sequence

| GGT | TCT | TGT | AGT | TGC | CAG | GCT | TCT | AGC | TCA |
|---|---|---|---|---|---|---|---|---|---|
| G | S | C | S | C | Q | A | S | S | S |

| TGT | GCA | CAA | CCA | TAA |
|---|---|---|---|---|
| C | A | Q | P | Stop |

[Fig.4]
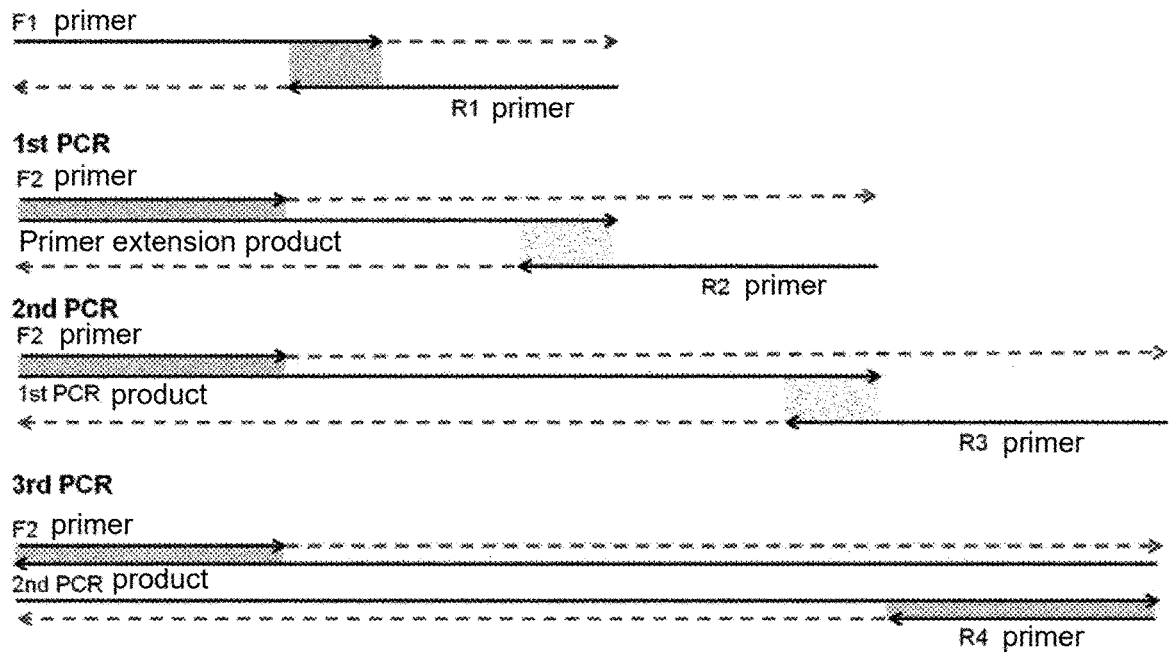
[Fig.5]
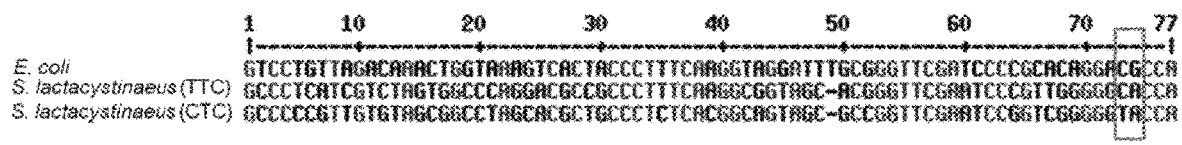
[Fig.6]
DNA template for tRNA$^{Glu}$ synthesis
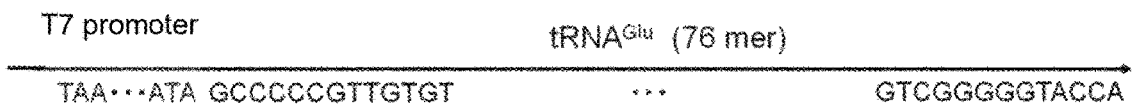

[Fig.7]
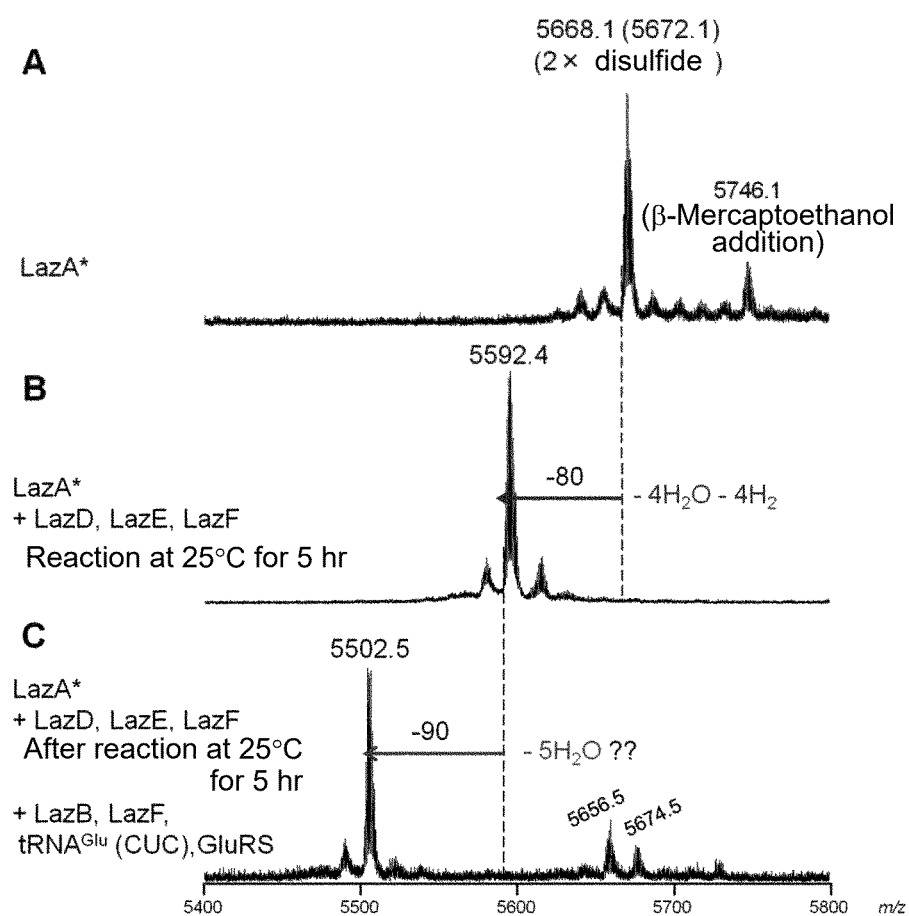

[Fig.8]
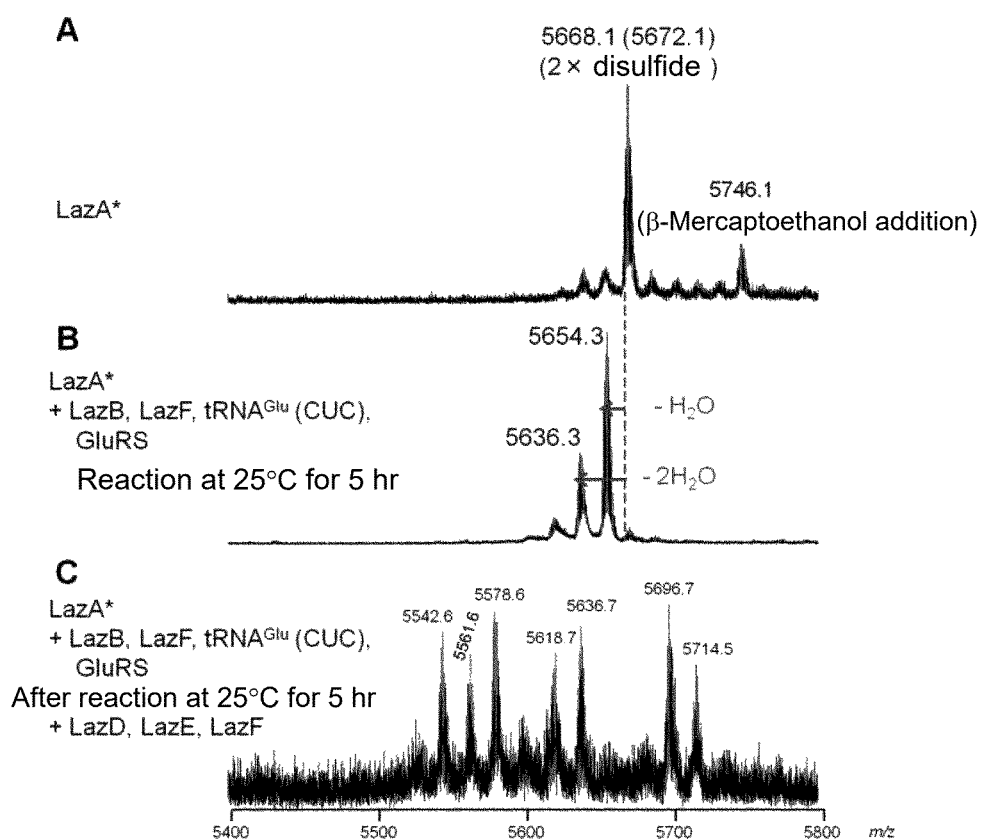

[Fig.9]
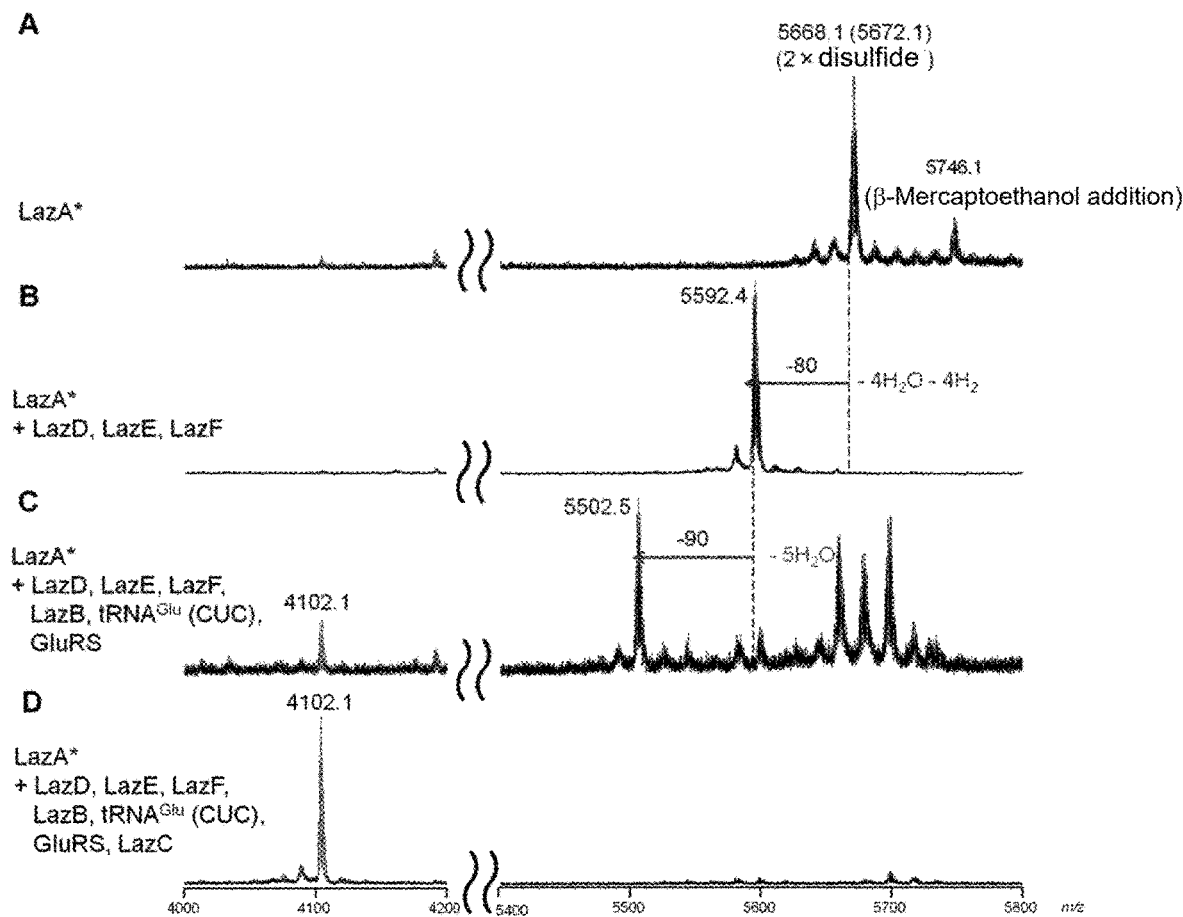
[Fig.10]
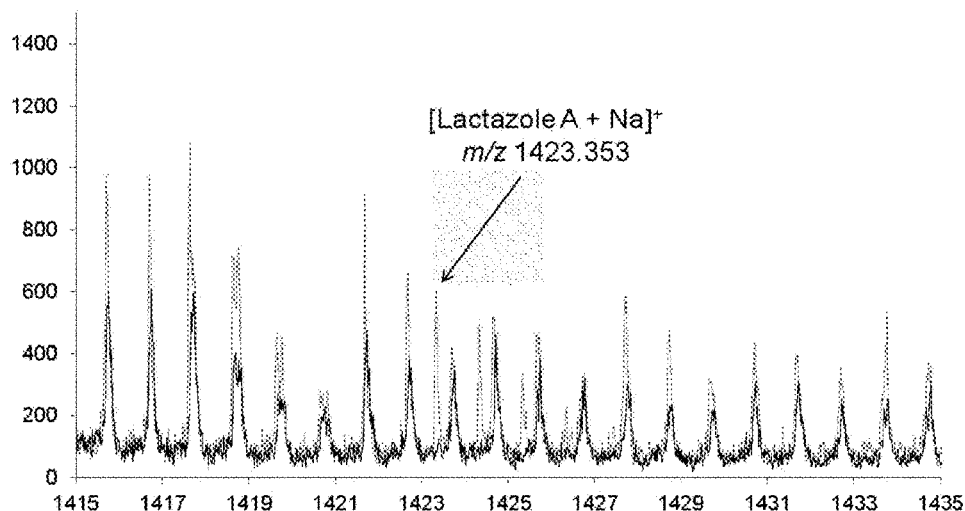

[Fig.11]
Leader peptides
m/z 1026.268 [M+4H]$^{4+}$
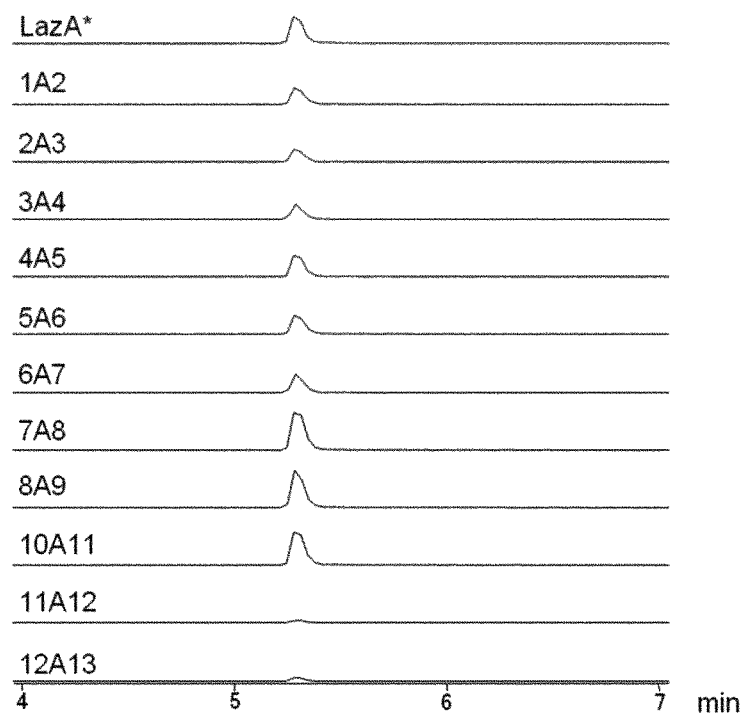
[Fig.12]
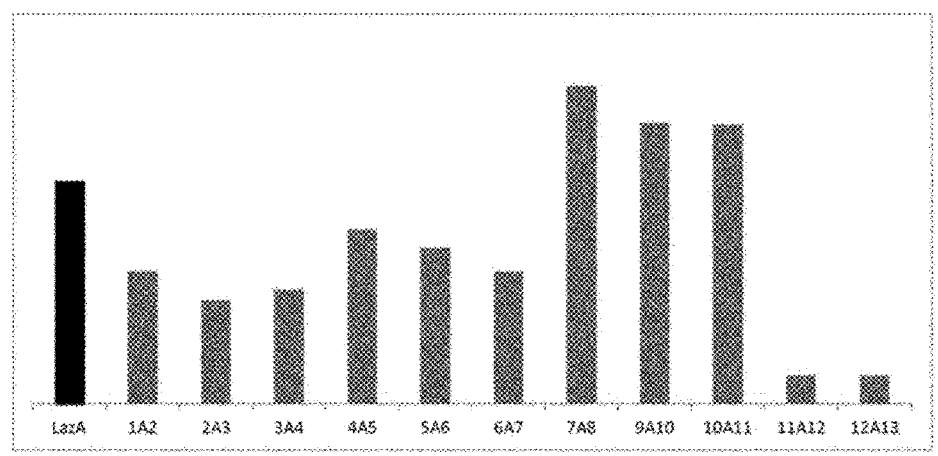

[Fig.13]
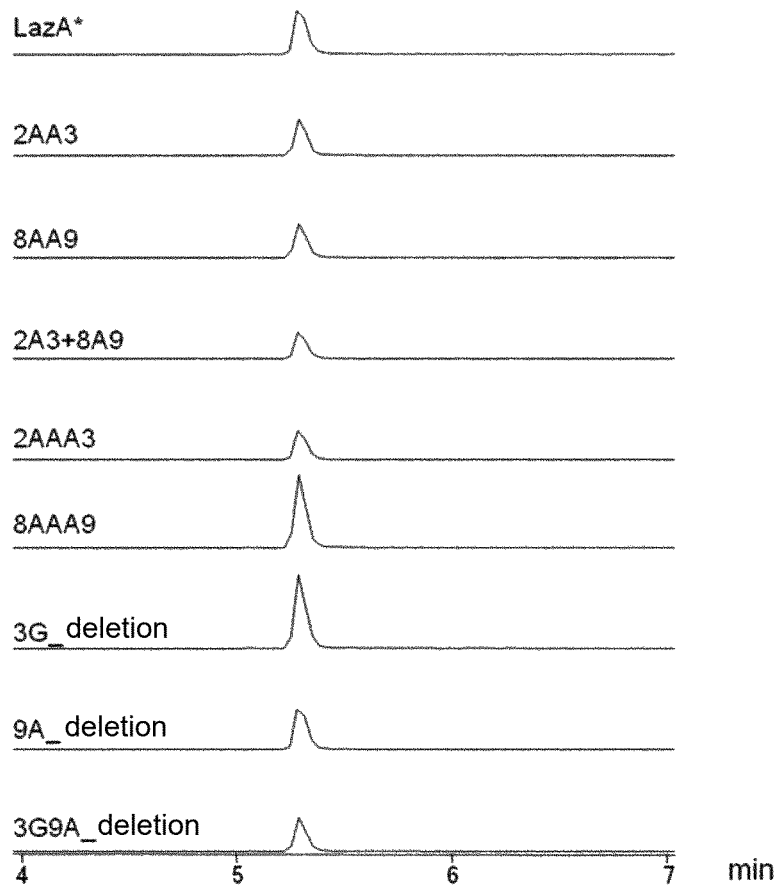
[Fig.14]
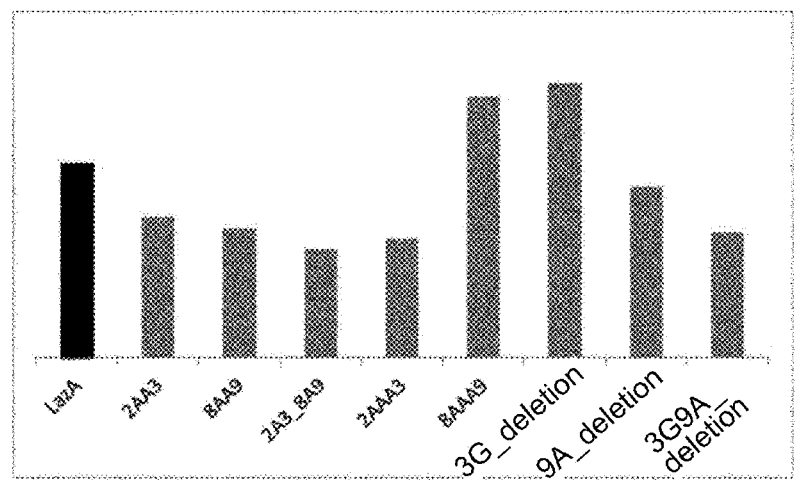

[Fig.15]
Leader peptides
$m/z$ 1026.268 $[M+4H]^{4+}$
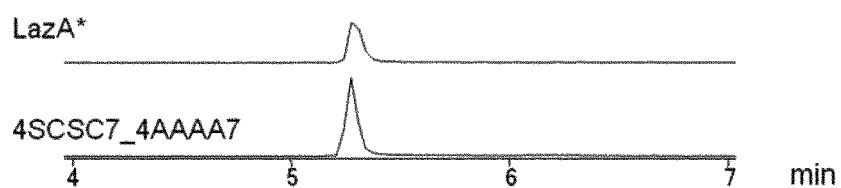
[Fig.16]
Leader peptides
$m/z$ 1026.268 $[M+4H]^{4+}$
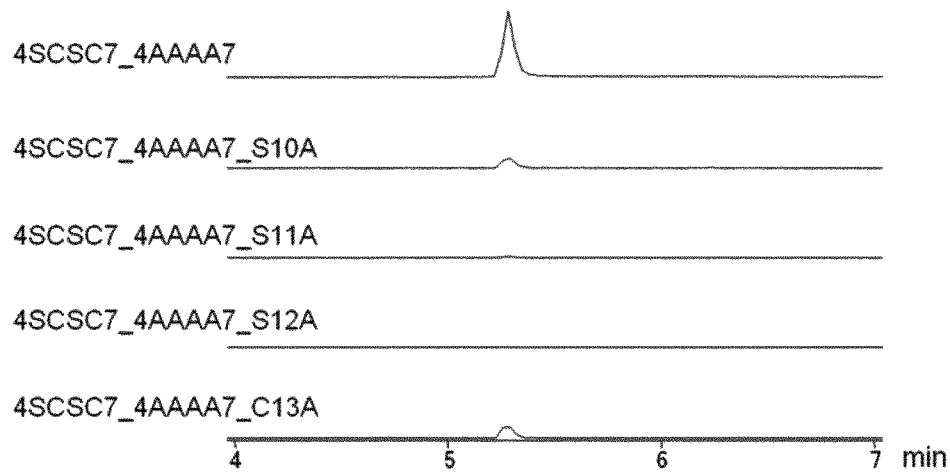

[Fig.17]
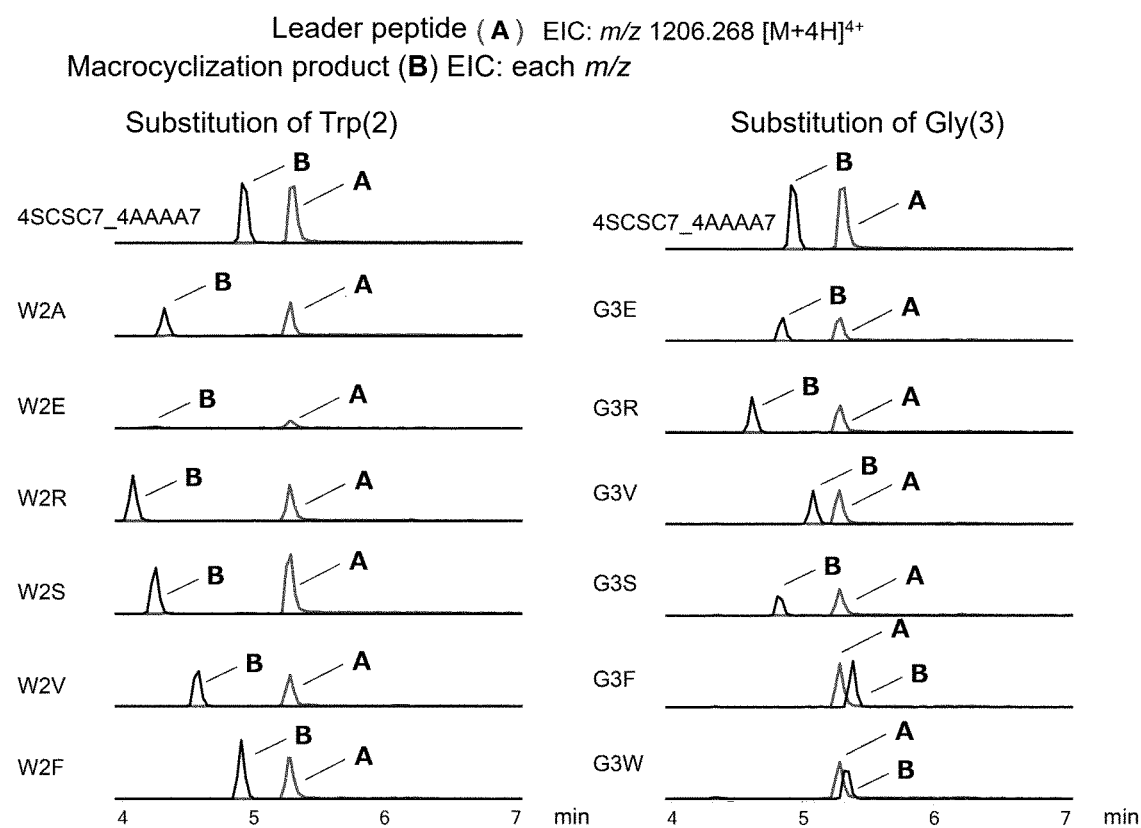

[Fig.18]
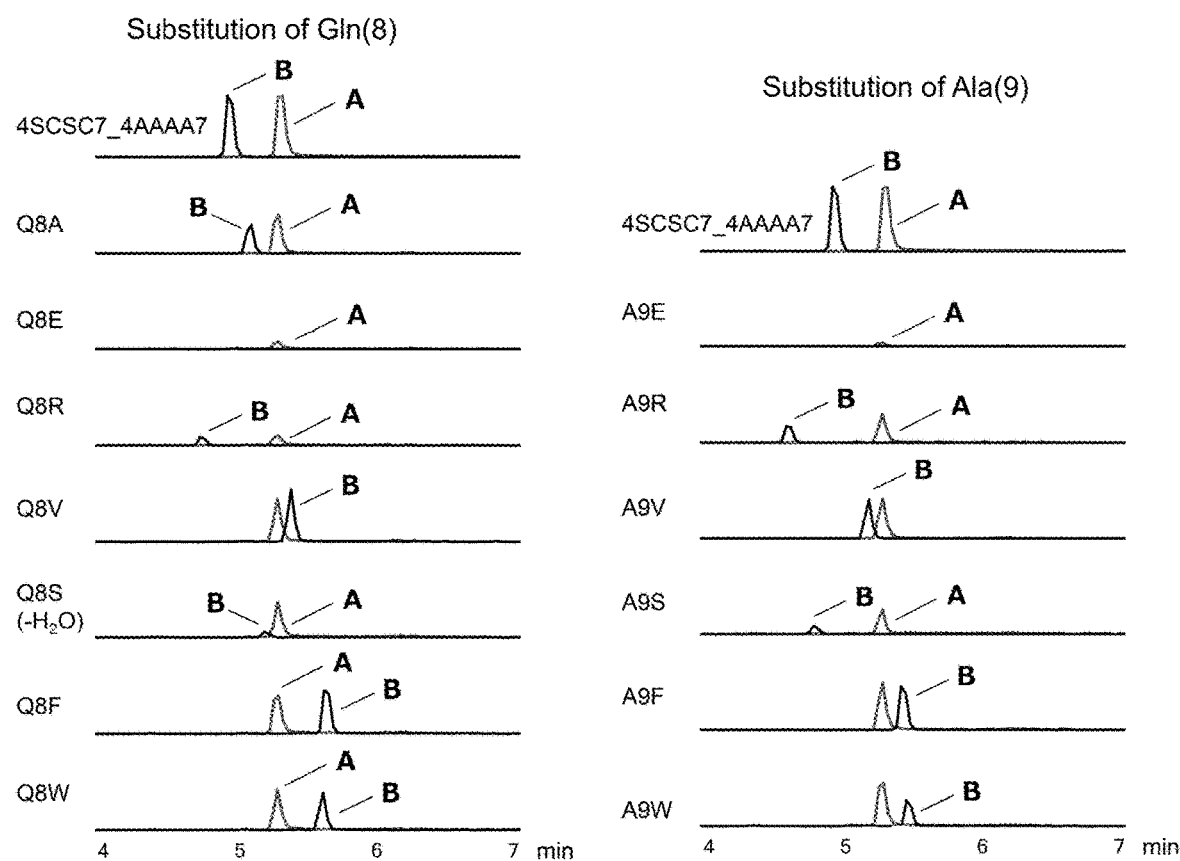

[Fig.19]
Leader peptide (A) EIC: $m/z$ 1206.268 $[M+4H]^{4+}$
Macrocyclization product (B) EIC: each $m/z$
Substitution of Gln(15) and Pro(16)
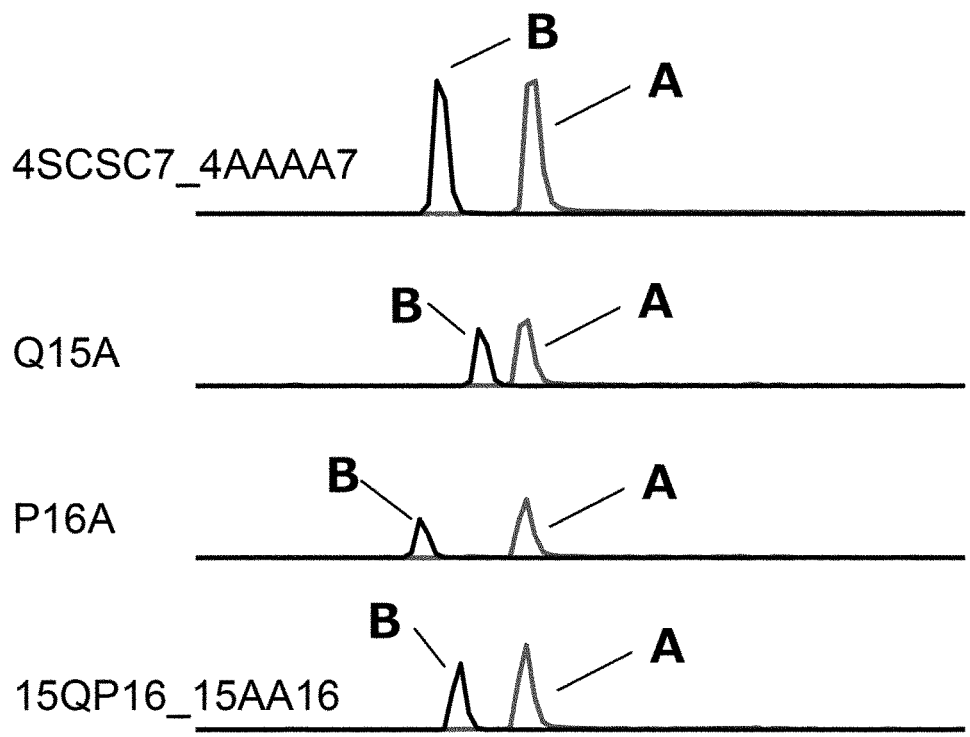

[Fig.20]
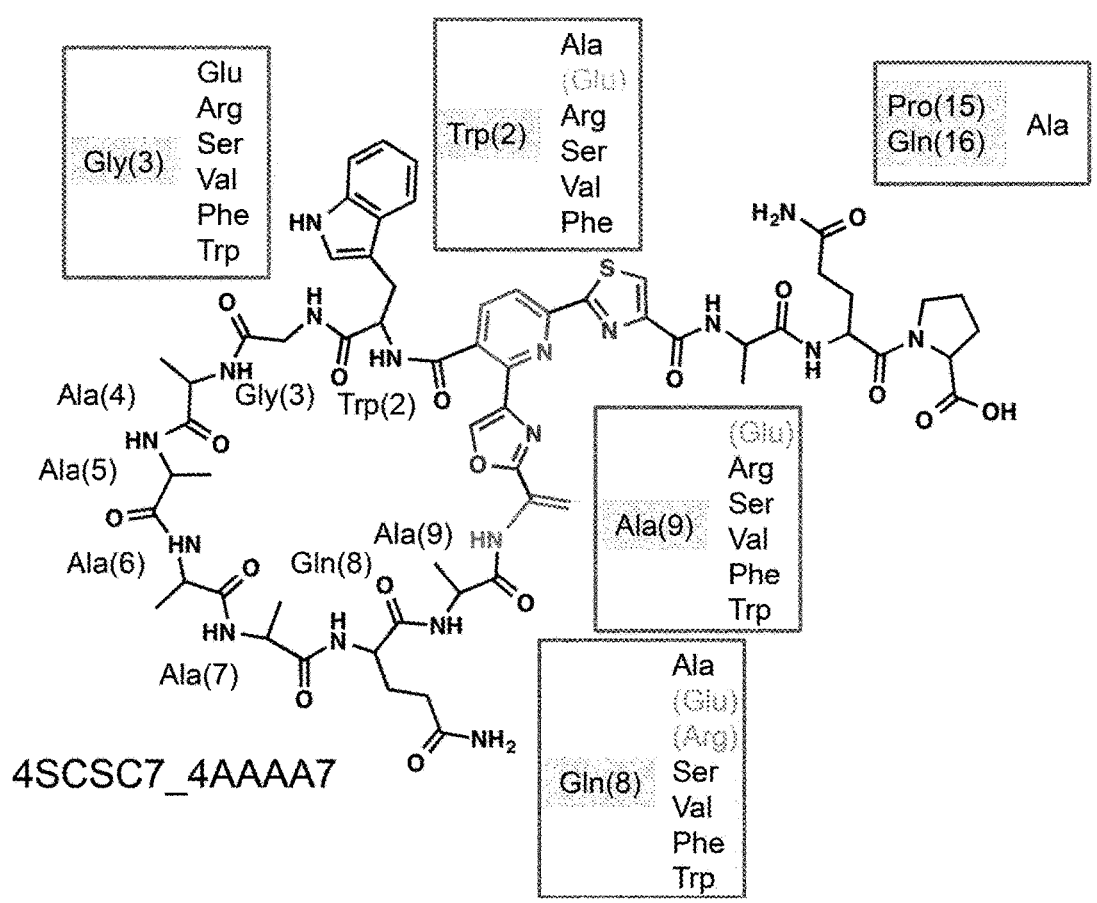

[Fig.21]
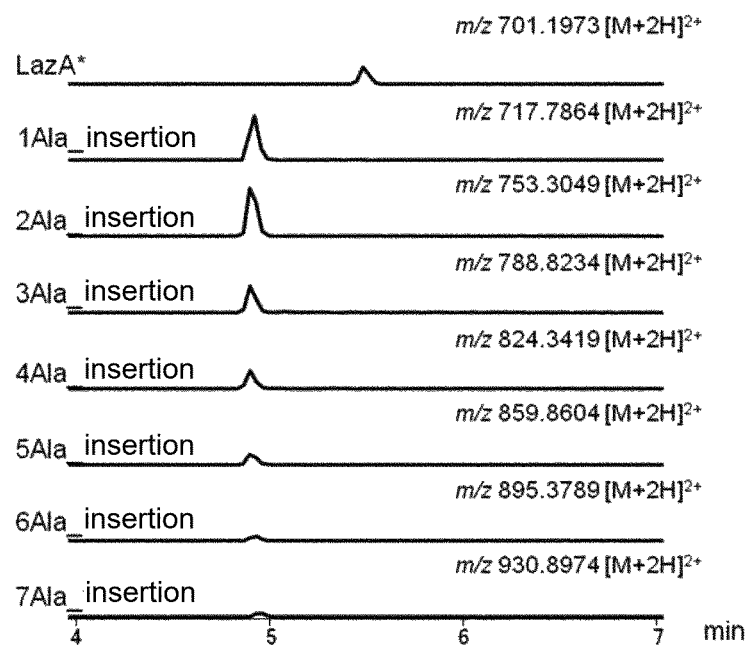
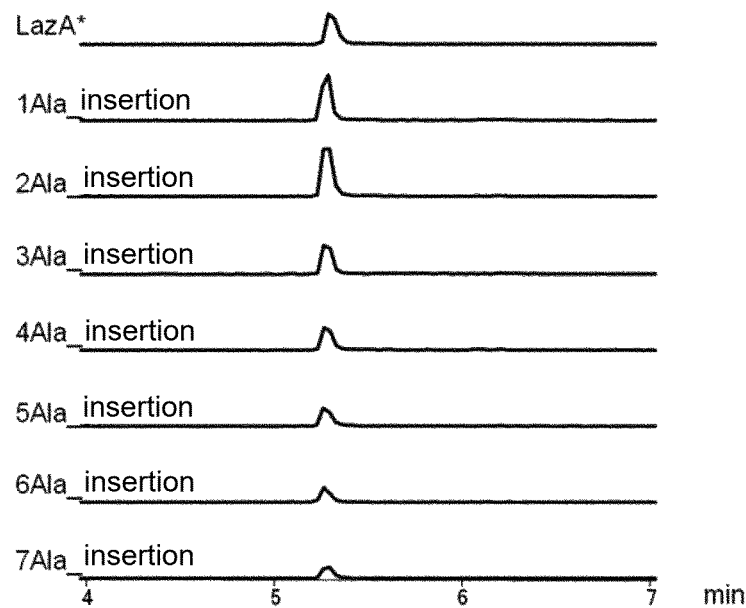

[Fig.22]
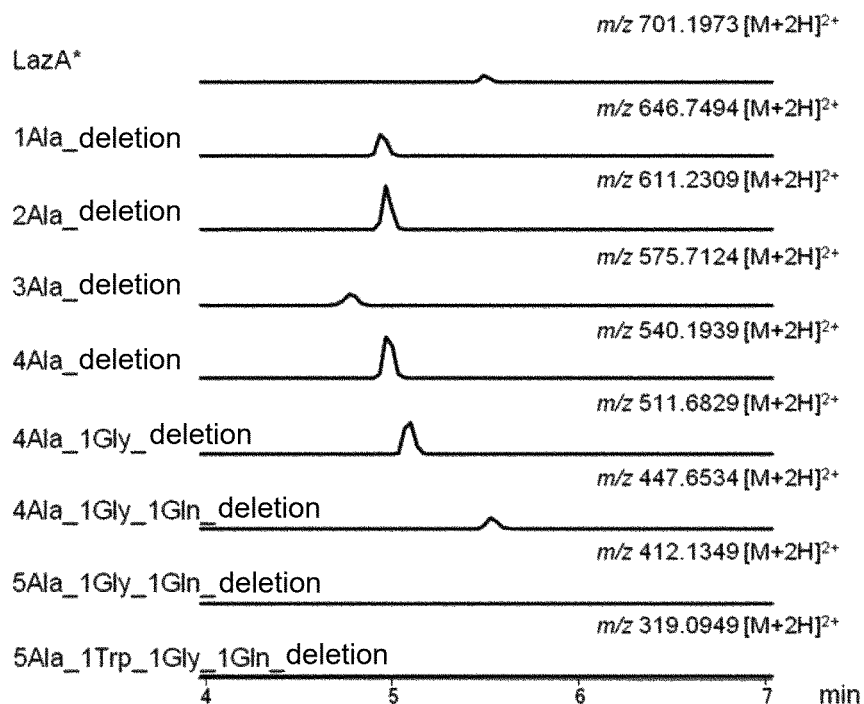
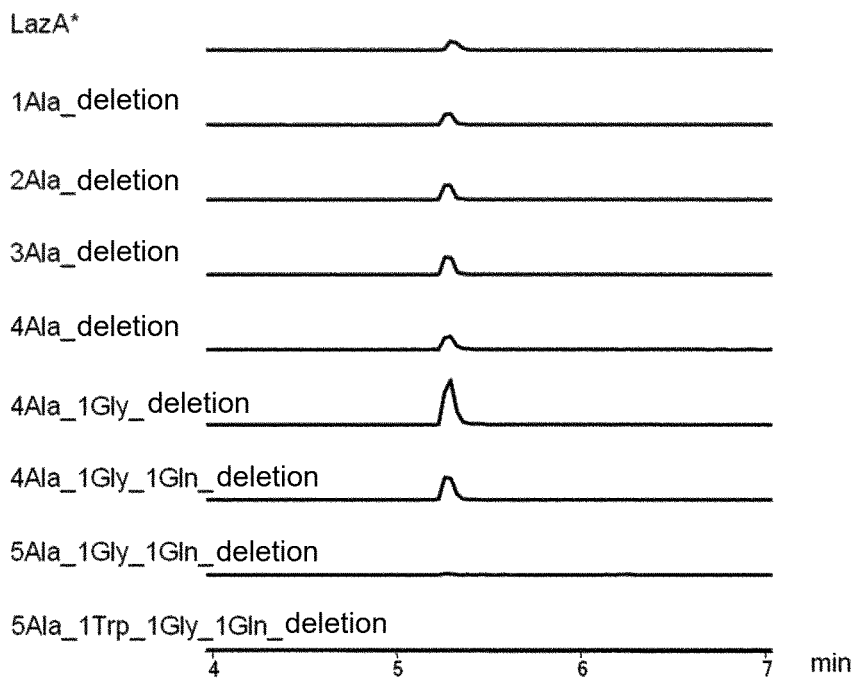

[Fig.23]
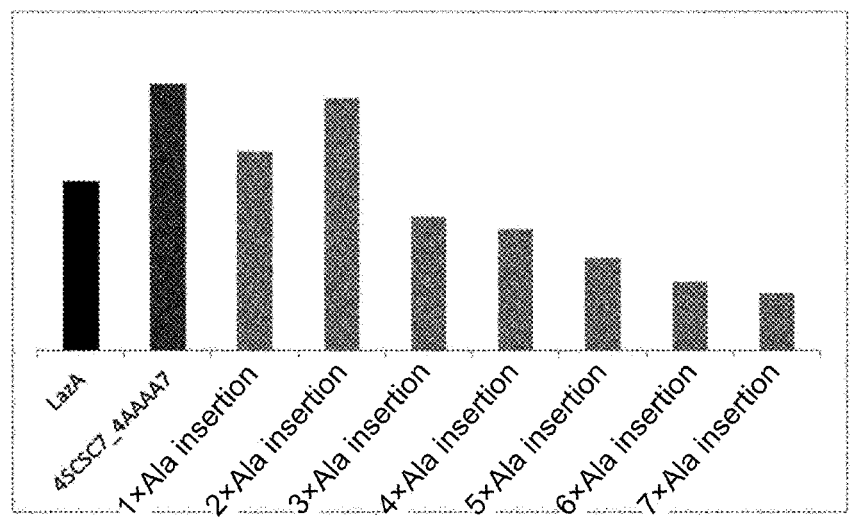
[Fig.24]
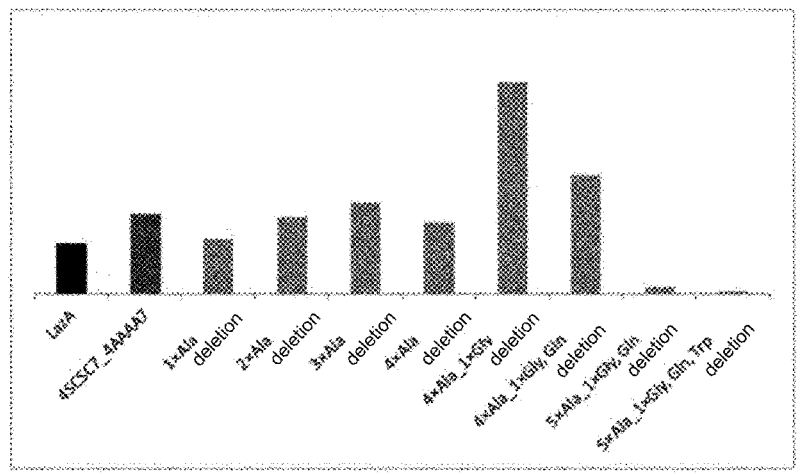

[Fig.25]
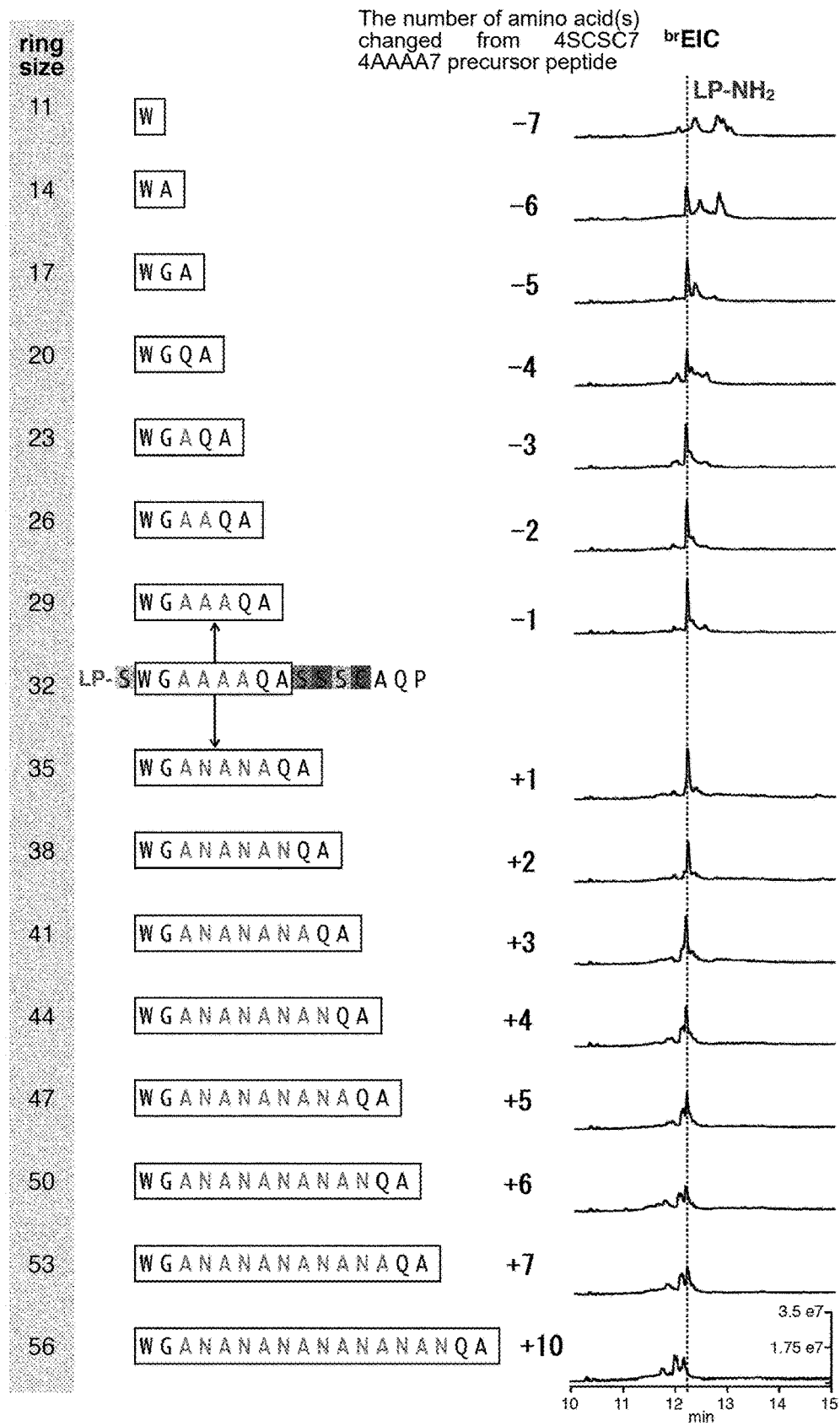

[Fig.26]
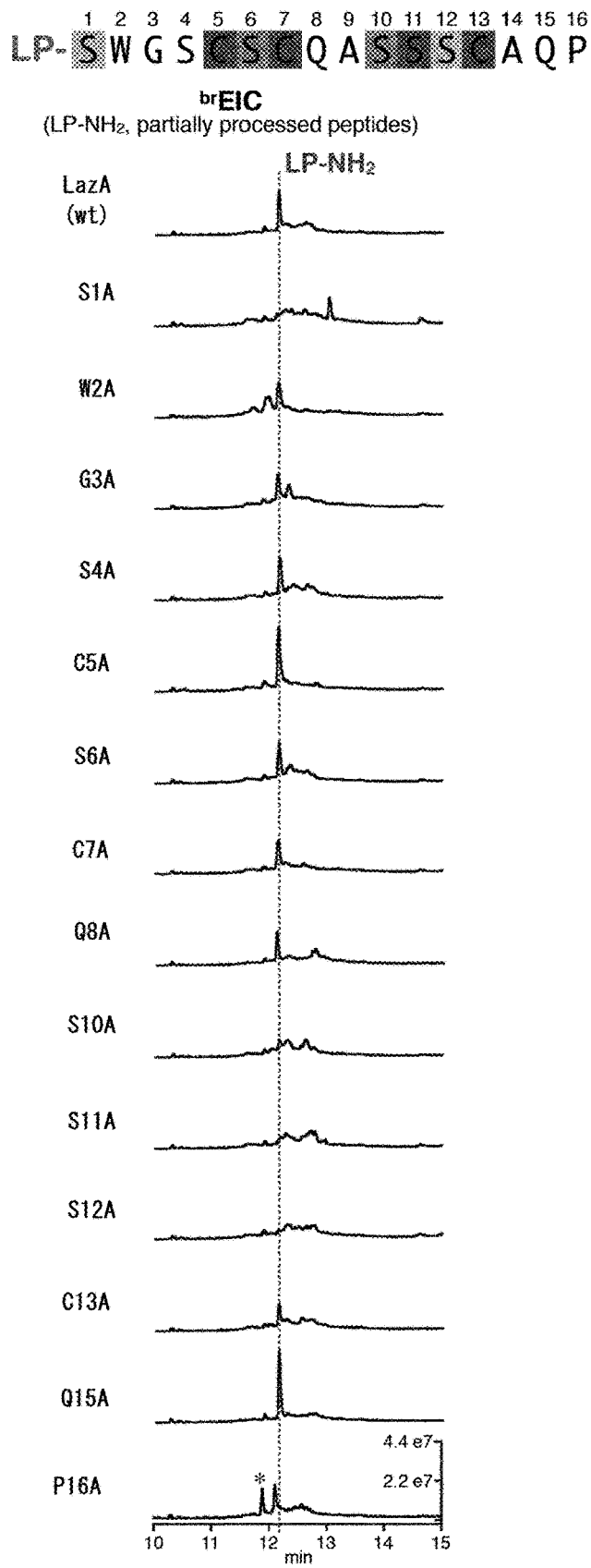

[Fig.27]
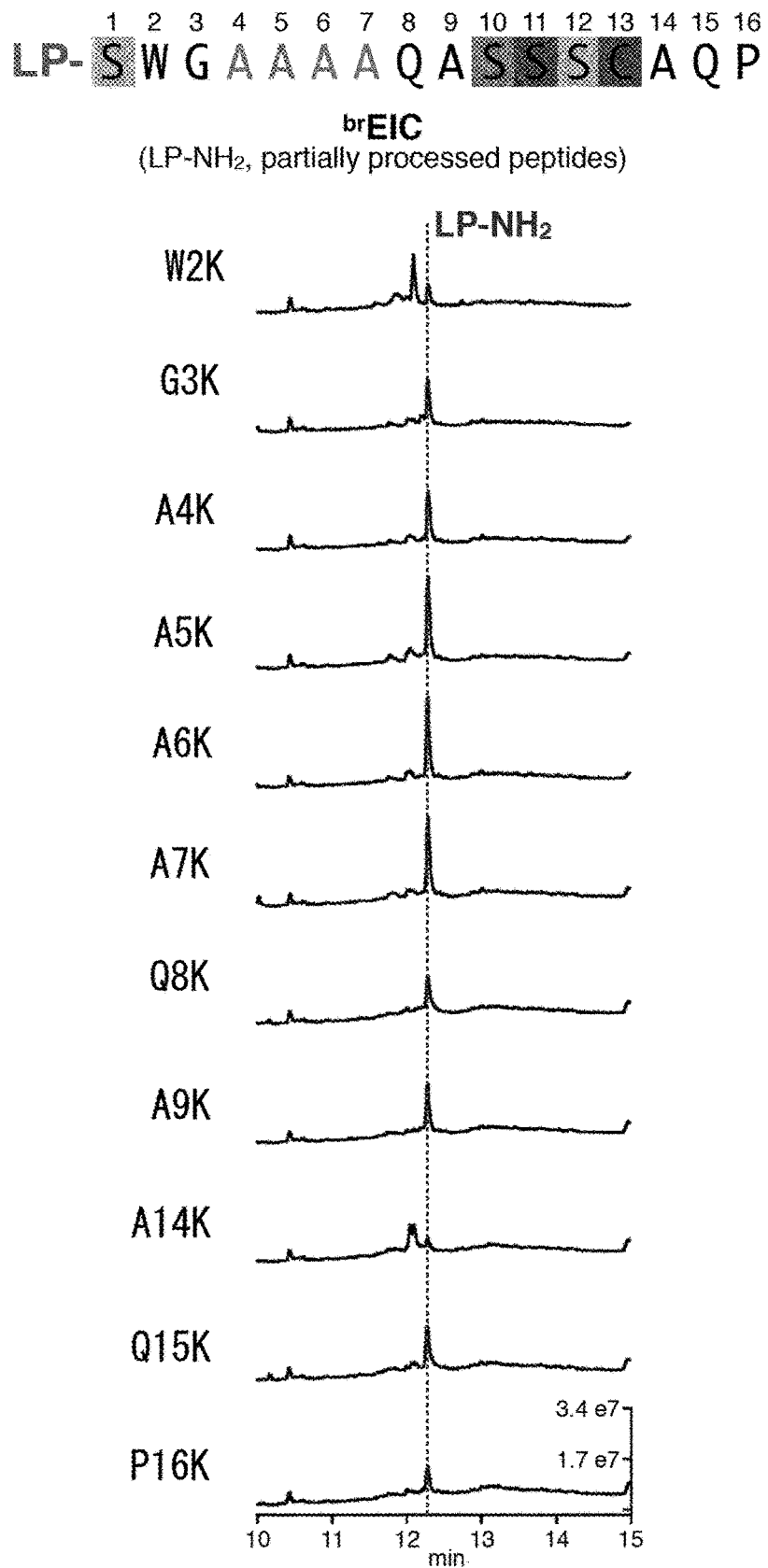

[Fig.28]
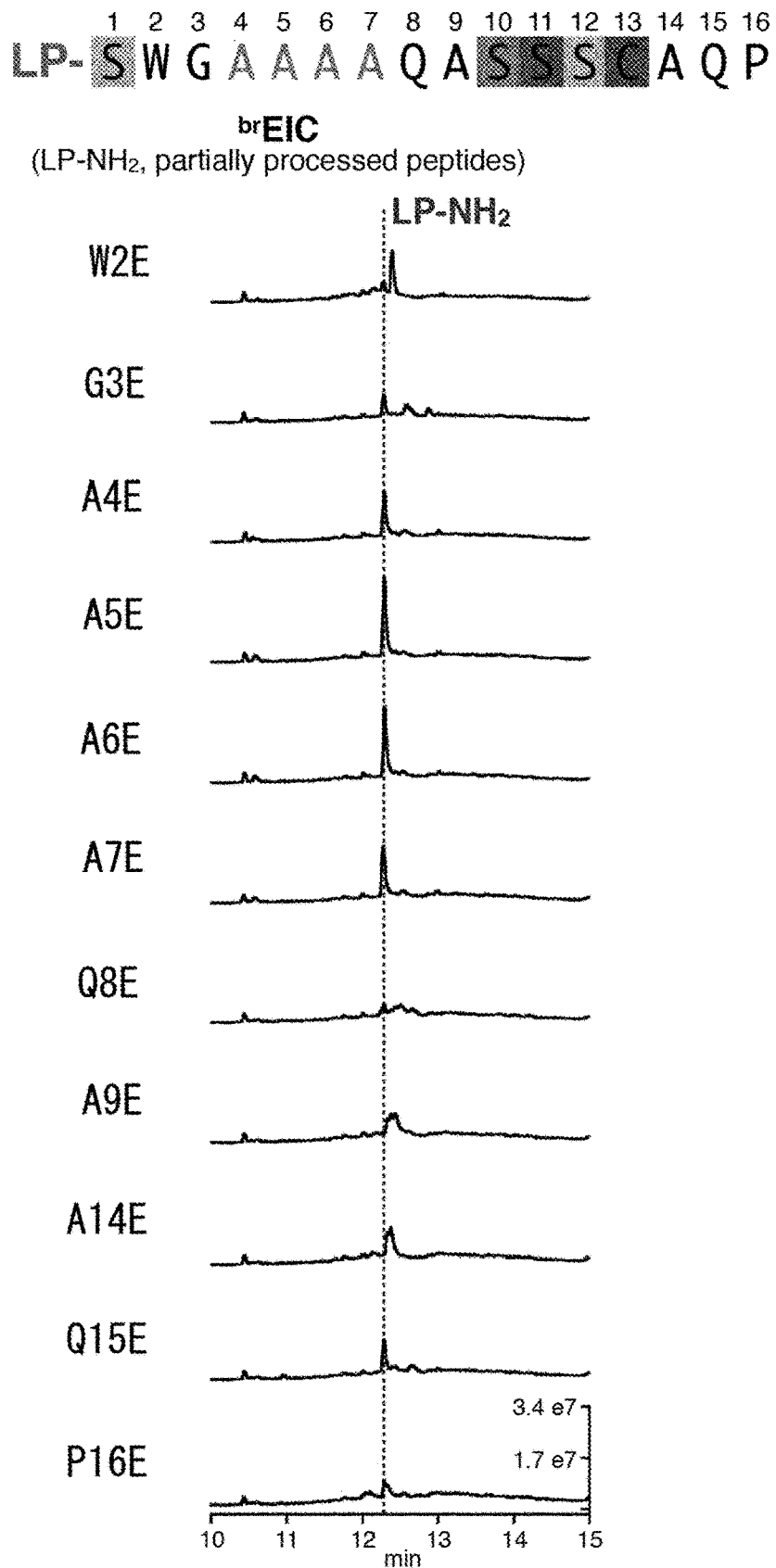

[Fig.29]
Leader peptide
EIC: *m/z* 1026.268 $[M+4H]^{4+}$
4AAAA7
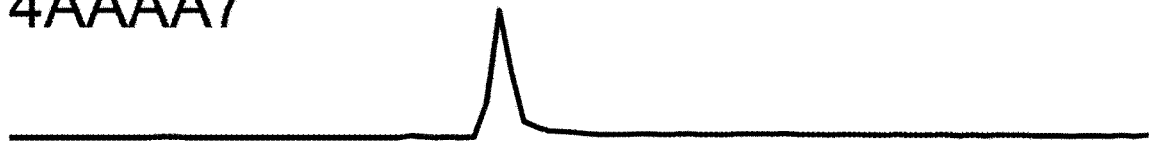
4AAAA7_S10T
4AAAA7_S11T
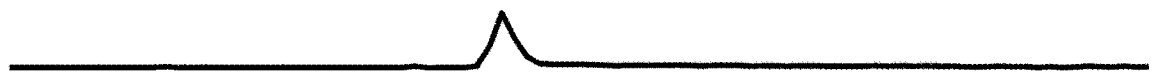
4AAAA7_S11C
4AAAA7_C13S
4AAAA7_C13T

[Fig.30]
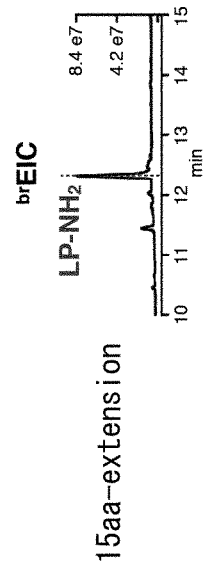
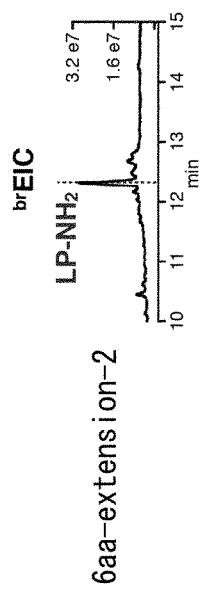
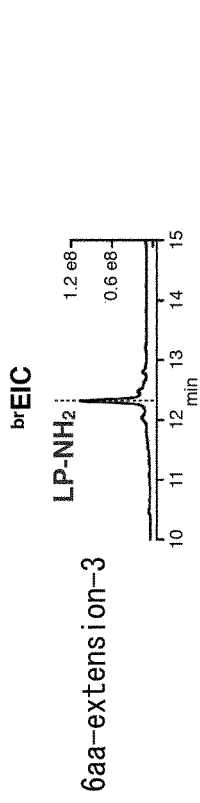

[Fig.31]
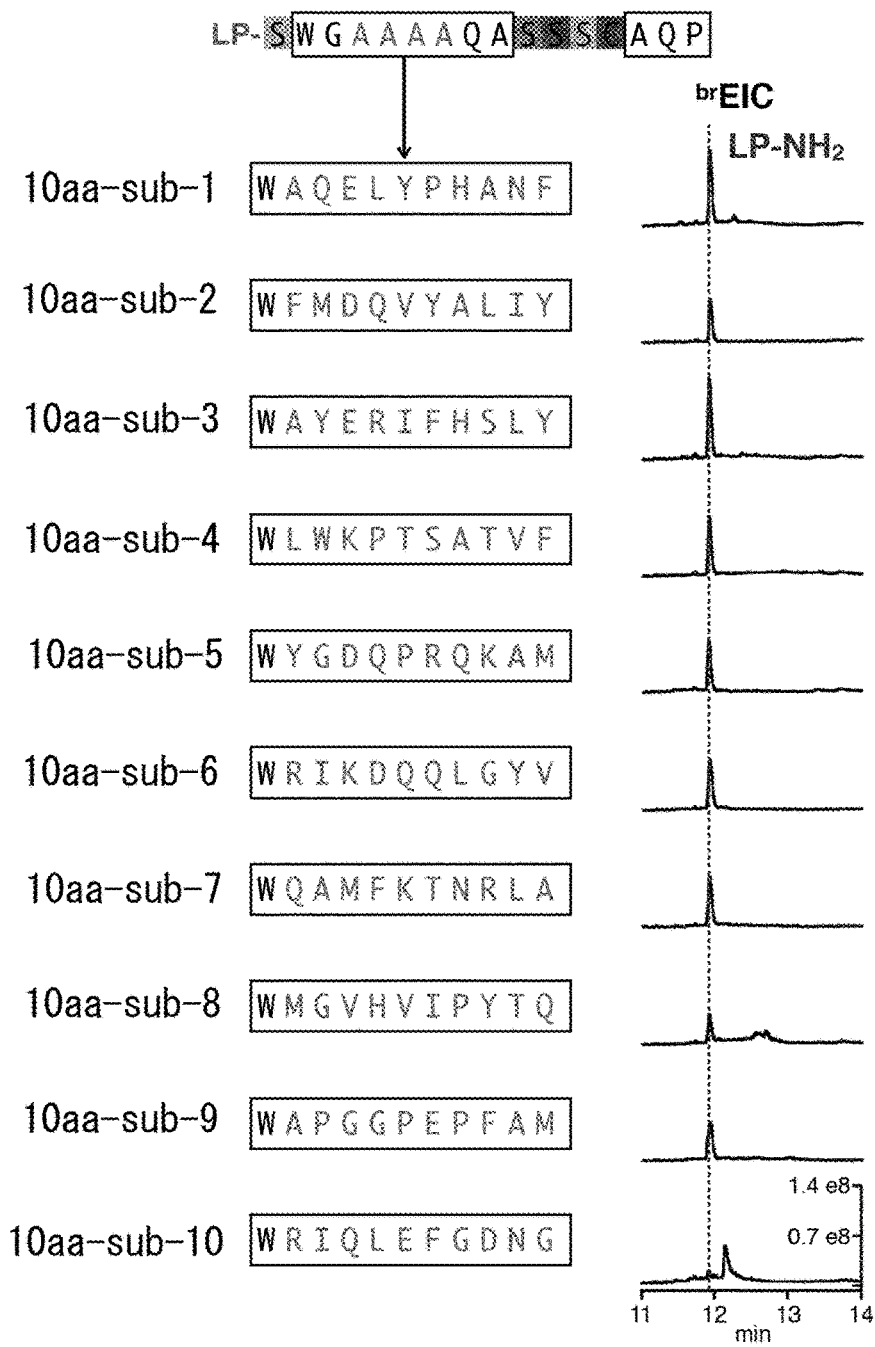
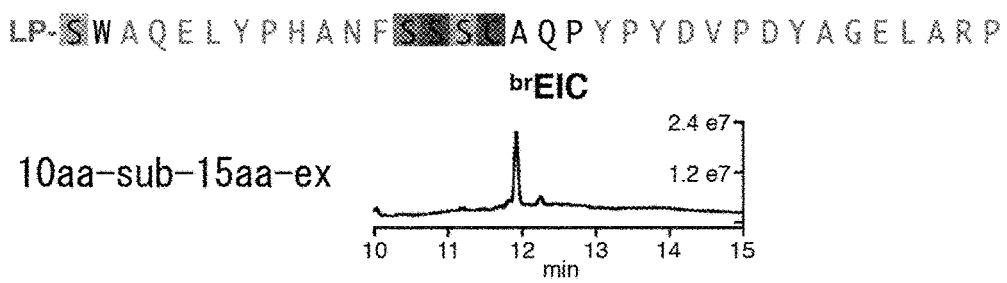

[Fig.32]
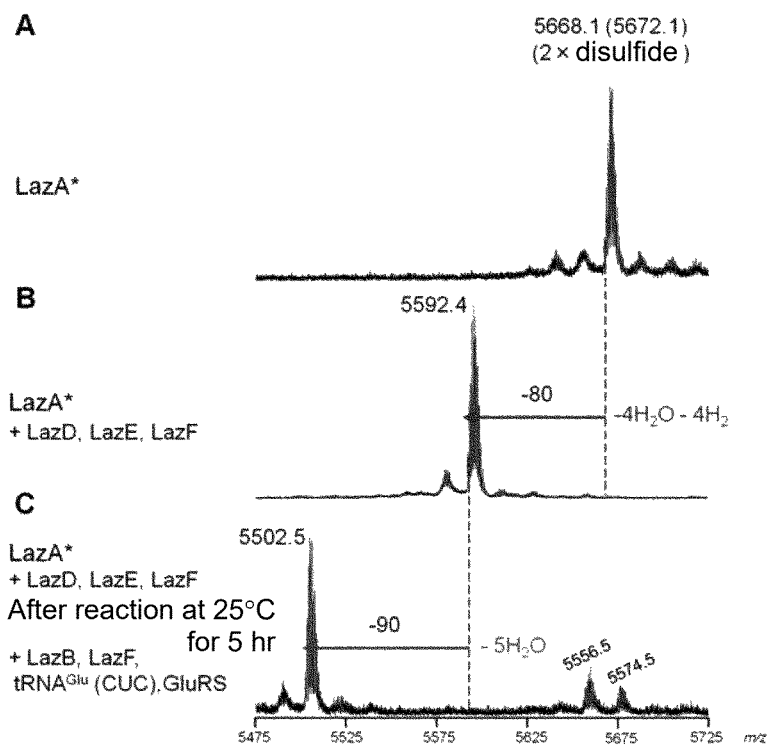
[Fig.33]
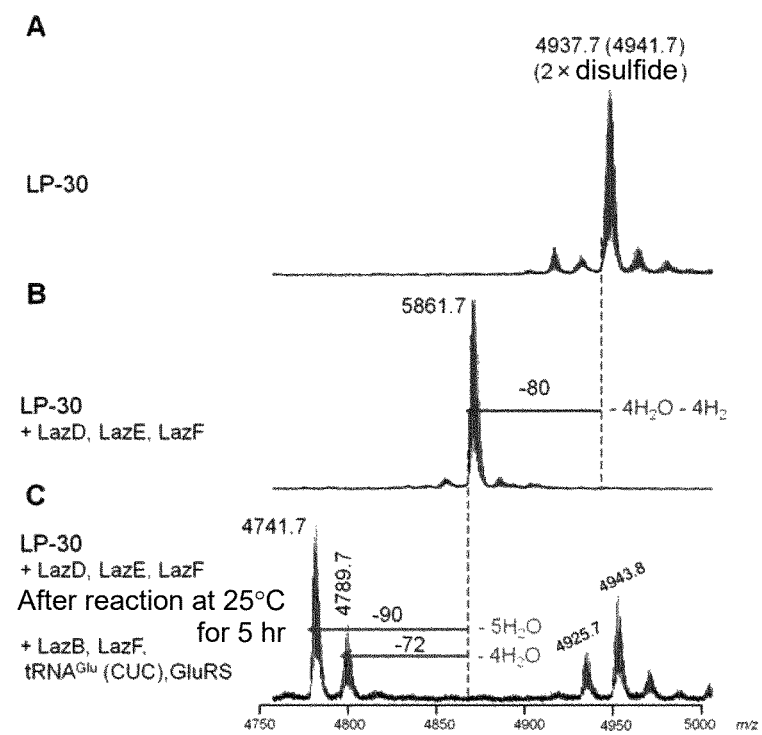

[Fig.34]
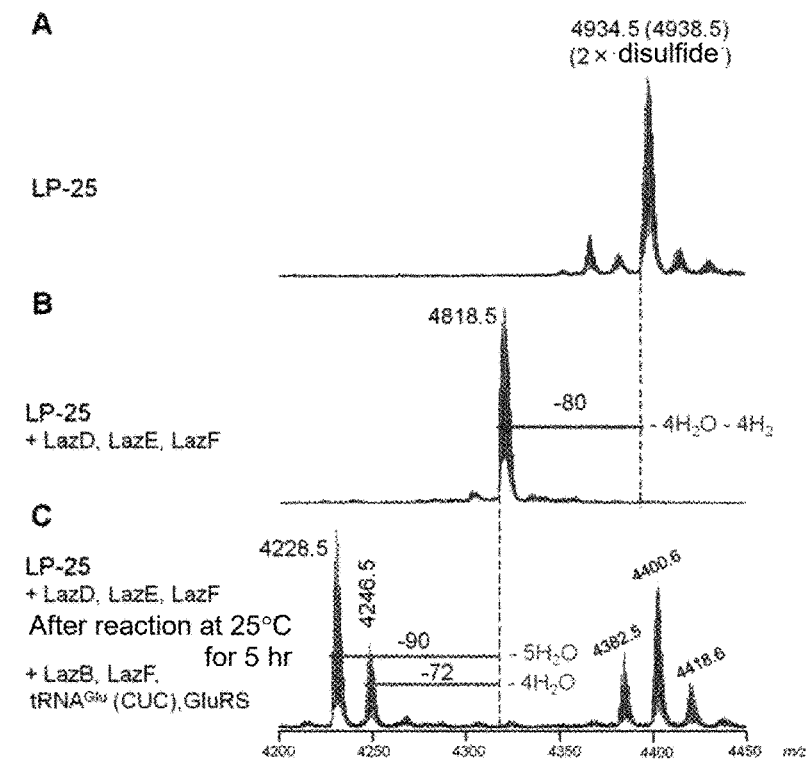
[Fig.35]
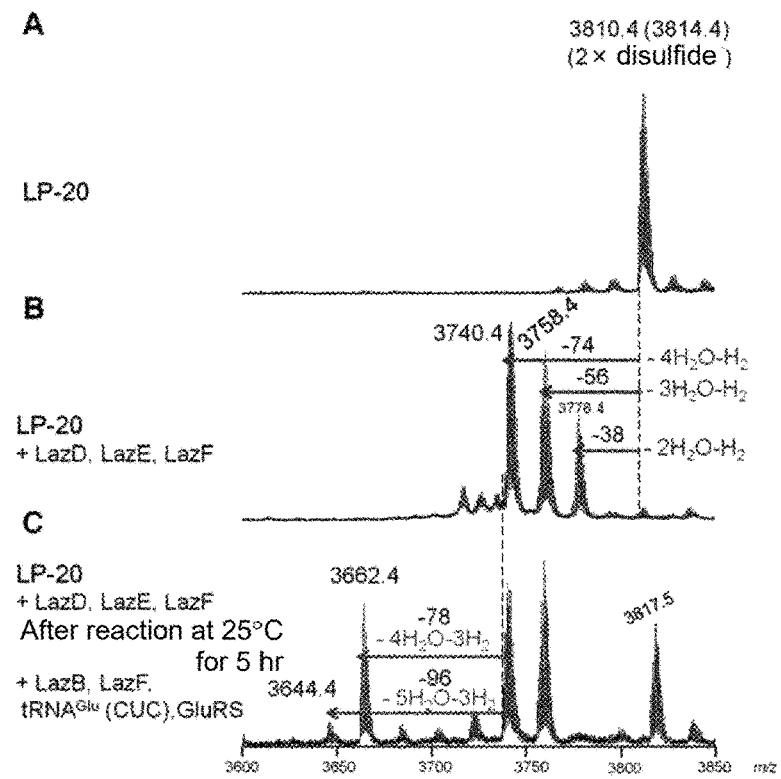

[Fig.36]
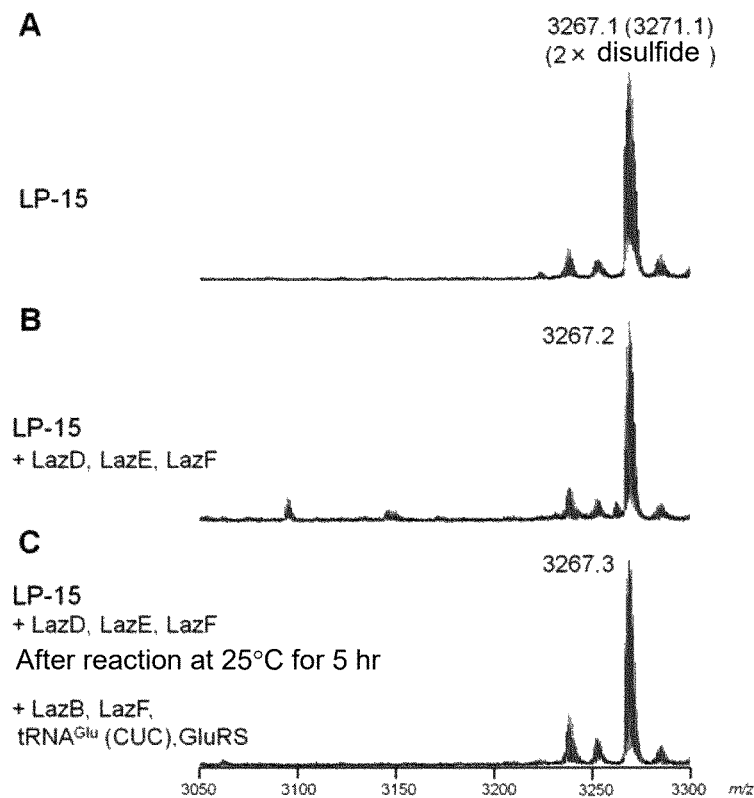
[Fig.37]
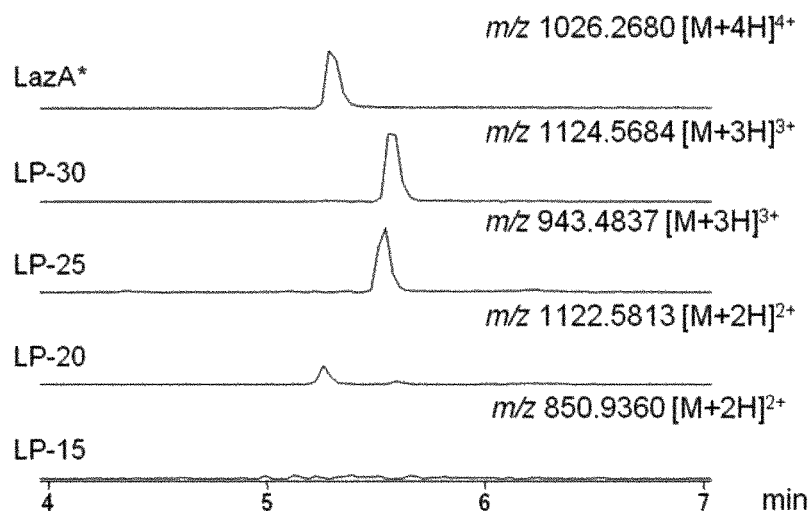

```
     -25       -20         -10          -1 1     5         10        15
     MLQDLDLSELTVTSLRDTVALPENGASWGSCSCQASSSCAQP
            Leader peptide                 Core peptide
```

Substituted by Ala one by one

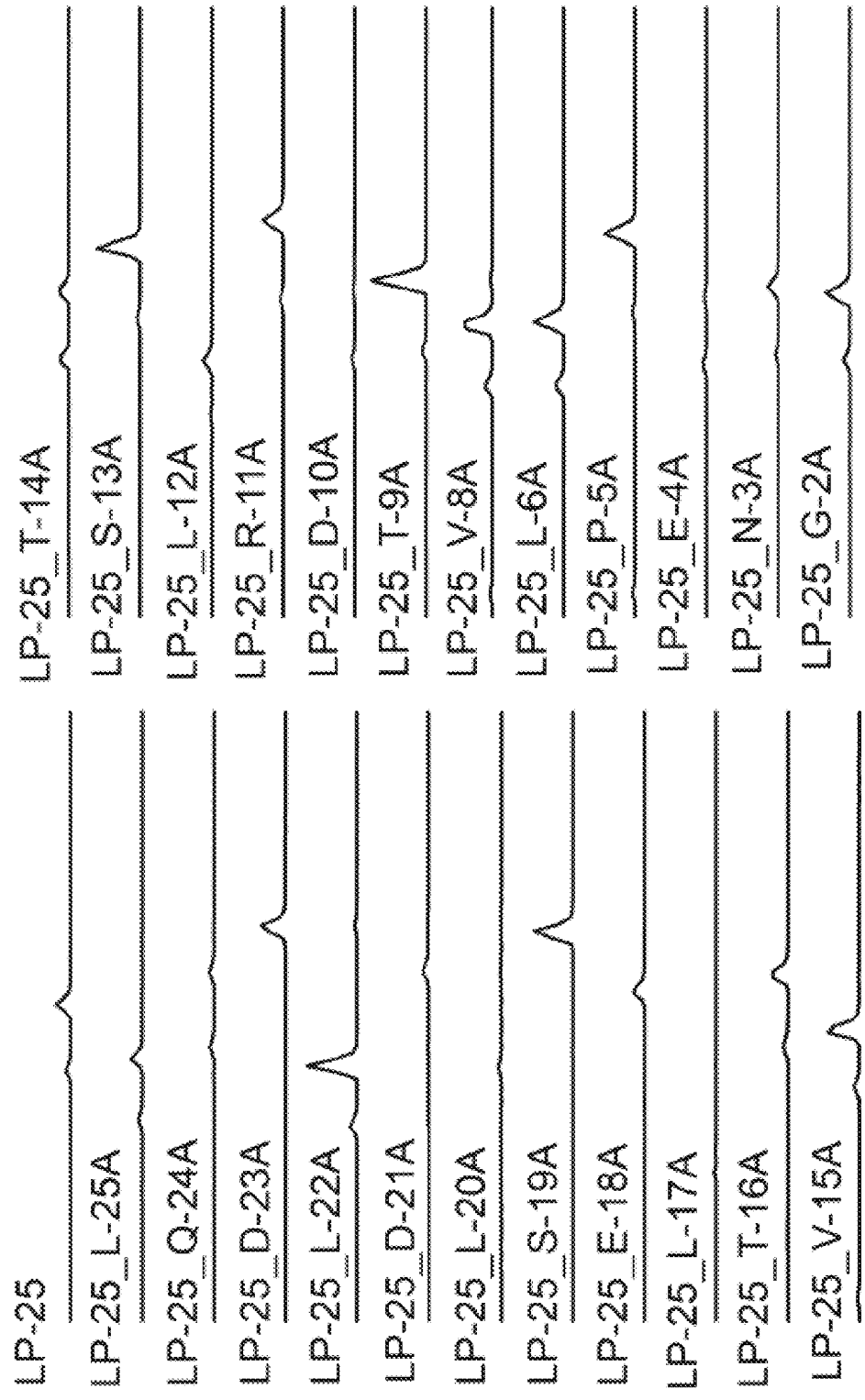
[Fig.39]

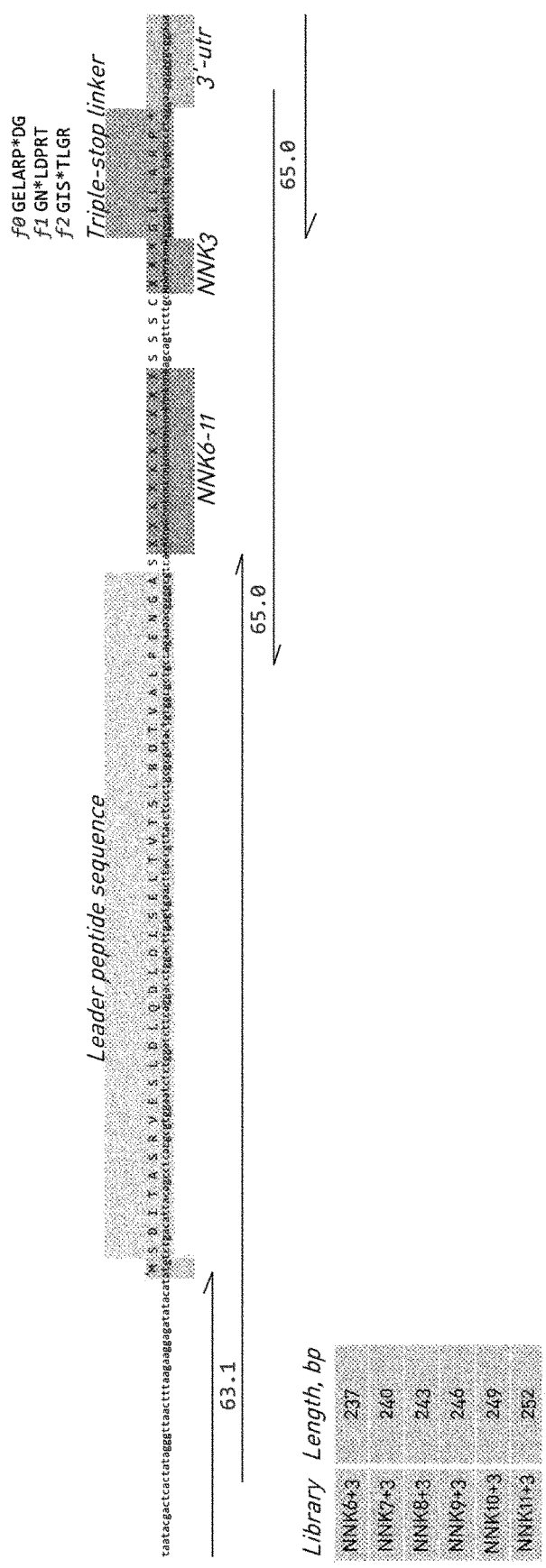
[Fig. 40]

[Fig.41]
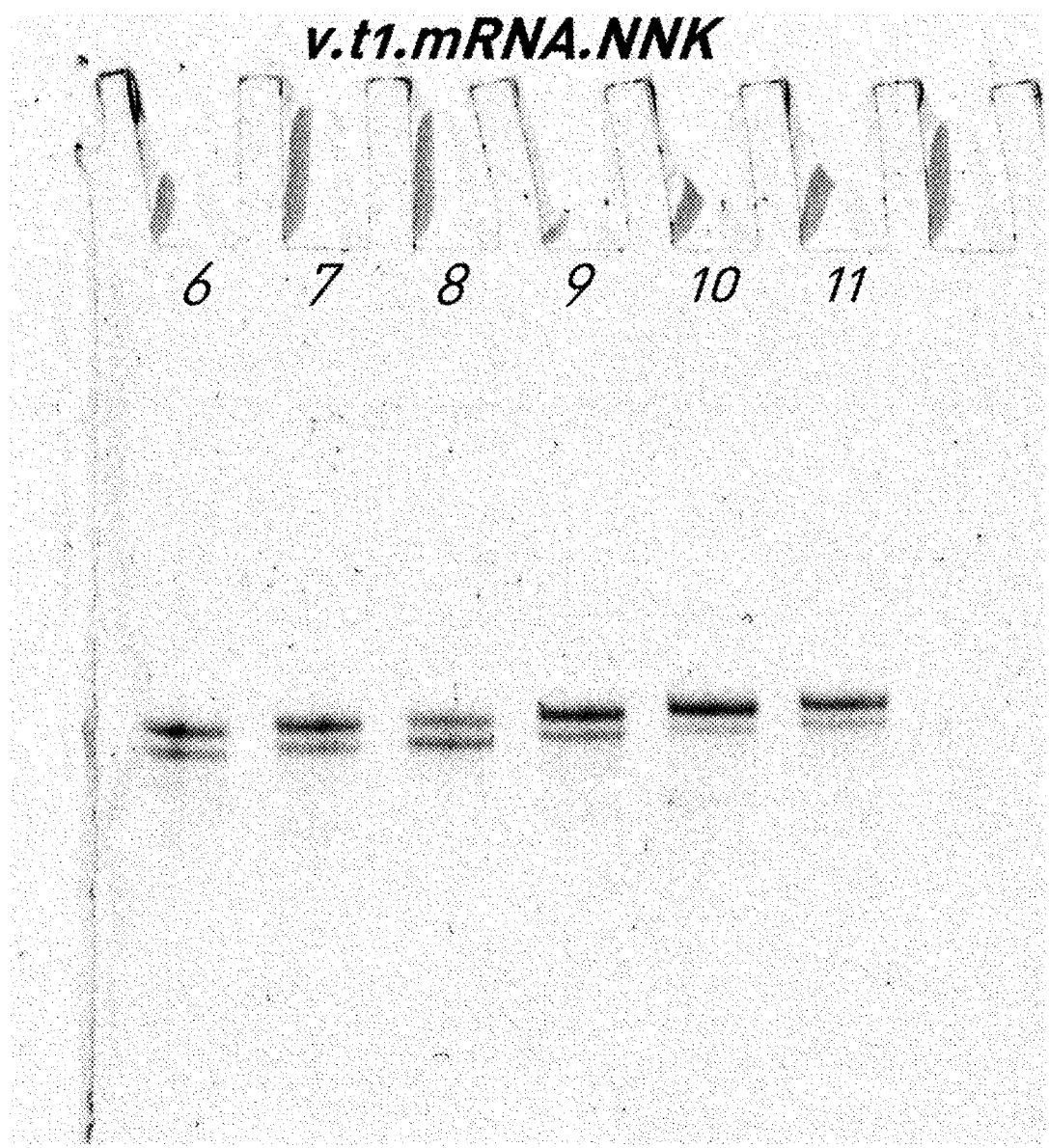

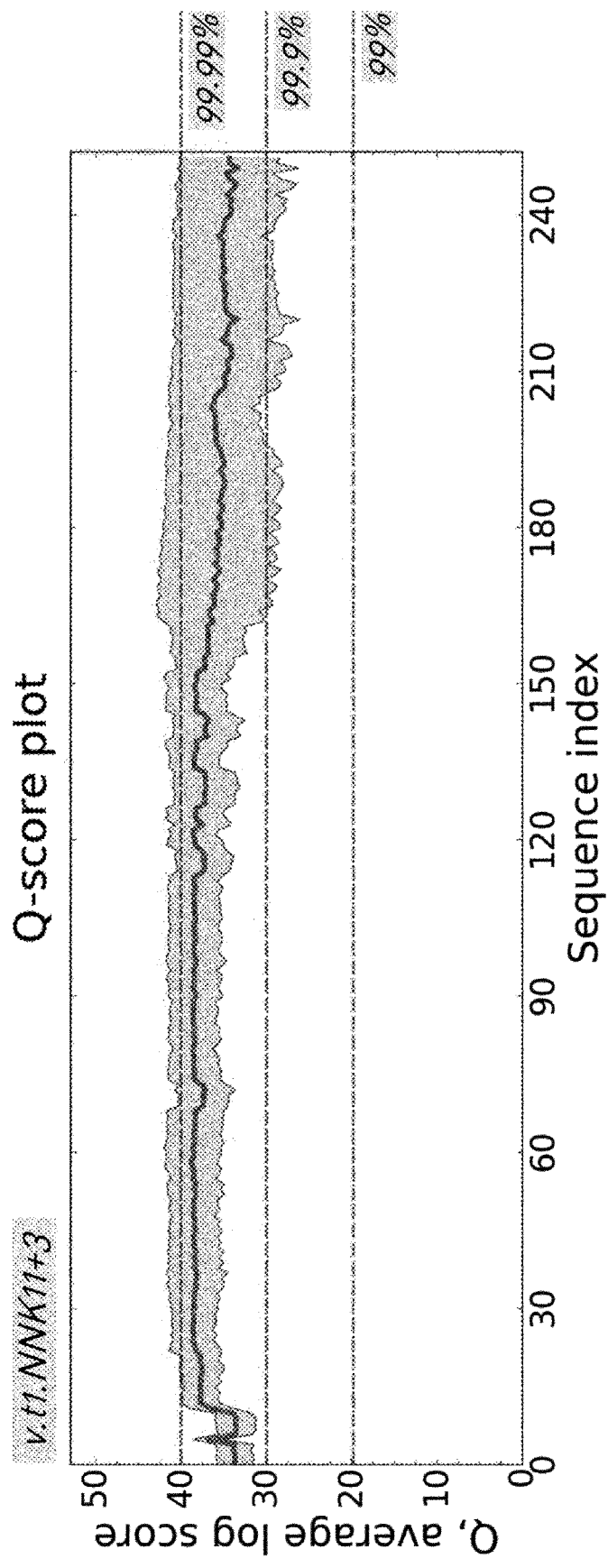
[Fig.42]

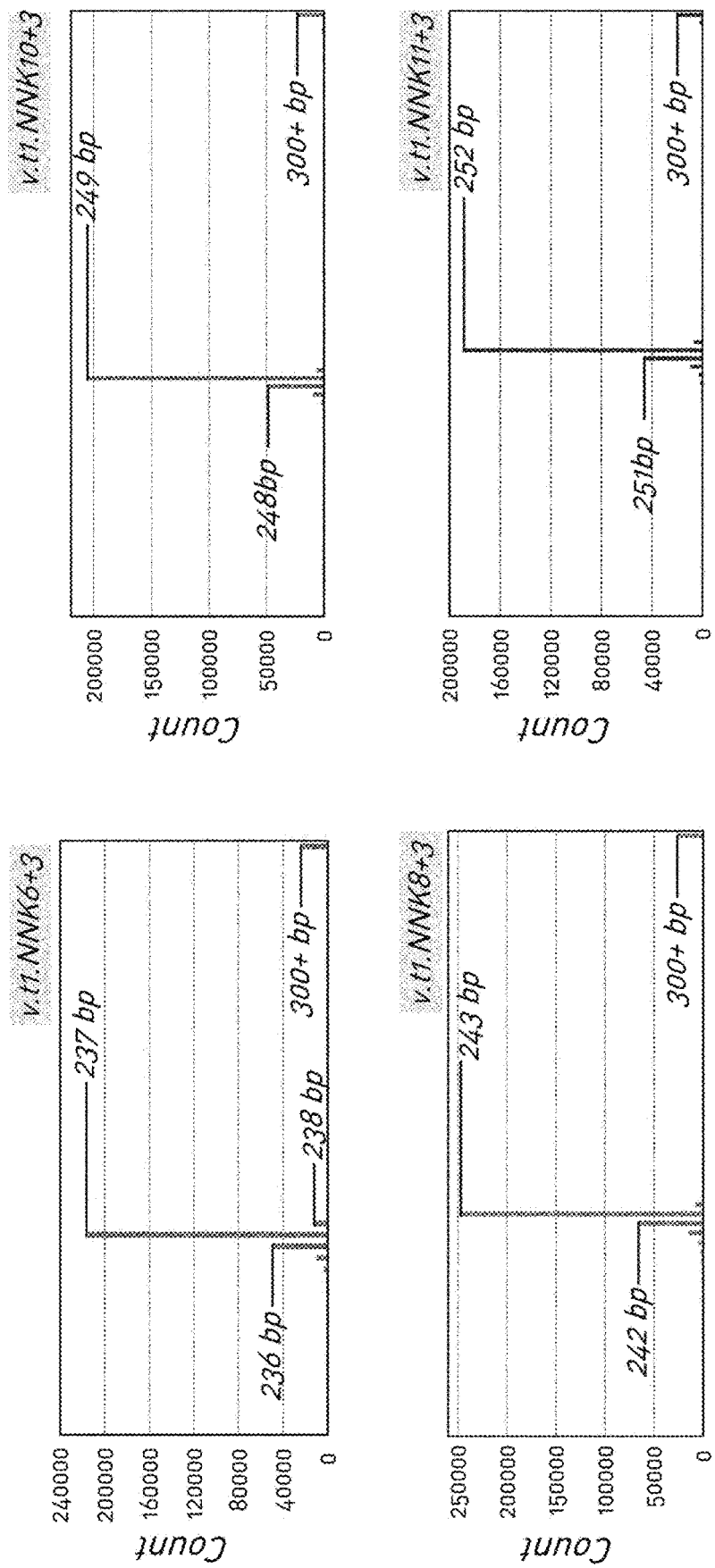
[Fig.43]

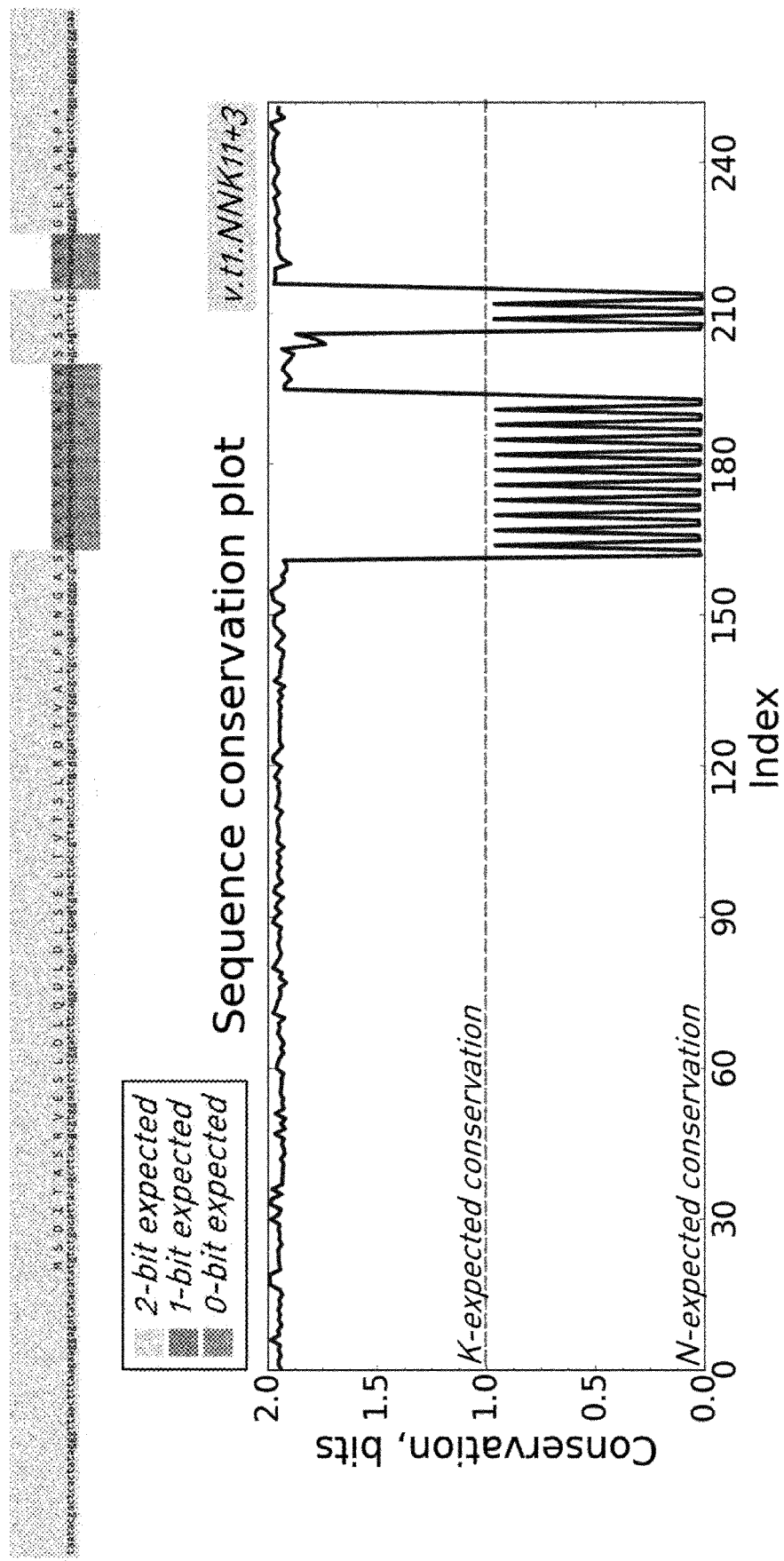
[Fig.44]

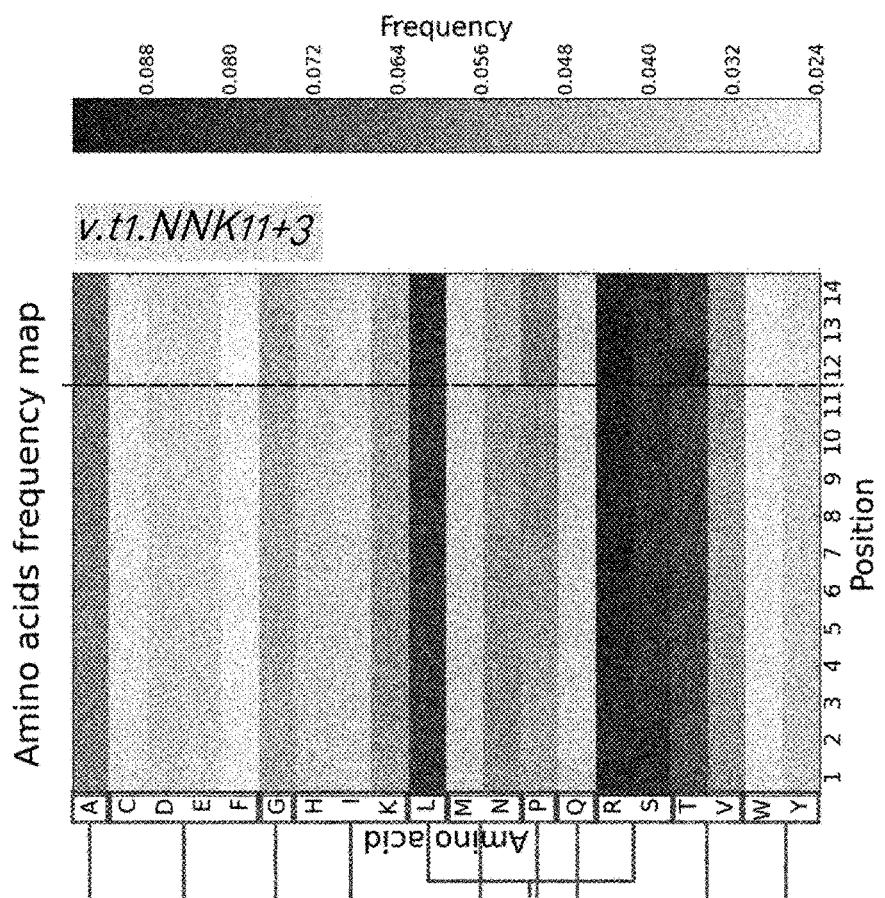
[Fig.45]
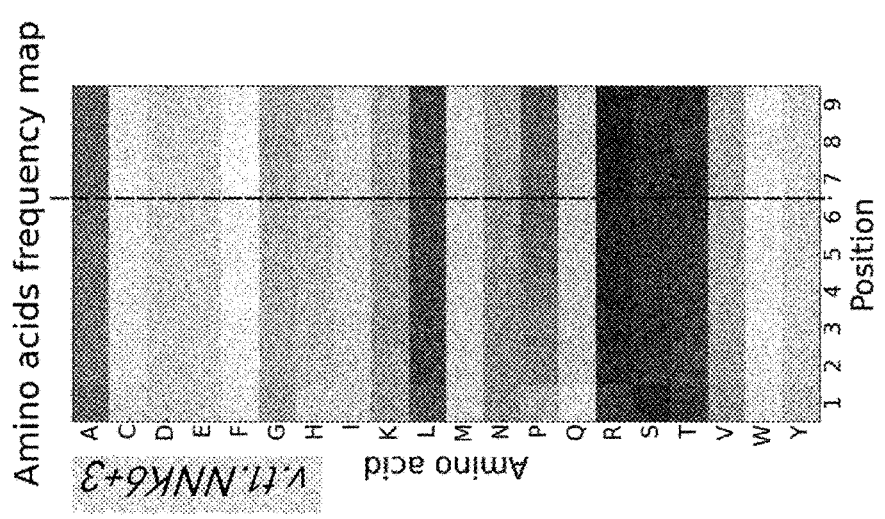

[Fig.46]
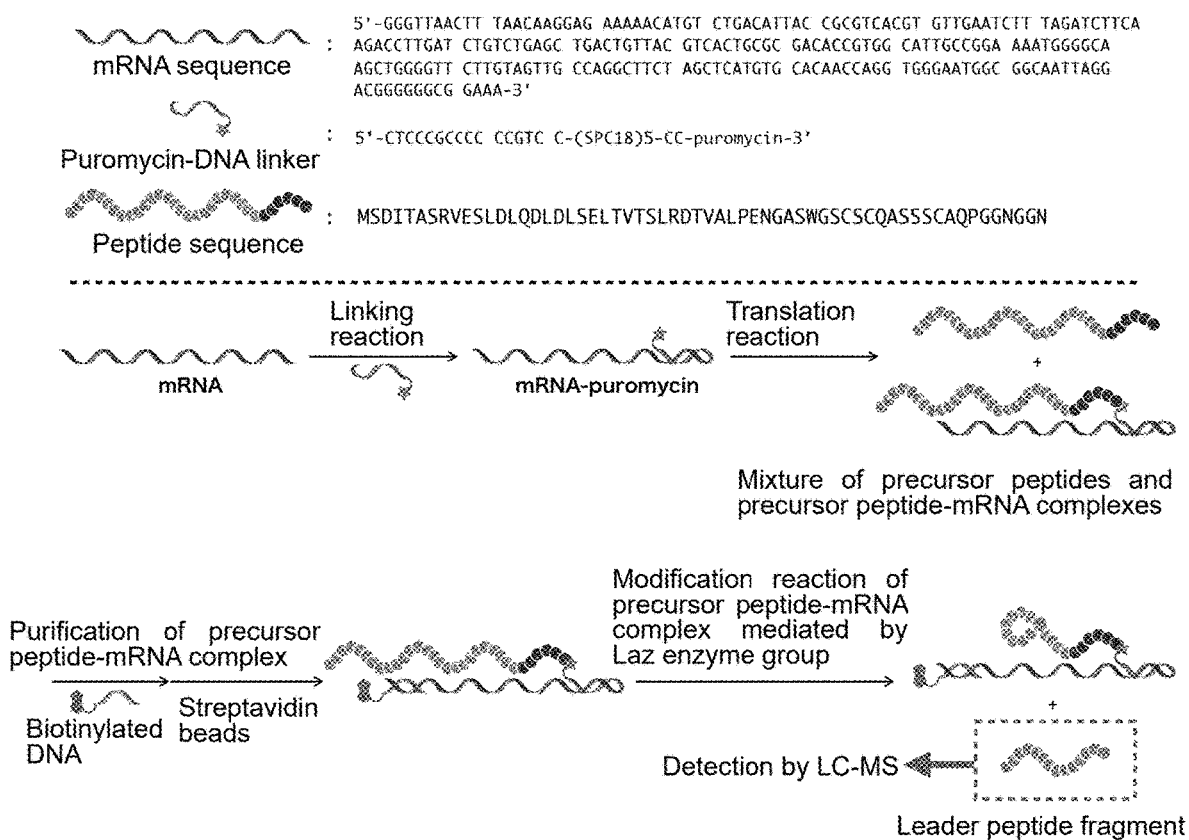

[Fig.47]
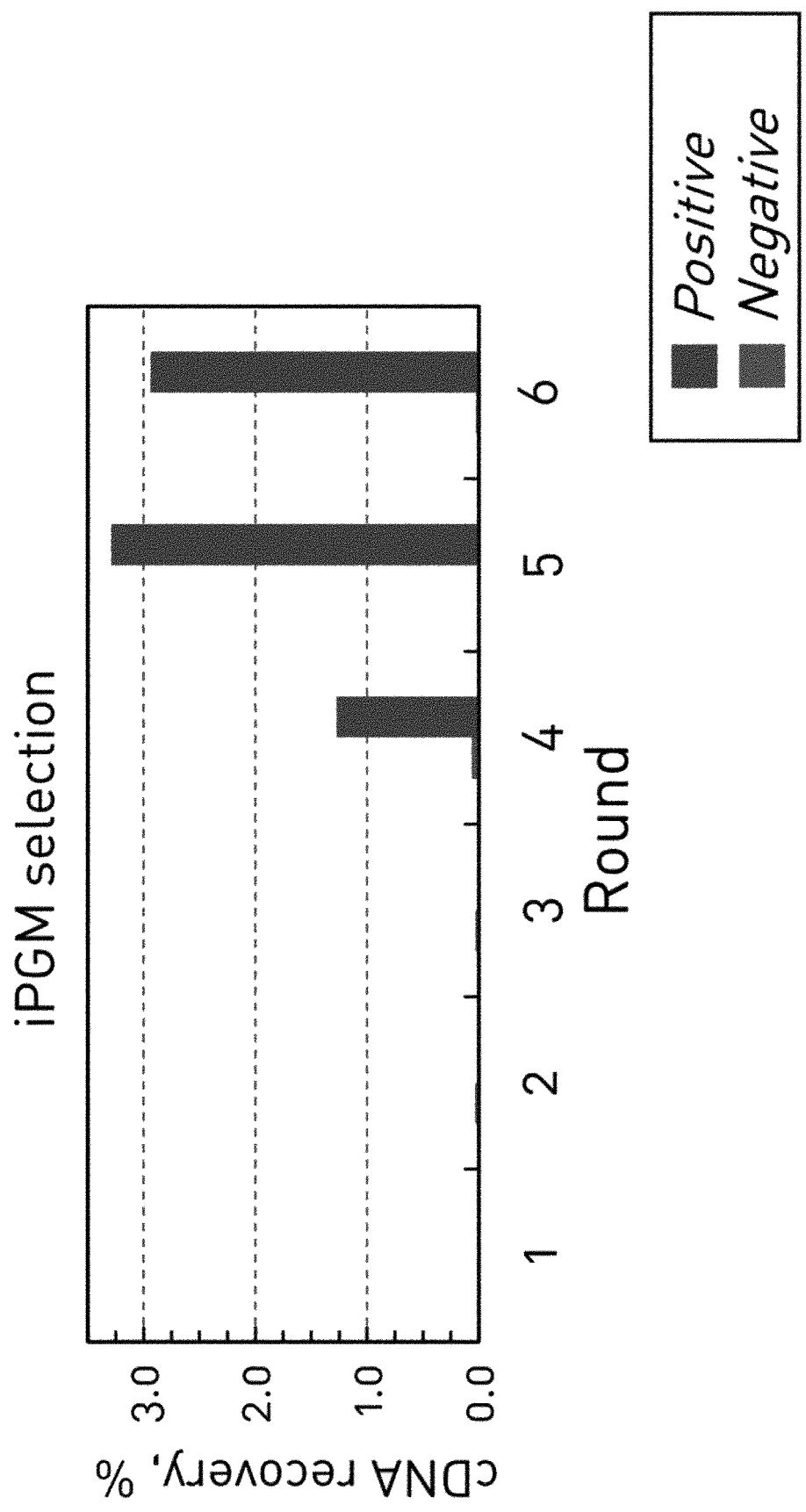

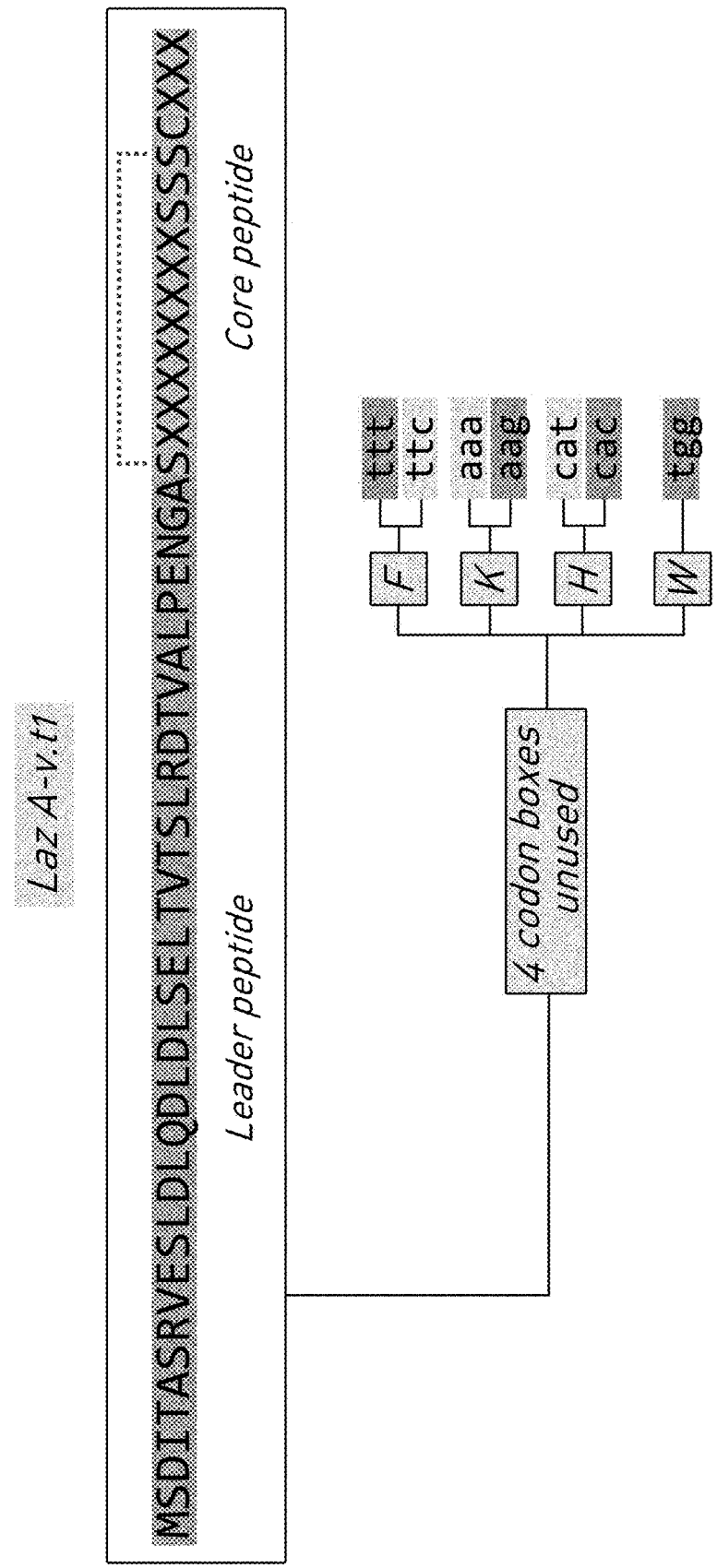
[Fig. 48]

[Fig.49]

```
                                                  v.061                                                  v.077
LP  S W G A A A A Q A S S S C A Q P *              LP  S A G A A A A Q A S S S C W Q P *
tca.ggggcggcagcggcccaagcgagcagttcttgcgcgcagccttaagcttcg   tcagcggggcggcagcggcccaggcgagcagttcttgc..agccttaagcttcg v.070                                                  v.080
LP  S A W A A A A Q A S S S C A Q P *              LP  S A G A A A A Q A S S S C A W P *
tcagc..gcgcagcgcccaagcgagcagttcttgcgcgcagccttaagcttcg   tcagcggggcggcagcggcccaggcgtctagttcttgcgc..ccttaagcttcg v.086                                                  v.081
LP  S A G W A A A Q A S S S C A Q P *              LP  S A G A A A A Q A S S S C A Q W *
tcagcggg..gcagcggcccaggcgtctagttcttgcgcgcagccttaagcttcg   tcagcggggcggcagcggcccaggcgtctagttcttgcgcgcag..taagcttcg v.087                                                  v.071
LP  S A G A W A A Q A S S S C A Q P *              LP  S A W A A A W Q A S S S C A Q P *
tcagcggggca..cggcccaggcgtctagttcttgcgcgcagccttaagcttcg   tcagc..gcgcagcg..aagcgagcagttcttgcgcgcagccttaagcttcg v.088                                                  v.072
LP  S A G A A W A Q A S S S C A Q P *              LP  S A W A K A W Q A S S S C A Q P *
tcagcggggcagc..cccaggcgtctagttcttgcgcgcagccttaagcttcg   tcagc..gc..gc..aagcgagcagttcttgcgcgcagccttaagcttcg v.089                                                  v.073
LP  S A G A A A W Q A S S S C A Q P *              LP  S W K W K W K Q A S S S C A Q P *
tcagcggggcagcggcc..caggcgtctagttcttgcgcgcagccttaagcttcg   tca..aagcgagcagttcttgcgcgcagccttaagcttcg v.074                                                  v.100
LP  S A G A A A A W A S S S C A Q P *              LP  S A W A H A F Q A S S S C A Q K *
tcagcggggcggcagcggcc..gcagcagttcttgcgcgcagccttaagcttcg   tcagc..gca..gc..caggcgtctagttcttgcgcgcag..taagcttcg v.075                                                  v.101
LP  S A G A A A A A W S S S C A Q P *              LP  S A K A W A H Q A S S S C A Q F *
tcagcggggcggcagcggccgc..agcagttcttgcgcgcagccttaagcttcg   tcagc..gca..gcc..aggcgtctagttcttgcgcag..taagcttcg
```

[Fig.50]
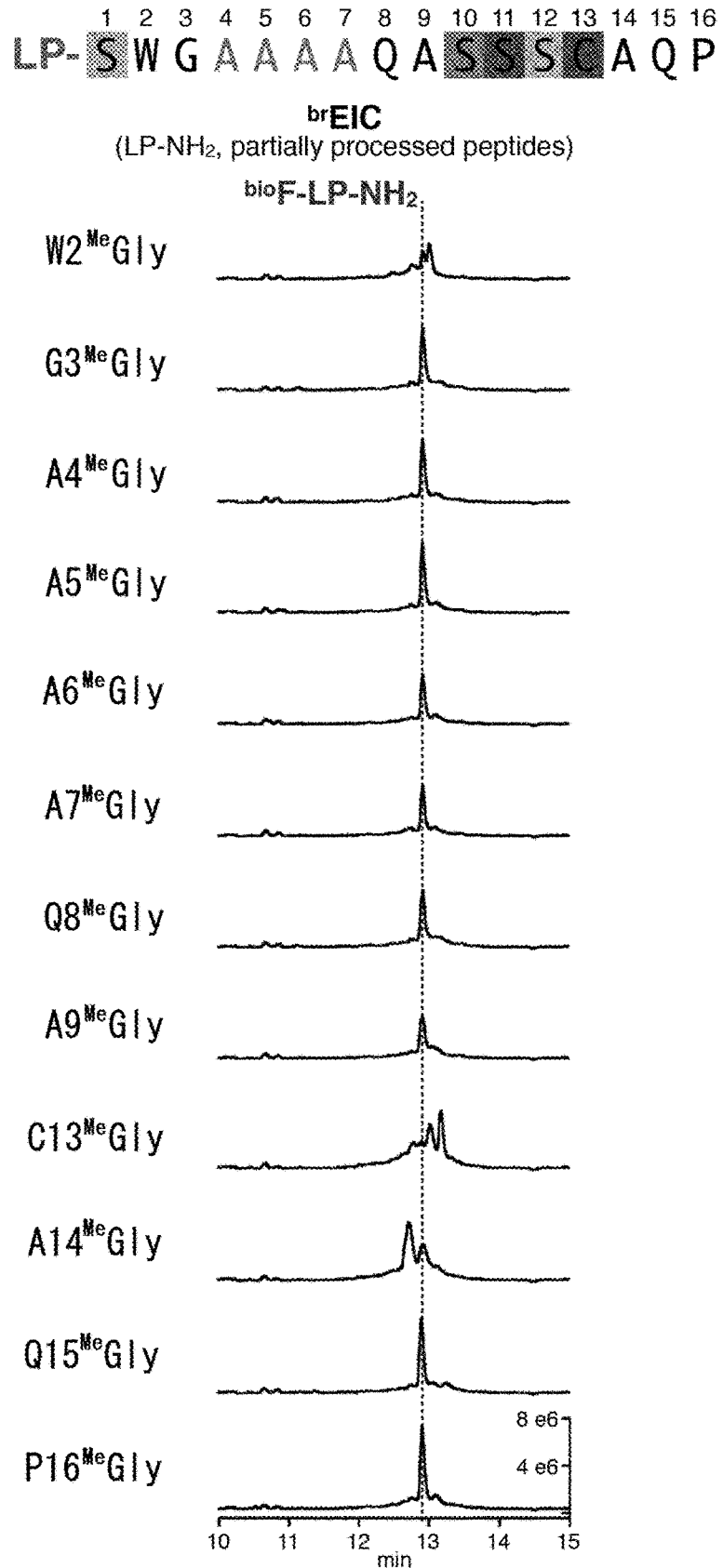

[Fig.51]
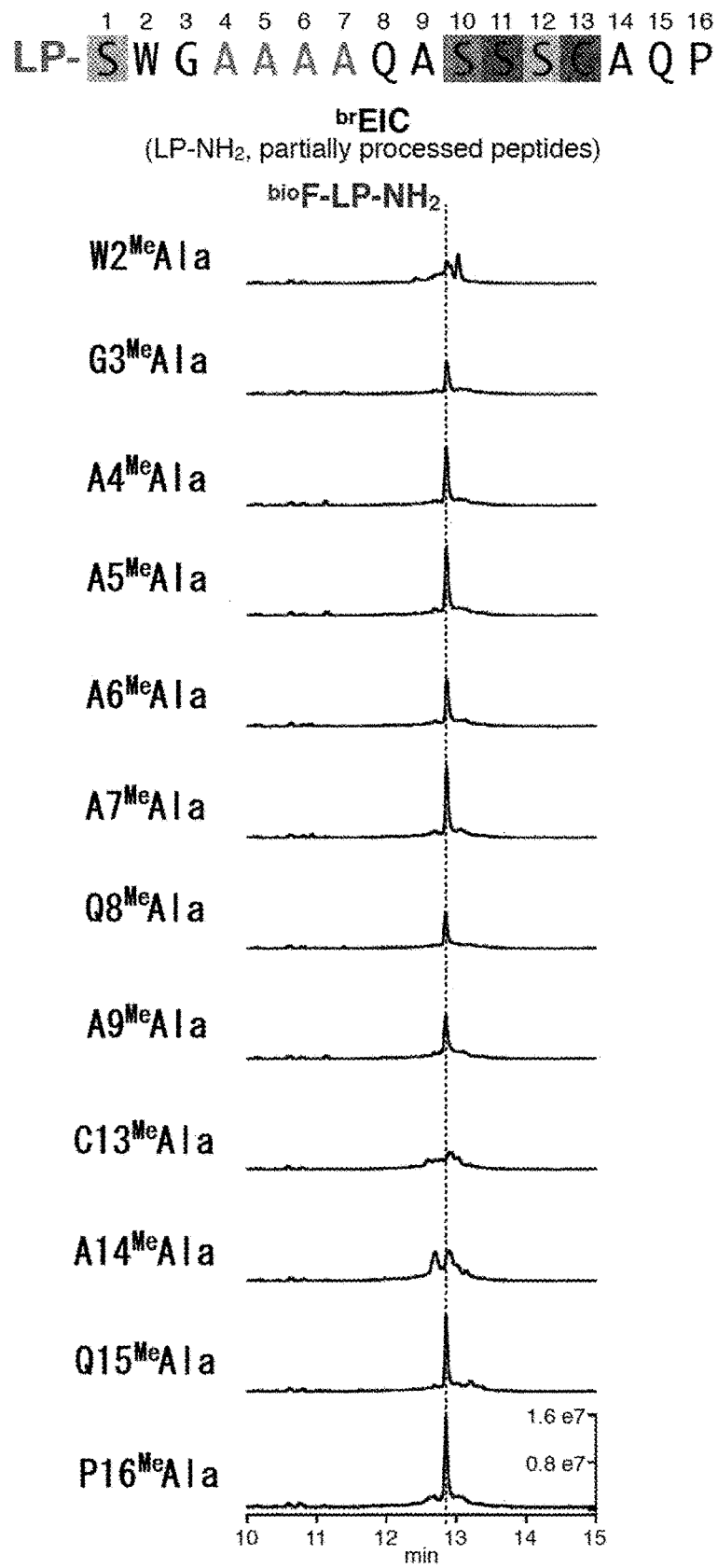

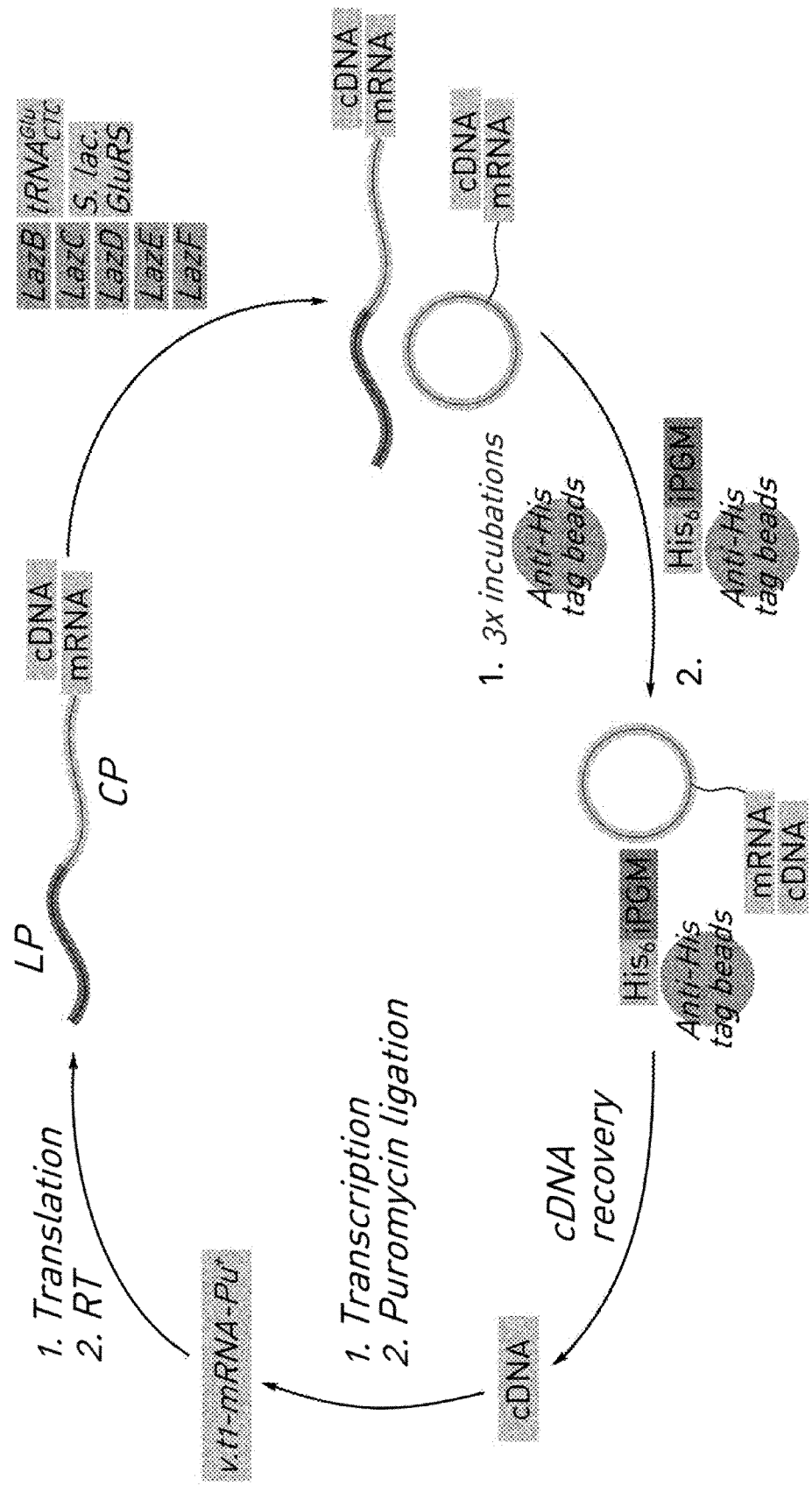
[Fig.52]

[Fig.53]
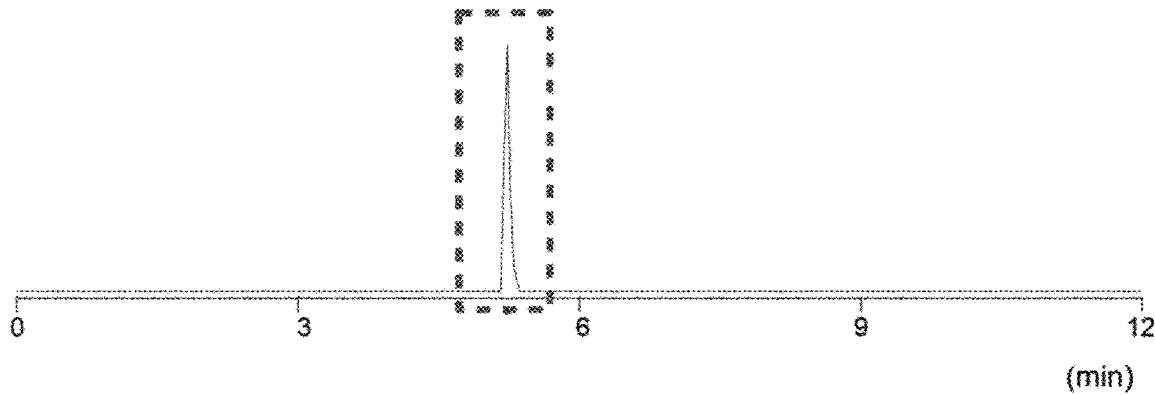
[Fig.54]
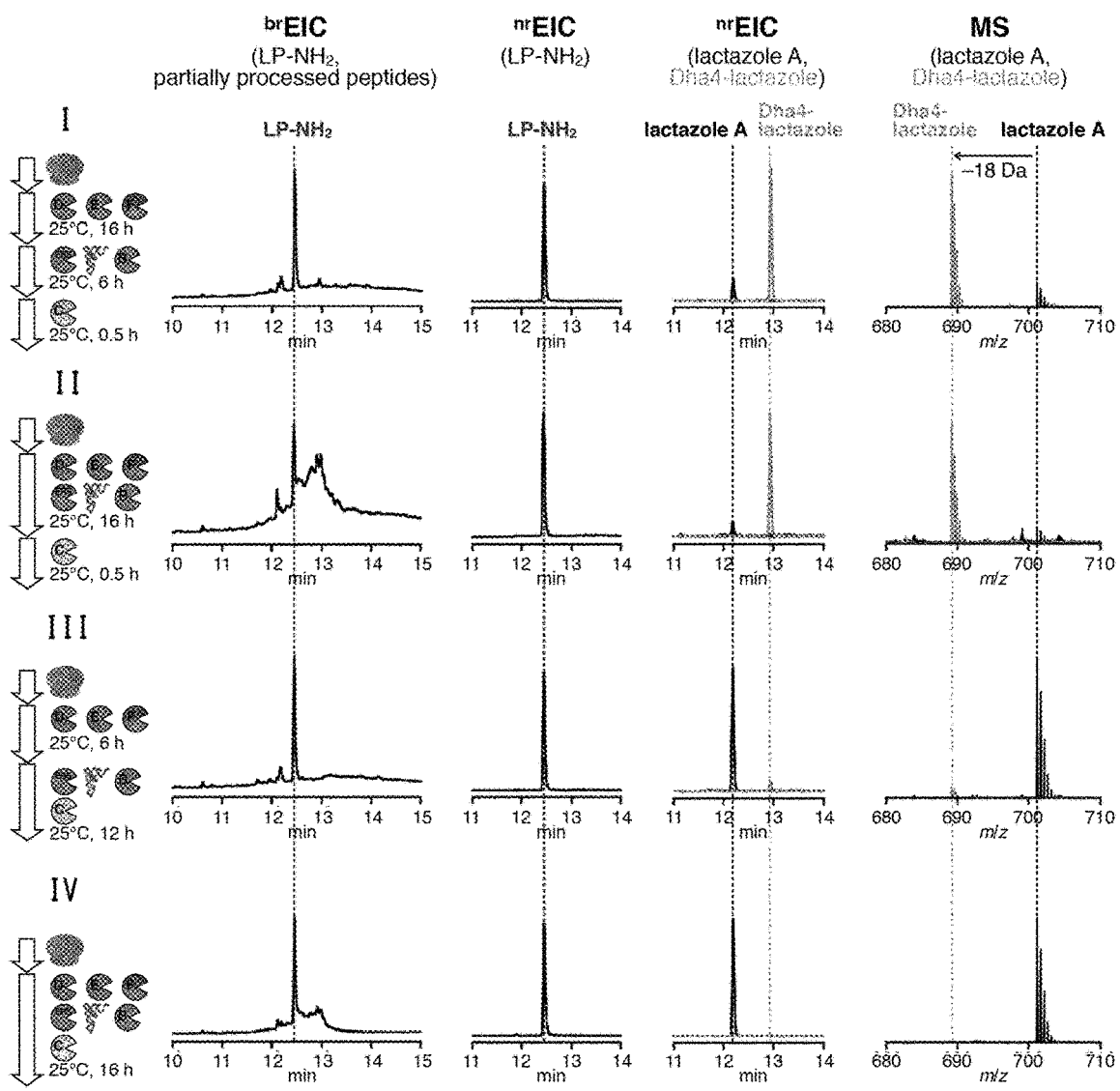

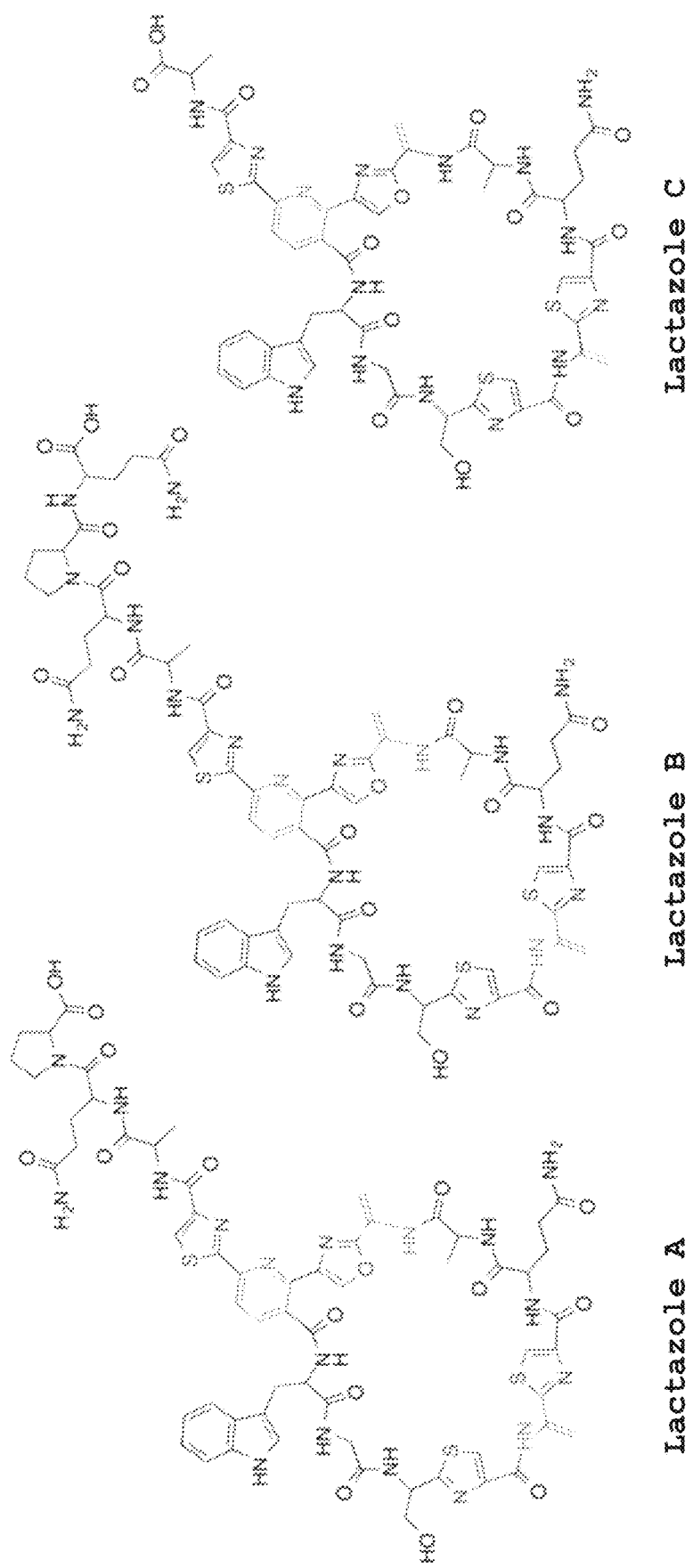
[Fig. 55]

[Fig. 56]
[Table 1]

| Entry | Name | Amino-acid sequences of LPs (-34 to -1) | Number of azoles | Number of Dhas |
|---|---|---|---|---|
| 1 | GodA* | M K K E N V Q T L A I D D I E N I D A E V T I E E L S S T N G A E | 6 | 1,2 |
| 2 | GodA*LP(-25)-(-1) | M K K K           L A I D D I E N I D A E V T I E E L S S T N G A E | 6 | 1,2 |
| 3 | GodA*LP(-20)-(-1) | M K K K                   I E N I D A E V T I E E L S S T N G A E | 6 | 1,2 |
| 4 | GodA*LP(-15)-(-1) | M K K K                            A E V T I E E L S S T N G A E | 4,5,6 | 1 |
| 5 | GodA*LP(-10)-(-1) | M K K K                                   E E L S S T N G A E | 0 | 0 |
| 6 | GodA*LP(-5)-(-1) | M K K K                                           S T N G A E | 0 | 0 |

From top to bottom, the sequence identifiers are SEQ ID NOs: 9 to 13.

[Fig. 57]
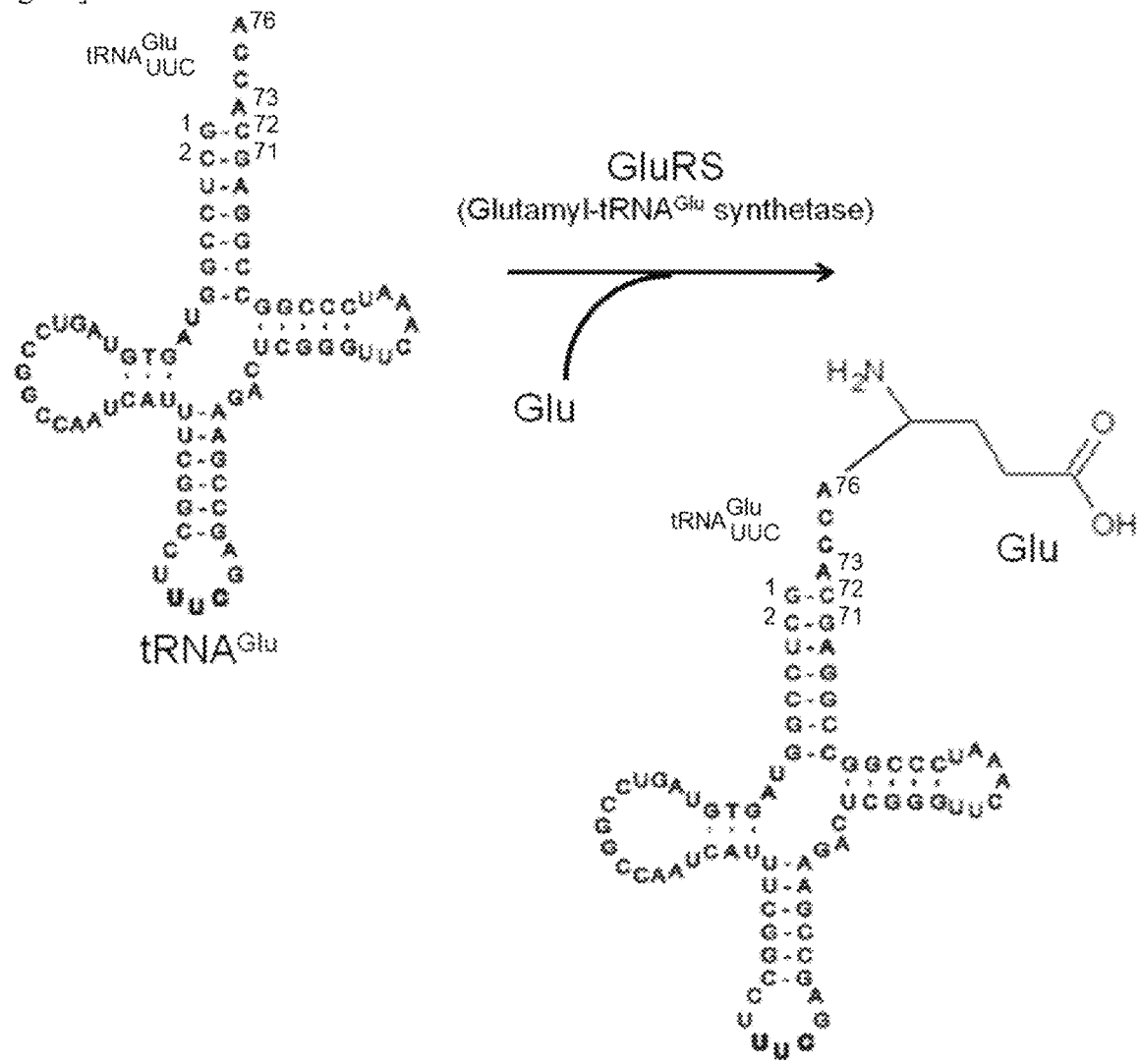
The sequence identifier of tRNA^Glu is SEQ ID NO: 277.

[Fig. 58]
[Table 31]

| Analog name | Amino acid sequence | | | | | | | | | | | | | | | | | The number of azole moieties formed | The number of dehydroalanine moieties formed |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | | |
| Native | S | W | G | S | C | S | C | Q | A | S | S | S | C | A | Q | P | P | | |
| 1A2 | S | A | G | S | C | S | C | Q | A | S | S | S | C | A | Q | P | P | 4 | 5 |
| 2A3 | S | W | A | S | C | S | C | Q | A | S | S | S | C | A | Q | P | P | 4 | 5 |
| 3A4 | S | W | G | A | C | S | C | Q | A | S | S | S | C | A | Q | P | P | 4 | 5 |
| 4A5 | S | W | G | S | A | S | C | Q | A | S | S | S | C | A | Q | P | P | 4, 5 | 5 |
| 5A6 | S | W | G | S | C | A | C | Q | A | S | S | S | C | A | Q | P | P | 4 | 5 |
| 6A7 | S | W | G | S | C | S | A | Q | A | S | S | S | C | A | Q | P | P | 4 | 5 |
| 7A8 | S | W | G | S | C | S | C | A | A | S | S | S | C | A | Q | P | P | 4 | 5 |
| 8A9 (9A10) | S | W | G | S | C | S | C | Q | A | A | S | S | C | A | Q | P | P | 3, 4 | 5 |
| 10A11 | S | W | G | S | C | S | C | Q | A | S | A | S | C | A | Q | P | P | 3, 4 | 5 |
| 11A12 | S | W | G | S | C | S | C | Q | A | S | S | A | C | A | Q | P | P | 4 | 5 |
| 12A13 | S | W | G | S | C | S | C | Q | A | S | S | S | A | A | Q | P | P | 4 | 5 |

From top to bottom, the sequence identifiers are SEQ ID NOs: 18 to 29.

[Fig. 59]
[Table 32]

| Analog name | Amino acid sequence |||||||||||||||||||
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| LazA* | S | W | G | S | C | S | C | Q | A | S | S | S | C | A | Q | P | | | |
| 2AA3 | S | W | A | A | G | S | C | S | C | Q | A | S | S | S | C | A | Q | P | |
| 8AA9 | S | W | G | S | C | S | C | Q | A | A | A | S | S | S | C | A | Q | P | |
| 2A3+8A9 | S | W | A | G | S | C | S | C | Q | A | A | S | S | S | C | A | Q | P | |
| 2AAA3 | S | W | A | A | A | G | S | C | S | C | A | A | A | S | C | A | Q | P | |
| 8AAA9 | S | W | G | S | C | S | C | Q | A | A | A | A | S | S | C | A | Q | P | |
| 3G_deletion | S | W | S | C | S | C | Q | A | S | S | S | C | A | Q | P | | | | |
| 9A_deletion | S | W | G | S | C | S | C | Q | S | S | S | C | A | Q | P | | | | |
| 3G9A_deletion | S | W | S | C | S | C | Q | S | S | S | C | A | Q | P | | | | | |

From top to bottom, the sequence identifiers are SEQ ID NOs: 18, and 30 to 37.

[Fig. 60]
[Table 33]

| Analog name | Amino acid sequence ||||||||||||||||
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| LazA* | S | W | G | S | C | S | C | Q | A | S | S | S | C | A | Q | P |
| 4SCSC7_4AAAA7 | S | W | G | A | A | A | A | Q | A | S | S | S | C | A | Q | P |

From top to bottom, the sequence identifiers are SEQ ID NOs: 18, and 38.

[Fig. 61]
[Table 34]

| Analog name | Amino acid sequence | | | | | | | | | | | | | | | | The number of azole moieties formed | The number of dehydroalanine moieties formed |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | | |
| LazA* | S | W | G | S | C | S | C | Q | A | S | S | S | C | A | Q | P | 4 | 5 |
| 4SCSC7_4AAAA7 | S | W | G | A | A | A | A | Q | A | S | S | S | C | A | Q | P | 2 | 3 |
| 4SCSC7_4AAAA7_S10A | S | W | G | A | A | A | A | Q | A | A | S | S | C | A | Q | P | 2 | 2 |
| 4SCSC7_4AAAA7_S11A | S | W | G | A | A | A | A | Q | A | S | A | S | C | A | Q | P | 1 | 3 |
| 4SCSC7_4AAAA7_S12A | S | W | G | A | A | A | A | Q | A | S | S | A | C | A | Q | P | 2 | 2 |
| 4SCSC7_4AAAA7_C13A | S | W | G | A | A | A | A | Q | A | S | S | S | A | A | Q | P | 1 | 3 |

From top to bottom, the sequence identifiers are SEQ ID NOs: 18, 38, and 39 to 42.

[Fig. 62]
[Table 35]

| Analog name | 1 | 2 | 3 | 4 | 5 | 6 | 7 | 8 | 9 | 10 | 11 | 12 | 13 | 14 | 15 | 16 | Azole ring | Dehydroalanine |
|---|---|---|---|---|---|---|---|---|---|---|---|---|---|---|---|---|---|---|
| 4SCSC7_4AAAA7_W2A | S | A | G | A | A | A | A | Q | A | S | S | S | C | A | Q | P | 2 | 3(2) |
| 4SCSC7_4AAAA7_W2E | S | E | G | A | A | A | A | Q | A | S | S | S | C | A | Q | P | 2 | 3 |
| 4SCSC7_4AAAA7_W2R | S | R | G | A | A | A | A | Q | A | S | S | S | C | A | Q | P | 2 | 3 |
| 4SCSC7_4AAAA7_W2S | S | S | G | A | A | A | A | Q | A | S | S | S | C | A | Q | P | 2 | 4,3 |
| 4SCSC7_4AAAA7_W2V | S | V | G | A | A | A | A | Q | A | S | S | S | C | A | Q | P | 2 | 3(2) |
| 4SCSC7_4AAAA7_W2F | S | F | G | A | A | A | A | Q | A | S | S | S | C | A | Q | P | 2 | 3 |
| 4SCSC7_4AAAA7_G3E | S | W | E | A | A | A | A | Q | A | S | S | S | C | A | Q | P | 2 | 3 |
| 4SCSC7_4AAAA7_G3R | S | W | R | A | A | A | A | Q | A | S | S | S | C | A | Q | P | 2 | 3 |
| 4SCSC7_4AAAA7_G3V | S | W | V | A | A | A | A | Q | A | S | S | S | C | A | Q | P | 2 | 3 |
| 4SCSC7_4AAAA7_G3S | S | W | S | A | A | A | A | Q | A | S | S | S | C | A | Q | P | 2 | 4,3 |
| 4SCSC7_4AAAA7_G3F | S | W | F | A | A | A | A | Q | A | S | S | S | C | A | Q | P | 2 | 3 |
| 4SCSC7_4AAAA7_G3W | S | W | W | A | A | A | A | Q | A | S | S | S | C | A | Q | P | 2 | 3 |
| 4SCSC7_4AAAA7_Q8A | S | W | G | A | A | A | A | A | A | S | S | S | C | A | Q | P | 1(2) | 3 |
| 4SCSC7_4AAAA7_Q8E | S | W | G | A | A | A | A | E | A | S | S | S | C | A | Q | P | 1 | 4 |
| 4SCSC7_4AAAA7_Q8R | S | W | G | A | A | A | A | R | A | S | S | S | C | A | Q | P | 1,2 | 3 |
| 4SCSC7_4AAAA7_Q8V | S | W | G | A | A | A | A | V | A | S | S | S | C | A | Q | P | 1,2 | 3 |
| 4SCSC7_4AAAA7_Q8S | S | W | G | A | A | A | A | S | A | S | S | S | C | A | Q | P | 1,2(3) | 3(azole 3+Dha3) |
| 4SCSC7_4AAAA7_Q8F | S | W | G | A | A | A | A | F | A | S | S | S | C | A | Q | P | 2 | 3 |
| 4SCSC7_4AAAA7_Q8W | S | W | G | A | A | A | A | W | A | S | S | S | C | A | Q | P | 2 | 3 |
| 4SCSC7_4AAAA7_A9E | S | W | G | A | A | A | A | Q | E | S | S | S | C | A | Q | P | 1(2) | 0 |
| 4SCSC7_4AAAA7_A9R | S | W | G | A | A | A | A | Q | R | S | S | S | C | A | Q | P | 2,1 | 3 |
| 4SCSC7_4AAAA7_A9V | S | W | G | A | A | A | A | Q | V | S | S | S | C | A | Q | P | 2,1 | 3 |
| 4SCSC7_4AAAA7_A9S | S | W | G | A | A | A | A | Q | S | S | S | S | C | A | Q | P | 2 | 4 |
| 4SCSC7_4AAAA7_A9F | S | W | G | A | A | A | A | Q | F | S | S | S | C | A | Q | P | 2,1 | 3 |
| 4SCSC7_4AAAA7_A9W | S | W | G | A | A | A | A | Q | W | S | S | S | C | A | Q | P | 2 | 3 |
| 4SCSC7_4AAAA7_Q15A | S | W | G | A | A | A | A | Q | A | S | S | S | C | A | A | P | 2 | 3 |
| 4SCSC7_4AAAA7_P16A | S | W | G | A | A | A | A | Q | A | S | S | S | C | A | Q | A | 2 | 3 |
| 4SCSC7_4AAAA7_15QP16_16AA16 | S | W | G | A | A | A | A | Q | A | S | S | S | C | A | A | A | 2 | 3 |

From top to bottom, the sequence identifiers are SEQ ID NOs: 43 to 70.

[Fig. 63]
[Table 36]

| Analog name | Amino acid sequence | | | | | | | | | | | | | | | | | | | | | | | The number of azole moieties formed | The number of dehydroalanine moieties formed |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | | |
| LazA* | S | W | G | S | C | S | C | Q | A | S | S | S | C | A | Q | P | | | | | | | | 4 | 4 |
| 4SCSC7_4AAAA7 | S | W | G | A | A | A | A | Q | A | S | S | S | C | A | Q | P | | | | | | | | 2 | 3 |
| 4SCSC7_4AAAA7_1× Ala insertion | S | W | G | A | A | A | A | Q | A | A | A | S | S | C | A | Q | P | | | | | | | 2,(1) | 3 |
| 4SCSC7_4AAAA7_2× Ala insertion | S | W | G | A | A | A | A | Q | A | A | A | A | S | S | C | A | Q | P | | | | | | 2,(1) | 3 |
| 4SCSC7_4AAAA7_3× Ala insertion | S | W | G | A | A | A | A | Q | A | A | A | A | A | S | S | C | A | Q | P | | | | | 2,(1) | 3 |
| 4SCSC7_4AAAA7_4× Ala insertion | S | W | G | A | A | A | A | Q | A | A | A | A | A | A | S | S | C | A | Q | P | | | | 2,(1) | 3 |
| 4SCSC7_4AAAA7_5× Ala insertion | S | W | G | A | A | A | A | Q | A | A | A | A | A | A | A | S | S | C | A | Q | P | | | 2,(1) | 3 |
| 4SCSC7_4AAAA7_6× Ala insertion | S | W | G | A | A | A | A | Q | A | A | A | A | A | A | A | A | S | S | C | A | Q | P | | 2,1 | 3 |
| 4SCSC7_4AAAA7_7× Ala insertion | S | W | G | A | A | A | A | Q | A | A | A | A | A | A | A | A | A | S | S | C | A | Q | P | 2,(1) | 3 |
| 4SCSC7_4AAAA7_1× Ala deletion | S | W | G | A | A | A | Q | A | S | S | S | C | A | Q | P | | | | | | | | | 2 | 3,(2) |
| 4SCSC7_4AAAA7_2× Ala deletion | S | W | G | A | A | Q | A | S | S | S | C | A | Q | P | | | | | | | | | | 2 | 3,(2) |
| 4SCSC7_4AAAA7_3× Ala deletion | S | W | A | A | Q | A | S | S | S | C | A | Q | P | | | | | | | | | | | 2 | 3 |
| 4SCSC7_4AAAA7_4× Ala deletion | S | W | Q | A | S | S | S | C | A | Q | P | | | | | | | | | | | | | 2 | 3,(2) |
| 4SCSC7_4AAAA7_4× Ala_1×Gly deletion | S | W | A | S | S | S | C | A | Q | P | | | | | | | | | | | | | | 2 | 2,(3) |
| 4SCSC7_4AAAA7_5× Ala_1×Gly, Gln deletion | S | S | S | S | C | A | Q | P | | | | | | | | | | | | | | | | 2 | 2,3 |
| 4SCSC7_4AAAA7_5× Ala_1×Gly, Gln, Trp deletion | S | S | S | C | A | Q | P | | | | | | | | | | | | | | | | | 2,1 | 3,(2) |

From top to bottom, the sequence identifiers are SEQ ID NOs: 18, 38, and 71 to 85.

[Fig. 64]
[Table 37]

| Analog name | Amino acid sequence | | | | | | | | | | | | | | | | The number of azole moieties formed |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | |
| Native | S | W | G | S | C | S | C | Q | A | S | S | S | C | A | Q | P | 4 |
| S1C | C | W | G | S | C | S | C | Q | A | S | S | S | C | A | Q | P | 4 |
| W2C | S | C | G | S | C | S | C | Q | A | S | S | S | C | A | Q | P | 4 |
| G3C | S | W | C | S | C | S | C | Q | A | S | S | S | C | A | Q | P | 4 |
| S4C | S | W | G | C | C | S | C | Q | A | S | S | S | C | A | Q | P | 4 |
| S6C | S | W | G | S | C | C | C | Q | A | S | S | S | C | A | Q | P | 4 |
| Q8C | S | W | G | S | C | S | C | C | A | S | S | S | C | A | Q | P | 4, 5 |
| A9C | S | W | G | S | C | S | C | Q | C | S | S | S | C | A | Q | P | 4, 5 |
| S10C | S | W | G | S | C | S | C | Q | A | C | S | S | C | A | Q | P | 5, (4) |
| S11C | S | W | G | S | C | S | C | Q | A | S | C | S | C | A | Q | P | 4 |
| S12C | S | W | G | S | C | S | C | Q | A | S | S | C | C | A | Q | P | 4 |
| A14C | S | W | G | S | C | S | C | Q | A | S | S | S | C | C | Q | P | 4 |
| Q15C | S | W | G | S | C | S | C | Q | A | S | S | S | C | A | C | P | 4 |
| P16C | S | W | G | S | C | S | C | Q | A | S | S | S | C | A | Q | C | 4 |

From top to bottom, the sequence identifiers are SEQ ID NOs: 18, and 86 to 97.

[Fig. 65]
[Table 38]

| Name | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 4SCSC7_4AAAA7 | S | W | G | A | A | A | A | Q | A | S | S | S | C | A | Q | P |
| 4SCSC7_4AAAA7_S10T | S | W | G | A | A | A | A | Q | A | T | S | S | C | A | Q | P |
| 4SCSC7_4AAAA7_S11T | S | W | G | A | A | A | A | Q | A | S | T | S | C | A | Q | P |
| 4SCSC7_4AAAA7_S11C | S | W | G | A | A | A | A | Q | A | S | C | S | C | A | Q | P |
| 4SCSC7_4AAAA7_C13S | S | W | G | A | A | A | A | Q | A | S | S | S | S | A | Q | P |
| 4SCSC7_4AAAA7_C13T | S | W | G | A | A | A | A | Q | A | S | S | S | T | A | Q | P |

From top to bottom, the sequence identifiers are SEQ ID NOs: 38, and 98 to 102.

SEQUENCE LISTING

<160> NUMBER OF SEQ ID NOS: 277

<210> SEQ ID NO 1
<211> LENGTH: 4
<212> TYPE: PRT
<213> ORGANISM: Artificial Sequence
<220> FEATURE:
<223> OTHER INFORMATION: partial structure of precursor peptide
      represented by fomula (III)
<220> FEATURE:
<221> NAME/KEY: misc_feature
<222> LOCATION: (1)..(1)
<223> OTHER INFORMATION: Xaa is one of optional amino acids and analogs
      thereof
<220> FEATURE:
<221> NAME/KEY: misc_feature
<222> LOCATION: (2)..(2)
<223> OTHER INFORMATION: Xaa is Ser, Cys, Thr, or diaminopropionic acid
      or analogs thereof
<220> FEATURE:
<221> NAME/KEY: misc_feature
<222> LOCATION: (3)..(3)
<223> OTHER INFORMATION: Xaa is Ser or Thr or analogs thereof
<220> FEATURE:
<221> NAME/KEY: misc_feature
<222> LOCATION: (4)..(4)
<223> OTHER INFORMATION: Xaa is one of optional amino acids and analogs
      thereof

<400> SEQUENCE: 1

Xaa Xaa Xaa Xaa
1

<210> SEQ ID NO 2
<211> LENGTH: 4
<212> TYPE: PRT
<213> ORGANISM: Artificial Sequence
<220> FEATURE:
<223> OTHER INFORMATION: partial structure of precursor peptide
      represented by fomula (III)
<220> FEATURE:
<221> NAME/KEY: misc_feature
<222> LOCATION: (1)..(1)
<223> OTHER INFORMATION: Xaa is Ser or Thr or analogs thereof
<220> FEATURE:
<221> NAME/KEY: misc_feature
<222> LOCATION: (2)..(2)
<223> OTHER INFORMATION: Xaa is Ser, Cys, Thr, or diaminopropionic acid
      or analogs thereof
<220> FEATURE:
<221> NAME/KEY: misc_feature
<222> LOCATION: (3)..(3)
<223> OTHER INFORMATION: Xaa is Ser or Thr or analogs thereof
<220> FEATURE:
<221> NAME/KEY: misc_feature
<222> LOCATION: (4)..(4)
<223> OTHER INFORMATION: Xaa is Ser, Cys, Thr, or diaminopropionic acid
      or analogs thereof

<400> SEQUENCE: 2

Xaa Xaa Xaa Xaa
1

<210> SEQ ID NO 3
<211> LENGTH: 4
<212> TYPE: PRT
<213> ORGANISM: Artificial Sequence
<220> FEATURE:
<223> OTHER INFORMATION: partial structure of precursor peptide
      represented by fomula (III)
<220> FEATURE:
<221> NAME/KEY: misc_feature
<222> LOCATION: (1)..(1)
<223> OTHER INFORMATION: Xaa is one of optional amino acids and analogs

```
      thereof
<220> FEATURE:
<221> NAME/KEY: misc_feature
<222> LOCATION: (2)..(2)
<223> OTHER INFORMATION: Xaa is Ser, Cys, or Thr or analogs thereof
<220> FEATURE:
<221> NAME/KEY: misc_feature
<222> LOCATION: (3)..(3)
<223> OTHER INFORMATION: Xaa is Ser or Thr or analogs thereof
<220> FEATURE:
<221> NAME/KEY: misc_feature
<222> LOCATION: (4)..(4)
<223> OTHER INFORMATION: Xaa is one of optional amino acids and analogs
      thereof

<400> SEQUENCE: 3

Xaa Xaa Xaa Xaa
1

<210> SEQ ID NO 4
<211> LENGTH: 4
<212> TYPE: PRT
<213> ORGANISM: Artificial Sequence
<220> FEATURE:
<223> OTHER INFORMATION: partial structure of precursor peptide
      represented by fomula (III)
<220> FEATURE:
<221> NAME/KEY: misc_feature
<222> LOCATION: (1)..(1)
<223> OTHER INFORMATION: Xaa is Ser or Thr or analogs thereof
<220> FEATURE:
<221> NAME/KEY: misc_feature
<222> LOCATION: (2)..(2)
<223> OTHER INFORMATION: Xaa is Ser, Cys, or Thr or analogs thereof
<220> FEATURE:
<221> NAME/KEY: misc_feature
<222> LOCATION: (3)..(3)
<223> OTHER INFORMATION: Xaa is Ser or Thr or analogs thereof
<220> FEATURE:
<221> NAME/KEY: misc_feature
<222> LOCATION: (4)..(4)
<223> OTHER INFORMATION: Xaa is Ser, Cys, Thr, or diaminopropionic acid
      or analogs thereof

<400> SEQUENCE: 4

Xaa Xaa Xaa Xaa
1

<210> SEQ ID NO 5
<211> LENGTH: 4
<212> TYPE: PRT
<213> ORGANISM: Artificial Sequence
<220> FEATURE:
<223> OTHER INFORMATION: partial structure of precursor peptide
      represented by fomula (III)
<220> FEATURE:
<221> NAME/KEY: misc_feature
<222> LOCATION: (1)..(1)
<223> OTHER INFORMATION: Xaa is one of optional amino acids and analogs
      thereof
<220> FEATURE:
<221> NAME/KEY: misc_feature
<222> LOCATION: (2)..(2)
<223> OTHER INFORMATION: Xaa is Ser, Cys, or Thr or analogs thereof
<220> FEATURE:
<221> NAME/KEY: misc_feature
<222> LOCATION: (3)..(3)
<223> OTHER INFORMATION: Xaa is Ser or analogs thereof
<220> FEATURE:
<221> NAME/KEY: misc_feature
<222> LOCATION: (4)..(4)
<223> OTHER INFORMATION: Xaa is one of optional amino acids and analogs
      thereof

<400> SEQUENCE: 5
```

```
Xaa Xaa Xaa Xaa
1

<210> SEQ ID NO 6
<211> LENGTH: 4
<212> TYPE: PRT
<213> ORGANISM: Artificial Sequence
<220> FEATURE:
<223> OTHER INFORMATION: partial structure of precursor peptide
      represented by fomula (III)
<220> FEATURE:
<221> NAME/KEY: misc_feature
<222> LOCATION: (1)..(1)
<223> OTHER INFORMATION: Xaa is Ser or Thr or analogs thereof
<220> FEATURE:
<221> NAME/KEY: misc_feature
<222> LOCATION: (2)..(2)
<223> OTHER INFORMATION: Xaa is Ser, Cys, or Thr or analogs thereof
<220> FEATURE:
<221> NAME/KEY: misc_feature
<222> LOCATION: (3)..(3)
<223> OTHER INFORMATION: Xaa is Ser or analogs thereof
<220> FEATURE:
<221> NAME/KEY: misc_feature
<222> LOCATION: (4)..(4)
<223> OTHER INFORMATION: Xaa is Ser, Cys, Thr, or diaminopropionic acid
      or analogs thereof

<400> SEQUENCE: 6

Xaa Xaa Xaa Xaa
1

<210> SEQ ID NO 7
<211> LENGTH: 4
<212> TYPE: PRT
<213> ORGANISM: Artificial Sequence
<220> FEATURE:
<223> OTHER INFORMATION: partial structure of precursor peptide
      represented by fomula (III)
<220> FEATURE:
<221> NAME/KEY: misc_feature
<222> LOCATION: (1)..(1)
<223> OTHER INFORMATION: Xaa is Ser or Thr or analogs thereof
<220> FEATURE:
<221> NAME/KEY: misc_feature
<222> LOCATION: (2)..(2)
<223> OTHER INFORMATION: Xaa is Ser, Cys, or Thr or analogs thereof
<220> FEATURE:
<221> NAME/KEY: misc_feature
<222> LOCATION: (4)..(4)
<223> OTHER INFORMATION: Xaa is Ser, Cys or Thr, or analogs thereof

<400> SEQUENCE: 7

Xaa Xaa Ser Xaa
1

<210> SEQ ID NO 8
<211> LENGTH: 34
<212> TYPE: PRT
<213> ORGANISM: Artificial Sequence
<220> FEATURE:
<223> OTHER INFORMATION: GodA leader peptide

<400> SEQUENCE: 8

Met Lys Lys Lys Glu Asn Val Gln Thr Leu Ala Ile Asp Asp Ile Glu
1               5                   10                  15

Asn Ile Asp Ala Glu Val Thr Ile Glu Glu Leu Ser Ser Thr Asn Gly
            20                  25                  30

Ala Glu
```

```
<210> SEQ ID NO 9
<211> LENGTH: 25
<212> TYPE: PRT
<213> ORGANISM: Artificial Sequence
<220> FEATURE:
<223> OTHER INFORMATION: GodA leader peptide -25 to -1

<400> SEQUENCE: 9

Leu Ala Ile Asp Asp Ile Glu Asn Ile Asp Ala Glu Val Thr Ile Glu
1               5                   10                  15

Glu Leu Ser Ser Thr Asn Gly Ala Glu
            20                  25

<210> SEQ ID NO 10
<211> LENGTH: 20
<212> TYPE: PRT
<213> ORGANISM: Artificial Sequence
<220> FEATURE:
<223> OTHER INFORMATION: GodA leader peptide -20 to -1

<400> SEQUENCE: 10

Ile Glu Asn Ile Asp Ala Glu Val Thr Ile Glu Glu Leu Ser Ser Thr
1               5                   10                  15

Asn Gly Ala Glu
            20

<210> SEQ ID NO 11
<211> LENGTH: 15
<212> TYPE: PRT
<213> ORGANISM: Artificial Sequence
<220> FEATURE:
<223> OTHER INFORMATION: GodA leader peptide -15 to -1

<400> SEQUENCE: 11

Ala Glu Val Thr Ile Glu Glu Leu Ser Ser Thr Asn Gly Ala Glu
1               5                   10                  15

<210> SEQ ID NO 12
<211> LENGTH: 10
<212> TYPE: PRT
<213> ORGANISM: Artificial Sequence
<220> FEATURE:
<223> OTHER INFORMATION: GodA leader peptide -10 to -1

<400> SEQUENCE: 12

Glu Glu Leu Ser Ser Thr Asn Gly Ala Glu
1               5                   10

<210> SEQ ID NO 13
<211> LENGTH: 6
<212> TYPE: PRT
<213> ORGANISM: Artificial Sequence
<220> FEATURE:
<223> OTHER INFORMATION: GodA leader peptide -6 to -1

<400> SEQUENCE: 13

Ser Thr Asn Gly Ala Glu
1               5

<210> SEQ ID NO 14
<211> LENGTH: 20
<212> TYPE: PRT
<213> ORGANISM: Artificial Sequence
<220> FEATURE:
<223> OTHER INFORMATION: leader peptide -20 to -1, LP in formula (II)
```

```
<400> SEQUENCE: 14

Leu Ser Glu Leu Thr Val Thr Ser Leu Arg Asp Thr Val Ala Leu Pro
1               5                   10                  15

Glu Asn Gly Ala
            20

<210> SEQ ID NO 15
<211> LENGTH: 25
<212> TYPE: PRT
<213> ORGANISM: Artificial Sequence
<220> FEATURE:
<223> OTHER INFORMATION: leader peptide -25 to -1, LP' in formula (III)

<400> SEQUENCE: 15

Leu Gln Asp Leu Asp Leu Ser Glu Leu Thr Val Thr Ser Leu Arg Asp
1               5                   10                  15

Thr Val Ala Leu Pro Glu Asn Gly Ala
            20                  25

<210> SEQ ID NO 16
<211> LENGTH: 30
<212> TYPE: PRT
<213> ORGANISM: Artificial Sequence
<220> FEATURE:
<223> OTHER INFORMATION: leader peptide -30 to -1, LP in formula (II)
      and LP' in formula (III)

<400> SEQUENCE: 16

Val Glu Ser Leu Asp Leu Gln Asp Leu Asp Leu Ser Glu Leu Thr Val
1               5                   10                  15

Thr Ser Leu Arg Asp Thr Val Ala Leu Pro Glu Asn Gly Ala
            20                  25                  30

<210> SEQ ID NO 17
<211> LENGTH: 38
<212> TYPE: PRT
<213> ORGANISM: Artificial Sequence
<220> FEATURE:
<223> OTHER INFORMATION: leadar peptide of LazA

<400> SEQUENCE: 17

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala
        35

<210> SEQ ID NO 18
<211> LENGTH: 16
<212> TYPE: PRT
<213> ORGANISM: Artificial Sequence
<220> FEATURE:
<223> OTHER INFORMATION: core peptide of LazA*, native

<400> SEQUENCE: 18

Ser Trp Gly Ser Cys Ser Cys Gln Ala Ser Ser Ser Cys Ala Gln Pro
1               5                   10                  15

<210> SEQ ID NO 19
<211> LENGTH: 17
<212> TYPE: PRT
<213> ORGANISM: Artificial Sequence
<220> FEATURE:
```

```
<223> OTHER INFORMATION: analog 1A2

<400> SEQUENCE: 19

Ser Ala Trp Gly Ser Cys Ser Cys Gln Ala Ser Ser Cys Ala Gln
1               5                   10                  15

Pro

<210> SEQ ID NO 20
<211> LENGTH: 17
<212> TYPE: PRT
<213> ORGANISM: Artificial Sequence
<220> FEATURE:
<223> OTHER INFORMATION: analog 2A3

<400> SEQUENCE: 20

Ser Trp Ala Gly Ser Cys Ser Cys Gln Ala Ser Ser Cys Ala Gln
1               5                   10                  15

Pro

<210> SEQ ID NO 21
<211> LENGTH: 17
<212> TYPE: PRT
<213> ORGANISM: Artificial Sequence
<220> FEATURE:
<223> OTHER INFORMATION: analog 3A4

<400> SEQUENCE: 21

Ser Trp Gly Ala Ser Cys Ser Cys Gln Ala Ser Ser Cys Ala Gln
1               5                   10                  15

Pro

<210> SEQ ID NO 22
<211> LENGTH: 17
<212> TYPE: PRT
<213> ORGANISM: Artificial Sequence
<220> FEATURE:
<223> OTHER INFORMATION: analog 4A5

<400> SEQUENCE: 22

Ser Trp Gly Ser Ala Cys Ser Cys Gln Ala Ser Ser Cys Ala Gln
1               5                   10                  15

Pro

<210> SEQ ID NO 23
<211> LENGTH: 17
<212> TYPE: PRT
<213> ORGANISM: Artificial Sequence
<220> FEATURE:
<223> OTHER INFORMATION: analog 5A6

<400> SEQUENCE: 23

Ser Trp Gly Ser Cys Ala Ser Cys Gln Ala Ser Ser Cys Ala Gln
1               5                   10                  15

Pro

<210> SEQ ID NO 24
<211> LENGTH: 17
<212> TYPE: PRT
<213> ORGANISM: Artificial Sequence
<220> FEATURE:
<223> OTHER INFORMATION: analog 6A7

<400> SEQUENCE: 24
```

Ser Trp Gly Ser Cys Ser Ala Cys Gln Ala Ser Ser Cys Ala Gln
1               5                   10                  15

Pro

<210> SEQ ID NO 25
<211> LENGTH: 17
<212> TYPE: PRT
<213> ORGANISM: Artificial Sequence
<220> FEATURE:
<223> OTHER INFORMATION: analog 7A8

<400> SEQUENCE: 25

Ser Trp Gly Ser Cys Ser Cys Ala Gln Ala Ser Ser Ser Cys Ala Gln
1               5                   10                  15

Pro

<210> SEQ ID NO 26
<211> LENGTH: 17
<212> TYPE: PRT
<213> ORGANISM: Artificial Sequence
<220> FEATURE:
<223> OTHER INFORMATION: analog 8A9 (9A10)

<400> SEQUENCE: 26

Ser Trp Gly Ser Cys Ser Cys Gln Ala Ala Ser Ser Ser Cys Ala Gln
1               5                   10                  15

Pro

<210> SEQ ID NO 27
<211> LENGTH: 17
<212> TYPE: PRT
<213> ORGANISM: Artificial Sequence
<220> FEATURE:
<223> OTHER INFORMATION: analog 10A11

<400> SEQUENCE: 27

Ser Trp Gly Ser Cys Ser Cys Gln Ala Ser Ala Ser Ser Cys Ala Gln
1               5                   10                  15

Pro

<210> SEQ ID NO 28
<211> LENGTH: 17
<212> TYPE: PRT
<213> ORGANISM: Artificial Sequence
<220> FEATURE:
<223> OTHER INFORMATION: analog 11A12

<400> SEQUENCE: 28

Ser Trp Gly Ser Cys Ser Cys Gln Ala Ser Ser Ala Ser Cys Ala Gln
1               5                   10                  15

Pro

<210> SEQ ID NO 29
<211> LENGTH: 17
<212> TYPE: PRT
<213> ORGANISM: Artificial Sequence
<220> FEATURE:
<223> OTHER INFORMATION: analog 12A13

<400> SEQUENCE: 29

Ser Trp Gly Ser Cys Ser Cys Gln Ala Ser Ser Ser Ala Cys Ala Gln
1               5                   10                  15

Pro

<210> SEQ ID NO 30
<211> LENGTH: 18
<212> TYPE: PRT
<213> ORGANISM: Artificial Sequence
<220> FEATURE:
<223> OTHER INFORMATION: analog 2AA3

<400> SEQUENCE: 30

Ser Trp Ala Ala Gly Ser Cys Ser Cys Gln Ala Ser Ser Ser Cys Ala
1               5                   10                  15

Gln Pro

<210> SEQ ID NO 31
<211> LENGTH: 18
<212> TYPE: PRT
<213> ORGANISM: Artificial Sequence
<220> FEATURE:
<223> OTHER INFORMATION: analog 8AA9

<400> SEQUENCE: 31

Ser Trp Gly Ser Cys Ser Cys Gln Ala Ala Ala Ser Ser Ser Cys Ala
1               5                   10                  15

Gln Pro

<210> SEQ ID NO 32
<211> LENGTH: 18
<212> TYPE: PRT
<213> ORGANISM: Artificial Sequence
<220> FEATURE:
<223> OTHER INFORMATION: analog 2A3+8A9

<400> SEQUENCE: 32

Ser Trp Ala Gly Ser Cys Ser Cys Gln Ala Ala Ser Ser Ser Cys Ala
1               5                   10                  15

Gln Pro

<210> SEQ ID NO 33
<211> LENGTH: 19
<212> TYPE: PRT
<213> ORGANISM: Artificial Sequence
<220> FEATURE:
<223> OTHER INFORMATION: analog 2AAA3

<400> SEQUENCE: 33

Ser Trp Ala Ala Ala Gly Ser Cys Ser Cys Gln Ala Ser Ser Ser Cys
1               5                   10                  15

Ala Gln Pro

<210> SEQ ID NO 34
<211> LENGTH: 19
<212> TYPE: PRT
<213> ORGANISM: Artificial Sequence
<220> FEATURE:
<223> OTHER INFORMATION: analog 8AAA9

<400> SEQUENCE: 34

Ser Trp Gly Ser Cys Ser Cys Gln Ala Ala Ala Ala Ser Ser Ser Cys
1               5                   10                  15

Ala Gln Pro

<210> SEQ ID NO 35
<211> LENGTH: 15

```
<212> TYPE: PRT
<213> ORGANISM: Artificial Sequence
<220> FEATURE:
<223> OTHER INFORMATION: analog 3G_deletion

<400> SEQUENCE: 35

Ser Trp Ser Cys Ser Cys Gln Ala Ser Ser Cys Ala Gln Pro
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: analog 9A_deletion

<400> SEQUENCE: 36

Ser Trp Gly Ser Cys Ser Cys Gln Ser Ser Cys Ala Gln Pro
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: analog 3G9A_deletion

<400> SEQUENCE: 37

Ser Trp Ser Cys Ser Cys Gln Ser Ser Cys Ala Gln Pro
1               5                   10

<210> SEQ ID NO 38
<211> LENGTH: 16
<212> TYPE: PRT
<213> ORGANISM: Artificial Sequence
<220> FEATURE:
<223> OTHER INFORMATION: analog 4SCSC7_4AAAA7

<400> SEQUENCE: 38

Ser Trp Gly Ala Ala Ala Ala Gln Ala Ser Ser Cys Ala Gln Pro
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: analog 4SCSC7_4AAAA7_S10A

<400> SEQUENCE: 39

Ser Trp Gly Ala Ala Ala Ala Gln Ala Ala Ser Cys Ala Gln Pro
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: analog 4SCSC7_4AAAA7_S11A

<400> SEQUENCE: 40

Ser Trp Gly Ala Ala Ala Ala Gln Ala Ser Ala Cys Ala Gln Pro
1               5                   10                  15

<210> SEQ ID NO 41
<211> LENGTH: 16
<212> TYPE: PRT
```

<213> ORGANISM: Artificial Sequence
<220> FEATURE:
<223> OTHER INFORMATION: analog 4SCSC7_4AAAA7_S12A

<400> SEQUENCE: 41

Ser Trp Gly Ala Ala Ala Ala Gln Ala Ser Ser Ala Cys Ala Gln Pro
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: analog 4SCSC7_4AAAA7_C13A

<400> SEQUENCE: 42

Ser Trp Gly Ala Ala Ala Ala Gln Ala Ser Ser Ser Ala Ala Gln Pro
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: analog 4SCSC7_4AAAA7_W2A

<400> SEQUENCE: 43

Ser Ala Gly Ala Ala Ala Ala Gln Ala Ser Ser Ser Cys Ala Gln Pro
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: analog 4SCSC7_4AAAA7_W2E

<400> SEQUENCE: 44

Ser Glu Gly Ala Ala Ala Ala Gln Ala Ser Ser Ser Cys Ala Gln Pro
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: analog 4SCSC7_4AAAA7_W2R

<400> SEQUENCE: 45

Ser Arg Gly Ala Ala Ala Ala Gln Ala Ser Ser Ser Cys Ala Gln Pro
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: analog 4SCSC7_4AAAA7_W2S

<400> SEQUENCE: 46

Ser Ser Gly Ala Ala Ala Ala Gln Ala Ser Ser Ser Cys Ala Gln Pro
1               5                   10                  15

<210> SEQ ID NO 47
<211> LENGTH: 16
<212> TYPE: PRT
<213> ORGANISM: Artificial Sequence

```
<220> FEATURE:
<223> OTHER INFORMATION: analog 4SCSC7_4AAAA7_W2V

<400> SEQUENCE: 47

Ser Val Gly Ala Ala Ala Ala Gln Ala Ser Ser Ser Cys Ala Gln Pro
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: analog 4SCSC7_4AAAA7_W2F

<400> SEQUENCE: 48

Ser Phe Gly Ala Ala Ala Ala Gln Ala Ser Ser Ser Cys Ala Gln Pro
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: analog 4SCSC7_4AAAA7_G3E

<400> SEQUENCE: 49

Ser Trp Glu Ala Ala Ala Ala Gln Ala Ser Ser Ser Cys Ala Gln Pro
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: analog 4SCSC7_4AAAA7_G3R

<400> SEQUENCE: 50

Ser Trp Arg Ala Ala Ala Ala Gln Ala Ser Ser Ser Cys Ala Gln Pro
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: analog 4SCSC7_4AAAA7_G3V

<400> SEQUENCE: 51

Ser Trp Val Ala Ala Ala Ala Gln Ala Ser Ser Ser Cys Ala Gln Pro
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: analog 4SCSC7_4AAAA7_G3S

<400> SEQUENCE: 52

Ser Trp Ser Ala Ala Ala Ala Gln Ala Ser Ser Ser Cys Ala Gln Pro
1               5                   10                  15

<210> SEQ ID NO 53
<211> LENGTH: 16
<212> TYPE: PRT
<213> ORGANISM: Artificial Sequence
<220> FEATURE:
```

```
<223> OTHER INFORMATION: analog 4SCSC7_4AAAA7_G3F

<400> SEQUENCE: 53

Ser Trp Phe Ala Ala Ala Ala Gln Ala Ser Ser Ser Cys Ala Gln Pro
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: analog 4SCSC7_4AAAA7_G3W

<400> SEQUENCE: 54

Ser Trp Trp Ala Ala Ala Ala Gln Ala Ser Ser Ser Cys Ala Gln Pro
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: analog 4SCSC7_4AAAA7_Q8A

<400> SEQUENCE: 55

Ser Trp Gly Ala Ala Ala Ala Ala Ala Ser Ser Ser Cys Ala Gln Pro
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: analog 4SCSC7_4AAAA7_Q8E

<400> SEQUENCE: 56

Ser Trp Gly Ala Ala Ala Ala Glu Ala Ser Ser Ser Cys Ala Gln Pro
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: analog 4SCSC7_4AAAA7_Q8R

<400> SEQUENCE: 57

Ser Trp Gly Ala Ala Ala Ala Arg Ala Ser Ser Ser Cys Ala Gln Pro
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: analog 4SCSC7_4AAAA7_Q8V

<400> SEQUENCE: 58

Ser Trp Gly Ala Ala Ala Ala Val Ala Ser Ser Ser Cys Ala Gln Pro
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: analog 4SCSC7_4AAAA7_Q8S
```

```
<400> SEQUENCE: 59

Ser Trp Gly Ala Ala Ala Ala Ser Ala Ser Ser Ser Cys Ala Gln Pro
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: analog 4SCSC7_4AAAA7_Q8F

<400> SEQUENCE: 60

Ser Trp Gly Ala Ala Ala Ala Phe Ala Ser Ser Ser Cys Ala Gln Pro
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: analog 4SCSC7_4AAAA7_Q8W

<400> SEQUENCE: 61

Ser Trp Gly Ala Ala Ala Ala Trp Ala Ser Ser Ser Cys Ala Gln Pro
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: analog 4SCSC7_4AAAA7_A9E

<400> SEQUENCE: 62

Ser Trp Gly Ala Ala Ala Ala Gln Glu Ser Ser Ser Cys Ala Gln Pro
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: analog 4SCSC7_4AAAA7_A9R

<400> SEQUENCE: 63

Ser Trp Gly Ala Ala Ala Ala Gln Arg Ser Ser Ser Cys Ala Gln Pro
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: analog 4SCSC7_4AAAA7_A9V

<400> SEQUENCE: 64

Ser Trp Gly Ala Ala Ala Ala Gln Val Ser Ser Ser Cys Ala Gln Pro
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: analog 4SCSC7_4AAAA7_A9S
```

```
<400> SEQUENCE: 65

Ser Trp Gly Ala Ala Ala Ala Gln Ser Ser Ser Cys Ala Gln Pro
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: analog 4SCSC7_4AAAA7_A9F

<400> SEQUENCE: 66

Ser Trp Gly Ala Ala Ala Ala Gln Phe Ser Ser Ser Cys Ala Gln Pro
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: analog 4SCSC7_4AAAA7_A9W

<400> SEQUENCE: 67

Ser Trp Gly Ala Ala Ala Ala Gln Trp Ser Ser Ser Cys Ala Gln Pro
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: analog 4SCSC7_4AAAA7_Q15A

<400> SEQUENCE: 68

Ser Trp Gly Ala Ala Ala Ala Gln Ala Ser Ser Ser Cys Ala Ala Pro
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: analog 4SCSC7_4AAAA7_P16A

<400> SEQUENCE: 69

Ser Trp Gly Ala Ala Ala Ala Gln Ala Ser Ser Ser Cys Ala Gln Ala
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: analog 4SCSC7_4AAAA7_15QP16_15AA16

<400> SEQUENCE: 70

Ser Trp Gly Ala Ala Ala Ala Gln Ala Ser Ser Ser Cys Ala Ala Ala
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: analog 4SCSC7_4AAAA7_Ala insertion

<400> SEQUENCE: 71
```

Ser Trp Gly Ala Ala Ala Ala Gln Ala Ser Ser Ser Cys Ala Gln
1               5                   10                  15

Pro

<210> SEQ ID NO 72
<211> LENGTH: 18
<212> TYPE: PRT
<213> ORGANISM: Artificial Sequence
<220> FEATURE:
<223> OTHER INFORMATION: analog 4SCSC7_4AAAA7_2Ala insertion

<400> SEQUENCE: 72

Ser Trp Gly Ala Ala Ala Ala Ala Ala Gln Ala Ser Ser Ser Cys Ala
1               5                   10                  15

Gln Pro

<210> SEQ ID NO 73
<211> LENGTH: 19
<212> TYPE: PRT
<213> ORGANISM: Artificial Sequence
<220> FEATURE:
<223> OTHER INFORMATION: analog 4SCSC7_4AAAA7_3Ala insertion

<400> SEQUENCE: 73

Ser Trp Gly Ala Ala Ala Ala Ala Ala Ala Gln Ala Ser Ser Ser Cys
1               5                   10                  15

Ala Gln Pro

<210> SEQ ID NO 74
<211> LENGTH: 20
<212> TYPE: PRT
<213> ORGANISM: Artificial Sequence
<220> FEATURE:
<223> OTHER INFORMATION: analog 4SCSC7_4AAAA7_4Ala insertion

<400> SEQUENCE: 74

Ser Trp Gly Ala Ala Ala Ala Ala Ala Ala Ala Gln Ala Ser Ser Ser
1               5                   10                  15

Cys Ala Gln Pro
        20

<210> SEQ ID NO 75
<211> LENGTH: 21
<212> TYPE: PRT
<213> ORGANISM: Artificial Sequence
<220> FEATURE:
<223> OTHER INFORMATION: analog 4SCSC7_4AAAA7_5Ala insertion

<400> SEQUENCE: 75

Ser Trp Gly Ala Ala Ala Ala Ala Ala Ala Ala Ala Gln Ala Ser Ser
1               5                   10                  15

Ser Cys Ala Gln Pro
        20

<210> SEQ ID NO 76
<211> LENGTH: 22
<212> TYPE: PRT
<213> ORGANISM: Artificial Sequence
<220> FEATURE:
<223> OTHER INFORMATION: analog 4SCSC7_4AAAA7_6Ala insertion

<400> SEQUENCE: 76

Ser Trp Gly Ala Ala Ala Ala Ala Ala Ala Ala Ala Ala Gln Ala Ser

```
                1               5                  10                  15

Ser Ser Cys Ala Gln Pro
            20

<210> SEQ ID NO 77
<211> LENGTH: 23
<212> TYPE: PRT
<213> ORGANISM: Artificial Sequence
<220> FEATURE:
<223> OTHER INFORMATION: analog 4SCSC7_4AAAA7_7Ala insertion

<400> SEQUENCE: 77

Ser Trp Gly Ala Ala Ala Ala Ala Ala Ala Ala Ala Ala Gln Ala
1               5                  10                  15

Ser Ser Ser Cys Ala Gln Pro
            20

<210> SEQ ID NO 78
<211> LENGTH: 15
<212> TYPE: PRT
<213> ORGANISM: Artificial Sequence
<220> FEATURE:
<223> OTHER INFORMATION: analog 4SCSC7_4AAAA7_Ala deletion

<400> SEQUENCE: 78

Ser Trp Gly Ala Ala Ala Gln Ala Ser Ser Ser Cys Ala Gln Pro
1               5                  10                  15

<210> SEQ ID NO 79
<211> LENGTH: 14
<212> TYPE: PRT
<213> ORGANISM: Artificial Sequence
<220> FEATURE:
<223> OTHER INFORMATION: analog 4SCSC7_4AAAA7_2Ala deletion

<400> SEQUENCE: 79

Ser Trp Gly Ala Ala Gln Ala Ser Ser Ser Cys Ala Gln Pro
1               5                  10

<210> SEQ ID NO 80
<211> LENGTH: 13
<212> TYPE: PRT
<213> ORGANISM: Artificial Sequence
<220> FEATURE:
<223> OTHER INFORMATION: analog 4SCSC7_4AAAA7_3Ala deletion

<400> SEQUENCE: 80

Ser Trp Gly Ala Gln Ala Ser Ser Ser Cys Ala Gln Pro
1               5                  10

<210> SEQ ID NO 81
<211> LENGTH: 12
<212> TYPE: PRT
<213> ORGANISM: Artificial Sequence
<220> FEATURE:
<223> OTHER INFORMATION: analog 4SCSC7_4AAAA7_4Ala deletion

<400> SEQUENCE: 81

Ser Trp Gly Gln Ala Ser Ser Ser Cys Ala Gln Pro
1               5                  10

<210> SEQ ID NO 82
<211> LENGTH: 11
<212> TYPE: PRT
<213> ORGANISM: Artificial Sequence
<220> FEATURE:
```

```
<223> OTHER INFORMATION: analog 4SCSC7_4AAAA7_4Ala Gly deletion

<400> SEQUENCE: 82

Ser Trp Gln Ala Ser Ser Ser Cys Ala Gln Pro
1               5                   10

<210> SEQ ID NO 83
<211> LENGTH: 10
<212> TYPE: PRT
<213> ORGANISM: Artificial Sequence
<220> FEATURE:
<223> OTHER INFORMATION: analog 4SCSC7_4AAAA7_4Ala Gly Gln deletion

<400> SEQUENCE: 83

Ser Trp Ala Ser Ser Ser Cys Ala Gln Pro
1               5                   10

<210> SEQ ID NO 84
<211> LENGTH: 9
<212> TYPE: PRT
<213> ORGANISM: Artificial Sequence
<220> FEATURE:
<223> OTHER INFORMATION: analog 4SCSC7_4AAAA7_5Ala Gly Gln deletion

<400> SEQUENCE: 84

Ser Trp Ser Ser Ser Cys Ala Gln Pro
1               5

<210> SEQ ID NO 85
<211> LENGTH: 8
<212> TYPE: PRT
<213> ORGANISM: Artificial Sequence
<220> FEATURE:
<223> OTHER INFORMATION: analog 4SCSC7_4AAAA7_5Ala Gly Gln Trp deletion

<400> SEQUENCE: 85

Ser Ser Ser Ser Cys Ala Gln Pro
1               5

<210> SEQ ID NO 86
<211> LENGTH: 16
<212> TYPE: PRT
<213> ORGANISM: Artificial Sequence
<220> FEATURE:
<223> OTHER INFORMATION: analog S1C

<400> SEQUENCE: 86

Cys Trp Gly Ser Cys Ser Cys Gln Ala Ser Ser Ser Cys Ala Gln Pro
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: analog W2C

<400> SEQUENCE: 87

Ser Cys Gly Ser Cys Ser Cys Gln Ala Ser Ser Ser Cys Ala Gln Pro
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: analog G3C
```

<400> SEQUENCE: 88

Ser Trp Cys Ser Cys Ser Cys Gln Ala Ser Ser Ser Cys Ala Gln Pro
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: analog S4C

<400> SEQUENCE: 89

Ser Trp Gly Cys Cys Ser Cys Gln Ala Ser Ser Ser Cys Ala Gln Pro
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: analog S6C

<400> SEQUENCE: 90

Ser Trp Gly Ser Cys Cys Cys Gln Ala Ser Ser Ser Cys Ala Gln Pro
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: analog Q8C

<400> SEQUENCE: 91

Ser Trp Gly Ser Cys Ser Cys Cys Ala Ser Ser Ser Cys Ala Gln Pro
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: analog A9C

<400> SEQUENCE: 92

Ser Trp Gly Ser Cys Ser Cys Gln Cys Ser Ser Ser Cys Ala Gln Pro
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: analog S10C

<400> SEQUENCE: 93

Ser Trp Gly Ser Cys Ser Cys Gln Ala Cys Ser Ser Cys Ala Gln Pro
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: analog S11C

```
<400> SEQUENCE: 94

Ser Trp Gly Ser Cys Ser Cys Gln Ala Ser Cys Ser Cys Ala Gln Pro
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: analog S12C

<400> SEQUENCE: 95

Ser Trp Gly Ser Cys Ser Cys Gln Ala Ser Ser Cys Cys Ala Gln Pro
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: analog Q15C

<400> SEQUENCE: 96

Ser Trp Gly Ser Cys Ser Cys Gln Ala Ser Ser Ser Cys Ala Cys Pro
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: analog P16C

<400> SEQUENCE: 97

Ser Trp Gly Ser Cys Ser Cys Gln Ala Ser Ser Ser Cys Ala Gln Cys
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: analog 4SCSC7_S10T

<400> SEQUENCE: 98

Ser Trp Gly Ala Ala Ala Ala Gln Ala Thr Ser Cys Ala Gln Pro
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: analog 4SCSC7_S11T

<400> SEQUENCE: 99

Ser Trp Gly Ala Ala Ala Ala Gln Ala Ser Thr Ser Cys Ala Gln Pro
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: analog 4SCSC7_S11C

<400> SEQUENCE: 100
```

Ser Trp Gly Ala Ala Ala Ala Gln Ala Ser Cys Ser Cys Ala Gln Pro
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: analog 4SCSC7_C13S

<400> SEQUENCE: 101

Ser Trp Gly Ala Ala Ala Ala Gln Ala Ser Ser Ser Ser Ala Gln Pro
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: analog 4SCSC7_C13T

<400> SEQUENCE: 102

Ser Trp Gly Ala Ala Ala Ala Gln Ala Ser Ser Ser Thr Ala Gln Pro
1               5                   10                  15

<210> SEQ ID NO 103
<211> LENGTH: 54
<212> TYPE: PRT
<213> ORGANISM: Artificial Sequence
<220> FEATURE:
<223> OTHER INFORMATION: LazA*

<400> SEQUENCE: 103

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
                20                  25                  30

Leu Pro Glu Asn Gly Ala Ser Trp Gly Ser Cys Ser Cys Gln Ala Ser
            35                  40                  45

Ser Ser Cys Ala Gln Pro
        50

<210> SEQ ID NO 104
<211> LENGTH: 47
<212> TYPE: PRT
<213> ORGANISM: Artificial Sequence
<220> FEATURE:
<223> OTHER INFORMATION: LazA* LP-30

<400> SEQUENCE: 104

Met Val Glu Ser Leu Asp Leu Gln Asp Leu Asp Leu Ser Glu Leu Thr
1               5                   10                  15

Val Thr Ser Leu Arg Asp Thr Val Ala Leu Pro Glu Asn Gly Ala Ser
                20                  25                  30

Trp Gly Ser Cys Ser Cys Gln Ala Ser Ser Ser Cys Ala Gln Pro
            35                  40                  45

<210> SEQ ID NO 105
<211> LENGTH: 42
<212> TYPE: PRT
<213> ORGANISM: Artificial Sequence
<220> FEATURE:
<223> OTHER INFORMATION: LazA* LP-25

```
<400> SEQUENCE: 105

Met Leu Gln Asp Leu Asp Leu Ser Glu Leu Thr Val Thr Ser Leu Arg
1               5                   10                  15

Asp Thr Val Ala Leu Pro Glu Asn Gly Ala Ser Trp Gly Ser Cys Ser
            20                  25                  30

Cys Gln Ala Ser Ser Ser Cys Ala Gln Pro
        35                  40

<210> SEQ ID NO 106
<211> LENGTH: 37
<212> TYPE: PRT
<213> ORGANISM: Artificial Sequence
<220> FEATURE:
<223> OTHER INFORMATION: LazA* LP-20

<400> SEQUENCE: 106

Met Leu Ser Glu Leu Thr Val Thr Ser Leu Arg Asp Thr Val Ala Leu
1               5                   10                  15

Pro Glu Asn Gly Ala Ser Trp Gly Ser Cys Ser Cys Gln Ala Ser Ser
            20                  25                  30

Ser Cys Ala Gln Pro
        35

<210> SEQ ID NO 107
<211> LENGTH: 32
<212> TYPE: PRT
<213> ORGANISM: Artificial Sequence
<220> FEATURE:
<223> OTHER INFORMATION: LazA* LP-15

<400> SEQUENCE: 107

Met Val Thr Ser Leu Arg Asp Thr Val Ala Leu Pro Glu Asn Gly Ala
1               5                   10                  15

Ser Trp Gly Ser Cys Ser Cys Gln Ala Ser Ser Ser Cys Ala Gln Pro
            20                  25                  30

<210> SEQ ID NO 108
<211> LENGTH: 54
<212> TYPE: PRT
<213> ORGANISM: Artificial Sequence
<220> FEATURE:
<223> OTHER INFORMATION: precursor peptide

<400> SEQUENCE: 108

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Trp Gly Ala Ala Ala Gln Ala Ser
        35                  40                  45

Ser Ser Cys Ala Gln Pro
    50

<210> SEQ ID NO 109
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (40)..(40)
<223> OTHER INFORMATION: MeGly
```

-continued

<400> SEQUENCE: 109

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Gly Gly Ala Ala Ala Gln Ala Ser
        35                  40                  45

Ser Ser Cys Ala Gln Pro
    50

<210> SEQ ID NO 110
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (40)..(40)
<223> OTHER INFORMATION: N-MethylAlanine

<400> SEQUENCE: 110

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Ala Gln Pro
    50

<210> SEQ ID NO 111
<211> LENGTH: 54
<212> TYPE: PRT
<213> ORGANISM: Artificial Sequence
<220> FEATURE:
<223> OTHER INFORMATION: precursor peptide

<400> SEQUENCE: 111

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Trp Ala Ala Ala Gln Ala Ser
        35                  40                  45

Ser Ser Cys Ala Gln Pro
    50

<210> SEQ ID NO 112
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: MeGly

<400> SEQUENCE: 112

Met Ser Asp Ile Thr Ala Ser Arg Val Glu Ser Leu Asp Leu Gln Asp
1               5                   10                  15

```
Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Ala Gln Pro
    50

<210> SEQ ID NO 113
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: N-MethylAlanine

<400> SEQUENCE: 113

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Ala Ala Ala Ala Gln Ala Ser
        35                  40                  45

Ser Ser Cys Ala Gln Pro
    50

<210> SEQ ID NO 114
<211> LENGTH: 54
<212> TYPE: PRT
<213> ORGANISM: Artificial Sequence
<220> FEATURE:
<223> OTHER INFORMATION: precursor peptide

<400> SEQUENCE: 114

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Trp Ala Ala Ala Gln Ala Ser
        35                  40                  45

Ser Ser Cys Ala Gln Pro
    50

<210> SEQ ID NO 115
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (42)..(42)
<223> OTHER INFORMATION: MeGly

<400> SEQUENCE: 115

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Gly Ala Ala Ala Gln Ala Ser
```

-continued

```
                 35                  40                  45

Ser Ser Cys Ala Gln Pro
        50

<210> SEQ ID NO 116
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (42)..(42)
<223> OTHER INFORMATION: N-MethylAlanine

<400> SEQUENCE: 116

Met Ser Asp Ile Thr Ala Ser Arg Val Glu Ser Leu Asp Leu Gln Asp
1               5                  10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Ala Gln Pro
        50

<210> SEQ ID NO 117
<211> LENGTH: 54
<212> TYPE: PRT
<213> ORGANISM: Artificial Sequence
<220> FEATURE:
<223> OTHER INFORMATION: precursor peptide

<400> SEQUENCE: 117

Met Ser Asp Ile Thr Ala Ser Arg Val Glu Ser Leu Asp Leu Gln Asp
1               5                  10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Trp Ala Ala Gln Ala Ser
        35                  40                  45

Ser Ser Cys Ala Gln Pro
        50

<210> SEQ ID NO 118
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (43)..(43)
<223> OTHER INFORMATION: MeGly

<400> SEQUENCE: 118

Met Ser Asp Ile Thr Ala Ser Arg Val Glu Ser Leu Asp Leu Gln Asp
1               5                  10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Gly Ala Ala Gln Ala Ser
        35                  40                  45

Ser Ser Cys Ala Gln Pro
        50
```

```
<210> SEQ ID NO 119
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (43)..(43)
<223> OTHER INFORMATION: N-MethylAlanine

<400> SEQUENCE: 119

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Ala Gln Pro
    50

<210> SEQ ID NO 120
<211> LENGTH: 54
<212> TYPE: PRT
<213> ORGANISM: Artificial Sequence
<220> FEATURE:
<223> OTHER INFORMATION: precursor peptide

<400> SEQUENCE: 120

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Trp Ala Gln Ala Ser
        35                  40                  45

Ser Ser Cys Ala Gln Pro
    50

<210> SEQ ID NO 121
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (44)..(44)
<223> OTHER INFORMATION: N-MethylAlanine

<400> SEQUENCE: 121

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gln Ala Ser
        35                  40                  45

Ser Ser Cys Ala Gln Pro
    50

<210> SEQ ID NO 122
<211> LENGTH: 54
<212> TYPE: PRT
<213> ORGANISM: Artificial Sequence
```

<220> FEATURE:
<223> OTHER INFORMATION: precursor peptide

<400> SEQUENCE: 122

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Trp Gln Ala Ser
        35                  40                  45

Ser Ser Cys Ala Gln Pro
    50

<210> SEQ ID NO 123
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (45)..(45)
<223> OTHER INFORMATION: N-MethylAlanine

<400> SEQUENCE: 123

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Ala Gln Pro
    50

<210> SEQ ID NO 124
<211> LENGTH: 54
<212> TYPE: PRT
<213> ORGANISM: Artificial Sequence
<220> FEATURE:
<223> OTHER INFORMATION: precursor peptide

<400> SEQUENCE: 124

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Trp Ala Ser
        35                  40                  45

Ser Ser Cys Ala Gln Pro
    50

<210> SEQ ID NO 125
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: MeGly

<400> SEQUENCE: 125

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gly Ala Ser
        35                  40                  45

Ser Ser Cys Ala Gln Pro
    50

<210> SEQ ID NO 126
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: N-MethylAlanine

<400> SEQUENCE: 126

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Ala Ala Ser
        35                  40                  45

Ser Ser Cys Ala Gln Pro
    50

<210> SEQ ID NO 127
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: F5Phe

<400> SEQUENCE: 127

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Phe Ala Ser
        35                  40                  45

Ser Ser Cys Ala Gln Pro
    50

<210> SEQ ID NO 128
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: cLeu

<400> SEQUENCE: 128

Met Ser Asp Ile Thr Ala Ser Arg Val Glu Ser Leu Asp Leu Gln Asp

```
  1               5                  10                  15
Leu Asp Leu Ser Glu Leu Thr Val Thr Ser Leu Arg Asp Thr Val Ala
        20                  25                  30

Leu Pro Glu Asn Gly Ala Ser Ala Gly Ala Ala Ala Ala Leu Ala Ser
        35                  40                  45

Ser Ser Cys Ala Gln Pro
        50

<210> SEQ ID NO 129
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: HydroxyAlanine

<400> SEQUENCE: 129

Met Ser Asp Ile Thr Ala Ser Arg Val Glu Ser Leu Asp Leu Gln Asp
1               5                  10                  15

Leu Asp Leu Ser Glu Leu Thr Val Thr Ser Leu Arg Asp Thr Val Ala
        20                  25                  30

Leu Pro Glu Asn Gly Ala Ser Ala Gly Ala Ala Ala Ala Ala Ala Ser
        35                  40                  45

Ser Ser Cys Ala Gln Pro
        50

<210> SEQ ID NO 130
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: OHPhe

<400> SEQUENCE: 130

Met Ser Asp Ile Thr Ala Ser Arg Val Glu Ser Leu Asp Leu Gln Asp
1               5                  10                  15

Leu Asp Leu Ser Glu Leu Thr Val Thr Ser Leu Arg Asp Thr Val Ala
        20                  25                  30

Leu Pro Glu Asn Gly Ala Ser Ala Gly Ala Ala Ala Ala Phe Ala Ser
        35                  40                  45

Ser Ser Cys Ala Gln Pro
        50

<210> SEQ ID NO 131
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: D-alanine

<400> SEQUENCE: 131

Met Ser Asp Ile Thr Ala Ser Arg Val Glu Ser Leu Asp Leu Gln Asp
1               5                  10                  15
```

```
Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Ala Ser
            35                  40                  45

Ser Ser Cys Ala Gln Pro
    50

<210> SEQ ID NO 132
<211> LENGTH: 54
<212> TYPE: PRT
<213> ORGANISM: Artificial Sequence
<220> FEATURE:
<223> OTHER INFORMATION: precursor peptide

<400> SEQUENCE: 132

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Ala Trp Ser
            35                  40                  45

Ser Ser Cys Ala Gln Pro
    50

<210> SEQ ID NO 133
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (47)..(47)
<223> OTHER INFORMATION: MeGly

<400> SEQUENCE: 133

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Ala Gly Ser
            35                  40                  45

Ser Ser Cys Ala Gln Pro
    50

<210> SEQ ID NO 134
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (47)..(47)
<223> OTHER INFORMATION: N-MethylAlanine

<400> SEQUENCE: 134

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Ala Ala Ser
```

Ser Ser Cys Ala Gln Pro
    50

<210> SEQ ID NO 135
<211> LENGTH: 54
<212> TYPE: PRT
<213> ORGANISM: Artificial Sequence
<220> FEATURE:
<223> OTHER INFORMATION: precursor peptide

<400> SEQUENCE: 135

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gln Ala Ser
        35                  40                  45

Ser Ser Cys Ala Gln Pro
    50

<210> SEQ ID NO 136
<211> LENGTH: 54
<212> TYPE: PRT
<213> ORGANISM: Artificial Sequence
<220> FEATURE:
<223> OTHER INFORMATION: precursor peptide

<400> SEQUENCE: 136

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gln Ala Ser
        35                  40                  45

Ser Ser Cys Met Gln Pro
    50

<210> SEQ ID NO 137
<211> LENGTH: 54
<212> TYPE: PRT
<213> ORGANISM: Artificial Sequence
<220> FEATURE:
<223> OTHER INFORMATION: precursor peptide

<400> SEQUENCE: 137

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gln Ala Ser
        35                  40                  45

Ser Ser Cys Ala Trp Pro
    50

<210> SEQ ID NO 138
<211> LENGTH: 54
<212> TYPE: PRT
<213> ORGANISM: Artificial Sequence
<220> FEATURE:
<223> OTHER INFORMATION: precursor peptide
<220> FEATURE:

```
<221> NAME/KEY: MOD_RES
<222> LOCATION: (53)..(53)
<223> OTHER INFORMATION: MeGly

<400> SEQUENCE: 138

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gln Ala Ser
        35                  40                  45

Ser Ser Cys Ala Gly Pro
    50

<210> SEQ ID NO 139
<211> LENGTH: 54
<212> TYPE: PRT
<213> ORGANISM: Artificial Sequence
<220> FEATURE:
<223> OTHER INFORMATION: precursor peptide

<400> SEQUENCE: 139

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gln Ala Ser
        35                  40                  45

Ser Ser Cys Ala Gln Trp
    50

<210> SEQ ID NO 140
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (54)..(54)
<223> OTHER INFORMATION: MeGly

<400> SEQUENCE: 140

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ala Gln Ala Ser
        35                  40                  45

Ser Ser Cys Ala Gln Gly
    50

<210> SEQ ID NO 141
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (54)..(54)
<223> OTHER INFORMATION: N-MethylAlanine

<400> SEQUENCE: 141
```

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
                20                  25                  30

Leu Pro Glu Asn Gly Ala Ser Ala Gly Ala Ala Ala Gln Ala Ser
            35                  40                  45

Ser Ser Cys Ala Gln Ala
    50
```

<210> SEQ ID NO 142
<211> LENGTH: 54
<212> TYPE: PRT
<213> ORGANISM: Artificial Sequence
<220> FEATURE:
<223> OTHER INFORMATION: precursor peptide

<400> SEQUENCE: 142

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
                20                  25                  30

Leu Pro Glu Asn Gly Ala Ser Ala Trp Ala Ala Ala Trp Gln Ala Ser
            35                  40                  45

Ser Ser Cys Ala Gln Pro
    50
```

<210> SEQ ID NO 143
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: MeGly
<220> FEATURE:
<221> NAME/KEY: MOD_RES
<222> LOCATION: (45)..(45)
<223> OTHER INFORMATION: MeGly

<400> SEQUENCE: 143

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
                20                  25                  30

Leu Pro Glu Asn Gly Ala Ser Ala Gly Ala Ala Ala Gly Gln Ala Ser
            35                  40                  45

Ser Ser Cys Ala Gln Pro
    50
```

<210> SEQ ID NO 144
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: N-MethylAlanine
<220> FEATURE:
<221> NAME/KEY: MOD_RES
<222> LOCATION: (45)..(45)

<223> OTHER INFORMATION: N-MethylAlanine

<400> SEQUENCE: 144

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Ala Ala Ala Ala Gln Ala Ser
        35                  40                  45

Ser Ser Cys Ala Gln Pro
    50

<210> SEQ ID NO 145
<211> LENGTH: 54
<212> TYPE: PRT
<213> ORGANISM: Artificial Sequence
<220> FEATURE:
<223> OTHER INFORMATION: precursor peptide

<400> SEQUENCE: 145

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Trp Ala Lys Ala Trp Gln Ala Ser
        35                  40                  45

Ser Ser Cys Ala Gln Pro
    50

<210> SEQ ID NO 146
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: N-MethylAlanine
<220> FEATURE:
<221> NAME/KEY: MOD_RES
<222> LOCATION: (45)..(45)
<223> OTHER INFORMATION: N-MethylAlanine

<400> SEQUENCE: 146

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Ala Ala Lys Ala Ala Gln Ala Ser
        35                  40                  45

Ser Ser Cys Ala Gln Pro
    50

<210> SEQ ID NO 147
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (43)..(43)
<223> OTHER INFORMATION: MeGly

<400> SEQUENCE: 147

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Trp Ala Gly Ala Trp Gln Ala Ser
        35                  40                  45

Ser Ser Cys Ala Gln Pro
    50

<210> SEQ ID NO 148
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: N-MethylAlanine
<220> FEATURE:
<221> NAME/KEY: MOD_RES
<222> LOCATION: (43)..(43)
<223> OTHER INFORMATION: MeGly
<220> FEATURE:
<221> NAME/KEY: MOD_RES
<222> LOCATION: (45)..(45)
<223> OTHER INFORMATION: N-MethylAlanine

<400> SEQUENCE: 148

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Ala Ala Gly Ala Ala Gln Ala Ser
        35                  40                  45

Ser Ser Cys Ala Gln Pro
    50

<210> SEQ ID NO 149
<211> LENGTH: 54
<212> TYPE: PRT
<213> ORGANISM: Artificial Sequence
<220> FEATURE:
<223> OTHER INFORMATION: precursor peptide

<400> SEQUENCE: 149

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Trp Lys Trp Lys Trp Lys Gln Ala Ser
        35                  40                  45

Ser Ser Cys Ala Gln Pro
    50

<210> SEQ ID NO 150
<211> LENGTH: 54
<212> TYPE: PRT
<213> ORGANISM: Artificial Sequence
<220> FEATURE:
<223> OTHER INFORMATION: precursor peptide
<220> FEATURE:

```
<221> NAME/KEY: MOD_RES
<222> LOCATION: (41)..(41)
<223> OTHER INFORMATION: MeGly
<220> FEATURE:
<221> NAME/KEY: MOD_RES
<222> LOCATION: (43)..(43)
<223> OTHER INFORMATION: MeGly
<220> FEATURE:
<221> NAME/KEY: MOD_RES
<222> LOCATION: (45)..(45)
<223> OTHER INFORMATION: MeGly

<400> SEQUENCE: 150

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Trp Gly Trp Gly Trp Gly Gln Ala Ser
        35                  40                  45

Ser Ser Cys Ala Gln Pro
    50

<210> SEQ ID NO 151
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (54)..(54)
<223> OTHER INFORMATION: MeGly

<400> SEQUENCE: 151

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Trp Ala His Ala Phe Gln Ala Ser
        35                  40                  45

Ser Ser Cys Ala Gln Gly
    50

<210> SEQ ID NO 152
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: F5Phe
<220> FEATURE:
<221> NAME/KEY: MOD_RES
<222> LOCATION: (43)..(43)
<223> OTHER INFORMATION: cLeu
<220> FEATURE:
<221> NAME/KEY: MOD_RES
<222> LOCATION: (45)..(45)
<223> OTHER INFORMATION: N-MethylAlanine
<220> FEATURE:
<221> NAME/KEY: MOD_RES
<222> LOCATION: (54)..(54)
<223> OTHER INFORMATION: MeGly

<400> SEQUENCE: 152

Met Ser Asp Ile Thr Ala Ser Arg Val Glu Ser Leu Asp Leu Gln Asp
```

```
                1               5                   10                  15
Leu Asp Leu Ser Glu Leu Thr Val Thr Ser Leu Arg Asp Thr Val Ala
                20                  25                  30

Leu Pro Glu Asn Gly Ala Ser Ala Phe Ala Leu Ala Ala Gln Ala Ser
            35                  40                  45

Ser Ser Cys Ala Gln Gly
        50
```

<210> SEQ ID NO 153
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (41)..(41)
<223> OTHER INFORMATION: MeGly
<220> FEATURE:
<221> NAME/KEY: MOD_RES
<222> LOCATION: (43)..(43)
<223> OTHER INFORMATION: F5Phe
<220> FEATURE:
<221> NAME/KEY: MOD_RES
<222> LOCATION: (45)..(45)
<223> OTHER INFORMATION: cLeu
<220> FEATURE:
<221> NAME/KEY: MOD_RES
<222> LOCATION: (54)..(54)
<223> OTHER INFORMATION: N-MethylAlanine

<400> SEQUENCE: 153

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
                20                  25                  30

Leu Pro Glu Asn Gly Ala Ser Ala Gly Ala Phe Ala Leu Gln Ala Ser
            35                  40                  45

Ser Ser Cys Ala Gln Ala
        50
```

<210> SEQ ID NO 154
<211> LENGTH: 62
<212> TYPE: PRT
<213> ORGANISM: Artificial Sequence
<220> FEATURE:
<223> OTHER INFORMATION: precursor peptide

<400> SEQUENCE: 154

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
                20                  25                  30

Leu Pro Glu Asn Gly Ala Ser Trp Gly Ala Ala Ala Ala Ala Ala Gln
            35                  40                  45

Ala Ser Ser Ser Cys Ala Gln Pro Asn Asn Leu Asn Val Gly
        50                  55                  60
```

<210> SEQ ID NO 155
<211> LENGTH: 60
<212> TYPE: PRT
<213> ORGANISM: Artificial Sequence
<220> FEATURE:
<223> OTHER INFORMATION: precursor peptide

<400> SEQUENCE: 155

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Ala Gln Pro Gly Glu Leu Ala Arg Pro
    50                  55                  60

<210> SEQ ID NO 156
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (44)..(44)
<223> OTHER INFORMATION: MeGly

<400> SEQUENCE: 156

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Gly Ala Gln Ala Ser
        35                  40                  45

Ser Ser Cys Ala Gln Pro
    50

<210> SEQ ID NO 157
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (45)..(45)
<223> OTHER INFORMATION: MeGly

<400> SEQUENCE: 157

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Gly Gln Ala Ser
        35                  40                  45

Ser Ser Cys Ala Gln Pro
    50

<210> SEQ ID NO 158
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (46)..(46)
<223> OTHER INFORMATION: D-serine

<400> SEQUENCE: 158

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Ser Ala Ser
        35                  40                  45

Ser Ser Cys Ala Gln Pro
    50
```

<210> SEQ ID NO 159
<211> LENGTH: 54
<212> TYPE: PRT
<213> ORGANISM: Artificial Sequence
<220> FEATURE:
<223> OTHER INFORMATION: precursor peptide

<400> SEQUENCE: 159

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Phe Gln Pro
    50
```

<210> SEQ ID NO 160
<211> LENGTH: 54
<212> TYPE: PRT
<213> ORGANISM: Artificial Sequence
<220> FEATURE:
<223> OTHER INFORMATION: precursor peptide

<400> SEQUENCE: 160

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45

Ser Ser Cys Arg Gln Pro
    50
```

<210> SEQ ID NO 161
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (53)..(53)
<223> OTHER INFORMATION: N-MethylAlanine

<400> SEQUENCE: 161

```
Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Gly Ala Ala Ala Gln Ala Ser
        35                  40                  45
```

Ser Ser Cys Ala Ala Pro
    50

<210> SEQ ID NO 162
<211> LENGTH: 54
<212> TYPE: PRT
<213> ORGANISM: Artificial Sequence
<220> FEATURE:
<223> OTHER INFORMATION: precursor peptide

<400> SEQUENCE: 162

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Trp Ala His Ala Phe Gln Ala Ser
        35                  40                  45

Ser Ser Cys Ala Gln Lys
    50

<210> SEQ ID NO 163
<211> LENGTH: 54
<212> TYPE: PRT
<213> ORGANISM: Artificial Sequence
<220> FEATURE:
<223> OTHER INFORMATION: precursor peptide
<220> FEATURE:
<221> NAME/KEY: MOD_RES
<222> LOCATION: (43)..(43)
<223> OTHER INFORMATION: cLeu

<400> SEQUENCE: 163

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Ala Trp Ala Leu Ala Phe Gln Ala Ser
        35                  40                  45

Ser Ser Cys Ala Gln Lys
    50

<210> SEQ ID NO 164
<211> LENGTH: 57
<212> TYPE: PRT
<213> ORGANISM: Actinomycete

<400> SEQUENCE: 164

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Trp Gly Ser Cys Ser Cys Gln Ala Ser
        35                  40                  45

Ser Ser Cys Ala Gln Pro Gln Asp Met
    50              55

<210> SEQ ID NO 165
<211> LENGTH: 77
<212> TYPE: DNA
<213> ORGANISM: Escherichia coli

<400> SEQUENCE: 165

-continued gtcctgttag acaaactggt aaagtcacta cccttttcaag gtaggatttg cgggttcgat    60
ccccgcacag gacgcca    77

<210> SEQ ID NO 166
<211> LENGTH: 76
<212> TYPE: DNA
<213> ORGANISM: Actinomycete

<400> SEQUENCE: 166
gccctcatcg tctagtggcc caggacgccg cccttttcaag gcggtagcac gggttcgaat    60
cccgttgggg gcacca    76

<210> SEQ ID NO 167
<211> LENGTH: 76
<212> TYPE: DNA
<213> ORGANISM: Actinomycete

<400> SEQUENCE: 167 gccccgttg tgtagcggcc tagcacgctg ccctctcacg gcagtagcgc cggttcgaat    60
ccggtcgggg gtacca    76

<210> SEQ ID NO 168
<211> LENGTH: 11
<212> TYPE: PRT
<213> ORGANISM: Artificial Sequence
<220> FEATURE:
<223> OTHER INFORMATION: analog 4SCSC7_4AAAA7_-5 deletion

<400> SEQUENCE: 168

Ser Trp Gly Ala Ser Ser Ser Cys Ala Gln Pro
1               5                   10

<210> SEQ ID NO 169
<211> LENGTH: 17
<212> TYPE: PRT
<213> ORGANISM: Artificial Sequence
<220> FEATURE:
<223> OTHER INFORMATION: analog 4SCSC7_4AAAA7_+1 insertion

<400> SEQUENCE: 169

Ser Trp Gly Ala Asn Ala Asn Ala Gln Ala Ser Ser Ser Cys Ala Gln
1               5                   10                  15

Pro

<210> SEQ ID NO 170
<211> LENGTH: 18
<212> TYPE: PRT
<213> ORGANISM: Artificial Sequence
<220> FEATURE:
<223> OTHER INFORMATION: analog 4SCSC7_4AAAA7_+2 insertion

<400> SEQUENCE: 170

Ser Trp Gly Ala Asn Ala Asn Ala Asn Gln Ala Ser Ser Ser Cys Ala
1               5                   10                  15

Gln Pro

<210> SEQ ID NO 171
<211> LENGTH: 19
<212> TYPE: PRT
<213> ORGANISM: Artificial Sequence
<220> FEATURE:
<223> OTHER INFORMATION: analog 4SCSC7_4AAAA7_+3 insertion -continued

```
<400> SEQUENCE: 171

Ser Trp Gly Ala Asn Ala Asn Ala Asn Ala Gln Ala Ser Ser Ser Cys
1               5                   10                  15

Ala Gln Pro

<210> SEQ ID NO 172
<211> LENGTH: 20
<212> TYPE: PRT
<213> ORGANISM: Artificial Sequence
<220> FEATURE:
<223> OTHER INFORMATION: analog 4SCSC7_4AAAA7_+4 insertion

<400> SEQUENCE: 172

Ser Trp Gly Ala Asn Ala Asn Ala Asn Ala Asn Gln Ala Ser Ser Ser
1               5                   10                  15

Cys Ala Gln Pro
            20

<210> SEQ ID NO 173
<211> LENGTH: 21
<212> TYPE: PRT
<213> ORGANISM: Artificial Sequence
<220> FEATURE:
<223> OTHER INFORMATION: analog 4SCSC7_4AAAA7_+5 insertion

<400> SEQUENCE: 173

Ser Trp Gly Ala Asn Ala Asn Ala Asn Ala Asn Ala Gln Ala Ser Ser
1               5                   10                  15

Ser Cys Ala Gln Pro
            20

<210> SEQ ID NO 174
<211> LENGTH: 22
<212> TYPE: PRT
<213> ORGANISM: Artificial Sequence
<220> FEATURE:
<223> OTHER INFORMATION: analog 4SCSC7_4AAAA7_+6 insertion

<400> SEQUENCE: 174

Ser Trp Gly Ala Asn Ala Asn Ala Asn Ala Asn Ala Asn Gln Ala Ser
1               5                   10                  15

Ser Ser Cys Ala Gln Pro
            20

<210> SEQ ID NO 175
<211> LENGTH: 23
<212> TYPE: PRT
<213> ORGANISM: Artificial Sequence
<220> FEATURE:
<223> OTHER INFORMATION: analog 4SCSC7_4AAAA7_+7 insertion

<400> SEQUENCE: 175

Ser Trp Gly Ala Asn Ala Asn Ala Asn Ala Asn Ala Asn Ala Gln Ala
1               5                   10                  15

Ser Ser Ser Cys Ala Gln Pro
            20

<210> SEQ ID NO 176
<211> LENGTH: 26
<212> TYPE: PRT
<213> ORGANISM: Artificial Sequence
<220> FEATURE:
<223> OTHER INFORMATION: analog 4SCSC7_4AAAA7_+10 insertion
```

```
<400> SEQUENCE: 176

Ser Trp Gly Ala Asn Ala Asn Ala Asn Ala Asn Ala Asn Ala
1               5                   10                  15

Asn Gln Ala Ser Ser Ser Cys Ala Gln Pro
            20                  25

<210> SEQ ID NO 177
<211> LENGTH: 16
<212> TYPE: PRT
<213> ORGANISM: Artificial Sequence
<220> FEATURE:
<223> OTHER INFORMATION: analog S1A

<400> SEQUENCE: 177

Ala Trp Gly Ser Cys Ser Cys Gln Ala Ser Ser Ser Cys Ala Gln Pro
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: analog W2A

<400> SEQUENCE: 178

Ser Ala Gly Ser Cys Ser Cys Gln Ala Ser Ser Ser Cys Ala Gln Pro
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: analog G3A

<400> SEQUENCE: 179

Ser Trp Ala Ser Cys Ser Cys Gln Ala Ser Ser Ser Cys Ala Gln Pro
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: analog S4A

<400> SEQUENCE: 180

Ser Trp Gly Ala Cys Ser Cys Gln Ala Ser Ser Ser Cys Ala Gln Pro
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: analog C5A

<400> SEQUENCE: 181

Ser Trp Gly Ser Ala Ser Cys Gln Ala Ser Ser Ser Cys Ala Gln Pro
1               5                   10                  15

<210> SEQ ID NO 182
<211> LENGTH: 16
<212> TYPE: PRT
<213> ORGANISM: Artificial Sequence
```

```
<220> FEATURE:
<223> OTHER INFORMATION: analog S6A

<400> SEQUENCE: 182

Ser Trp Gly Ser Cys Ala Cys Gln Ala Ser Ser Ser Cys Ala Gln Pro
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: analog C7A

<400> SEQUENCE: 183

Ser Trp Gly Ser Cys Ser Ala Gln Ala Ser Ser Ser Cys Ala Gln Pro
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: analog Q8A

<400> SEQUENCE: 184

Ser Trp Gly Ser Cys Ser Cys Ala Ala Ser Ser Ser Cys Ala Gln Pro
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: analog S10A

<400> SEQUENCE: 185

Ser Trp Gly Ser Cys Ser Cys Gln Ala Ala Ser Ser Cys Ala Gln Pro
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: analog S11A

<400> SEQUENCE: 186

Ser Trp Gly Ser Cys Ser Cys Gln Ala Ser Ala Ser Cys Ala Gln Pro
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: analog S12A

<400> SEQUENCE: 187

Ser Trp Gly Ser Cys Ser Cys Gln Ala Ser Ser Ala Cys Ala Gln Pro
1               5                   10                  15

<210> SEQ ID NO 188
<211> LENGTH: 16
<212> TYPE: PRT
<213> ORGANISM: Artificial Sequence
<220> FEATURE:
```

```
<223> OTHER INFORMATION: analog C13A

<400> SEQUENCE: 188

Ser Trp Gly Ser Cys Ser Cys Gln Ala Ser Ser Ser Ala Ala Gln Pro
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: analog Q15A

<400> SEQUENCE: 189

Ser Trp Gly Ser Cys Ser Cys Gln Ala Ser Ser Ser Cys Ala Ala Pro
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: analog P16A

<400> SEQUENCE: 190

Ser Trp Gly Ser Cys Ser Cys Gln Ala Ser Ser Ser Cys Ala Gln Ala
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: analog W2K

<400> SEQUENCE: 191

Ser Lys Gly Ala Ala Ala Ala Gln Ala Ser Ser Ser Cys Ala Gln Pro
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: analog G3K

<400> SEQUENCE: 192

Ser Trp Lys Ala Ala Ala Ala Gln Ala Ser Ser Ser Cys Ala Gln Pro
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: analog A4K

<400> SEQUENCE: 193

Ser Trp Gly Lys Ala Ala Ala Gln Ala Ser Ser Ser Cys Ala Gln Pro
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: analog A5K
```

<400> SEQUENCE: 194

Ser Trp Gly Ala Lys Ala Gln Ala Ser Ser Ser Cys Ala Gln Pro
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: analog A6K

<400> SEQUENCE: 195

Ser Trp Gly Ala Ala Lys Gln Ala Ser Ser Ser Cys Ala Gln Pro
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: analog A7K

<400> SEQUENCE: 196

Ser Trp Gly Ala Ala Ala Lys Gln Ala Ser Ser Ser Cys Ala Gln Pro
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: analog Q8K

<400> SEQUENCE: 197

Ser Trp Gly Ala Ala Ala Ala Lys Ala Ser Ser Ser Cys Ala Gln Pro
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: analog A9K

<400> SEQUENCE: 198

Ser Trp Gly Ala Ala Ala Ala Gln Lys Ser Ser Ser Cys Ala Gln Pro
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: analog A14K

<400> SEQUENCE: 199

Ser Trp Gly Ala Ala Ala Ala Gln Ala Ser Ser Ser Cys Lys Gln Pro
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: analog Q15K

<400> SEQUENCE: 200

Ser Trp Gly Ala Ala Ala Ala Gln Ala Ser Ser Ser Cys Ala Lys Pro
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: analog P16K

<400> SEQUENCE: 201

Ser Trp Gly Ala Ala Ala Ala Gln Ala Ser Ser Ser Cys Ala Gln Lys
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: analog W2E

<400> SEQUENCE: 202

Ser Glu Gly Ala Ala Ala Ala Gln Ala Ser Ser Ser Cys Ala Gln Pro
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: analog G3E

<400> SEQUENCE: 203

Ser Trp Glu Ala Ala Ala Ala Gln Ala Ser Ser Ser Cys Ala Gln Pro
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: analog A4E

<400> SEQUENCE: 204

Ser Trp Gly Glu Ala Ala Ala Gln Ala Ser Ser Ser Cys Ala Gln Pro
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: analog A5E

<400> SEQUENCE: 205

Ser Trp Gly Ala Glu Ala Ala Gln Ala Ser Ser Ser Cys Ala Gln Pro
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: analog A6E

<400> SEQUENCE: 206

```
Ser Trp Gly Ala Ala Glu Ala Gln Ala Ser Ser Ser Cys Ala Gln Pro
1               5                   10                  15

<210> SEQ ID NO 207
<211> LENGTH: 16
<212> TYPE: PRT
<213> ORGANISM: Artificial Sequence
<220> FEATURE:
<223> OTHER INFORMATION: analog A7E

<400> SEQUENCE: 207

Ser Trp Gly Ala Ala Ala Glu Gln Ala Ser Ser Ser Cys Ala Gln Pro
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: analog Q8E

<400> SEQUENCE: 208

Ser Trp Gly Ala Ala Ala Ala Glu Ala Ser Ser Ser Cys Ala Gln Pro
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: analog A9E

<400> SEQUENCE: 209

Ser Trp Gly Ala Ala Ala Ala Gln Glu Ser Ser Ser Cys Ala Gln Pro
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: analog Q15E

<400> SEQUENCE: 210

Ser Trp Gly Ala Ala Ala Ala Gln Ala Ser Ser Ser Cys Ala Glu Pro
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: analog P16E

<400> SEQUENCE: 211

Ser Trp Gly Ala Ala Ala Ala Gln Ala Ser Ser Ser Cys Ala Gln Glu
1               5                   10                  15

<210> SEQ ID NO 212
<211> LENGTH: 31
<212> TYPE: PRT
<213> ORGANISM: Artificial Sequence
<220> FEATURE:
<223> OTHER INFORMATION: analog 15aa-extension

<400> SEQUENCE: 212
```

```
Ser Trp Gly Ala Ala Ala Gln Ala Ser Ser Cys Ala Gln Pro
1               5                   10                  15

Tyr Pro Tyr Asp Val Pro Asp Tyr Ala Gly Glu Leu Ala Arg Pro
            20                  25                  30
```

<210> SEQ ID NO 213
<211> LENGTH: 22
<212> TYPE: PRT
<213> ORGANISM: Artificial Sequence
<220> FEATURE:
<223> OTHER INFORMATION: analog 6aa-extension-2

<400> SEQUENCE: 213

```
Ser Trp Gly Leu Ala Gly Gln Gln Ala Ser Ser Cys Ala Leu Gly
1               5                   10                  15

Gly Glu Leu Ala Arg Pro
            20
```

<210> SEQ ID NO 214
<211> LENGTH: 24
<212> TYPE: PRT
<213> ORGANISM: Artificial Sequence
<220> FEATURE:
<223> OTHER INFORMATION: analog 6aa-extension-1

<400> SEQUENCE: 214

```
Ser Trp Gly Ala Ala Ala Ala Ala Gln Ser Ser Ser Cys Ala
1               5                   10
```

```
Ser Trp Gly Ala Ala Ala Ala Ala Gln Ser Ser Ser Cys Ala
1               5                   10                  15

Gln Pro Asn Asn Leu Asn Val Gly
            20
```

<210> SEQ ID NO 215
<211> LENGTH: 22
<212> TYPE: PRT
<213> ORGANISM: Artificial Sequence
<220> FEATURE:
<223> OTHER INFORMATION: analog 6aa-extension-3

<400> SEQUENCE: 215

```
Ser Trp Gly Lys Ala Phe Asn Gln Ala Ser Ser Cys Ala Trp Pro
1               5                   10                  15

Gly Glu Leu Ala Arg Pro
            20
```

<210> SEQ ID NO 216
<211> LENGTH: 19
<212> TYPE: PRT
<213> ORGANISM: Artificial Sequence
<220> FEATURE:
<223> OTHER INFORMATION: analog 10aa-sub-1

<400> SEQUENCE: 216

```
Ser Trp Ala Gln Glu Leu Tyr Pro His Ala Asn Phe Ser Ser Cys
1               5                   10                  15

Ala Gln Pro
```

<210> SEQ ID NO 217
<211> LENGTH: 19
<212> TYPE: PRT
<213> ORGANISM: Artificial Sequence
<220> FEATURE:
<223> OTHER INFORMATION: analog 10aa-sub-2

<400> SEQUENCE: 217

Ser Trp Phe Met Asp Gln Val Tyr Ala Leu Ile Tyr Ser Ser Ser Cys
1               5                   10                  15

Ala Gln Pro

<210> SEQ ID NO 218
<211> LENGTH: 19
<212> TYPE: PRT
<213> ORGANISM: Artificial Sequence
<220> FEATURE:
<223> OTHER INFORMATION: analog 10aa-sub-3

<400> SEQUENCE: 218

Ser Trp Ala Tyr Glu Arg Ile Phe His Ser Leu Tyr Ser Ser Ser Cys
1               5                   10                  15

Ala Gln Pro

<210> SEQ ID NO 219
<211> LENGTH: 19
<212> TYPE: PRT
<213> ORGANISM: Artificial Sequence
<220> FEATURE:
<223> OTHER INFORMATION: analog 10aa-sub-4

<400> SEQUENCE: 219

Ser Trp Leu Trp Lys Pro Thr Ser Ala Thr Val Phe Ser Ser Ser Cys
1               5                   10                  15

Ala Gln Pro

<210> SEQ ID NO 220
<211> LENGTH: 19
<212> TYPE: PRT
<213> ORGANISM: Artificial Sequence
<220> FEATURE:
<223> OTHER INFORMATION: analog 10aa-sub-5

<400> SEQUENCE: 220

Ser Trp Tyr Gly Asp Gln Pro Arg Gln Lys Ala Met Ser Ser Ser Cys
1               5                   10                  15

Ala Gln Pro

<210> SEQ ID NO 221
<211> LENGTH: 19
<212> TYPE: PRT
<213> ORGANISM: Artificial Sequence
<220> FEATURE:
<223> OTHER INFORMATION: analog 10aa-sub-6

<400> SEQUENCE: 221

Ser Trp Arg Ile Lys Asp Gln Gln Leu Gly Tyr Val Ser Ser Ser Cys
1               5                   10                  15

Ala Gln Pro

<210> SEQ ID NO 222
<211> LENGTH: 19
<212> TYPE: PRT
<213> ORGANISM: Artificial Sequence
<220> FEATURE:
<223> OTHER INFORMATION: analog 10aa-sub-7

<400> SEQUENCE: 222

Ser Trp Gln Ala Met Phe Lys Thr Asn Arg Leu Ala Ser Ser Ser Cys
1               5                   10                  15

Ala Gln Pro

```
<210> SEQ ID NO 223
<211> LENGTH: 19
<212> TYPE: PRT
<213> ORGANISM: Artificial Sequence
<220> FEATURE:
<223> OTHER INFORMATION: analog 10aa-sub-8

<400> SEQUENCE: 223

Ser Trp Met Gly Val His Val Ile Pro Tyr Thr Gln Ser Ser Ser Cys
1               5                   10                  15

Ala Gln Pro

<210> SEQ ID NO 224
<211> LENGTH: 19
<212> TYPE: PRT
<213> ORGANISM: Artificial Sequence
<220> FEATURE:
<223> OTHER INFORMATION: analog 10aa-sub-9

<400> SEQUENCE: 224

Ser Trp Ala Pro Gly Gly Pro Glu Pro Phe Ala Met Ser Ser Ser Cys
1               5                   10                  15

Ala Gln Pro

<210> SEQ ID NO 225
<211> LENGTH: 19
<212> TYPE: PRT
<213> ORGANISM: Artificial Sequence
<220> FEATURE:
<223> OTHER INFORMATION: analog 10aa-sub-10

<400> SEQUENCE: 225

Ser Trp Arg Ile Gln Leu Glu Phe Gly Asp Asn Gly Ser Ser Ser Cys
1               5                   10                  15

Ala Gln Pro

<210> SEQ ID NO 226
<211> LENGTH: 34
<212> TYPE: PRT
<213> ORGANISM: Artificial Sequence
<220> FEATURE:
<223> OTHER INFORMATION: analog 10aa-sub-15aa-ex

<400> SEQUENCE: 226

Ser Trp Ala Gln Glu Leu Tyr Pro His Ala Asn Phe Ser Ser Ser Cys
1               5                   10                  15

Ala Gln Pro Tyr Pro Tyr Asp Val Pro Asp Tyr Ala Gly Glu Leu Ala
            20                  25                  30

Arg Pro

<210> SEQ ID NO 227
<211> LENGTH: 16
<212> TYPE: PRT
<213> ORGANISM: Artificial Sequence
<220> FEATURE:
<223> OTHER INFORMATION: analog W2MeGly
<220> FEATURE:
<221> NAME/KEY: MOD_RES
<222> LOCATION: (2)..(2)
<223> OTHER INFORMATION: MeGly

<400> SEQUENCE: 227

Ser Gly Gly Ala Ala Ala Ala Gln Ala Ser Ser Ser Cys Ala Gln Pro
```

-continued

```
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: analog G3MeGly
<220> FEATURE:
<221> NAME/KEY: MOD_RES
<222> LOCATION: (3)..(3)
<223> OTHER INFORMATION: MeGly

<400> SEQUENCE: 228

Ser Trp Gly Ala Ala Ala Ala Gln Ala Ser Ser Ser Cys Ala Gln Pro
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: analog A4MeGly
<220> FEATURE:
<221> NAME/KEY: MOD_RES
<222> LOCATION: (4)..(4)
<223> OTHER INFORMATION: MeGly

<400> SEQUENCE: 229

Ser Trp Gly Gly Ala Ala Ala Gln Ala Ser Ser Ser Cys Ala Gln Pro
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: analog A5MeGly
<220> FEATURE:
<221> NAME/KEY: MOD_RES
<222> LOCATION: (5)..(5)
<223> OTHER INFORMATION: MeGly

<400> SEQUENCE: 230

Ser Trp Gly Ala Gly Ala Ala Gln Ala Ser Ser Ser Cys Ala Gln Pro
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: analog A6MeGly
<220> FEATURE:
<221> NAME/KEY: MOD_RES
<222> LOCATION: (6)..(6)
<223> OTHER INFORMATION: MeGly

<400> SEQUENCE: 231

Ser Trp Gly Ala Ala Gly Ala Gln Ala Ser Ser Ser Cys Ala Gln Pro
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: analog A7MeGly
<220> FEATURE:
<221> NAME/KEY: MOD_RES
```

```
<222> LOCATION: (7)..(7)
<223> OTHER INFORMATION: MeGly

<400> SEQUENCE: 232

Ser Trp Gly Ala Ala Ala Gly Gln Ala Ser Ser Ser Cys Ala Gln Pro
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: analog Q8MeGly
<220> FEATURE:
<221> NAME/KEY: MOD_RES
<222> LOCATION: (8)..(8)
<223> OTHER INFORMATION: MeGly

<400> SEQUENCE: 233

Ser Trp Gly Ala Ala Ala Ala Gly Ala Ser Ser Ser Cys Ala Gln Pro
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: analog A9MeGly
<220> FEATURE:
<221> NAME/KEY: MOD_RES
<222> LOCATION: (9)..(9)
<223> OTHER INFORMATION: MeGly

<400> SEQUENCE: 234

Ser Trp Gly Ala Ala Ala Ala Gln Gly Ser Ser Ser Cys Ala Gln Pro
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: analog C13MeGly
<220> FEATURE:
<221> NAME/KEY: MOD_RES
<222> LOCATION: (13)..(13)
<223> OTHER INFORMATION: MeGly

<400> SEQUENCE: 235

Ser Trp Gly Ala Ala Ala Ala Gln Ala Ser Ser Ser Gly Ala Gln Pro
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: analog A14MeGly
<220> FEATURE:
<221> NAME/KEY: MOD_RES
<222> LOCATION: (14)..(14)
<223> OTHER INFORMATION: MeGly

<400> SEQUENCE: 236

Ser Trp Gly Ala Ala Ala Ala Gln Ala Ser Ser Ser Cys Gly Gln Pro
1               5                   10                  15

<210> SEQ ID NO 237
<211> LENGTH: 16
```

```
<212> TYPE: PRT
<213> ORGANISM: Artificial Sequence
<220> FEATURE:
<223> OTHER INFORMATION: analog Q15MeGly
<220> FEATURE:
<221> NAME/KEY: MOD_RES
<222> LOCATION: (15)..(15)
<223> OTHER INFORMATION: MeGly

<400> SEQUENCE: 237

Ser Trp Gly Ala Ala Ala Ala Gln Ala Ser Ser Ser Cys Ala Gly Pro
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: analog P16MeGly
<220> FEATURE:
<221> NAME/KEY: MOD_RES
<222> LOCATION: (16)..(16)
<223> OTHER INFORMATION: MeGly

<400> SEQUENCE: 238

Ser Trp Gly Ala Ala Ala Ala Gln Ala Ser Ser Ser Cys Ala Gln Gly
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: analog W2MeAla
<220> FEATURE:
<221> NAME/KEY: MOD_RES
<222> LOCATION: (2)..(2)
<223> OTHER INFORMATION: N-MethylAlanine

<400> SEQUENCE: 239

Ser Ala Gly Ala Ala Ala Ala Gln Ala Ser Ser Ser Cys Ala Gln Pro
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: analog G3MeAla

<400> SEQUENCE: 240

Ser Trp Ala Ala Ala Ala Ala Gln Ala Ser Ser Ser Cys Ala Gln Pro
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: analog A4MeAla

<400> SEQUENCE: 241

Ser Trp Gly Ala Ala Ala Ala Gln Ala Ser Ser Ser Cys Ala Gln Pro
1               5                   10                  15

<210> SEQ ID NO 242
<211> LENGTH: 16
<212> TYPE: PRT
<213> ORGANISM: Artificial Sequence
```

```
<220> FEATURE:
<223> OTHER INFORMATION: analog A5MeAla

<400> SEQUENCE: 242

Ser Trp Gly Ala Ala Ala Ala Gln Ala Ser Ser Ser Cys Ala Gln Pro
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: analog A6MeAla

<400> SEQUENCE: 243

Ser Trp Gly Ala Ala Ala Ala Gln Ala Ser Ser Ser Cys Ala Gln Pro
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: analog A7MeAla

<400> SEQUENCE: 244

Ser Trp Gly Ala Ala Ala Ala Gln Ala Ser Ser Ser Cys Ala Gln Pro
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: analog Q8MeAla

<400> SEQUENCE: 245

Ser Trp Gly Ala Ala Ala Ala Ala Ala Ser Ser Ser Cys Ala Gln Pro
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: analog A9MeAla

<400> SEQUENCE: 246

Ser Trp Gly Ala Ala Ala Ala Gln Ala Ser Ser Ser Cys Ala Gln Pro
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: analog C13MeAla

<400> SEQUENCE: 247

Ser Trp Gly Ala Ala Ala Ala Gln Ala Ser Ser Ser Ala Ala Gln Pro
1               5                   10                  15

<210> SEQ ID NO 248
<211> LENGTH: 16
<212> TYPE: PRT
<213> ORGANISM: Artificial Sequence
<220> FEATURE:
```

<223> OTHER INFORMATION: analog A14MeAla

<400> SEQUENCE: 248

Ser Trp Gly Ala Ala Ala Ala Gln Ala Ser Ser Ser Cys Ala Gln Pro
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: analog Q15MeAla

<400> SEQUENCE: 249

Ser Trp Gly Ala Ala Ala Ala Gln Ala Ser Ser Ser Cys Ala Ala Pro
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: analog P16MeAla

<400> SEQUENCE: 250

Ser Trp Gly Ala Ala Ala Ala Gln Ala Ser Ser Ser Cys Ala Gln Ala
1               5                   10                  15

<210> SEQ ID NO 251
<211> LENGTH: 57
<212> TYPE: PRT
<213> ORGANISM: Artificial Sequence
<220> FEATURE:
<223> OTHER INFORMATION: LazA

<400> SEQUENCE: 251

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
                20                  25                  30

Leu Pro Glu Asn Gly Ala Ser Trp Gly Ser Cys Ser Cys Gln Ala Ser
            35                  40                  45

Ser Ser Cys Ala Gln Pro Gln Asp Met
        50                  55

<210> SEQ ID NO 252
<211> LENGTH: 165
<212> TYPE: DNA
<213> ORGANISM: Artificial Sequence
<220> FEATURE:
<223> OTHER INFORMATION: LazA DNA template

<400> SEQUENCE: 252
atgtctgaca ttaccgcgtc acgtgttgaa tctttagatc ttcaagacct tgatctgtct      60
gagctgactg ttacgtcact gcgcgacacc gtggcattgc cggaaaatgg ggcaagctgg     120
ggttcttgta gttgccaggc ttctagctca tgtgcacaac ataa                      165

<210> SEQ ID NO 253
<211> LENGTH: 23
<212> TYPE: DNA
<213> ORGANISM: Artificial Sequence
<220> FEATURE:
<223> OTHER INFORMATION: Translation enhancer sequence, SD sequence, and
       start codon of Laz A DNA template

```
<400> SEQUENCE: 253
ttaactttaa aggagaaatg tct                                            23

<210> SEQ ID NO 254
<211> LENGTH: 77
<212> TYPE: DNA
<213> ORGANISM: Escherichia coli

<400> SEQUENCE: 254
gtcctgttag acaractggt aaagtcacta cccttcaag gtaggatttg cgggttcgat    60
ccccgcacag gacgcca                                                   77

<210> SEQ ID NO 255
<211> LENGTH: 76
<212> TYPE: DNA
<213> ORGANISM: S. lactacystinaeus

<400> SEQUENCE: 255
gccctcatcg tctagtggcc caggacgccg cccttcaag gcggtagcac gggttcgaat    60
cccgttgggg gcacca                                                    76

<210> SEQ ID NO 256
<211> LENGTH: 76
<212> TYPE: DNA
<213> ORGANISM: S. lactacystinaeus

<400> SEQUENCE: 256 gccccgttg tgtagcggcc tagcacgctg ccctctcacg gcagtagcgc cggttcgaat    60
ccggtcgggg gtacca                                                    76

<210> SEQ ID NO 257
<211> LENGTH: 13
<212> TYPE: DNA
<213> ORGANISM: Artificial Sequence
<220> FEATURE:
<223> OTHER INFORMATION: part of tRNA Glu

<400> SEQUENCE: 257 gccccgttg tgt                                                        13

<210> SEQ ID NO 258
<211> LENGTH: 13
<212> TYPE: DNA
<213> ORGANISM: Artificial Sequence
<220> FEATURE:
<223> OTHER INFORMATION: part of tRNA Glu

<400> SEQUENCE: 258 gtcggggta cca                                                        13

<210> SEQ ID NO 259
<211> LENGTH: 224
<212> TYPE: RNA
<213> ORGANISM: Artificial Sequence
<220> FEATURE:
<223> OTHER INFORMATION: example of mRNA in the mRNA library

<400> SEQUENCE: 259
ggguuaacuu uaacaaggag aaaaacaugu cugacauuac cgcgucacgu guugaaucuu    60
uagaucuuca agaccuugau cugucugagc ugacuguuac gucacugcgc gacaccgugg   120
```
cauugccgga aaaugggca agcuggggu cuuguaguug ccaggcuucu agcucaugug    180
cacaaccagg ugggaauggc ggcaauuagg acggggggcg gaaa    224

<210> SEQ ID NO 260
<211> LENGTH: 16
<212> TYPE: DNA
<213> ORGANISM: Artificial Sequence
<220> FEATURE:
<223> OTHER INFORMATION: part of puromycin-DNA linker

<400> SEQUENCE: 260
ctcccgcccc ccgtcc    16

<210> SEQ ID NO 261
<211> LENGTH: 60
<212> TYPE: PRT
<213> ORGANISM: Artificial Sequence
<220> FEATURE:
<223> OTHER INFORMATION: exapmle of peptide in the peptide library

<400> SEQUENCE: 261

Met Ser Asp Ile Thr Ala Ser Arg Val Glu Ser Leu Asp Leu Gln Asp
1               5                   10                  15

Leu Asp Leu Ser Glu Leu Thr Val Thr Ser Leu Arg Asp Thr Val Ala
            20                  25                  30

Leu Pro Glu Asn Gly Ala Ser Trp Gly Ser Cys Ser Cys Gln Ala Ser
        35                  40                  45

Ser Ser Cys Ala Gln Pro Gly Gly Asn Gly Gly Asn
    50                  55                  60

<210> SEQ ID NO 262
<211> LENGTH: 16
<212> TYPE: PRT
<213> ORGANISM: Artificial Sequence
<220> FEATURE:
<223> OTHER INFORMATION: amino acid sequence of template v.070

<400> SEQUENCE: 262

Ser Ala Trp Ala Ala Ala Ala Gln Ala Ser Ser Ser Cys Ala Gln Pro
1               5                   10                  15

<210> SEQ ID NO 263
<211> LENGTH: 16
<212> TYPE: PRT
<213> ORGANISM: Artificial Sequence
<220> FEATURE:
<223> OTHER INFORMATION: amino acid sequence of template v.086

<400> SEQUENCE: 263

Ser Ala Gly Trp Ala Ala Ala Gln Ala Ser Ser Ser Cys Ala Gln Pro
1               5                   10                  15

<210> SEQ ID NO 264
<211> LENGTH: 16
<212> TYPE: PRT
<213> ORGANISM: Artificial Sequence
<220> FEATURE:
<223> OTHER INFORMATION: amino acid sequence of template v.087

<400> SEQUENCE: 264

Ser Ala Gly Ala Trp Ala Ala Gln Ala Ser Ser Ser Cys Ala Gln Pro
1               5                   10                  15

<210> SEQ ID NO 265

```
<211> LENGTH: 16
<212> TYPE: PRT
<213> ORGANISM: Artificial Sequence
<220> FEATURE:
<223> OTHER INFORMATION: amino acid sequence of template v.088

<400> SEQUENCE: 265

Ser Ala Gly Ala Ala Trp Ala Gln Ala Ser Ser Ser Cys Ala Gln Pro
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: amino acid sequence of template v.089

<400> SEQUENCE: 266

Ser Ala Gly Ala Ala Ala Trp Gln Ala Ser Ser Ser Cys Ala Gln Pro
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: amino acid sequence of template v.074

<400> SEQUENCE: 267

Ser Ala Gly Ala Ala Ala Ala Trp Ala Ser Ser Ser Cys Ala Gln Pro
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: amino acid sequence of template v.075

<400> SEQUENCE: 268

Ser Ala Gly Ala Ala Ala Ala Ala Trp Ser Ser Ser Cys Ala Gln Pro
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: amino acid sequence of template v.077

<400> SEQUENCE: 269

Ser Ala Gly Ala Ala Ala Ala Gln Ala Ser Ser Ser Cys Trp Gln Pro
1               5                   10                  15

<210> SEQ ID NO 270
<211> LENGTH: 16
<212> TYPE: PRT
<213> ORGANISM: Artificial Sequence
<220> FEATURE:
<223> OTHER INFORMATION: amino acid sequence of template v.080

<400> SEQUENCE: 270

Ser Ala Gly Ala Ala Ala Ala Gln Ala Ser Ser Ser Cys Ala Trp Pro
1               5                   10                  15

<210> SEQ ID NO 271
<211> LENGTH: 16
```

```
<212> TYPE: PRT
<213> ORGANISM: Artificial Sequence
<220> FEATURE:
<223> OTHER INFORMATION: amino acid sequence of template v.081

<400> SEQUENCE: 271

Ser Ala Gly Ala Ala Ala Gln Ala Ser Ser Ser Cys Ala Gln Trp
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: amino acid sequence of template v.071

<400> SEQUENCE: 272

Ser Ala Trp Ala Ala Ala Trp Gln Ala Ser Ser Ser Cys Ala Gln Pro
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: amino acid sequence of template v.072

<400> SEQUENCE: 273

Ser Ala Trp Ala Lys Ala Trp Gln Ala Ser Ser Ser Cys Ala Gln Pro
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: amino acid sequence of template v.073

<400> SEQUENCE: 274

Ser Trp Lys Trp Lys Trp Lys Gln Ala Ser Ser Ser Cys Ala Gln Pro
1               5                   10                  15

<210> SEQ ID NO 275
<211> LENGTH: 16
<212> TYPE: PRT
<213> ORGANISM: Artificial Sequence
<220> FEATURE:
<223> OTHER INFORMATION: amino acid sequence of template v.100

<400> SEQUENCE: 275

Ser Ala Trp Ala His Ala Phe Gln Ala Ser Ser Ser Cys Ala Gln Lys
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: amino acid sequence of template v.101

<400> SEQUENCE: 276

Ser Ala Lys Ala Trp Ala His Gln Ala Ser Ser Ser Cys Ala Gln Phe
1               5                   10                  15

<210> SEQ ID NO 277
<211> LENGTH: 78
<212> TYPE: DNA
```

-continued

```
<213> ORGANISM: Artificial Sequence
<220> FEATURE:
<223> OTHER INFORMATION: tRNA Glu

<400> SEQUENCE: 277
gcuccgguag tguaguccgg ccaaucauuu cggccuuucg agccgaagac ucgggguucaa     60 aucccggccg gagcacca                                                   78
```

COMPOUND LIBRARY AND METHOD FOR PRODUCING COMPOUND LIBRARY

REFERENCE TO SEQUENCE LISTING SUBMITTED VIA PATENTCENTER

The content of the text file of the sequence listing named "20240508_034574_028US1_ST25_sub" which is 99,012 bytes in size was created on Apr. 30, 2024 and electronically submitted via Patent Center herewith the application is incorporated herein by reference in its entirety.

REFERENCE TO LARGE TABLES ASCII FILE SUBMITTED VIA PATENTCENTER

The content of the text file containing Tables 3, 4, 5A, 5B, 6, and 7, which has the filename "20250603_034574_028US1_tables" is 1,056,989 bytes in size was created on Jun. 3, 2025 and electronically submitted via Patent Center herewith the application is incorporated herein by reference in its entirety.

TECHNICAL FIELD

The present invention relates to a compound library and a method for producing a compound library, etc.

BACKGROUND ART

With the development of genome sequencing technology in recent years, a peptide compound group called RiPPs (ribosomally synthesized and post-translationally modified peptides) has received attention, which is synthesized in ribosomes and biosynthesized through post-translational modifications (Non-Patent Document 1). For RiPPs, biosynthetic genes called structural gene which reside in biosynthetic gene clusters are translated by ribosomes to synthesize precursor peptides. Then, the precursor peptides are subjected to a plurality of diverse modifications such as azole ring formation or dehydroamino acid formation by post-translationally modifying enzymes encoded by other biosynthetic genes, so that mature products are synthesized.

Thiopeptides, one of the RiPPs, have interesting physiological activity such as strong translation inhibitory activity, an antimicrobial effect on multi-drug-resistant organisms, an antiparasitic effect, an antiviral effect, an immunosuppressive effect, an anticancer effect and the like. For examples, lactazoles A, B and C are known as the thiopeptides. It has also been reported that lazA-F, a lactazole biosynthetic gene cluster, was found in the genome of an actinomycete *Streptomyces* lactacystinaeus (Non-Patent Document 2).

See FIG. 55 for the structures of Lactazole A, Lactazole B, and Lactazole C.

Thiopeptides have interesting activity, as mentioned above, and therefore have received attention as medicament candidates or tools for research. Various attempts have been made to develop libraries containing peptides having diverse structures and screen for thiopeptides having affinity for target substances.

An attempt to prepare thiopeptide analogs through the use of a mechanism of thiopeptide biosynthesis has been made by Walsh et al., who have prepared thiopeptide analogs in vivo by introducing mutations to structural genes using GE37468 and a thiocillin biosynthesis pathway (Non-Patent Documents 3 and 4).

In Non-Patent Document 4, *Bacillus cereus* ATCC 14579 is used as a host for thiocillin. In this document, an attempt has been made to prepare analogs so as to change the size of the macrocycle. As Thiocillin has a macrocyclic structure of a 26-membered ring, it has been reported that analogs having a 23-, 26-, 29-, 32-, or 35-membered macrocycle were able to be prepared by adding mutations to structural genes.

In vitro methods are known as methods for obtaining a library of compounds having a peptide structure.

Cell-free translation systems are systems for synthesizing peptides or proteins of interest in vitro through the use of protein-synthesis functions extracted from cells. The cell-free translation systems include systems directly using translational factors extracted from cells such as rabbit reticulocytes, wheat germs or *E. coli*, and systems called reconstituted cell-free translation systems, which prepare 31 kinds of proteins for translation other than a ribosome one by one as recombinant proteins and mix these proteins (Non-Patent Document 5).

The reconstituted cell-free translation systems, as compared with the systems directly using cell extracts, have the advantage that peptides or proteins can be synthesized with high efficiency because of involving neither nuclease nor protease.

The cell-free translation systems are excellent in convenience because their approaches for synthesizing proteins, as compared with chemical synthesis methods or production methods based on genetically recombinant organisms, etc., have a rapid synthesis speed. Hence, the cell-free translation systems are also employed in drug discovery research. For example, "flexible in vitro translation system (FIT system)" is known (Non-Patent Document 6). The FIT system can construct a system for preparing peptides containing non-proteinogenic amino acids by a cell-free translation system, and a special peptide library having a cyclic structure or the like by using this system.

CITATION LIST

Non-Patent Document

Non-Patent Document 1: Arnison, P. G. et al. Ribosomally synthesized and post-translationally modified peptide natural products: overview and recommendations for a universal nomenclature. Nat Prod Rep 30, 108-160, (2013).

Non-Patent Document 2: Hayashi, S. et al. Genome mining reveals a minimum gene set for the biosynthesis of 32-membered macrocyclic thiopeptides lactazoles. Chem Biol 21, 679-688, (2014).

Non-Patent Document 3: Young, T. S., Dorrestein, P. C. & Walsh, C. T. Codon randomization for rapid exploration of chemical space in thiopeptide antibiotic variants. Chem Biol 19, 1600-1610, (2012).

Non-Patent Document 4: Bowers, A. A., Acker, M. G., Young, T. S. & Walsh, C. T. Generation of thiocillin ring size variants by prepeptide gene replacement and in vivo processing by *Bacillus cereus*. J Am Chem Soc 134, 10313-10316, (2012).

Non-Patent Document 5: Shimizu, Y. et al. Cell-free translation reconstituted with purified components. Nat Biotechnol 19, 751-755, (2001).

Non-Patent Document 6: Goto, Y., Katoh, T. & Suga, H. Flexizymes for genetic code reprogramming. Nat Protoc 6, 779-790, (2011).

SUMMARY

Technical Problem

In cell-free translation systems, peptides or proteins of interest can be synthesized in just 30 minutes, and, if many DNA or mRNA templates can be synthesized, many types of peptides or proteins can be readily synthesized according thereto. Thus, the cell-free translation systems are useful for obtaining compound libraries because many types of proteins can be synthesized conveniently and rapidly. However, any approach has not yet been known, which involves constructing a peptide compound library having diverse structures in vitro by exploiting the advantages of the cell-free translation systems and linking the cell-free translation systems to thiopeptide-biosynthesis systems.

Non-Patent Document 2 discloses that lazA-F, a lactazole biosynthetic gene cluster, was found. Nonetheless, an enzyme LazB-F expressed from lazB-F has not been functionally determined. Besides, this document does not disclose in vitro reaction using these enzymes.

The possibility (substrate tolerance) is unclear that thiopeptide-biosynthetic enzymes such as the enzyme LazB-F may form thiopeptides from diverse amino acid sequences including non-natural sequences. Also, the possibility is unknown that the thiopeptide-biosynthetic enzymes can be applied to library construction.

The present invention has been made in light of the problems described above. An objective of the present invention is to provide a method for producing a peptide compound library using a thiopeptide-biosynthesis system.

Solution to Problem

The present inventors have conducted diligent studies to attain the objective and consequently completed the present invention by finding that: peptide compounds having diverse structures can be synthesized by using predetermined thiopeptide-biosynthetic enzymes; and peptide compound libraries can be developed using cell-free translation systems and the thiopeptide-biosynthesis systems.

Specifically, the present invention is as follows.

[1]

A method for producing a compound library comprising two or more cyclic compounds represented by the formula (I):

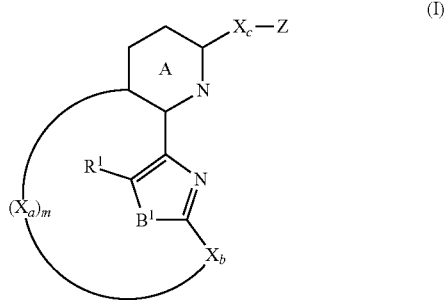

(I)

wherein m number of $X_a$, and $X_b$ and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, $B^1$ is an oxygen atom, a sulfur atom, or a NH group, and $R^1$ is a hydrogen atom or a hydrocarbon group, comprising a step of allowing a macrocyclase in vitro to act on two or more peptides represented by the formula (II):

$$LP\text{-}X\text{-}(Xa)_m\text{-}Y\text{-}Z \qquad (II)$$

wherein

X represents a group represented by the formula (1):

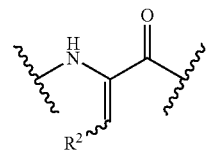

(1)

(wherein $R^2$ is a hydrogen atom or a hydrocarbon group),

Y is a peptide residue consisting of four amino acids and/or analogs thereof and contains a group represented by the formula (2):

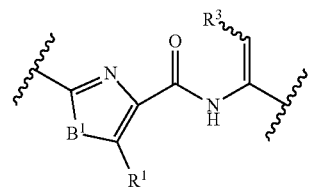

(2)

(wherein $R^1$ and $B^1$ are as defined above, and $R^3$ represents a hydrogen or a hydrocarbon group), m number of $X_a$, m and Z are as defined above, and LP is present or absent and, when present, represents a peptide residue consisting of 1 to 100 amino acids and/or analogs thereof, and forming the nitrogen-containing 6-membered ring A while eliminating LP, if present, to form the two or more cyclic compounds represented by the formula (I).

[2]

The production method according to [1], wherein LP is a peptide residue consisting of 11 or more and 100 or less amino acids and/or analogs thereof.

[3]

The production method according to [1] or [2], wherein m is an integer selected from 2 to 24.

[4]

The production method according to any of [1] to [3], wherein Y is a group represented by the following formula (3):

(3)

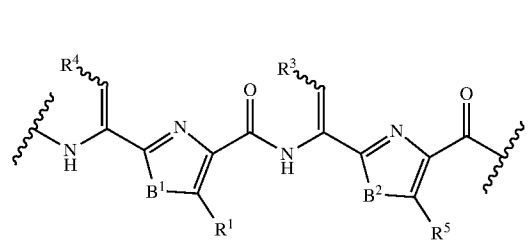

wherein $R^1$, $R^3$, $R^4$ and $R^5$ each independently represent a hydrogen atom or a hydrocarbon group, and $B^1$ and $B^2$ each independently represent an oxygen atom, a sulfur atom, or a NH group.

[5]

The production method according to any of [1] to [4], wherein Y is a group represented by the following formula (3'):

(3')

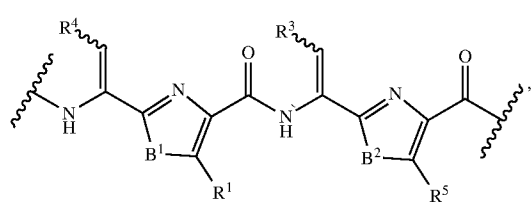

wherein $R^1$, $R^3$, $R^4$ and $R^5$ each independently represent a hydrogen atom or a methyl group, and $B^1$ and $B^2$ each independently represent an oxygen atom or a sulfur atom, with the proviso that when $B^1$ and/or $B^2$ is a sulfur atom, each of $R^1$ and $R^5$ is a hydrogen.

[6]

The production method according to any of [1] to [5], wherein Y is a group represented by the following formula (3"):

(3")

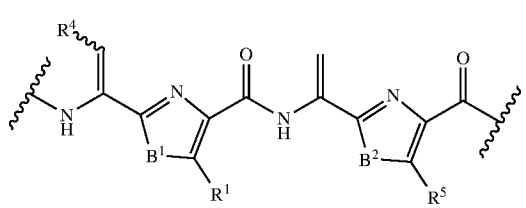

wherein $R^1$, $R^4$ and $R^5$ each independently represent a hydrogen atom or a methyl group, and $B^1$ and $B^2$ each independently represent an oxygen atom or a sulfur atom, with the proviso that when $B^1$ and/or $B^2$ is a sulfur atom, each of $R^1$ and $R^5$ is a hydrogen.

[7]

The production method according to any of [1] to [6], wherein Y is a group represented by the following formula (3-1):

(3-1)

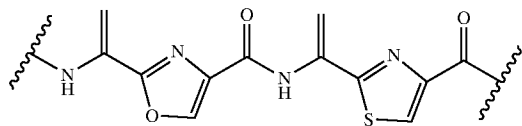

[8]

The production method according to any of [1] to [7], wherein the macrocyclase comprises LazC and/or an enzyme having homology with LazC.

[9]

A method for producing a compound library comprising two or more cyclic compounds represented by the formula (I):

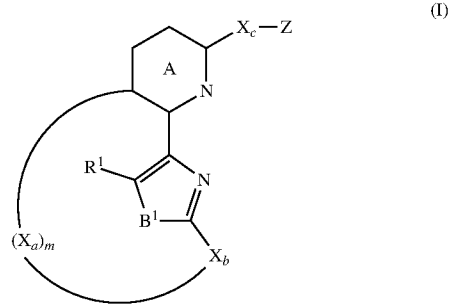

(I)

wherein m number of $X_a$, and $X_b$ and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, $B^1$ is an oxygen atom, a sulfur atom, or a NH group, and $R^1$ is a hydrogen atom or a hydrocarbon group, the method comprising:

a step of producing a mRNA library encoding precursor peptides represented by the formula (III):

$$LP' - X' - (Xa')_{m'} - Y' - Z'$$ (III)

wherein

X' is serine or threonine, or an analog thereof,

Y' is a peptide consisting of four amino acids represented by -Y'(10)-Y'(11)-Y'(12)-Y'(13)- and/or analogs thereof, wherein Y'(10) is an amino acid residue selected from the group consisting of any amino acids and analogs thereof, Y'(11) is serine, cysteine, threonine, or diaminopropionic acid or an analog thereof, Y'(12) is serine or threonine or an analog thereof, and Y'(13) is an amino acid residue selected from the group consisting of any amino acids and analogs thereof, m' number of $X_a$', m' and Z' are the same as defined as m number of $X_a$, m and Z, respectively, in the formula (I), and LP' is present or absent and, when present, represents a peptide consisting of 1 to 100 amino acids and/or analogs thereof;

a step of expressing the precursor peptides by a cell-free translation system with the mRNA library to produce a first peptide library;

a step of reacting an enzyme for forming azole ring(s) with the first peptide library, so that at least an azole ring is formed on Y'(11) in the precursor peptides to produce a second peptide library;

a step of reacting an enzyme for forming $\alpha,\beta$-unsaturated amino acid(s) with the second peptide library in the presence of cosubstrate tRNA$^{Glu}$ for glutamylation reaction and aminoacylation enzyme GluRS, so that at least X' and Y'(12) in the precursor peptides are converted to $\alpha,\beta$-unsaturated amino acid residues to produce a third peptide library; and a step of reacting a macrocyclase with the third peptide library and forming a nitrogen-containing 6-membered ring while eliminating LP', if present, to form the two or more cyclic compounds represented by the formula (I).

A method for producing a compound library comprising two or more cyclic compounds represented by the formula (I):

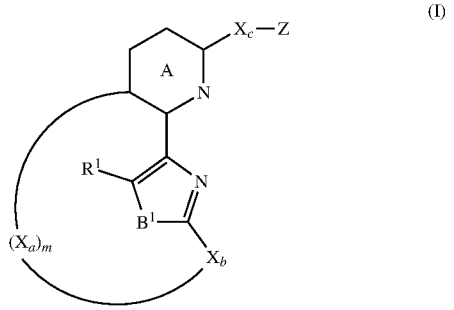

wherein m number of $X_a$, and $X_b$ and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, $B^1$ is an oxygen atom, a sulfur atom, or a NH group, and $R^1$ is a hydrogen atom or a hydrocarbon group, the method comprising:

a step of producing a mRNA library encoding precursor peptides represented by the formula (III):

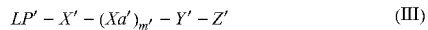

wherein

X' is serine or threonine, or an analog thereof,

Y' is a peptide consisting of four amino acids represented by -Y'(10)-Y'(11)-Y'(12)-Y'(13)- and/or analogs thereof, wherein Y'(10) is an amino acid residue selected from the group consisting of any amino acids and analogs thereof, Y'(11) is serine, cysteine, threonine, or diaminopropionic acid or an analog thereof, Y'(12) is serine or threonine or an analog thereof, and Y'(13) is an amino acid residue selected from the group consisting of any amino acids and analogs thereof, m' number of $X_a$', m' and Z' are as the same defined as m number of $X_a$, m and Z, respectively, in the formula (I), and LP' is present or absent and, when present, represents a peptide consisting of 1 to 100 amino acids and/or analogs thereof;

a step of binding puromycin to the 3' end of each mRNA of the mRNA library to produce a puromycin-bound mRNA library;

a step of expressing the precursor peptides by a cell-free translation system with the puromycin-bound mRNA library to produce a first peptide-mRNA complex library;

a step of reacting an enzyme for forming azole ring(s) with the first peptide-mRNA complex library, so that an azole ring is formed on at least Y'(11) in the precursor peptides to produce a second peptide-mRNA complex library;

a step of reacting an enzyme for forming $\alpha,\beta$-unsaturated amino acid(s) with the second peptide-mRNA complex library in the presence of cosubstrate tRNA$^{Glu}$ for glutamylation reaction and aminoacylation enzyme GluRS, so that at least X' and Y'(12) in the precursor peptides are converted to $\alpha,\beta$-unsaturated amino acid residues to produce a third peptide-mRNA complex library; and a step of reacting a macrocyclase with the third peptide-mRNA complex library and forming a nitrogen-containing 6-membered ring while eliminating LP', if present, to form the two or more cyclic compounds represented by the formula (I).

[11]

The production method according to [9] or [10], wherein LP' is a peptide consisting of 11 or more and 100 or less amino acids and/or analogs thereof.

[12]

The production method according to any of [9] to [11], wherein m is an integer selected from 2 to 24.

[13]

The production method according to any of [9] to [12], wherein Y'(10) is serine or threonine or an analog thereof, and Y'(13) is serine, cysteine, threonine, or diaminopropionic acid or an analog thereof.

[14]

The production method according to any of [9] to [13], wherein Y'(11) is serine, cysteine, or threonine, or an analog thereof, and Y'(12) is serine or threonine, or an analog thereof.

[15]

The production method according to any of [9] to [14], wherein Y'(11) is serine, cysteine, or threonine, or an analog thereof, and Y'(12) is serine or an analog thereof.

[16]

The production method according to any of [9] to [15], wherein Y'(10) is serine or threonine or an analog thereof, Y'(11) is serine, cysteine, or threonine, or an analog thereof, Y'(12) is serine, and Y'(13) is serine, cysteine, or threonine, or an analog thereof.

[17]

The production method according to any of [9] to [16], wherein in $(X_a')$ m' in the formula (III), amino acid residue $X_a'(1)$ adjacent to X' is an amino acid other than an acidic amino acid or an analog thereof.

[18]

The production method according to any of [9] to [17], wherein in $(X_a')$ m' in the formula (III), amino acid residue $X_a'(m')$ at m'-th position is an amino acid other than an acidic amino acid or an analog thereof.

[19]

The production method according to any of [9] to [18], wherein in $(X_a')$ m' in the formula (III), amino acid residue $X_a'(m'-1)$ at (m'-1)-th position is an amino acid other than an acidic amino acid and a basic amino acid or an analog thereof.

[20]

The production method according to any of [9] to [19], wherein the enzyme for forming azole ring(s) comprises LazD, LazE and LazF, and/or enzymes having homology with any of them.

[21]

The production method according to any of [9] to [20], wherein the enzyme for forming α,β-unsaturated amino acid(s) comprises LazB and LazF, and/or enzymes having homology with any of them.

[22]

The production method according to any of [9] to [21], wherein the macrocyclase comprises LazC and/or an enzyme having homology with LazC.

[23]

The production method according to any of [9] to [22], wherein the cosubstrate tRNA$^{Glu}$ for glutamylation reaction is actinomycete-derived tRNA$^{Glu}$, and the aminoacylation enzyme GluRS is actinomycete-derived GluRS.

[24]

A compound library comprising two or more cyclic compounds represented by the formula (I):

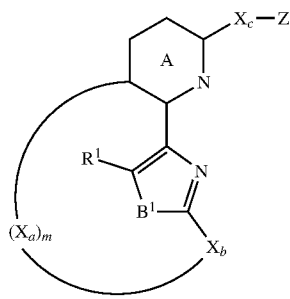

(I)

wherein m number of $X_a$, and $X_b$ and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, B¹ is an oxygen atom, a sulfur atom, or a NH group, and R¹ is a hydrogen atom or a hydrocarbon group, wherein at least one of the cyclic compounds represented by the formula (I) is in a non-natural form.

[25]

A screening method for identifying a cyclic compound represented by the formula (I) binding to a target substance, comprising:

a step of contacting a compound library produced by the production method according to any of [1] to [23] or the compound library according to with the target substance, followed by incubation; and a step of selecting a cyclic compound represented by the formula (I) bound to the target substance.

[26]

A screening kit for identifying a cyclic compound represented by the formula (I) binding to a target substance, comprising a compound library produced by the production method according to any of [1] to [23] or the compound library according to [24].

[27]

A method for producing a cyclic compound represented by the formula (I):

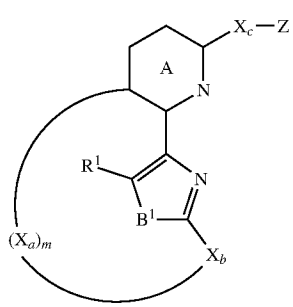

(I)

wherein m number of $X_a$, and $X_b$ and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, B¹ is an oxygen atom, a sulfur atom, or a NH group, and R¹ is a hydrogen atom or a hydrocarbon group, comprising a step of allowing a macrocyclase in vitro to act on a peptide represented by the formula (II):

$$LP - X - (Xa)_m - Y - Z \qquad (II)$$

wherein
X represents a group represented by the formula (1):

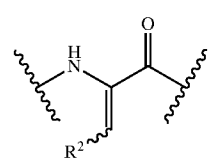

(1)

(wherein R² is a hydrogen or a hydrocarbon group),

Y is a peptide consisting of four amino acids and/or analogs thereof and contains a group represented by the formula (2):

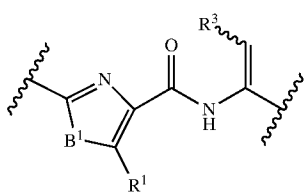

(2)

(wherein $R^1$ and $R^3$ each represent hydrogen or a hydrocarbon group, and $B^1$ represents an oxygen atom, a sulfur atom, or a NH group), m number of $X_a$, m and Z are as defined above, and LP is present or absent and, when present, represents a peptide residue consisting of 1 to 100 amino acids and/or analogs thereof, and forming the nitrogen-containing 6-membered ring A while eliminating LP, if present, to form the cyclic compound represented by the formula (I).

A method for producing a cyclic compound represented by the formula (I):

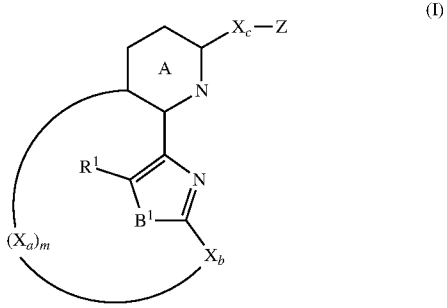

(I)

wherein m number of $X_a$, $X_b$, and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, $B^1$ is an oxygen atom, a sulfur atom, or a NH group, and $R^1$ is a hydrogen atom or a hydrocarbon group, the method comprising:

a step of producing mRNA encoding a precursor peptide represented by the formula (III):

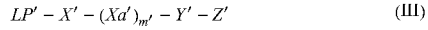

$$LP' - X' - (Xa')_{m'} - Y' - Z'$$

(III)

wherein

X' is serine or threonine, or an analog thereof,

Y' is a peptide consisting of four amino acids represented by -Y'(10)-Y'(11)-Y'(12)-Y'(13)- and/or analogs thereof, wherein Y'(10) is an amino acid residue selected from the group consisting of any amino acids and analogs thereof, Y'(11) is serine, cysteine, threonine, or diaminopropionic acid or an analog thereof, Y'(12) is serine or threonine or an analog thereof, and Y'(13) is an amino acid residue selected from the group consisting of any amino acids and analogs thereof, m' number of $X_a$', m' and Z' are the same as defined as m number of $X_a$, m and Z, respectively, in the formula (I), and LP' is present or absent and, when present, represents a peptide consisting of 1 to 100 amino acids and/or analogs thereof;

a step of expressing the precursor peptide by a cell-free translation system with the mRNA to produce a first peptide;

a step of reacting an enzyme for forming azole ring(s) with the first peptide, so that an azole ring is formed on at least Y'(11) in the precursor peptide to produce a second peptide;

a step of reacting an enzyme for forming α,β-unsaturated amino acid(s) with the second peptide in the presence of cosubstrate $tRNA^{Glu}$ for glutamylation reaction and aminoacylation enzyme GluRS, so that at least X' and Y'(12) in the precursor peptide are converted to α,β-unsaturated amino acid residues to produce a third peptide; and a step of reacting a macrocyclase with the third peptide and forming a nitrogen-containing 6-membered ring while eliminating LP', if present, to form a cyclic compound represented by the formula (I).

According to the present invention, a compound library much more diverse than that prepared by synthesis or in vivo can be obtained by a rapid and convenient method. Use of this compound library enables a compound binding to a target substance to be screened for.

Furthermore, a mRNA display method can be applied to the compound library of the present invention to prepare a library of complexes with mRNAs encoding the peptide moieties of the compounds, so that nucleic acid sequences encoding compounds identified by screening can be determined, and the relationship between the structures and activities of the compounds can be readily analyzed.

BRIEF DESCRIPTION OF DRAWINGS

FIG. 1 is a diagram showing the sequences of LazA and LazA*. The sequence identifiers of LazA and LazA* are SEQ ID NOs: 251 and 103.

FIG. 2 is a schematic view of a lazA DNA template. This template contains a T7 promoter sequence, a translation enhancer sequence, a SD sequence and a DNA template encoding LazA* and has a total length of 214 base pairs. The sequence identifier of translation enhancer sequence, SD sequence, and start codon of the Laz A DNA template is SEQ ID NOs: 253.

FIG. 3 is a diagram showing the nucleotide sequence of lazA having codons changed to E. coli type. The sequence identifiers of the DNA and the amino acid corresponding to the DNA are SEQ ID NOs: 252 and 103.

FIG. 4 is a schematic view of primer extension and PCR.

FIG. 5 is a diagram showing the alignment of $tRNA^{Glu}$ nucleotide sequences of E. coli and lactazole-producing microbes. The 72nd and 73rd bases, which were important for the substrate recognition of MibB, are emphasized with a box. From top to bottom, the sequence identifiers are SEQ ID NOs: 254 to 256.

FIG. 6 is a diagram showing a $tRNA^{Glu}$ DNA template (a total length of 97 bp) for in vitro transcription. From left to right, the sequence identifiers are SEQ ID NOs: 257 and 258.

FIG. 7 is a diagram showing results of performing azole ring formation reaction (5 hr) followed by α,β-unsaturated amino acid formation reaction. A. A reaction system of LazA* alone; B. A system in which LazD, LazE and LazF were added to LazA* and reacted for 5 hours; and C. A reaction system in which LazB, LazF, tRNA$^{Glu}$ (CUC) and GluRS were added after the reaction of B. It is considered that: m/z 5656.5 is derived from a peptide obtained by the Michael addition of DTT (molecular weight: 154) to dehydroalanine of m/z 5502.5; and m/z 5674.5 is derived from a peptide obtained by the Michael addition of DTT (molecular weight: 154) to a tetradehydrate.

FIG. 8 is a diagram showing results of performing α,β-unsaturated amino acid formation reaction (5 hr) followed by azole ring formation reaction. A. A reaction system of LazA* alone; B. A system in which LazB, LazF, tRNAGlu (CUC) and GluRS were added to LazA* and reacted for 5 hours; and C. A reaction system in which LazD, LazE and LazF were added after the reaction of B.

FIG. 9 is a diagram showing results of reaction of LazC (m/z 2000 to). A. A reaction system of LazA* alone; B. A reaction system in which LazD, LazE and LazF were added to LazA*; C. A reaction system in which LazD, LazE, LazF, LazB, IRNA$^{Glu}$ and GluRS were added to LazA*; and D. A reaction system in which LazD, LazE, LazF, LazB, tRNA$^{Glu}$, GluRS and LazC were added to LazA*.

FIG. 10 shows that the same MS spectra as those of FIG. 9D in the range of m/z 1415 to 1435 were enlarged and overlaid. A signal of a Na adduct (calcd. 1423.369) of lactazole A was specifically seen in the system of LazC (+).

FIG. 11 shows the LC-MS chromatograms (EIC) of leader peptides cleaved off during Ala-inserted analog formation.

FIG. 12 is a diagram showing the peak areas of leader peptides cleaved off during Ala-inserted analog formation.

FIG. 13 shows the LC-MS chromatograms (EIC) of leader peptides cleaved off during Ala multiply-inserted analog and -deleted analog formation.

FIG. 14 is a diagram showing the peak areas of leader peptides cleaved off during Ala multiply-insert ed analog and -deleted analog formation.

FIG. 15 shows the LC-MS chromatogram (EIC) of a leader peptide cleaved off during 4SCSC7_4AAAA7 analog formation.

FIG. 16 shows the LC-MS chromatograms (EIC) of leader peptides cleaved off through LazC reaction with Ala-substituted precursor peptides as substrates.

FIG. 17 shows the LC-MS chromatograms (EIC) of reaction products by Laz enzyme group with a Trp (2) or Gly (3)-substituted analog as a substrate.

FIG. 18 shows the LC-MS chromatograms (EIC) of reaction products by Laz enzyme group with a Gln (8) or Ala (9)-substituted analog as a substrate.

FIG. 19 shows the LC-MS chromatograms (EIC) of reaction products by Laz enzyme group with a Gln (15) or Pro (16)-substituted analog as a substrate.

FIG. 20 is a diagram showing results of reaction in substituting a residue (Trp (2), Gly (3), Gln (8), Ala (9), Gln (15) or Pro (16)) in a macrocycle.

FIG. 21 shows the LC-MS chromatograms (EIC) of reaction products by Laz enzyme group with Ala multiply-inserted precursor peptides as substrates.

FIG. 22 shows the LC-MS chromatograms (EIC) of reaction products by Laz enzyme group with multiply-deleted precursor peptides as a substrate.

FIG. 23 shows the peak areas of leader peptides cleaved off from reaction products by Laz enzyme group with Ala multiply-inserted precursor peptides as substrates.

FIG. 24 shows the peak areas of leader peptides cleaved off from reaction products by Laz enzyme group with multiply-deleted precursor peptides as substrates.

FIG. 25 shows the LC-MS chromatograms (brEIC) of reaction products mediated by a Laz enzyme group with Ala and Asn multiply-inserted precursor peptides or multiply-deleted precursor peptides as substrates. From top to bottom, the sequence identifiers are SEQ ID NOs: 84, 83, 82, 81, 80, 79, 78, 70, and 169 to 176.

FIG. 26 shows the LC-MS chromatograms (brEIC) of reaction products mediated by a Laz enzyme group for Ala-substituted analogs. The sequence identifier of the amino acid sequence is SEQ ID NO: 18.

FIG. 27 shows the LC-MS chromatograms (brEIC) of reaction products mediated by a Laz enzyme group for Lys-substituted analogs. The sequence identifier of the amino acid sequence is SEQ ID NO: 38.

FIG. 28 shows the LC-MS chromatograms (brEIC) of reaction products mediated by a Laz enzyme group for Glu-substituted analogs. The sequence identifier of the amino acid sequence is SEQ ID NO: 38.

FIG. 29 is a diagram showing the LC-MS chromatograms (EIC) of leader peptides cleaved off through LazC reaction with a Ser (10), Ser (11) or Cys (13)-substituted analog as a substrate.

FIG. 30 shows the LC-MS chromatograms (brEIC) of reaction products mediated by a Laz enzyme group for analogs (substitution and extension) as to a C-terminal region. From top to bottom, the sequence identifiers are SEQ ID NOs: 212 to 215.

FIG. 31 shows the LC-MS chromatograms (brEIC) of reaction products mediated by a Laz enzyme group for analogs having a randomized intra-ring sequence, and an analog having a randomized intra-ring sequence and an extended C-terminal region. From top to bottom, the sequence identifiers are SEQ ID NOs: 38, and 216 to 226.

FIG. 32 shows results of azole ring formation reaction mediated by LazD, LazE and LazF, and α,β-unsaturated amino acid formation reaction mediated by LazB and LazF when LazA* was used as a substrate.

FIG. 33 shows results of azole ring formation reaction mediated by LazD, LazE and LazF, and α,β-unsaturated amino acid formation reaction mediated by LazB and LazF when LP-30 was used as a substrate.

FIG. 34 shows results of azole ring formation reaction mediated by LazD, LazE and LazF, and α,β-unsaturated amino acid formation reaction mediated by LazB and LazF when LP-25 was used as a substrate.

FIG. 35 shows results of azole ring formation reaction mediated by LazD, LazE and LazF, and α,β-unsaturated amino acid formation reaction mediated by LazB and LazF when LP-20 was used as a substrate.

FIG. 36 shows results of azole ring formation reaction mediated by LazD, LazE and LazF, and α,β-unsaturated amino acid formation reaction mediated by LazB and LazF when LP-15 was used as a substrate.

FIG. 37 shows the LC-MS chromatograms (EIC) of leader peptides using leader peptide-truncated precursor peptides as substrates.

FIG. 38 is a schematic view of altered precursor peptides prepared by substituting each of their amino acid residues positioned from −25 to −1 of a leader peptide in LP-25 by Ala. The sequence identifier of the amino acid sequence is SEQ ID NO: 105.

FIG. 39 is a diagram showing the LC-MS chromatograms (EIC) of leader peptides in reaction products of altered precursor peptides prepared by the substitution of each of their amino acid residues positioned from −25 to −1.

FIG. 40 is a diagram showing the design of compound libraries. The sequence identifier of the amino acid sequence is SEQ ID NO: 17.

FIG. 41 is a diagram of an electrophoretic gel showing that mRNA libraries were prepared. In the diagram, 6 to 11 denote mRNA libraries containing any amino acid sequences consisting of 5, 6, 7, 8, 9 and 10 residues, respectively.

FIG. 42 is a graph showing sequencing quality score Q in sequencing the DNA sequences of reverse transcription products of prepared mRNA libraries.

FIG. 43 is a diagram showing results of evaluating the lengths of prepared mRNA libraries and analyzing the degree of frameshift.

FIG. 44 is a diagram showing results of evaluating the sequence conservation of prepared mRNA libraries in order to confirm that: invariable regions of the libraries correctly had particular sequences; and variable regions evenly had random sequences. The sequence identifier of the amino acid sequence is SEQ ID NO: 17.

FIG. 45 is a diagram showing results of analyzing the frequency of each amino acid in random regions contained in prepared mRNA libraries.

FIG. 46 is a diagram showing a scheme in obtaining a cyclic peptide binding to iPGM, comprising a step of constructing a peptide-mRNA complex library from a mRNA library and further constructing a compound library containing cyclic peptides by the action of LazB-F enzyme. From top to bottom, the sequence identifiers are SEQ ID NOs: 259 to 261.

FIG. 47 is a diagram showing a graph of the rate of recovery of cDNA obtained by a selection experiment carried out by the scheme of FIG. 52.

FIG. 48 is a schematic view showing four types of codons reprogrammable for the introduction of non-proteinogenic amino acid(s) in the preparation of analogs containing the non-proteinogenic amino acid(s). The sequence identifier of the amino acid sequence is SEQ ID NO: 17.

FIG. 49 is a schematic view of DNA templates provided for the preparation of analogs containing non-proteinogenic amino acid(s). tgg and aag codons corresponding to the boxed W and K were reprogrammed to introduce non-proteinogenic amino acid(s) to a substrate peptide. In left column, from top to bottom, the sequence identifiers are SEQ ID NOs: 38 and 262 to 268. In right column, from top to bottom, the sequence identifiers are SEQ ID NOs: 269 to 276.

FIG. 50 shows the LC-MS chromatograms (brEIC) of reaction products mediated by a Laz enzyme group for non-proteinogenic amino acid-substituted analog N$^{Me}$Gly. The sequence identifier of the amino acid sequence is SEQ ID NO: 38.

FIG. 51 shows the LC-MS chromatograms (brEIC) of reaction products mediated by a Laz enzyme group for non-proteinogenic amino acid-substituted analog NMcAla. The sequence identifier of the amino acid sequence is SEQ ID NO: 38.

FIG. 52 is a schematic view showing a experimental procedure for revealing that a precursor peptides displayed on mRNA is modified by a lactazole biosynthetic enzyme.

FIG. 53 is a diagram showing the LC-MS chromatogram of a leader peptide cleaved off through LazC reaction with a peptide-mRNA complex as a substrate.

FIG. 54 is a diagram showing results of reaction in enzyme addition patterns I, II, III and IV.

FIG. 55 shows structures of Lactazole A, Lactazole B, and Lactazole C.

FIG. 56 is Table 1.

FIG. 57 schematically shows the aminoacylation enzyme GluRS aminoacylating tRNA$^{Glu}$ with glutamic acid.

FIG. 58 is Table 31.

FIG. 59 is Table 32.

FIG. 60 is Table 33.

FIG. 61 is Table 34.

FIG. 62 is Table 35.

FIG. 63 is Table 36.

FIG. 64 is Table 37.

FIG. 65 is Table 38.

DESCRIPTION OF EMBODIMENTS

Hereinafter, embodiments of the present invention will be described in detail. However, the present invention is not limited by the following present embodiment and can be carried out through various changes or modifications without departing from the spirit of the present invention.

One embodiment of the method for producing a compound library according to the present invention is a method for producing a compound library containing two or more cyclic compounds represented by the formula (I):

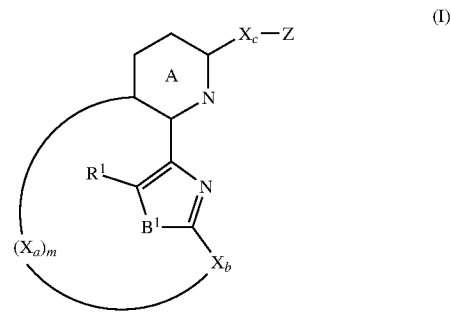

(I)

wherein m number of $X_a$, and $X_b$ and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, $B^1$ is an oxygen atom, a sulfur atom, or a NH group, and $R^1$ is a hydrogen atom or a hydrocarbon group, the method including a step of allowing a macrocyclase in vitro to act on two or more peptides represented by the formula (II):

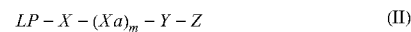

$$LP - X - (Xa)_m - Y - Z \qquad (II)$$

wherein

X represents a group represented by the formula (1):

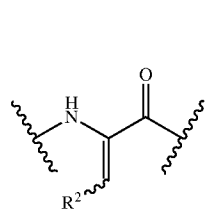
(1)

(wherein $R^2$ is a hydrogen atom or a hydrocarbon group),

Y is a peptide residue consisting of four amino acids and/or analogs thereof and contains a group represented by the formula (2):

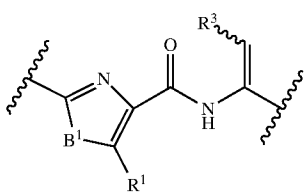
(2)

(wherein $R^1$ and $R^3$ each represent a hydrogen or a hydrocarbon group, and B' represents an oxygen atom, a sulfur atom, or a NH group), m number of $X_a$ each independently represents an amino acid residue selected from the group consisting of any amino acids and analogs thereof, LP is present or absent and, when present, represents a peptide consisting of 1 to 100 amino acids and/or analogs thereof, Z is present or absent and, when present, represents a peptide consisting of 1 to 100 amino acids and/or analogs thereof, and m is an integer selected from 2 to 40, and forming the nitrogen-containing 6-membered ring A while eliminating LP, if present, to form the two or more cyclic compounds represented by the formula (I).

In the formula (1) and the formula (II), m number of $X_a$ may be the same or different and each independently represents an amino acid residue selected from the group consisting of any amino acids and analogs thereof.

In the formula (1) and the formula (2), the unsaturated double bond containing $R^2$ or $R^3$ may be a single isomer in E or Z form or may be a mixture of E and Z forms. The formula (1) is preferably represented by

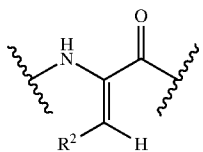

and the formula (2) is preferably represented by

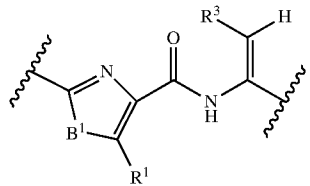

One embodiment of the method for producing a compound library according to the present invention is a method for producing a compound library containing two or more cyclic compounds represented by the formula (I), including:

a step of producing a mRNA library encoding precursor peptides represented by the formula (III):

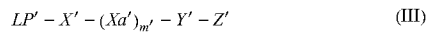
(III)

wherein

X' is serine or threonine, or an analog thereof,

Y' is a peptide consisting of four amino acids represented by -Y'(10)-Y'(11)-Y'(12)-Y'(13)-and/or analogs thereof, wherein Y'(10) is an amino acid residue selected from the group consisting of any amino acids and analogs thereof, Y'(11) is serine, cysteine, threonine, or diaminopropionic acid or an analog thereof, Y'(12) is serine or threonine or an analog thereof, and Y'(13) is an amino acid residue selected from the group consisting of any amino acids and analogs thereof, m' number of $X_a$' each independently represents an amino acid residue selected from the group consisting of any amino acids and analogs thereof, LP' is present or absent and, when present, represents a peptide consisting of 1 to 100 amino acids and/or analogs thereof, Z' is present or absent and, when present, represents a peptide consisting of 1 to 100 amino acids and/or analogs thereof, and m' is an integer selected from 2 to 40;

a step of expressing the precursor peptides by a cell-free translation system with the mRNA library to produce a first peptide library;

a step of reacting an azole ring-forming enzyme with the first peptide library, so that an azole ring is formed on at least Y'(11) in the precursor peptides to produce a second peptide library; and a step of reacting an α,β-unsaturated amino acid-forming enzyme with the second peptide library in the presence of cosubstrate tRNA$^{Glu}$ for glutamylation reaction and aminoacylation enzyme GluRS, so that at least X' and Y'(12) in the precursor peptides are converted to α,β-unsaturated amino acid residues to produce a third peptide library; and a step of reacting a macrocyclase with the third peptide library and forming a nitrogen-containing 6-membered ring while eliminating LP', if present, to form the two or more cyclic compounds represented by the formula (I).

In the formula (III), m' number of $X_a$' may be the same or different and each independently represents an amino acid residue selected from the group consisting of any amino acids and analogs thereof.

The "α,β-unsaturated amino acid" in the α,β-unsaturated amino acid-forming enzyme refers to an amino acid having an unsaturated double bond formed between a carbon at position a and a carbon at position β adjacent to the carbon at position a in an amino acid or an analog thereof, as shown in [Formula 21] given below. The unsaturated double bond may be a single isomer in E or Z form or may be a mixture of E and Z forms.

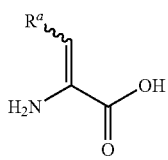

In the formula, Ra is any organic group.

One embodiment of the method for producing a compound library according to the present invention is a method for producing a compound library containing two or more cyclic compounds represented by the formula (I), including:
 a step of producing a mRNA library encoding precursor peptides represented by the formula (III);
 a step of binding puromycin to the 3' end of each mRNA of the mRNA library to produce a puromycin-bound mRNA library;
 a step of expressing the precursor peptides by a cell-free translation system with the puromycin-bound mRNA library to produce a first peptide-mRNA complex library;
 a step of reacting an azole ring-forming enzyme with the first peptide-mRNA complex library, so that an azole ring is formed on at least Y'(11) in the precursor peptides to produce a second peptide-mRNA complex library;
 a step of reacting an α,β-unsaturated amino acid-forming enzyme with the second peptide-mRNA complex library in the presence of cosubstrate tRNA$^{Glu}$ for glutamylation reaction and aminoacylation enzyme GluRS, so that at least X' and Y'(12) in the precursor peptides are converted to α,β-unsaturated amino acid residues to produce a third peptide-mRNA complex library; and
 a step of reacting a macrocyclase with the third peptide-mRNA complex library and forming a nitrogen-containing 6-membered ring while eliminating LP', if present, to form the two or more cyclic compounds represented by the formula (I).

The method for producing a compound library according to the present invention can conveniently produce a compound library of post-translationally modified and macrocyclized compounds without including a step of removing leader peptides, whereas the leader peptides usually need to be removed for in vitro use of enzymes in a post-translational modification reaction step.

In the present specification, the "amino acid" is a proteinogenic amino acid. In the present specification, the "proteinogenic amino acid" means an amino acid constituting a protein (Arg, His, Lys, Asp, Glu, Ser, Thr, Asn, Gln, Cys, Gly, Pro, Ala, Ile, Leu, Met, Phe, Trp, Tyr, and Val). In the present specification, the amino acid is also indicated by a conventional single-letter code or three-letter code.

In the present specification, the "analog of an amino acid" includes a natural or non-natural amino acid other than a proteinogenic amino acid. The natural or non-natural amino acid other than a proteinogenic amino acid is also referred to as a "non-proteinogenic amino acid". Examples of the non-proteinogenic amino acid include, but are not limited to: α,α-disubstituted amino acids (α-methylalanine, etc.), N-alkyl-α-amino acids, D-amino acids, β-amino acids and α-hydroxylic acid, which differ in backbone structure from natural forms; amino acids differing in side chain structure from natural forms (norleucine, homohistidine, etc.); amino acids having extra methylene on a side chain ("homo" amino acids, homophenylalanine, diaminopropionic acid, β-methylcysteine, β-isopropylserine, β-phenylserine, etc.); and amino acids obtained by substituting a carboxylic acid functional group amino acid in a side chain by sulfonic acid (cysteic acid, etc.). In the present specification, the "analog of an amino acid" also encompasses a mutant or a derivative of a proteinogenic amino acid or a non-proteinogenic amino acid and, specifically, also includes derivatives, such as an α,β-unsaturated amino acid and azole, formed from a proteinogenic amino acid or a non-proteinogenic amino acid.

When the peptide according to the present invention contains an α,β-unsaturated amino acid as an amino acid analog, examples of the α,β-unsaturated amino acid as the amino acid analog specifically include analog (I) having the following structure:

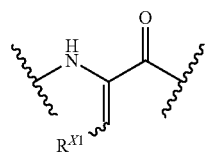

analog (I)

wherein $R^{X1}$ is a hydrogen atom or a hydrocarbon group.

When the peptide according to the present invention contains azole as an amino acid analog, examples of the azole as the amino acid analog specifically include analog (II) having the following structure:

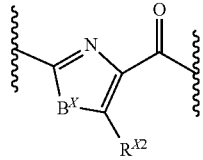

analog (II)

wherein BX is an oxygen atom, a sulfur atom or a NH group, and $R^{X2}$ is a hydrogen atom or a hydrocarbon group.

In the present specification, a chemical structural formula encompasses a tautomer, a geometric isomer, an optical isomer and the like.

Particularly, examples of the analog of Cys include, but are not limited to, an analog represented by a formula given below. Alternatively, the analog of Cys may be analog (I) or analog (II), as mentioned above, derived from the following formula:

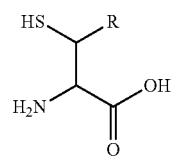

wherein R represents a hydrogen atom, an alkyl group having 1 to 10 carbon atoms and optionally having a substituent, or an aromatic group optionally having a substituent.

Particularly, examples of the analog of Ser or Thr include, but are not limited to, an analog represented by a formula given below. Alternatively, the analog of Ser or Thr may be analog (I) or analog (II), as mentioned above, derived from the following formula:

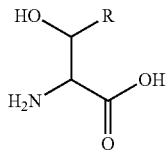

wherein R represents a hydrogen atom, an alkyl group having 1 to 10 carbon atoms and optionally having a substituent, or an aromatic group optionally having a substituent.

Particularly, examples of the analog of diaminopropionic acid (Dap) include, but are not limited to, an analog given below. Alternatively, the analog of diaminopropionic acid may be analog (I) or analog (II), as mentioned above, derived from the following formula:

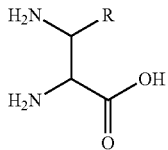

wherein R represents a hydrogen atom, an alkyl group having 1 to 10 carbon atoms and optionally having a substituent, or an aromatic group optionally having a substituent.

In the present specification, examples of the hydrocarbon group preferably include an alkyl group having 1 to 10 carbon atoms and optionally having a substituent, and an aromatic group optionally having a substituent. In the present specification, the hydrocarbon group is preferably an alkyl group having 1 to 6 carbon atoms or a phenyl group optionally having a substituent, more preferably an alkyl group having 1 to 4 carbon atoms or a phenyl group, and further preferably a methyl group.

In the present specification, examples of the substituent include an alkyl group, an aromatic group, a halogen group, an azide group and an amino group. The substituent is preferably an alkyl group having 1 to 4 carbon atoms, and more preferably a methyl group.

The nitrogen-containing 6-membered ring optionally having a substituent in the formula (I) is not particularly limited as long as the nitrogen-containing 6-membered ring results from a reaction between the formula (1) and the formula (2), i.e., 2+4 cycloaddition. Specifically, examples thereof include the following structures:

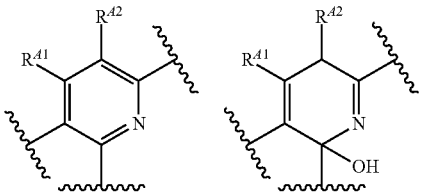

wherein $R^{41}$ and $R^{42}$ are each independently hydrogen or a hydrocarbon group, and each of RAI and $R^{42}$ is preferably a hydrogen or an alkyl group having 1 to 4 carbon atoms, and more preferably a hydrogen or a methyl group.

Each of LP and LP' is also referred to as a leader peptide and represents a peptide consisting of 1 to 100 amino acids and/or analogs thereof. LP and LP' may be present or absent. The presence of LP or LP' tends to facilitate recognizing a precursor peptide by an enzyme such as a macrocyclase, an azole ring-forming enzyme, an α,β-unsaturated amino acid-forming enzyme and the like, so that the reaction proceeds smoothly.

The number of amino acids and/or analogs thereof constituting LP or LP' is preferably 11 or more and 100 or less, more preferably 11 or more and 60 or less, further preferably 16 or more and 45 or less, as to LP, and preferably 11 or more and 100 or less, more preferably 11 or more and 60 or less, further preferably 16 or more and 45 or less, as to LP' for sufficient substrate recognition by a modifying enzyme.

An important leader peptide region for the azole ring-forming enzyme has been revealed in goadsporin, which has a thiopeptide-like modified structure (Ozaki, T. et al. Dissection of goadsporin biosynthesis by in vitro reconstitution leading to designer analogues expressed in vivo. Nat Commun 8, 14207, doi: 10.1038/ncomms14207 (2017).). Table 1 shows results of a leader peptide truncation experiment for biosynthesis of goadsporin.

See FIG. 56 for Table 1.

As shown in the table, leader-truncated precursor peptides obtained by N-terminally truncating a leader peptide region of precursor peptide GodA of goadsporin are used as substrates. For the leader peptide region having 20 residues (LP-20) or more, six azole rings are formed. For the leader peptide region having 15 residues (LP-15), the efficiency of azole ring formation is reduced. Azole ring formation is no longer seen in shorter ones (LP-10 and LP-5).

LP is not particularly limited by its sequence and is preferably a peptide of -(-20th) LSELTVTSLRDTVAL-PENGA (-1st)-(SEQ ID NO: 14) from the −20th to −1st (the −1st amino acid is adjacent to X) amino acids in order from the N terminus with X in the formula (II) defined as position 1, or a peptide having homology with this peptide. For LP, the homology with the peptide of -LSELTVTSLRDTVAL-PENGA-(SEQ ID NO: 14) is preferably 50% or more, more preferably 70% or more, further preferably 90% or more.

LP' is not particularly limited by its sequence and is preferably a peptide of -(-25th) LQDLDLSELTVT-SLRDTVALPENGA (-1st)-(SEQ ID NO: 15) from the −25th to −1st amino acids in order from the N terminus with X in the formula (III) defined as position 1, or a peptide having homology with this peptide. For LP', the homology with the peptide of -LQDLDLSELTVTSLRDTVAL-PENGA-(SEQ ID NO: 15) is preferably 50% or more, more preferably 70% or more, and further preferably 90% or more.

Each of the sequences of LP and LP' is more preferably a peptide of -(-30th) VESLDLQDLDLSELTVT- SLRDTVALPENGA (-1st)-(SEQ ID NO: 16) from the −30th to −1 st amino acids in order from the N terminus with X defined as position 1, or a peptide having homology with this peptide, and further preferably a peptide of -(-38th) MSDITASRVESLDLQDLDLSELTVTSLRDTVAL-PENGA (-1st)-(SEQ ID NO: 17) from the −38th to −1st amino acids in order from the N terminus with X defined as position 1, or a peptide having homology with this peptide. The homology with these peptides is preferably 50% or more, more preferably 70% or more, and further preferably 90% or more.

LP' preferably has a hydrophobic amino acid or a derivative thereof, more preferably leucine or an analog thereof, further preferably leucine, at position −17 with X in the formula (III) defined as position 1.

LP' preferably has a hydrophobic amino acid or a derivative thereof, more preferably leucine or a derivative thereof, further preferably leucine, at position −20 with X in the formula (III) defined as position 1.

LP' preferably has an acidic amino acid or a derivative thereof, more preferably aspartic acid or a derivative thereof, further preferably aspartic acid, at position −21 with X in the formula (III) defined as position 1.

LP' preferably has a hydrophobic amino acid or a derivative thereof, more preferably leucine or a derivative thereof, further preferably leucine, at each of positions −17 and −20 with X in the formula (III) defined as position 1.

LP' preferably has a hydrophobic amino acid or a derivative thereof at each of positions −17 and −20 and an acidic amino acid or a derivative thereof at position −21, more preferably leucine or a derivative thereof at each of positions −17 and −20 and aspartic acid or a derivative thereof at position −21, further preferably leucine at each of positions −17 and −20 and aspartic acid at position −21, with X in the formula (III) defined as position 1.

Z in the formula (I) and the formula (II) or Z' in the formula (III) is present or absent and, when present, represents a peptide consisting of 1 to 100 amino acids and/or analogs thereof.

Each of Z and Z', if present, is not particularly limited by its sequence and types of amino acids and is preferably a peptide consisting of 1 to 100 amino acids and/or analogs thereof, more preferably a peptide consisting of 1 to 50 amino acids and/or analogs thereof, further preferably a peptide consisting of 1 to 40 amino acids and/or analogs thereof, still further preferably a peptide consisting of 3 to 30 amino acids and/or analogs thereof. In Z in the formula (I) and the formula (II) or Z' in the formula (III), the amino acid adjacent to Xc or Y is not particularly limited and is preferably an amino acid other than an acidic amino acid or an analog thereof.

m in the formula (I) and the formula (II) or m' in the formula (III) is an integer selected from 2 to 40, preferably an integer of 2 or larger and 24 or smaller, more preferably an integer of 2 or larger and 20 or smaller, further preferably an integer of 2 or larger and 16 or smaller. When each of m and m' is an integer selected from 2 to 40, cyclization tends to proceed smoothly by the action of macrocyclase.

Y in the formula (I) is a peptide residue consisting of four amino acids and/or analogs thereof and contains a group represented by the formula (2) given below. The group represented by the formula (2) is a residue corresponding to two amino acids and/or analogs thereof in the peptide residue consisting of four amino acids and/or analogs thereof. The peptide residue in Y except for the group represented by the formula (2) is a residue corresponding to any two amino acids and/or analogs thereof.

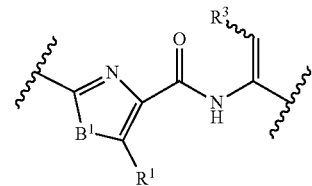

(2)

wherein R' and $R^3$ each represent a hydrogen or a hydrocarbon group, and $B^1$ represents an oxygen atom, a sulfur atom or a NH group.

Y in the formula (I) is a peptide residue consisting of four amino acids and/or analogs thereof and preferably contains a group represented by the following formula (2-1) or formula (2-2):

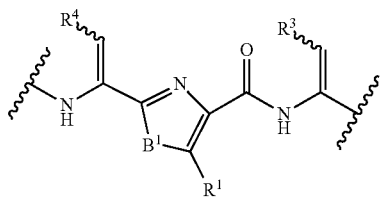

(2-1)

wherein $R^1$, $R^4$ and $R^5$ each represent a hydrogen atom or a hydrocarbon group, and B' represents an oxygen atom, a sulfur atom or a NH group.

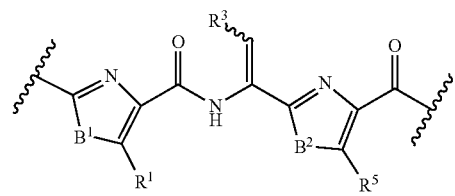

(2-2)

wherein $R^1$, $R^3$ and $R^5$ each represent a hydrogen atom or a hydrocarbon group, and B' and $B^2$ each represent an oxygen atom, a sulfur atom or a NH group.

Y in the formula (I) is preferably a group represented by the following formula (3):

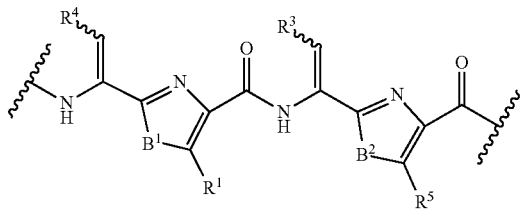

(3)

wherein $R^1$, $R^3$, $R^4$ and $R^5$ each independently represent a hydrogen atom or a hydrocarbon group, and B' and $B^2$ each represent an oxygen atom, a sulfur atom or a NH group.

Y in the formula (I) is more preferably a group represented by the following formula (3'):

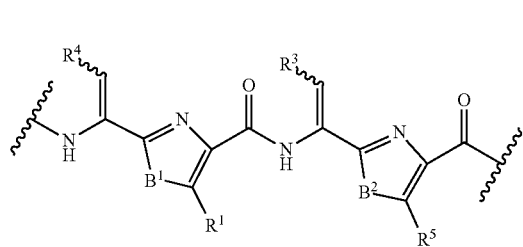

wherein $R^1$, $R^3$, $R^4$ and $R^5$ each independently represent a hydrogen atom or a methyl group, and $B^1$ and $B^2$ each represent an oxygen atom or a sulfur atom, with the proviso that when $B^1$ and/or $B^2$ is a sulfur atom, each of $R^1$ and $R^5$ is a hydrogen.

The group represented by the formula (3) or the formula (3') is preferably represented by the following formula:

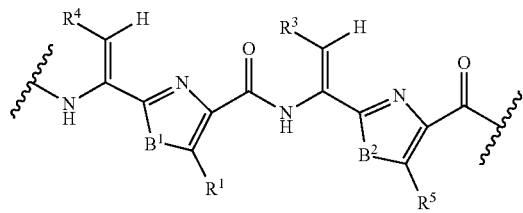

Y in the formula (I) is further preferably a group represented by the following formula (3"):

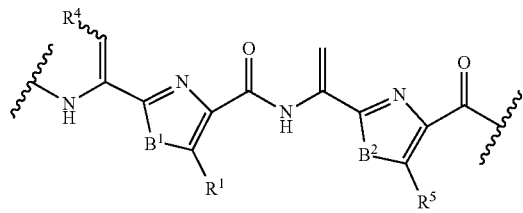

wherein $R^1$, $R^4$ and $R^5$ each independently represent a hydrogen atom or a methyl group, and $B^1$ and $B^2$ each represent an oxygen atom or a sulfur atom, with the proviso that when $B^1$ and/or $B^2$ is a sulfur atom, each of $R^1$ and $R^5$ is a hydrogen.

The group represented by the formula (3") is preferably represented by the following formula:

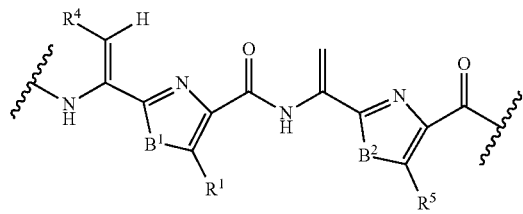

Y in the formula (I) is still further preferably a group represented by the following formula (3-1):

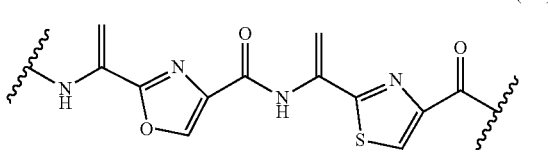

Y' in the formula (III) is a peptide consisting of four amino acids represented by -Y'(10)-Y'(11)-Y'(12)-Y'(13)- and/or analogs thereof, wherein Y'(10) is an amino acid residue selected from the group consisting of any amino acids and analogs thereof, Y'(11) is serine, cysteine, threonine or diaminopropionic acid, or an analog thereof, Y'(12) is serine or threonine, or an analog thereof, and Y'(13) is an amino acid residue selected from the group consisting of any amino acids and analogs thereof.

Y'(11) is preferably serine, cysteine or threonine, or an analog thereof, more preferably serine, cysteine or threonine, further preferably serine.

Y'(12) is preferably serine or threonine or an analog thereof, more preferably serine or an analog thereof, further preferably serine.

Preferably, Y'(11) is serine, cysteine or threonine, or an analog thereof, and Y'(12) is serine or an analog thereof.

Y'(10) is not particularly limited and is preferably serine or threonine, or an analog thereof from the viewpoint of the efficiency of the macrocyclization reaction. Y'(13) is not particularly limited and is preferably serine, cysteine, threonine or diaminopropionic acid, or an analog thereof from the viewpoint of the efficiency of the macrocyclization reaction.

Y'(10) is more preferably serine or threonine, further preferably serine.

Y'(13) is more preferably serine, cysteine or threonine, further preferably cysteine.

Preferably, Y'(10) is serine or threonine or an analog thereof, Y'(11) is serine, cysteine or threonine or an analog thereof, Y'(12) is serine or an analog thereof, and Y'(13) is serine, cysteine, threonine or diaminopropionic acid, or an analog thereof. More preferably, Y'(10) is serine or threonine, or an analog thereof, Y'(11) is serine, cysteine or threonine or an analog thereof, Y'(12) is serine, and Y'(13) is serine, cysteine or threonine, or an analog thereof. Further preferably, Y'(10) is serine, Y'(11) is serine, Y'(12) is serine, and Y'(13) is cysteine.

For $(X_a')$ m' in the formula (III), the efficiency of the enzymatic reaction tends to be reduced when amino acid $X_a'(1)$ is an acidic amino acid or an analog of the acidic amino acid.

Thus, in $(X_a')$ m' in the formula (III), the amino acid residue $X_a'(1)$ adjacent to X' is preferably an amino acid other than an acidic amino acid or an analog thereof.

For $(X_a')$ m' in the formula (III), the efficiency of the enzymatic reaction tends to be reduced when an amino acid residue adjacent to Y'(10) on an N-terminal side, i.e., amino acid residue $X_a'(m')$ at position m', is an acidic amino acid or an analog of the acidic amino acid.

Thus, in $(X_a')$ m' in the formula (III), the amino acid residue $X_a'(m')$ at position m' is preferably an amino acid other than an acidic amino acid or an analog thereof.

For $(X_a')$ m' in the formula (III), the efficiency of the enzymatic reaction tends to be reduced when an amino acid residue adjacent to $X_a'(m')$ described above on an N-terminal side, i.e., amino acid residue $X_a'(m'-1)$ at position m'-1, is an acidic amino acid or an analog of the acidic amino acid, or a basic amino acid or an analog of the basic amino acid.

Thus, in $(X_a')$ m' in the formula (III), the amino acid residue $X_a'(m'-1)$ at position m'-1 is preferably an amino acid other than an acidic amino acid and a basic amino acid or analogs thereof.

An amino acid adjacent to Y'(13) in Z' in the formula (III) is any amino acid or an analog thereof. However, the efficiency of the enzymatic reaction tends to be reduced when this amino acid is an acidic amino acid or an analog of the acidic amino acid.

Thus, the amino acid adjacent to Y'(13) in Z' in the formula (III) is preferably an amino acid other than an acidic amino acid or an analog thereof.

The method for producing a peptide library according to the present invention employs an azole ring-forming enzyme, an α,β-unsaturated amino acid-forming enzyme and macrocyclase.

The azole ring-forming enzyme in the method for producing a peptide library according to the present invention preferably includes LazD, LazE and LazF. An enzyme having homology with each of LazD, LazE and LazF can also be used as the azole ring-forming enzyme.

Examples of the enzyme having homology with each of LazD, LazE and LazF include enzymes shown in Table 2 below. Two or more of these enzymes may be used in combination. The enzyme having homology with each of LazD, LazE and LazF is also referred to as a homolog of LazD, LazE or LazF. The "homolog" means an enzyme that is an enzyme other than LazD, LazE and LazF and that enables a peptide having a formed azole ring to be detected when an similar azole ring formation reaction as described in Examples mentioned later is performed for an arbitrary peptide with the same concentration as that of LazD, LazE or LazF.

The homology of the homologs of LazD, LazE and LazF can be 20% or more with respect to the alignment of LazD, LazE and LazF, respectively. In the present specification, the "enzyme having homology" also includes an enzyme having homology (%) of 20% or more with respect to the alignment of the original enzyme. Found enzymes that can be used similarly to LazD, LazE or LazF on the basis of homology (%) with respect to the alignment of LazD, LazE or LazF are shown in Table 3 (for LazD), Table 4 (for LazE) and Table 5 (for LazF). The enzymes shown in these tables have been found by homology search using BLAST.

In the case of using LazD, LazE and LazF for the azole ring formation according to the present invention, LazD and LazE form azoline, and subsequently, LazF (a domain contained in LazF, close to C-terminal side, involved in azole ring formation) forms azole, thereby constructing an azole ring. The azole ring-forming enzyme according to the present invention is a group including enzymes involved in azoline formation and azole formation.

In this context, each of the homologs of LazD and LazE may be an enzyme containing a domain involved in azoline formation and a domain involved in an additional function together (also referred to as a bi-functional enzyme) or may be two or more separate enzymes each containing a domain involved in azoline formation. LazF contains a C-terminal domain involved in azole formation and an N-terminal domain involved in α,β-unsaturated amino acid formation. Thus, the homolog of LazF as the azole ring-forming enzyme can be an enzyme containing at least a domain involved in azole formation and may be two or more separate enzymes each containing a domain involved in azole formation.

As described above, the azole ring-forming enzyme is not particularly limited as long as the enzyme contains at least domains involved in azoline formation and azole formation. The homolog of LazD, LazE or LazF preferably contains a domain having homology of 80% or more, more preferably homology of 85% or more, further preferably homology of 90% or more, with each of the domains involved in azoline formation and azole formation in LazD, LazE and LazF.

The α,β-unsaturated amino acid-forming enzyme in the method for producing a peptide library according to the present invention preferably includes LazB and LazF. An enzyme having homology with each of LazB and LazF can also be used as the α,β-unsaturated amino acid-forming enzyme.

Examples of the enzyme having homology with each of LazB and LazF include enzymes shown in Table 6 (for LazB) and Table 5B (for LazF) below. Two or more of these enzymes may be used in combination.

The enzyme having homology with each of LazB and LazF is also referred to as a homolog of LazB or LazF. The "homolog" means an enzyme that is an enzyme other than LazB and LazF and that enables a peptide having a formed α,β-unsaturated amino acid to be detected when an similar α,β-unsaturated amino acid formation reaction as described in Examples mentioned later is performed for an arbitrary peptide with the same concentration as that of LazB or LazF.

The homology of the homologs of LazB and LazF can be 20% or more with LazB and LazF, respectively.

In the case of using LazB and LazF for the α,β-unsaturated amino acid formation according to the present invention, LazB performs glutamylation, and subsequently, LazF (a domain of LazF, close to N-terminal side, involved in α,β-unsaturated amino acid formation) causes glutamate elimination, thereby constructing an α,β-unsaturated amino acid. The α,β-unsaturated amino acid-forming enzyme according to the present invention is a group including enzymes involved in glutamylation and glutamate elimination.

In this context, each of the homologs of LazB and LazF may be an enzyme containing a domain involved in glutamylation or glutamate elimination and a domain involved in an additional function together (also referred to as a bi-functional enzyme) or may be two or more separate enzymes each containing a domain involved in glutamylation or glutamate elimination.

As described above, the α,β-unsaturated amino acid-forming enzyme is not particularly limited as long as the enzyme contains at least domains involved in glutamylation and glutamate elimination. The homologs of LazB and LazF preferably contain a domain having homology of 80% or more, more preferably homology of 85% or more, further preferably homology of 90% or more, with the domains involved in glutamylation and glutamate elimination in LazB and LazF, respectively.

The macrocyclase in the method for producing a peptide library according to the present invention preferably includes LazC. An enzyme having homology with LazC can also be used as the macrocyclase.

Examples of the enzyme having homology with LazC include enzymes shown in Table 7. Two or more of these enzymes may be used in combination.

The enzyme having homology with LazC is also referred to as a homolog of LazC. The "homolog" means an enzyme that is an enzyme other than LazC and that enables a peptide having a formed macrocycle to be detected when an similar macrocyclization reaction as described in Examples mentioned later is performed for an arbitrary peptide with the same concentration as that of LazC.

The homology of the homolog of LazC can be 20% or more with LazC.

The macrocyclase is not particularly limited as long as the enzyme contains at least a domain involved in macrocyclization. The homolog of LazC may be an enzyme containing a domain involved in macrocyclization and a domain involved in an additional function together (also referred to as a bi-functional enzyme) or may be two or more separate enzymes each containing a domain involved in macrocyclization. The homolog of LazC preferably contains a domain having homology of 80% or more, more preferably homology of 85% or more, further preferably homology of 90% or more, with the domain involved in macrocyclization in LazC.

In the present specification, the phrase "having homology of Y % or more with the amino acid sequence represented by SEQ ID NO: X" means that when two polypeptides are aligned so as to match their amino acid sequences to the maximum, the ratio of the number of common amino acid residues to the total number of amino acids shown in SEQ ID NO: X is Y % or more.

TABLE 2

| | Name of specific compound to be synthesized | Azoline cyclization (docking) | Azoline cyclization (cyclodehydration) | Azoline oxidation (azole cyclization) | Dehydroalanine formation (glutamic acid addition) | Dehydroalanine formation (glutamate elimination) | Macrocyclization |
|---|---|---|---|---|---|---|---|
| Thipeptide | Lactazole | LazD | LazE | LazF C-ter | LazB | LazF N-ter | LazC |
| | Micrococcin = Thiocillin | TclI | TclJ | TclN | TclK | TclL | TclM |
| | Thiocillin = Micrococcin | TclI | TclJ | TclN | TclK | TclL | TclM |
| | Berninamycin | BerE2 BerG1 | BerE2 BerG2 | BerE1 BerE2 | BerB | BerC | BerD |
| | Thiomuracin | TbtF | TbtG | TbtE | TbtB | TbtC | TbtD |
| | Thiomuracin | TpdF | TpdG | TpdE | TpdB | TpdC | TpdD |
| | GE2270 | PbtF | PbtG | PbtE | PbtB | PbtC | PbtD |
| | GE2270 | TpdF | TpdG | TpdE | TpdB | TpdC | TpdD |
| | Nosiheptide | NosH | NosG | NosF | NosE | NosD | NosO |
| | Thiostrepton | TsrN | TsrO | TsrM | TsrJ TsrS | TsrK | TsrL |
| | Siomycin | SioN | SioO | SioM | SioJ SioS | SioK | SioL |
| | TP-1161 | TpdG | TpaH TpaC TpaD | TpaE TpaF | TpaL | TpaK | TpaB |
| | Thiocillin | TclI | TclJ | TclN | TclK | TclL | TclM |
| | GE37468 | GetH | GetI | GetG GetK | GetD | GetE | GetF |
| | Cyclothiazomycin | CltD | CltB | CltC | CltE | CltF CltG | CltD |
| LAPs | Goadsporin | GodD | GodD | GodE | GodF | GodG | |
| | Plantazolicin | BamC | BamD | BamB | | | |
| cyanobactin | Patellamide | | PatD | PatG | | | |
| | unnamed cyanobactin | | LynD | LynG | | | |
| | Trichamide | | TriD | TriG | | | |
| | Tenuecyclamide | | TenD | TenG | | | |
| | Trunkamide | | TruD | TruG | | | |
| Lantipeptide | Nisin | | | | NisB | NisB | |
| | NAI-107 | | | | MibB | MibB | |

| | Name of specific compound to be synthesized | Producing microbe | Reference |
|---|---|---|---|
| Thipeptide | Lactazole | *Streptomyces lactacystinaeus* OM-6519 | Chem. Biol. 21 (5), 679-688 (2014) |
| | Micrococcin = Thiocillin | *Staphylococcus epidermidis* strain 115 | J. Bacteriol. 2016, 198, 2431-2438 |
| | Thiocillin = Micrococcin | *Bacillus cereus* ATCC 14579 | PNAS, 2009. 106 (8) 2549-2553 |
| | Berninamycin | *Streptomyces bernensis* UC 5144 | PNAS, 2013. 110 (21) 8483-8488 |
| | Thiomuracin | *Thermobispora bispora* DSM 43833 | J Am Chem Soc. 2015 137(51): 16012-16015. |
| | Thiomuracin | *Nonomuraea* Bp3714-39 | J Am Chem Soc. 2009; 131(16): 5946-55. |
| | GE2270 | *Planobispora rosea* ATCC53733 | J Am Chem Soc. 2015 137(51): 16012-16015. |
| | GE2270 | *Nonomuraea* strain WU8817 | J Am Chem Soc. 2009; 131(16): 5946-55. |
| | Nosiheptide | *Streptomyces actuosus* ATCC 25421 | ACS Chem. Biol., 2009, 4 (10), pp 855-864 |
| | Thiostrepton | *Streptomyces laurentii* ATCC 31255 | Chemistry & Biology, 16, 2009, 141-147 |
| | Siomycin | *Streptomyces sioyaensis* ATCC 13989 | Chemistry & Biology, 16, 2009, 141-147 |

TABLE 2-continued

| | | | |
|---|---|---|---|
| | TP-1161 | *Nocardiopsis* sp. TFS65-07 | Appl. Environ. Microbiol. 76 (21), 7093-7101 (2010) |
| | Thiocillin | *Bacillus cereus* ATCC 14579 | PNAS, 2009. 106 (8) 2549-2553 |
| | GE37468 | *Streptomyces* ATCC 55365 | PNAS, 2011. 108 (32) 13053-13058 |
| | Cyclothiazomycin | *Streptomyces hygroscopicus* 10-22 | Appl. Environ. Microbiol. 76 (7), 2335-2344 (2010) |
| LAPs | Goadsporin | *Streptomyces* sp. Tp-A0584 | Microbiology 151, 3923-3933 (2005) |
| | Plantazolicin | *Bacillus methylotrophicus* FZB42 | ACS Chem. Biol., 2016, 11, 2232-2243 |
| cyanobactin | Patellamide | | PNAS, 2005. 102 (20) 7315-7320 |
| | unnamed cyanobactin | | Nat Chem Biol. 2008 June; 4(6): 341-343. |
| | Trichamide | | Nat Chem Biol. 2008 June; 4(6): 341-343. |
| | Tenuecyclamide | | Nat Chem Biol. 2008 June; 4(6): 341-343. |
| | Trunkamide | *Prochloron didemni* | Nat Chem Biol. 2008 June; 4(6): 341-343. |
| Lantipeptide | Nisin | *Lactococcus lactis* 6F3 | Nature 517, 509-512 (2015) |
| | NAI-107 | *Microbispora corallina* | PNAS, 2010. 107 (30) 13461-13466 |

The reaction of the α,β-unsaturated amino acid-forming enzyme with a peptide according to the present invention is performed in the presence of a cosubstrate for glutamylation reaction and aminoacylation enzyme. In this context, the cosubstrate for glutamylation reaction and the aminoacylation enzyme may be derived from a cell-free translation system or may be other than those contained in the cell-free translation system. Specifically, the reaction of the α,β-unsaturated amino acid-forming enzyme with a peptide according to the present invention may be performed using a cosubstrate for glutamylation reaction and aminoacylation enzyme in a cell-free translation system when the cell-free translation system contains them, and may be performed in the presence of a cosubstrate for glutamylation reaction and/or aminoacylation enzyme that is not contained in the cell-free translation system, by separately adding them. Whether to use a cosubstrate and aminoacylation enzyme contained in a cell-free translation system or to use a cosubstrate and aminoacylation enzyme other than the cell-free translation system can be appropriately selected according to the type of the α,β-unsaturated amino acid-forming enzyme used, etc.

From homology information on amino acid sequences by HHpred, LazB has exhibited 13% identity to an N-terminal region of biosynthetic enzyme NisB for class I lantipeptide Nisin carried by *Lactococcus lactis*. NisB catalyzes the formation of an α,β-unsaturated amino acid such as dehydroalanine or dehydrobutyrine by the dehydration of Ser or Thr in Nisin biosynthesis.

For RiPPs compounds, it has been reported that the α,β-unsaturated amino acid such as dehydroalanine or dehydrobutyrine is formed through the dehydration reaction of Ser or Thr. The Ser or Thr dehydration mechanism is reportedly divided broadly into two different mechanisms. One of them is a tRNA-dependent dehydration mechanism seen in thiopeptides or class I lantipeptides, and the other one is an ATP-dependent dehydration mechanism seen in class II to IV lantipeptides.

The tRNA-type dehydration mechanism has been revealed for NisB. As shown below, a dehydroamino acid is formed by glutamylation which adds a glutamic acid aminoacylated to glutamyl-tRNA to a hydroxy group, and elimination of the glutamic acid.

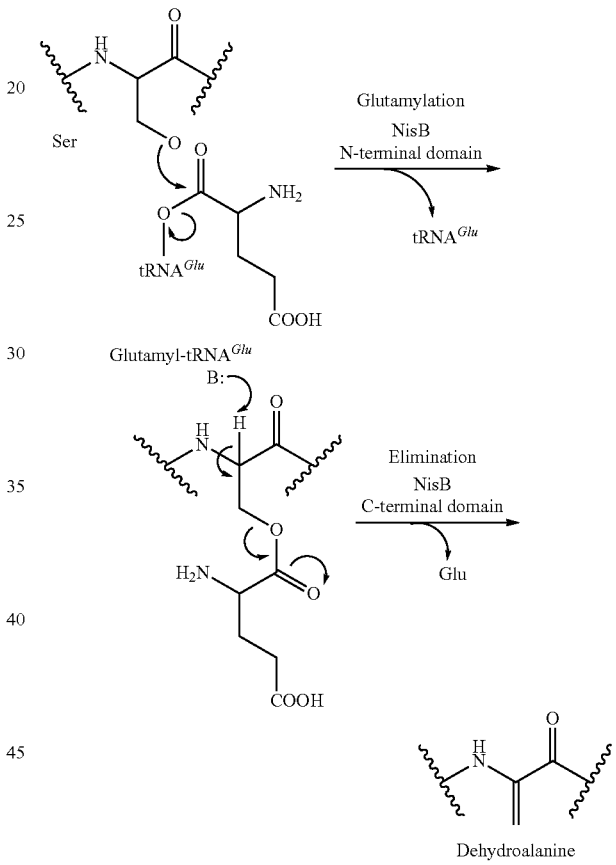

It is known that the α,β-unsaturated amino acid formation of other thiopeptides is based on the tRNA-type dehydration mechanism (Nature Volume 517, pages 509-512, (2015)). Since LazB has high homology with an N-terminal region of NisB, LazB presumably catalyzes glutamylation reaction using glutamyl-tRNA$^{Glu}$.

Thus, in the present invention, glutamyl-tRNA$^{Glu}$ is used as a cosubstrate for reaction in the formation of an α,β-unsaturated amino acid. In the present invention, particularly, when LazB and LazF, and/or enzymes having homology with them are used as the α,β-unsaturated amino acid-forming enzyme, tRNA$^{Glu}$ is not particularly limited as long as the tRNA$^{Glu}$ is at least accepted by the α,β-unsaturated amino acid-forming enzyme. From the viewpoint that the reaction proceeds efficiently, it is preferred to use actinomycete-derived tRNA$^{Glu}$ and/or *E. coli*-derived tRNA$^{Glu}$, and it is more preferred to use tRNA$^{Glu}$ derived from an actinomycete *Streptomyces* lactacystinaeus which is a lactazole-producing microbe and/or tRNA$^{Glu}$ derived from *Streptomyces lividans* which is used as a host heterologously expressing lactazole.

Also, aminoacylation enzyme GluRS is used for forming glutamyl-tRNA$^{Glu}$ from tRNA$^{Glu}$. Particularly, when LazB and LazF, and/or enzymes having homology with them are used as the α,β-unsaturated amino acid-forming enzyme, GluRS is not particularly limited as long as the tRNA$^{Glu}$ used is glutamylated. Actinomycete-derived GluRS and/or *E. coli*-derived GluRS is preferred, and GluRS derived from an actinomycete *Streptomyces* lactacystinaeus which is a lactazole-producing microbe and/or GluRS derived from *Streptomyces lividans* which is used as a host heterologously expressing lactazole is more preferred. The actinomycete-derived GluRS may be GluRS extracted from the actinomycete or may be obtained as a recombinant protein of GluRS within the actinomycete genome. The *E. coli*-derived GluRS may be GluRS extracted from *E. coli* or may be obtained as a recombinant protein of GluRS from the *E. coli* genome.

The peptide represented by the formula (II) may be prepared, for example, from a precursor peptide represented by the formula (III) by the action of the azole ring-forming enzyme, the α,β-unsaturated amino acid-forming enzyme and the macrocyclase, or may be prepared by an organic chemical approach known in the art with a precursor peptide represented by the formula (III) as a starting material. Alternatively, the peptide represented by the formula (II) may be prepared in accordance with a peptide synthesis method known in the art, for example, an organic chemical approach described in J. Am. Chem. Soc 2015, 137, 3494-3497, and J. Am. Chem. Soc. 2016, 138, 13461-13464.

Specifically, the peptide represented by the formula (II) can be obtained, for example, by allowing a general acid or base catalyst to act on the precursor peptide represented by the formula (III) so that a carbonyl group and a hydroxy group or a thiol group in the peptide are intramolecularly dehydrated and condensed to form an azole ring, then converting a hydroxy group in the peptide to a leaving group, and allowing a general base to act on the resultant to form an α,β-unsaturated amino acid. Alternatively, the precursor peptide represented by the formula (III) may be prepared using amino acids having a selenium atom at position y, such as selenocysteine, phenylselenocysteine and selenolysine, and induced into selenoxide by treatment with an oxidizing agent such as hydrogen peroxide, followed by β elimination to form an α,β-unsaturated amino acid.

In the present specification, the "cell-free translation system" refers to a translation system involving no cell. For example, *E. coli* extracts, wheat germ extracts, rabbit erythrocyte extracts or insect cell extracts can be used as the cell-free translation system. Alternatively, a reconstituted cell-free translation system may be used, which is constructed by reconstituting a ribosomal protein, aminoacyl-tRNA synthetase (aaRS), ribosomal RNA, amino acid, rRNA, GTP, ATP, translation initiation factor (IF) elongation factor (EF), release factor (RF) and ribosome recycling factor (RRF), respectively purified, and other factors necessary for translation.

The system may contain RNA polymerase in order to also perform transcription from DNA. A commercially available cell-free translation system can be used, for example, RTS-100 (registered trademark) from Roche Diagnostics K.K. as an *E. coli*-derived system, PURESYSTEM (registered trademark) from Post Genome Institute (PGI) and PURExpressR In Vitro Protein Synthesis Kit from New England BioLabs Inc. as a reconstituted translation system, and a system using wheat germ extracts from ZOEGENE Corp. or CellFree Sciences Co., Ltd.

For example, techniques described in the following documents are known in the art as systems using *E. coli* ribosome: H. F. Kung et al., 1977. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

According to the cell-free translation system, an expression product can be obtained with high purity without being purified.

The cell-free translation system of the present invention may be supplemented with factors necessary for transcription and thereby used not only in translation but in transcription.

One aspect of the present invention is a compound library containing two or more cyclic compounds represented by the formula (I), wherein at least one of the cyclic compounds represented by the formula (I) is in a non-natural form.

The non-natural form refers to a form structurally differing from naturally occurring lactazole or the like.

One aspect of the present invention is a screening method for identifying a cyclic compound represented by the formula (I) which binds to a target substance, including: a step of contacting a compound library produced by the production method of the present invention or the compound library of the present invention with the target substance, followed by incubation; and a step of selecting a cyclic compound represented by the formula (I) bound with the target substance.

One aspect of the present invention is a screening kit for identifying a cyclic compound represented by the formula (I) which binds to a target substance, containing a compound library produced by the production method of the present invention or the compound library of the present invention.

One aspect of the present invention is a method for producing a cyclic compound represented by the formula (I), including a step of allowing a macrocyclase in vitro to act on a peptide represented by the formula (II) and forming the nitrogen-containing 6-membered ring A while eliminating LP to form the cyclic compound represented by the formula (I).

One aspect of the present invention is a method for producing a cyclic compound represented by the formula (I), including: a step of producing mRNA encoding a precursor peptide represented by the formula (III); a step of expressing the precursor peptide by a cell-free translation system using the mRNA to produce a first peptide; a step of reacting an azole ring-forming enzyme with the first peptide, so that an azole ring is formed on at least Y'(11) in the precursor peptide to produce a second peptide; a step of reacting an α,β-unsaturated amino acid-forming enzyme with the second peptide in the presence of cosubstrate tRNA$^{Glu}$ for glutamylation reaction and aminoacylation enzyme GluRS, so that at least X' and Y'(12) in the precursor peptide are converted to α,β-unsaturated amino acid residues to produce a third peptide; and a step of reacting a macrocyclase with the third peptide and forming a nitrogen-containing 6-membered ring while eliminating LP to form a cyclic compound represented by the formula (I).

When the method for producing a compound library and the method for producing a cyclic compound according to the present invention include steps of producing a first peptide library or a first peptide, producing a second peptide library or a second peptide, producing a third peptide library or a third peptide and producing a cyclic compound, these steps also encompass an embodiment in which the reactions are performed at once by adding enzymes or cosubstrates to one system, i.e., an embodiment in which these production steps proceed in a series of reactions in the system, and also encompass an embodiment in which the reactions are performed stepwise by adding and reacting enzymes in order.

Specific embodiments encompassed by the method for producing a compound library and the method for producing a cyclic compound according to the present invention include:

an embodiment which includes first adding an azole ring-forming enzyme to a system containing precursor peptides or a puromycin-bound mRNA library, followed by reaction, next adding an α,β-unsaturated amino acid-forming enzyme, optionally with cosubstrate tRNA$^{Glu}$ for glutamylation reaction and/or aminoacylation enzyme GluRS, followed by reaction, and further adding a macrocyclase, followed by reaction (pattern I);

an embodiment which includes first adding cosubstrate tRNA$^{Glu}$ for glutamylation reaction and/or aminoacylation enzyme GluRS, if necessary, to a system containing precursor peptides or a puromycin-bound mRNA library, adding an azole ring-forming enzyme and an α,β-unsaturated amino acid-forming enzyme, followed by reaction, and next adding a macrocyclase, followed by reaction (pattern II);

an embodiment which includes first adding an azole ring-forming enzyme to a system containing precursor peptides or a puromycin-bound mRNA library, followed by reaction, next adding cosubstrate tRNA$^{Glu}$ for glutamylation reaction and/or aminoacylation enzyme GluRS, if necessary, adding an α,β-unsaturated amino acid-forming enzyme and macrocyclase, followed by reaction (pattern III); and an embodiment which includes first adding cosubstrate tRNA$^{Glu}$ for glutamylation reaction and/or aminoacylation enzyme GluRS, if necessary, to a system containing precursor peptides or a puromycin-bound mRNA library, and adding an azole ring-forming enzyme, an α,β-unsaturated amino acid-forming enzyme and a macrocyclase, followed by reaction (pattern IV).

EXAMPLES

<Synthesis of Precursor Peptide>

In order to reconstruct lactazole biosynthesis in vitro, a precursor peptide was prepared using a cell-free translation system. It is considered that C-terminal several amino acids of LazA are cleaved by cellular endogenous protease. Accordingly, LazA* tailored to a purified product of lactazole A was synthesized by truncating C-terminal three residues (QDM). The sequences of LazA and LazA* are shown in FIG. 1.

(Preparation of DNA Template)

In order to synthesize the precursor peptide using a cell-free translation system, a DNA template was first prepared.

An attempt was made to prepare a DNA template containing a nucleotide sequence encoding the precursor peptide LazA as well as a T7 promoter sequence, a SD sequence and a ribosomal binding sequence. For the promoter sequence, the SD sequence and the ribosomal binding sequence, a DNA template used in a FIT-GS system (goadsporin) was referred to (Ozaki, T. et al. Dissection of goadsporin biosynthesis by in vitro reconstitution leading to designer analogues expressed in vivo. Nat Commun 8, 14207, doi: 10.1038/ncomms14207 (2017).). FIG. 2 shows a schematic view of the laz.A DNA template.

The nucleotide sequence encoding the precursor peptide needed to be changed from actinomycete-type codons into *E. coli* type so that the cell-free translation system can utilize *E. coli*-derived RNA polymerase or ribosome. Hence, the DNA template was designed so as to optimize the nucleotide sequence on the basis of the usage frequency of *E. coli* codon as shown in Table 8. The designed nucleotide sequence encoding the precursor peptide is shown in FIG. 3.

TABLE 8

| Usage frequency of *E. coli* codon | | | | | |
|---|---|---|---|---|---|
| Order of precedence | 1 | 2 | 3 | 4 | 5 |
| Ala | GCA | GCT |  | GCG |  |
| Cys | TGT |  | TGC |  |  |
| Asp | GAC | GAT |  |  |  |
| Glu | GAA |  | GAG |  |  |
| Phe | TTT | TTC |  |  |  |
| Gly | GGT |  | GGC | GGG |  |
| His | CAT |  | CAC |  |  |
| Ile | ATT |  | ATC |  |  |
| Lys | AAG | AAA |  |  |  |
| Leu | CTG | TTA | CTT |  | TTG |
| Met | ATG |  |  |  |  |
| Asn | AAT |  | AAC |  |  |
| Pro | CCG | CCA | CCT |  |  |
| Gln | CAA | CAG |  |  |  |
| Arg | CGT |  | CGC |  |  |
| Ser | TCT | TCA | AGC |  | AGT |
| Thr | ACC | ACT |  | ACG | ACA |
| Val | GTT | GTG |  | GTA |  |
| Trp | TGG |  |  |  |  |
| Tyr | TAT | TAC |  |  |  |

Subsequently, the preparation of the designed DNA template was attempted. Since the nucleotide sequence of the DNA template was 214 base pairs, the DNA template was prepared by primer extension and PCR using six primers. FIG. 4 shows a schematic view of the primer extension. Tables 9 to 15 show the reaction composition and reaction conditions of the primer extension system, and the reaction composition and reaction conditions of the PCR system.

The prepared DNA template was confirmed by electrophoresis to have base pairs having the length of interest. The DNA template having the confirmed length was purified using FastGene/PCR Extraction Kit (Nippon Genetics Co., Ltd.) and eluted with 20 ul of MilliQ water.

TABLE 9

| Primer extension reaction composition | |
|---|---|
| KOD-Plus-neo (Toyobo Co., Ltd.) | 2.0 (μl) |
| 10 × KOD-Plus-neo Buffer | 10 |
| 2 mM dNTPs | 10 |
| 25 mM MgSO$_4$ | 6.0 |

TABLE 9-continued

Primer extension reaction composition

| | |
|---|---|
| 50 μM F1 primer | 2.0 |
| 50 μM R1 primer | 2.0 |
| MilliQ water | 68 |
| Total | 100 μl |

TABLE 10

Primer extension reaction conditions

| | |
|---|---|
| 94° C. | 1.0 min |
| 50° C. | 1.0 min ⎤ |
| 50° C. | 1.0 min ⎦ 5 cycles |

TABLE 11

1st PCR reaction composition

| | |
|---|---|
| KOD-Plus-neo | 2.0 (μl) |
| 10 × KOD-Plus-neo Buffer | 10 |
| 2 mM dNTPs | 10 |
| 25 mM MgSO$_4$ | 6.0 |
| 50 μM F2 primer | 1.0 |
| 50 μM R2 primer | 1.0 |
| MilliQ water | 65 |
| Extension product | 5.0 |
| Total | 100 μl |

TABLE 12

2nd PCR reaction composition

| | |
|---|---|
| KOD-Plus-neo | 2.0 (μl) |
| 10 × KOD-Plus-neo Buffer | 10 |
| 2 mM dNTPs | 10 |
| 25 mM MgSO$_4$ | 6.0 |
| 50 μM F2 primer | 1.0 |
| 50 μM R3 primer | 1.0 |
| MilliQ water | 69.5 |
| 1st PCR product | 0.5 |
| Total | 100 μl |

TABLE 13

3rd PCR reaction composition

| | |
|---|---|
| KOD-Plus-neo | 2.0 (μl) |
| 10 × KOD-Plus-neo Buffer | 10 |
| 2 mM dNTPs | 10 |
| 25 mM MgSO$_4$ | 6.0 |
| 50 μM F2 primer | 1.0 |
| 50 μM R4 primer | 1.0 |
| MilliQ water | 69.5 |
| 2nd PCR product | 0.5 |
| Total | 100 μl |

TABLE 14

1st PCR and 2nd PCR reaction conditions

| | | |
|---|---|---|
| 94° C. | 40 min | ⎤ |
| 50° C. | 40 min | ⎬ 5 cycles |
| 68° C. | 40 min | ⎦ |

TABLE 15

3rd PCR reaction conditions

| | | |
|---|---|---|
| 94° C. | 40 min | ⎤ |
| 50° C. | 40 min | ⎬ 14 cycles |
| 68° C. | 40 min | ⎦ |

(Translation Reaction in Cell-Free Translation System)

Next, translation reaction was performed in a cell-free translation system with the DNA template prepared in the preceding section (Preparation of DNA template) to prepare precursor peptide LazA.

The cell-free translation system used in this experiment was the one prepared by the Suga Laboratory of Department of Chemistry, School of Science, The University of Tokyo. The preparation of the cell-free translation system is described in Goto, Y., Katoh, T. & Suga, H. Flexizymes for genetic code reprogramming. Nat Protoc 6, 779-790, (2011). E. coli A19-derived ribosome, translation elongation factors (IF1, IF2, and IF3), translation elongation factors (EF-G, EF-Tu, and EF-Ts), translation release factors (RF2, RF3, and RRF), aminoacyl-tRNA synthetase, methionyl-tRNA formyltransferase, T7 RNA polymerase, creatine kinase, myokinase, inorganic pyrophosphatase and nucleoside diphosphate kinase were used as constituent proteins of the cell-free translation system.

The cell-free translation system employed two divided solutions, Solution A containing cofactors, etc. and Solution B containing proteins, preserved at −80° C. The composition of the Solution A and the Solution B used is as described in Nature Protocols, 2011. The N-terminal amino acid of the peptide to be synthesized becomes formylmethionine by the action of the methionyl-tRNA formyltransferase.

In vitro translation reaction was performed using the cell-free translation system with the prepared DNA template. The composition of the in vitro translation system is shown in Table 16. The reaction was performed by incubation at 37° C. for 30 minutes using a vapor-phase incubator.

After the in vitro translation reaction, desalting operation was performed using zip tip C18. Subsequently, the desalted translated peptide was analyzed by MALDI-TOFMS using sinapic acid as a matrix. As a result of the analysis by MALDI-TOF MS, a peak was observed at $[M+H]^+$5672.4 (calculated value is $[M+H]^+$5672.6), confirming that the precursor peptide LazA* of interest was able to be synthesized.

TABLE 16

Reaction conditions

| | |
|---|---|
| Solution A version 7S | 0.273 μl |
| Solution B version10.1 | 0.320 μl |

TABLE 16-continued

| Reaction conditions | |
| --- | --- |
| DNA template | 0.25 μl |
| 5 mM mixed solution of 20 amino acids | 0.25 μl |
| MilliQ | 1.407 μl |
| Total | 2.5 μl |

<Preparation of LazB, LazC, LazD, LazE, LazF, Cosubstrate and GluRS>

The enzymes used in the production of libraries were prepared as follows.
(Preparation of LazB)

lazB-opt/pET26b was transferred to *E. coli* BL21 (DE3) for protein expression by heat shock method to obtain transformants. One colony thereof was precultured at 37° C. for 16 hours using 6 ml of LB medium. 4 ml of the resulting cultures was inoculated to 200 ml of ZYM-5052 medium. Subsequently, main culture was performed at 180 rpm at 18° C. for 20 hours. The bacterial cells thus cultured were centrifuged at 4720×g for 10 minutes for harvest and then stored at −80° C. For the extraction of the recombinant protein, the bacterial cells were suspended in 50 mM Tris-HCl pH 8.0, 500 mM NaCl and 10 mM imidazole pH 8.0. The suspended bacterial cells were ultrasonically disrupted, and the suspension was centrifuged at 10300×g at 4° C. for 30 minutes. From the obtained supernatant, the protein was subjected to His-tag-purification using Bio-Scale TM Mini Profinity TM IMAC cartridge (Bio-Rad Laboratories, Inc.). The cartridge was washed with the same buffer as used in the suspension, followed by elution with a buffer having an imidazole concentration elevated to 200 mM. The elution fraction was desalted with Bio-Gel P-6 desalting cartridge (Bio-Rad Laboratories, Inc.). The buffer was replaced with 25 mM HEPES pH 8.0, 500 mM NaCl and 5% glycerol. The LazB purification fraction was subjected to polyacrylamide gel electrophoresis (SDS-PAGE). As a result, a band corresponding to His-Tag-bound LazB was observed at a molecular weight of approximately 96 kDa, confirming that the protein of interest was correctly obtained. The concentration calculated from absorbance at UV 280 nm was 17.9 μM (approximately 1.7 mg/ml).

(Preparation of LazC)

lazC-opt/pET26b was transferred to *E. coli* BL21 (DE3) for protein expression by heat shock method to obtain transformants. One colony thereof was precultured at 37° C. for 16 hours using 6 ml of LB medium. 4 ml of the resulting cultures was inoculated to 200 ml of ZYM-5052 medium. Subsequently, main culture was performed at 180 rpm at 18° C. for 20 hours. The bacterial cells thus cultured were purified and desalted in the same manner as in LazB. The buffer was replaced with 25 mM HEPES pH 6.8 and 500 mM NaCl. The LazC purification fraction was subjected to SDS-PAGE. As a result, a band corresponding to His-Tag-bound LazC was observed at a molecular weight of approximately 45 kDa, confirming that the protein of interest was correctly obtained. The concentration calculated from absorbance at UV 280 nm was 23.0 μM (approximately 1.0 mg/ml).

(Preparation of LazD)

Although coexpression with pET26b vector, pET16 vector and chaperon, etc. was attempted for the purification of LazD, no solubilized protein was obtained in any of the cases due to low expression levels and insolubilization. Accordingly, pCold vector of a cold-shock expression system was attempted.

lazD-opt/pColdII was transferred to *E. coli* BL21 (DE3) for protein expression by heat shock method to obtain transformants. One colony thereof was precultured at 37° C. for 16 hours using 20 ml of LB medium. 16 ml of the resulting cultures was inoculated to 800 ml of LB medium. Subsequently, the bacterial cells were cultured at 150 rpm at 37° C. for 2 hours and then cooled in ice. IPTG was added thereto with a final concentration of 0.1 mM, and the bacterial cells were cultured at 180 rpm at 15° C. for 18 hours. The bacterial cells thus cultured were centrifuged at 4720×g for 10 minutes for harvest and then immediately suspended in 50 mM Tris-HCl pH 8.0, 500 mM NaCl, 10 mM imidazole pH 8.0 and 2 mM DTT. The suspended bacterial cells were ultrasonically disrupted, and the suspension was centrifuged at 10300×g at 4° C. for 30 minutes. From the obtained supernatant, the protein was subjected to His-tag-purification using Bio-Scale TM Mini Profinity TM IMAC cartridge. The cartridge was washed with the same buffer as used in the suspension, followed by elution with a buffer having an imidazole concentration elevated to 200 mM. The elution fraction was desalted with Bio-Gel P-6 desalting cartridge. The buffer was replaced with 25 mM HEPES pH 8.0, 500 mM NaCl and 2 mM DTT. The LazD purification fraction was subjected to SDS-PAGE. As a result, a band corresponding to His-Tag-bound LazD was observed at a molecular weight of approximately 58 kDa, confirming that the protein of interest was correctly obtained. The fraction was concentrated approximately 4-fold by ultrafiltration using a 30 kDa ultrafiltration membrane. The concentration of the concentrated fraction calculated from absorbance at UV 280 nm was 41.7 μM (approximately 2.4 mg/ml).

(Preparation of LazE)

Although coexpression with pET26b vector, pET16 vector and chaperon, etc. was attempted for the expression and purification of LazE, as with LazD, no solubilized protein was obtained in any of the cases due to low expression levels and insolubilization. Accordingly, the pCold vector of a cold-shock expression system was attempted.

lazE-opt/pColdII was transferred to *E. coli* BL21 (DE3) for protein expression by heat shock method to obtain transformants. One colony thereof was precultured at 37° C. for 16 hours using 20 ml of LB medium. 16 ml of the resulting cultures was inoculated to 800 ml of LB medium. Subsequently, the bacterial cells were cultured at 150 rpm at 37° C. for 2 hours and then cooled in icc. IPTG was added thereto with a final concentration of 0.1 mM, and the bacterial cells were cultured at 180 rpm at 15° C. for 18 hours. The bacterial cells thus cultured were purified and desalted in the same manner as in LazD. The LazE purification fraction was subjected to SDS-PAGE. As a result, a band corresponding to His-Tag-bound LazE was observed at a molecular weight of approximately 74 kDa, confirming that the protein of interest was correctly obtained. The fraction was concentrated approximately 7-fold by ultrafiltration using a 30 kDa ultrafiltration membrane. The concentration of the concentrated fraction calculated from absorbance at UV 280 nm was 22.6 μM (approximately 1.7 mg/ml).

(Preparation of LazF)

lazF-opt/pET26b was transferred to *E. coli* BL21 (DE3) for protein expression by heat shock method to obtain transformants. One colony thereof was precultured at 37° C. for 16 hours using 6 ml of LB medium. 4 ml of the resulting cultures was inoculated to 200 ml of ZYM-5052 medium. Subsequently, main culture was performed at 180 rpm at 18° C. for 20 hours. The bacterial cells thus cultured were purified and desalted in the same manner as in LazB. The buffer was replaced with 25 mM HEPES pH 6.8 and 500 mM NaCl. The LazF purification fraction was subjected to SDS-PAGE. As a result, a band corresponding to His-Tag-bound LazF was observed at a molecular weight of approximately 61 kDa, confirming that the protein of interest was correctly obtained. The purified LazF assumed yellow color which indicated that LazF was bound with flavin. Yamashita et al. have revealed that FMN is noncovalently bound with LazF (Ozaki, T. et al. Dissection of goadsporin biosynthesis by in vitro reconstitution leading to designer analogues expressed in vivo. Nat Commun 8, 14207, (2017).). The concentration of LazF calculated by the Bradford method was 32.9 UM (approximately 2.0 mg/ml).

(Preparation of Cosubstrate)

$tRNA^{Glu}$ derived from Lactazole-producing microbe, which serves as a cosubstrate for glutamylation reaction mediated by LazB was prepared by in vitro transcription.

(1) Synthesis of DNA Template

First, a $tRNA^{Glu}$ sequence was found from the genome of an actinomycete Streptomyces lactacystinaeus, which is a lactazole-producing microbe. Four copies of $tRNA^{Glu}$ were encoded in the genome of S. lactacystinaeus. Three of these copies were $tRNA^{Glu}$ (CUC) having completely the same nucleotide sequence, and the other copy was $tRNA^{Glu}$ (UUC). FIG. 5 shows the alignment of the $tRNA^{Glu}$ nucleotide sequences of E. coli and the producing microbe. As shown in FIG. 5, $tRNA^{Glu}$ having the anticodon UUC had CA as the 72nd and 73rd bases, and $tRNA^{Glu}$ having the anticodon CUC had UA as the 72nd and 73rd bases.

The two types of $tRNA^{Glu}$ were prepared, and DNA templates of the two $tRNA^{Glu}$ (CUC and UUC) were each prepared (see FIG. 6). The synthesis of the DNA templates was performed by the same operation as in the DNA template synthesis for the precursor peptide. Tables 17 to 22 show the reaction composition and reaction conditions of the primer extension system, and the reaction composition and reaction conditions of the PCR system.

2 μl of the 2nd PCR products were electrophoresed to confirm that DNA templates having the length of interest were amplified. The 2nd PCR products confirmed to be amplified were subjected to phenol-chloroform extraction to remove proteins. Finally, pellets obtained by ethanol precipitation were dissolved in 400 μl of MilliQ water.

TABLE 17

Primer extension reaction composition

| | |
|---|---|
| Taq DNA polymerase | 0.75 (μl) |
| 10 × PCR Buffer | 10 |
| 5 mM dNTPs | 5 |
| 250 mM $MgCl_2$ | 1.0 |
| 200 μM F1 primer | 0.5 |
| 200 μM R1 primer | 0.5 |
| MilliQ water | 82.25 |
| Total | 100 μl |

TABLE 18

Primer extension reaction conditions

| | | |
|---|---|---|
| 94° C. | | 1.0 min |
| 50° C. | 5 cycles | 1.0 min |
| 68° C. | | 1.0 min |

TABLE 19

1st PCR reaction composition

| | |
|---|---|
| Taq DNA polymerase | 0.75 (μl) |
| 10 × PCR Buffer | 10 |
| 5 mM dNTPs | 5 |
| 250 mM $MgCl_2$ | 1.0 |
| 200 μM F2 primer | 0.5 |
| 200 μM R2 primer | 0.5 |
| MilliQ water | 81.75 |
| Extension product | 0.5 |
| Total | 100 μl |

TABLE 20

1st PCR reaction conditions

| | | |
|---|---|---|
| 94° C. | | 40 min |
| 50° C. | 5 cycles | 40 min |
| 68° C. | | 40 min |

TABLE 21

2nd PCR reaction composition

| | |
|---|---|
| Taq DNA polymerase | 30.0 (μl) |
| 10 × PCR Buffer | 400 |
| 5 mM dNTPs | 200 |
| 250 mM $MgCl_2$ | 40.0 |
| 50 μM F2 primer | 40.0 |
| 50 μM R3 primer | 40.0 |
| 1st PCR product | 20.0 |
| MilliQ water | 3230 |
| Total | 4000 μl |

TABLE 22

2nd PCR reaction conditions

| | | |
|---|---|---|
| 94° C. | | 40 min |
| 50° C. | 14 cycles | 40 min |
| 68° C. | | 40 min |

(2) In Vitro Transcription Reaction

In vitro transcription reaction was performed under the reaction conditions of Table 23 below with the synthesized DNA templates. The transcription reaction was performed by incubation at 37° C. for 20 hours.

After the completion of the in vitro transcription reaction, the template DNAs were degraded by DNase treatment. Then, proteins were removed by isopropanol precipitation. Pellets obtained by the isopropanol precipitation were dissolved in 400 µl of MilliQ and purified using a modified gel. The RNA solutions thus gel-purified were subjected to ethanol precipitation again. Then, these solutions were adjusted so as to attain 250 µM solutions while the concentration was measured using Nanodrop, which were then stored at −80° C.

TABLE 23

| In vitro transcription reaction composition | |
|---|---|
| T7 RNA polymerase | 80.0 (µl) |
| 10 × T7 Buffer | 400 |
| 25 mM NTPs | 600 |
| 250 mM MgCl$_2$ | 360 |
| 100 mM DTT | 400 |
| 2M KOH (well mixed after addition) | 45.0 |
| 100 mMGMP | 200 |
| 2nd PCR product | 400 |
| MilliQ water | 1515 |
| Total | 4000 µl |

(Preparation of GluRS)

Aminoacylation enzyme GluRS aminoacylates tRNA$^{Glu}$ with glutamic acid, as shown in FIG. 57. Actinomycete-type GluRS was obtained as a recombinant protein.

Since neither a strain nor genomic DNA of the lactazole-producing microbe S. lactacystinaeus was obtained, GluRS within the genome of S. lividans used as a host heterologously expressing lactazole was obtained as a recombinant protein (Hayashi, S. et al. Genome mining reveals a minimum gene set for the biosynthesis of 32-membered macrocyclic thiopeptides lactazoles. Chem Biol 21, 679-688, (2014).).

Specifically, a gluRS region was first amplified by PCR using primers gluRS-Fw-Ndel and gluRS-Rv-Xhol with S. lividans genome extracts as a template. The amplified fragment was cloned into pET26b vector through Ndel and Xhol to obtain gluRS/pET26b.

Next, gluRS/pET26b was transferred to E. coli BL21 (DE3) for protein expression by heat shock method to obtain transformants. One colony thereof was precultured at 37° C. for 16 hours using 6 ml of LB medium. 4 ml of the resulting cultures was inoculated to 200 ml of LB medium. Subsequently, the bacterial cells were shake-cultured at 150 rpm at 37° C. for 2 hours and then cooled in ice. IPTG was added thereto with a final concentration of 0.1 mM, and the bacterial cells were shake-cultured at 180 rpm at 18° C. for 20 hours. The bacterial cells thus cultured were centrifuged at 4720×g for 10 minutes for harvest and then stored at −80° C. For the extraction of a recombinant protein, the bacterial cells were suspended in 50 mM Tris-HCl pH 8.0, 300 mM NaCl and 20 mM imidazole pH 8.0. The suspended bacterial cells were ultrasonically disrupted, and the suspension was centrifuged at 10300×g at 4° C. for 30 minutes. From the obtained supernatant, the protein was subjected to His-tag-purification using Ni-NTA. The column was washed with the same buffer as used in the suspension, followed by elution with a buffer having an imidazole concentration elevated to 200 mM. The elution solution was dialyzed overnight against Tris-HCl pH 7.5. The actinomycete-type GluRS thus His-tag-purified was subjected to SDS-PAGE. As a result, a band corresponding to His-Tag-bound GluRS was observed at a molecular weight of approximately 55 kDa, confirming that the protein of interest was correctly obtained. The concentration calculated from absorbance at UV 280 nm was 39.0 µM (approximately 2.1 mg/ml).

<Preparation of Cyclic Compound>

Cyclic compounds represented by the formula (I) were formed from the precursor peptide obtained in the preceding section <Synthesis of precursor peptide>.

[Example 1] Azole Ring Formation and α,β-Unsaturated Amino Acid Formation

First, stepwise reaction was performed by allowing azole ring formation reaction to proceed completely using LazD, LazE and LazF, and after a lapse of given time, adding LazB and tRNA$^{Glu}$ to the reaction system so that α,β-unsaturated amino acid formation reaction proceeded.

LazA* was synthesized on the scale of 5.0 µl of a cell-free translation system. 25 µl of a reaction solution supplemented with a coenzyme and LazD, LazE and LazF was allowed to act at 25° C. for 5 hours. After 5-hour reaction, half the amount, i.e., 12.5 µl, was desalted using zip tip C18 and analyzed by MALDI-TOF MS. LazB, tRNA$^{Glu}$ and GluRS were added to the remaining half (12.5 µl) and reacted again at 25° C. for 15 hours.

Tables 24 and 25 show the composition of the azole ring formation reaction system and the composition of the α,β-unsaturated amino acid formation reaction system, respectively.

As a result of the analysis by MALDI-TOF MS, it was found, as shown in FIG. 7, that the formation reaction of four azole rings almost proceeded through the 5-hour reaction mediated by LazD, LazE and LazF. When LazB, LazF, tRNA$^{Glu}$ and GluRS were added thereto, a major reaction product was detected at m/z 5502.5 by MALDI-TOF MS. This indicates that a mass shift of −90 Da occurred by the α,β-unsaturated amino acid-forming enzymes. The dehydration of five H$_2$O molecules occurred, confirming that azole rings and dehydroalanine were formed from LazA*.

As described above, the in vitro reconstruction of azole ring formation and α,β-unsaturated amino acid formation in the lactazole biosynthesis pathway was achieved.

TABLE 24

| Azole ring formation reaction composition | |
|---|---|
| 5.0 µl | LazA* |
| 50 mM | Tris-HCl pH 8.0 |
| 5 mM | ATP (adjusted to pH 7.0 with NaOH) |
| 10 mM | MgCl$_2$ |
| 1 mM | DTT |
| 1 µM | LazD |
| 1 µM | LazE |
| 2 µM | LazF |
| Total volume | 25 µl |

TABLE 25

| α,β-Unsaturated amino acid formation reaction composition | |
|---|---|
| 12.5 µl | LazA* having azole rings formed |
| 10 µM | Producing microbe tRNA$^{Glu}$ |
| 1 µM | GluRS |
| 2 µM | LazB |
| 1 µM | LazF |
| Total volume | 15 µl |

[Comparative Example 1] Azole Ring Formation and α,β-Unsaturated Amino Acid Formation The azole ring-forming enzymes LazD, LazE and LazF and the α,β-unsaturated amino acid-forming enzymes LazB and LazF were reacted at the same time, and the reaction product was analyzed.

LazA* was synthesized on the scale of 2.5 µl of a cell-free translation system. LazD, LazE, LazF, LazB and the other cosubstrates were added thereto according to the composition given below, and reacted. The reaction was performed by incubation at 25° C. for 20 hours. After the reaction, the reaction solution was desalted using zip tip C18 and analyzed by MALDI-TOF MS.

Table 26 shows the composition of the azole ring and α,β-unsaturated amino acid formation reaction system.

As a result of the analysis by MALDI-TOF MS, four major reaction products were found at m/z 5502.6, 5656.6, 5675.6, and 5695.7, whereas a peak of the peptide of interest (m/z 5520) in which four azole rings and four dehydroalanine moieties were formed was not confirmed. These four observed peaks were not consistent with any of m/z. of possible intermediates (combinations of varying numbers of azole rings formed, varying numbers of α,β-unsaturated amino acids formed and varying numbers of glutamylation products). Three peaks at m/z 5656.6, 5675.6 and 5695.7 were presumably peaks derived from compounds resulting from Michael addition reaction of compounds having a strongly nucleophilic thiol group or the like with dehydroalanine.

TABLE 26

Azole ring and α,β-unsaturated amino
acid formation reaction composition

| | |
|---|---|
| 2.5 µl | LazA* |
| 50 mM | Tris-HCl pH 8.0 |
| 5 mM | ATP (adjusted to pH 7.0 with NaOH) |
| 10 mM | MgCl$_2$ |
| 1 mM | DTT |
| 1 µM | LazD |
| 1 µM | LazE |
| 2 µM | LazF |
| 10 µM | Producing microbe tRNA$^{Glu}$ |
| 1 µM | GluRS |
| 2 µM | LazB |
| Total volume | 15 µl |

[Comparative Example 2] Azole Ring Formation and α,β-Unsaturated Amino Acid Formation The stepwise reaction which involved allowing azole ring formation reaction and then α,β-unsaturated amino acid formation reaction to proceed in Example 1 was changed to a stepwise reaction which involved allowing α,β-unsaturated amino acid formation reaction and then azole ring formation reaction to proceed. Specifically, this reaction was performed as follows.

LazA* was synthesized on the scale of 5.0 µl of a cell-free translation system. LazB, tRNA$^{Glu}$ and GluRS were added thereto and reacted at 25° C. for 5 hours. After 5-hour reaction, half the amount was desalted using zip tip C18 and analyzed by MALDI-TOF MS. LazD, LazE and LazF were added to the remaining half and reacted again at 25° C. for 15 hours.

Tables 27 and 28 show the composition of the α,β-unsaturated amino acid formation reaction system and the composition of the azole ring formation reaction system, respectively.

As a result of the analysis by MALDI-TOF MS, the dehydration reaction of 1 or 2 molecules associated with α,β-unsaturated amino acid formation was confirmed, as shown in FIG. 8, in the 5-hour reaction mediated by LazB, LazF, tRNA$^{Glu}$ and GluRS. When the azole ring-forming enzymes LazD, LazE and LazF were added thereto, many peaks considered as peaks of peptides differing in modified state were detected, unlike the chart shown in FIG. 7. This means that when α,β-unsaturated amino acid formation reaction proceeds first, subsequent modification reaction does not proceed smoothly.

TABLE 27

α,β-Unsaturated amino acid formation reaction composition

| | |
|---|---|
| 5.0 µl | LazA* |
| 50 mM | Tris-HCl pH 8.0 |
| 5 mM | ATP (adjusted to pH 7.0 with NaOH) |
| 10 mM | MgCl$_2$ |
| 1 mM | DTT |
| 10 µM | Producing microbe tRNA$^{Glu}$ |
| 1 µM | GluRS |
| 2 µM | LazB |
| 2 µM | LazF |
| Total volume | 25 µl |

TABLE 28

Azole ring formation reaction composition

| | |
|---|---|
| 12.5 µl | LazA* having formed α,β-unsaturated amino acids |
| 1 µM | LazD |
| 1 µM | LazE |
| 1 µM | LazF |
| Total volume | 15 µl |

[Example 2] Macrocyclization Reaction

As mentioned in the preceding section [Example 1], the in vitro reconstruction of azole ring formation and α,β-unsaturated amino acid formation was achieved. Subsequently, macrocyclization reaction was performed using a prepared recombinant enzyme. The reaction was performed using biosynthetic enzyme LazC presumably involved in macrocyclization reaction.

LazA* was synthesized on the scale of 5.0 µl of a cell-free translation system. LazD, LazE, LazF, LazB, LazC and other cosubstrates were added thereto according to the composition given below, and reacted in 30 µl in total of a reaction system. The reaction was performed in reaction systems including four reaction systems: A. a reaction system of LazA* alone; B. LazA*+LazD, LazE and LazF; C. LazA*+LazD, LazE, LazF, LazB, tRNA$^{Glu}$ and GluRS; and D. LazA*+LazD, LazE, LazF, LazB, tRNA$^{Glu}$, GluRS and LazC. Each reaction was performed by incubation at 25° C. for 20 hours. The composition of the reaction systems is shown in Table 29.

After the reaction, each reaction solution was desalted using zip tip C18 and analyzed by MALDI-TOF MS. For the analysis, half the amount, i.e., 15 µl, was analyzed using sinapic acid (SA) as a matrix, and the remaining half was analyzed using CHCA (α-cyano-4-hydroxycinnamic acid) as a matrix. The samples with sinapic acid used as a matrix were measured in a region of molecular weights of 2000 or larger. The samples with CHCA used as a matrix were measured in a region of molecular weights of 3000 or smaller.

The results of the analysis by MALDI-TOF MS are shown in FIG. 9. As shown in FIG. 9, peptides in a region from m/z 5400 to 5800 disappeared in the system supplemented with LazC, and a peptide of m/z 4102.1 accumulated instead, demonstrating that LazC consumed the substrate. The signal of m/z 4102.1 was consistent with m/z of a leader peptide cleaved off by LazC (calcd. m/z 4102.1). This peak of m/z. 4102.1 was further analyzed by MALDI-TOF MS/MS. As a result, this peak was found to be derived from the leader peptide.

As shown in FIG. 10, a peak consistent with m/z of a Na adduct of lactazole A (calcd. 1423.369) was confirmed in the system of LazC (+) by the comparison of mass spectra between LazC (+) and LazC (−). It was also confirmed by LC-MS and LC/MS/MS that a cyclized compound was able to be synthesized as the enzymatic reaction product.

Since m/z of a leader peptide is easily detected, this m/z can serve as an index for conveniently determining whether a macrocyclization product has been formed.

As described above, a method for synthesizing a cyclized compound using enzymes for lactazole A in vitro was established.

TABLE 29

Azole ring, α,β-unsaturated amino acid, and macrocycle formation reaction composition

| | |
|---|---|
| 5.0 µl | LazA* |
| 50 mM | Tris-HCl pH 8.0 |
| 5 mM | ATP (adjusted to pH 7.0 with NaOH) |
| 10 mM | MgCl$_2$ |
| 1 mM | DTT |
| 1 µM | LazD |
| 1 µM | LazE |
| 2 µM | LazF |
| 10 µM | Producing microbe tRNA$^{Glu}$ (CUC) |
| 1 µM | GluRS |
| 2 µM | LazB |
| 2 µM | LazC |
| Total volume | 30 µl |

<Substrate Tolerance>

The constructed method for synthesizing a cyclized compound using enzymes for lactazole A in vitro as mentioned above was examined for applicable substrate tolerance.

[Example 3] Substrate Tolerance to Length of Precursor Peptide-1

In order to confirm the possibility of forming macrocycles other than a 32-membered ring by the macrocyclase LazC, precursor peptides inserted with Ala were prepared by inserting Ala to the core peptide region. Macrocyclization was performed with these precursor peptides as substrates.

As in Example 1, a mutant DNA template was prepared by primer extension and PCR and translated in a cell-free translation system to confirm that the precursor peptides of interest, inserted with Ala, were synthesized. Subsequently, LazD, LazE, LazF, LazB, tRNA$^{Glu}$ (CUC), GluRS and LazC were added to respective translationally-synthesized Ala-inserted precursor peptides and reacted. Table 30 shows the composition of azole ring, α,β-unsaturated amino acid and macrocycle formation reaction. The reaction was performed by incubation at 25° C. for 20 hours. The reaction product was analyzed by MALDI-TOF MS and LC-MS.

Table 31 shows the sequences of the prepared precursor peptides and the numbers of azole rings and α,β-unsaturated amino acids formed observed in each precursor peptide. Each of the precursor peptides exhibited the numbers of azole rings and α,β-unsaturated amino acids formed similar to those of the native one (LazA*). This demonstrated that the insertion of Ala hardly influences azole ring formation and α,β-unsaturated amino acid formation. In the table, symbols such as "4, 5" represent that two peaks have almost the same intensity. The same holds true for such symbols in the tables given below.

FIG. 11 shows mass chromatograms about the leader peptide cleaved off through LazC reaction which is a reaction product of macrocycle formation reaction. The leader peptides are basically cleaved off specifically for the macrocyclization reaction of LazC. Provided that ionic strengths in the chromatograms were not saturated and fell within a dynamic range, it was believed that the peak intensity of each leader peptide cleaved off was proportional to macrocyclization efficiency. Accordingly, the peak areas of the eliminated leader peptides for respective analogs are summarized in FIG. 12. As is evident from FIGS. 11 and 12, LazC was found to tolerate ring expansion.

TABLE 30

Azole ring, α,β-unsaturated amino acid, and macrocycle formation reaction composition

| | |
|---|---|
| 5.0 µl | LazA* |
| 50 mM | Tris-HCl pH 8.0 |
| 5 mM | ATP (adjusted to pH 7.0 with NaOH) |
| 10 mM | MgCl$_2$ |
| 1 mM | DTT |
| 1 µM | LazD |
| 1 µM | LazE |
| 2 µM | LazF |
| 10 µM | Producing microbe tRNA$^{Glu}$(CUC) |
| 1 µM | GluRS |
| 2 µM | LazB |
| 2 µM | LazC |
| Total volume | 30 µl |

See FIG. 58 for Table 31.

[Example 3] Substrate Tolerance to Length of Precursor Peptide-2

Most of the Ala-inserted precursor peptides in which one residue of Ala was inserted became a macrocyclic compound having an expanded ring in response to macrocyclization reaction mediated by LazC. Accordingly, in order to examine how large the ring formed by LazC could be or how small the ring formed by LazC could be, mutant precursor peptides were prepared by inserting two or three residues of Ala or by deleting one or two residues of amino acids from LazA*. These mutant precursor peptides were reacted as substrates with LazC.

In accordance with the method of Example 2, the precursor peptides shown in Table 32 were prepared, and each precursor peptide was subjected to azole ring, α,β-unsaturated amino acid and macrocycle formation reaction. FIG. 13 shows the chromatograms of leader peptides cleaved off by the macrocyclization of the analogs. FIG. 14 shows the peak areas of the leader peptides.

See FIG. 59 for Table 32.

As seen from Examples 3 and 4, LazC successfully formed macrocycles from 26-membered to 41-membered rings, demonstrating that LazC has substrate tolerance to the size of a macrocycle.

[Example 5] Ser (4), Cys (5), Ser (6), and Cys (7)-Substituted Analog

The 4SCSC7_4AAAA7 precursor peptide was prepared by substituting all the amino acid residues Ser (4), Cys (5), Ser (6) and Cys (7), which are converted to azole rings and α,β-unsaturated amino acids, by Ala. This precursor peptide was reacted as a substrate with LazC.

In according with the method of Example 3, a mutant DNA template encoding 4SCSC7_4AAAA7 was prepared and translated in the cell-free translation system to confirm that the mutant precursor peptide of interest was synthesized. Subsequently, LazD, LazE, LazF, LazB, tRNA$^{Glu}$ (CUC), GluRS and LazC were added to the translationally-synthesized mutant precursor peptide and reacted. The reaction product was analyzed by MALDI-TOF MS and LC-MS.

The amino acid sequence of the prepared 4SCSC7_4AAAA7 precursor peptide is shown in Table 33.

FIG. 15 shows the chromatogram of a leader peptide in the reaction product. Leader peptide elimination was also seen in the 4SCSC7_4AAAA7 precursor peptide at a level equivalent to LazA*, demonstrating that Ser (4), Cys (5), Ser (6) and Cys (7) are not important for the substrate recognition of LazC.

See FIG. 60 for Table 33.

[Example 6] Ser (11), Ser (12), Cys (13) or Ser (10)-Substituted Analog

Mutant precursor peptides were prepared by substituting each of Ser (11), Ser (12), Cys (13) and their neighboring Ser (10) one by one by Ala. These mutant precursor peptides were analyzed for whether to be recognized as a substrate by LazC.

In according with the method of Example 3, mutant DNA templates encoding respective analogs described in Table 34 were prepared and translated in a cell-free translation system to confirm that the mutant precursor peptides of interest were synthesized. Subsequently, LazD, LazE, LazF, LazB, tRNA$^{Glu}$ (CUC), GluRS and LazC were added to each translationally-synthesized mutant precursor peptide and reacted. The reaction products were analyzed by MALDI-TOF MS and LC-MS.

Table 34 shows the amino acid sequences of the prepared precursor peptides, and the numbers of azole rings and α,β-unsaturated amino acids formed.

FIG. 16 shows the chromatograms of leader peptides in the reaction products. A leader peptide cleaved off was slightly seen in S11A and C13A, whereas such a leader peptide was hardly seen in S11A and S12A. This demonstrated that for the recognition of a substrate by LazC, Ser (11) and Ser (12) are important and Ser (10) and Cys (13) are also relatively important.

See FIG. 61 for Table 34.

[Example 7] Trp (2), Gly (3), Gln (8), Ala (9), Gln (15) or Pro (16)-Substituted Analog Example 5 demonstrated that macrocyclization proceeds even if Ser (4), Cys (5), Ser (6) and Cys (7) are substituted. Example 6 demonstrated that for the recognition of a substrate by LazC, Ser (11) and Ser (12) are important and Ser (10) and Cys (13) are also relatively important.

The other amino acids Trp (2), Gly (3), Gln (8) and Ala (9) supposed to be contained in the macrocycle were studied for whether to be substitutable. Also, amino acids exterior to the macrocycle were studied for whether macrocyclization would also proceed in Gln (15) or Pro (16)-substituted analogs.

In according with the method of Example 3, mutant DNA templates encoding respective precursor peptides described in Table 35 were prepared and translated in the cell-free translation system to confirm that the mutant precursor peptides of interest were synthesized. Subsequently, LazD, LazE, LazF, LazB, tRNA$^{Glu}$ (CUC), GluRS and LazC were added to each translationally-synthesized mutant precursor peptide and reacted. The reaction product were analyzed by MALDI-TOF MS and LC-MS. The results of the LC-MS analysis (MS peaks of leader peptides and macrocyclization products) are shown in FIGS. 17, 18 and 19.

In the table, the symbol "( )" in "3, (2)", etc. represents a minor peak. The same holds true for such symbols in the tables given below.

Results about the reaction efficiency in substitution of the intra-macrocycle residues (Trp (2), Gly (3), Gln (8), Ala (9), Gln (15) and Pro (16)) are summarized in FIG. 20. In FIG. 20, the amino acid residues with parentheses mean residues having reduced reaction efficiency.

See FIG. 62 for Table 35.

[Example 8-1] Substrate Tolerance to Length of Precursor Peptide-3

In order to further study the size of the macrocycle that could be catalyzed by LazC, Ala multiply-inserted precursor peptides were prepared by inserting multiple Ala residues to the 4SCSC7_4AAAA7 precursor peptide, whereas multiply-deleted precursor peptides were prepared by deleting multiple residues therefrom.

In according with the method of Example 3, mutant DNA templates encoding respective precursor peptides with one to seven Ala residues inserted to the 4SCSC7_4AAAA7 precursor peptide and precursor peptides with one to eight amino acid residues deleted from the 4SCSC7_4AAAA7 precursor peptide were prepared and translated in the cell-free translation system to confirm that the mutant precursor peptides of interest were synthesized. Subsequently, LazD), LazE, LazF, LazB, tRNAGlu (CUC), GluRS and LazC were added to each translationally-synthesized mutant precursor peptide and reacted. The reaction product was analyzed by MALDI-TOF MS and LC-MS.

Table 36 shows the amino acid sequences of the prepared Ala multiply-inserted and multiply-deleted precursor peptides, and the numbers of azole rings and α,β-unsaturated amino acids formed. Similar azole ring formation and α,β-unsaturated amino acid formation were seen in the mutant precursor peptides, demonstrating that LazD, LazE, LazF and LazB tolerate these mutant precursor peptides as substrates. This suggests that for the substrate recognition of the azole ring-forming enzymes and the α,β-unsaturated amino acid-forming enzymes, distance from a leader peptide region is not important and the arrangement of an amino acid sequence surrounding the residues serving as a substrate is important.

FIGS. 21 and 22 show the chromatograms of the leader peptides in the reaction products. FIGS. 23 and 24 show the peak areas of the leader peptides.

See FIG. 63 for Table 36.

[Example 8-2] Substrate Tolerance to Length of Precursor Peptide-4

In order to further study the size of the macrocycle that could be formed by the Laz enzyme group, Ala and Asn multiply-inserted precursor peptides were prepared by inserting multiple Ala and Asn residues to the 4SCSC7_4AAAA7 precursor peptide, whereas multiply-deleted precursor peptides were prepared by deleting multiple residues therefrom.

In according with the method of Example 3, mutant DNA templates encoding respective precursor peptides with Ala and Asn inserted to the 4SCSC7_4AAAA7 precursor peptide and precursor peptides with amino acid residues deleted from the 4SCSC7_4AAAA7 precursor peptide were prepared and translated in the cell-free translation system to confirm that the mutant precursor peptides of interest were synthesized. Subsequently, LazD, LazE, LazF, LazB, tRNA-Glu (CUC), GluRS and LazC were added to each translationally-synthesized mutant precursor peptide and reacted. The reaction products were analyzed by LC-MS. In this experiment, modification reaction mediated by the Laz enzyme group and the formation of a macrocyclization product were confirmed by broad extracted ion chromatograms (brEIC) in which peak(s) detected in the range of +400 or +600 of the tetravalent or pentavalent m/z value of a precursor peptide were integrated. In the brEIC, the presence of a precursor peptide, a linear intermediate peptide having azoline/azole/dehydrated amino acid and a leader peptide fragment (LP-NH2) through LazC reaction can be confirmed at the same time. FIG. 25 shows brEIC of each reaction product.

[Example 9-1] Substrate Tolerance of Azole Ring-Forming Enzyme to Cys-Substituted Analog In order to determine the substrate recognition of the azole ring-forming enzymes, Cys-substituted precursor peptides were prepared by substituting residues of the core peptide region one by one by Cys, and reacted with the azole ring-forming enzymes.

In accordance with the method of Example 3, mutant DNA templates encoding respective Cys-substituted precursor peptides with amino acid residues of the core peptide region substituted one by one by Cys were prepared and translated in the cell-free translation system to confirm that the mutant precursor peptides of interest were synthesized. Subsequently, LazD, LazE and LazF were added to each translationally synthesized mutant precursor peptide and reacted. The reaction products were analyzed by MALDI-TOF MS.

Table 37 shows the amino acid sequences of the prepared Cys-substituted precursor peptides, and the observed number of azole rings formed. The azole ring-forming enzymes were found to recognize a region rich in Cys or Ser and tend to cause the azole cyclization of Cys or Ser residues in this region.

See FIG. 64 for Table 37.

[Example 9-2] Substrate Tolerance of Macrocyclization to Ala-Substituted Analog

As in Example 1, mutant DNA templates were prepared by primer extension and PCR and translated in the cell-free translation system to synthesize S1A, W2A, G3A, S4A, C5A, S6A, C7A, Q8A, S10A, S11A, S12A, C13A, Q15A and P16A altered precursor peptides (see FIG. 26) in which the 1st to 16th native amino acids, respectively, were replaced with Ala.

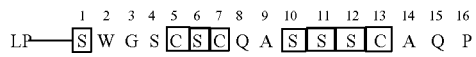

The sequence identifier of the amino acid sequence is SEQ ID NO: 18.

Subsequently, each altered precursor peptide mentioned above was reacted as in Example 8-2, and the reaction product was analyzed by LC-MS. Modification reaction mediated by the Laz enzyme group and the formation of macrocyclization products were confirmed by broad extracted ion chromatograms (brEIC) in which peaks detected in the range of +400 of the tetravalent m/z value of a precursor peptide were integrated. FIG. 26 shows brEIC of each reaction product. In the chromatograms, no peak of a macrocyclization product was observed for S1A, S11A, and S12A.

[Example 9-3] Substrate Tolerance of Macrocyclization to Lys-Substituted Analog

As in Example 1, mutant DNA templates were prepared by primer extension and PCR and translated in the cell-free translation system to synthesize W2K, G3K, A4K, A5K, A6K, A7K, Q8K, A9K, Q15K and P16K altered precursor peptides (see FIG. 27) in which the 2nd to 9th and 14th to 16th native amino acids, respectively, were replaced with Lys.

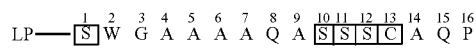

The sequence identifier of the amino acid sequence is SEQ ID NO: 38.

Subsequently, each altered precursor peptide mentioned above was reacted in accordance with the procedures described in Example 9-2, and the reaction product was analyzed by LC-MS. Modification reaction mediated by the Laz enzyme group and the formation of macrocyclization products were confirmed by broad extracted ion chromatograms (brEIC) in which peaks detected in the range of +400 of the tetravalent m/z value of a precursor peptide were integrated. FIG. 27 shows brEIC of each reaction product.

[Example 9-4] Substrate Tolerance of Macrocyclization to Glu-Substituted Analog

As in Example 9-3, W2E, G3E, A4E, A5E, A6E, A7E, Q8E, A9E, Q15E and P16E altered precursor peptides (see FIG. 28) were synthesized by replacing the 2nd to 9th, 15th, and 16th native amino acids, respectively, with Glu. Subsequently, each altered precursor peptide mentioned above was reacted in accordance with the procedures described in Example 9-2, and the reaction product was analyzed by LC-MS. Modification reaction mediated by the Laz enzyme group and the formation of macrocyclization products were confirmed by broad extracted ion chromatograms (brEIC) in which peaks detected in the range of +400 of the tetravalent m/z value of a precursor peptide were integrated. FIG. 28 shows brEIC of each reaction product.

[Example 10-1] Substrate Tolerance of Macrocyclization to Ser (10), Ser (11), or Cys (13)-Substituted Analog As in Example 1, mutant DNA templates were prepared by primer extension and PCR and translated in the cell-free translation system to confirm that the S10T, S11T, S11C, C13S and C13T altered precursor peptides of interest (see Table 38) were synthesized.

Subsequently, LazD, LazE, LazF, LazB, RNA$^{Glu}$ (CUC), GluRS and LazC were added to each of the translationally-synthesized S10T, S11T, S11C, C13S and C13T altered precursor peptides and reacted. Table 39 shows the composition of azole ring, α,β-unsaturated amino acid and macrocycle formation reaction. The reaction was performed by incubation at 25° C. for 20 hours. The reaction products were analyzed by MALDI-TOF MS and LC-MS. FIG. 29 shows the chromatograms of leader peptides in the reaction product.

See FIG. 65 for Table 38.

TABLE 39

Azole ring, α,β-unsaturated amino acid, and macrocycle formation reaction composition

| | |
|---|---|
| 5.0 µl | LazA* |
| 50 mM | Tris-HCl pH 8.0 |
| 5 mM | ATP (adjusted to pH 7.0 with NaOH) |
| 10 mM | MgCl$_2$ |
| 1 mM | DTT |
| 1 µM | LazD |
| 1 µM | LazE |
| 2 µM | LazF |
| 10 µM | Producing microbe tRNA$^{Glu}$ (CUC) |
| 1 µM | GluRS |
| 2 µM | LazB |
| 2 µM | LazC |
| Total volume | 30 µl |

[Example 10-2] Substrate Tolerance of Macrocyclization to Analog (Substitution and Extension) as to C-Terminal Region As in Example 1, mutant DNA templates were prepared by primer extension and PCR and translated in the cell-free translation system to obtain the precursor peptides altered in a C-terminal region shown in FIG. 30. Subsequently, each of the translationally-synthesized precursor peptides altered in a C-terminal region was reacted in accordance with the procedures described in Example 10-1, and the reaction product was analyzed by LC-MS. Modification reaction mediated by the Laz enzyme group and the formation of macrocyclization products were confirmed by broad extracted ion chromatograms (brEIC) in which peaks detected in the range of +400 of the pentavalent m/z value of a precursor peptide were integrated. FIG. 30 shows brEIC of each reaction product.

[Example 10-3] Substrate Tolerance of Macrocyclization to Analog Having Random Artificial Sequence as Intra-Ring Sequence, and Analog Having Randomized Intra-Ring Sequence and Having Extended C-Terminal Region As in Example 1, mutant DNA templates were prepared by primer extension and PCR and translated in the cell-free translation system to obtain the altered precursor peptides of interest having a randomized intra-ring sequence (FIG. 31a), and the altered precursor peptides of interest having a randomized intra-ring sequence and having an extended C-terminal region (FIG. 31b), as shown in FIG. 31. Subsequently, LazD, LazE and LazF were added to each of the translationally-synthesized precursor peptide altered in a C-terminal region, and reacted at 25° C. for 6 hours. Then, LazB, cosubstrate tRNA$^{Glu}$, aminoacylation enzyme GluRS and LazC were added thereto and reacted at 25° C. for 12 hours. The reaction products were analyzed by LC-MS. Modification reaction mediated by the Laz enzyme group and the formation of macrocyclization products were confirmed by broad extracted ion chromatograms (brEIC) in which peaks detected in the range of +600 of the tetravalent or pentavalent m/z value of a precursor peptide were integrated. FIG. 31 shows brEIC of each reaction product.

[Example 11] Recognition of Leader Peptide

In order to determine the role of leader peptides in the lactazole biosynthetic enzymes, leader peptide-truncated precursor peptides were prepared and reacted as substrates with each modifying enzyme.

Mutant precursor peptides were prepared by N-terminally truncating a leader peptide having 38 residues. The prepared mutant precursor peptides contained leader peptides having 30, 25, 20 and 15 residues and were designated as LP-30, LP-25, LP-20, and LP-15, respectively. Azole ring formation reaction, α,β-unsaturated amino acid formation reaction and macrocyclization reaction were performed with these four mutant precursor peptides as substrates. The reaction products were analyzed by MALDI-TOF MS and LC-MS to confirm whether the reaction has proceeded or not.

The amino acid sequences of the prepared leader peptide-truncated precursor peptides are shown in Table 40. The sequence SWGSCSCQASSSCAQP (SEQ ID NO:18) corresponds to the core peptide region. The N terminus is always formylmethionine because of synthesis by translation. As a result of the azole ring formation reaction mediated by LazD, LazE and LazF and the α,β-unsaturated amino acid formation reaction mediated by LazB and LazF with each of the mutant precursor peptides as a substrate, it was found that the azole ring formation and the α,β-unsaturated amino acid formation proceeded almost completely up to LP-25, whereas the efficiency of azole ring formation and α,β-unsaturated amino acid formation was reduced in LP-20. The results about mass chromatograms are shown in FIGS. 32 to 36.

FIG. 37 shows the mass chromatograms of leader peptides resulting from macrocyclization reaction mediated by LazC with each of the mutant precursor peptides as a substrate.

These results demonstrated that an important site of a leader peptide for the azole ring-forming enzymes and the α,β-unsaturated amino acid-forming enzymes in lactazole biosynthesis is a C-terminal side from Leu (-25). The results also demonstrated that as for the macrocyclase, reaction proceeds in the presence of at least a C-terminal region from Leu (-20).

TABLE 40

| Analog name | Amino acid sequence |
|---|---|
| LazA* | MSDITASRVESLDLQDLDLSELTVTSLRDTVALPENGASWGSCSCQASSSCAQP |
| LP-30 | MVESLDLQDLDLSELTVTSLRDTVALPENGASWGSCSCQASSSCAQP |

TABLE 40-continued

| Analog name | Amino acid sequence |
|---|---|
| LP-25 | MLQDLDLSELTVTSLRDTVALPENGASWGSCSCQASSSCAQP |
| LP-20 | MLSELTVTSLRDTVALPENGASWGSCSCQASSSCAQP |
| LP-15 | MVTSLRDTVALPENGASWGSCSCQASSSCAQP |

From top to bottom, the sequence identifiers are SEQ ID NOs: 103 to 107.

[Example 12] Ala Scanning Experiment of Leader Peptide

Altered precursor peptides were prepared by substituting each of the amino acid residues positioned from −1 to −25 of the leader peptide in LP-25 shown in FIG. 38 by Ala to confirm substrate tolerance thereof to azole ring, α,β-unsaturated amino acid and macrocycle formation reaction.

Specifically, as in Example 1, mutant DNA templates were prepared by primer extension and PCR and translated in the cell-free translation system to confirm that the altered precursor peptides of interest were synthesized as altered forms of the leader peptide site.

Subsequently, LazD, LazE, LazF, LazB, tRNA$^{Glu}$ (CUC), GluRS and LazC were added to each translationally-synthesized Ala-inserted precursor peptide and reacted. Table 41 shows the composition of azole ring, α,β-unsaturated amino acid and macrocycle formation reaction. The reaction was performed by incubation at 25° C. for 20 hours. The reaction products were analyzed by MALDI-TOF MS and LC-MS.

FIG. 39 shows the chromatograms of leader peptides in the reaction products of the altered precursor peptides prepared by the substitution of each of the amino acid residues positioned from −1 to −25. In FIG. 39, for example, "LP-25_S-19A" means an "altered precursor peptide in which the amino acid position at −19 (S) was substituted by Ala". The same holds true for the other altered precursor peptides.

TABLE 41

Azole ring, α,β-unsaturated amino acid, and macrocycle formation reaction composition

| | |
|---|---|
| 5.0 μl | LazA* |
| 50 mM | Tris-HCl pH 8.0 |
| 5 mM | ATP (adjusted to pH 7.0 with NaOH) |
| 10 mM | MgCl$_2$ |
| 1 mM | DTT |
| 1 μM | LazD |
| 1 μM | LazE |
| 2 μM | LazF |
| 10 μM | Producing microbe tRNA$^{Glu}$ (CUC) |
| 1 μM | GluRS |
| 2 μM | LazB |
| 2 μM | LazC |
| Total volume | 30 μl |

[Example 13] Preparation and Screening of Compound Library

As shown in FIG. 40, compound libraries were designed which were constituted by peptides containing "leader peptide-Ser-any amino acid sequence consisting of 5 to 10 residues-Ser-Ser-Ser-Cys-any amino acid sequence consisting of 3 residues". DNA libraries were prepared on the basis of the design of the compound libraries described above.

The preparation of the DNA libraries conformed to the method described in Chemistry & Biology 18, 1562-1570 (2011), and Chemistry & Biology 21, 766-774 (2014). The DNA libraries were transcribed in vitro to prepare mRNA libraries. It was confirmed that the mRNA libraries were able to be synthesized as shown in the electrophoretic gel of FIG. 41. In the drawing of the electrophoretic gel, 6 to 11 denote mRNA libraries containing any amino acid sequence consisting of 5, 6, 7, 8, 9 and 10 residues, respectively. In order to confirm that the prepared mRNA libraries had a correct sequence, the mRNA libraries were reverse-transcribed. Then, the obtained DNA sequences were analyzed using a high-throughput sequencer (MiSeq, Illumina K.K.). From results of sequencing quality score Q (FIG. 42) in the DNA sequencing, frameshift analysis (FIG. 43), sequence conservation plot (FIG. 44) and amino acid frequency analysis (FIG. 45), it was confirmed that the mRNA libraries were correctly constructed as designed.

According to the scheme shown in FIG. 46, peptide-mRNA complex libraries were constructed from the mRNA libraries mentioned above, and compound libraries containing thiopeptides were constructed by the action of LazB-F enzyme. Then, the compound libraries were subjected to a step of screening for a cyclic peptide interacting with enzyme iPGM. As seen from the graph of the rate of cDNA recovery shown in FIG. 47, cyclic peptides binding to iPGM were able to be obtained.

These results showed that the production method of the present invention including using an azole ring-forming enzyme, an α,β-unsaturated amino acid-forming enzyme and a macrocyclase can provide a compound library.

[Example 14-1] Synthesis of Cyclic Peptide Containing Non-Proteinogenic Amino Acid On the basis of the reprogramming scheme shown in FIG. 48, non-proteinogenic amino acids were introduced to the core peptide moieties of precursor peptides before azole ring formation, α,β-unsaturated amino acid formation and macrocyclization. FIG. 49 shows DNA templates and peptides formed from the templates. In FIG. 49, the boxed codons and amino acids refer to codons and amino acids to be reprogrammed, and are positions for the introduction of non-proteinogenic amino acids.

In accordance with the method described in Example 1, each DNA template described above was translated and further induced into a cyclic peptide through the step of allowing LazB, LazC, LazD, LazE and LazF enzymes to act. The products after translation and cyclic peptide-formation were measured by LC/MS to confirm whether the translation for the DNA templates harboring the non-proteinogenic amino acids have proceeded, and whether cyclic peptides have been formed. The results are shown in Tables 42 to 44. In the tables, m/z shown in the column "Observation results" is the observed value of MS, or the value of MS of the cyclic peptide.

The structures of the introduced non-natural amino acids are as described below.

In Table 43, v.064 and v.082 denote precursor peptides obtained from DNA templates containing no codon to be reprogrammed. MS of a cyclic peptide was also observed in v.064 and v.082. The obtainment of the cyclic peptides from v.064 and v.082 means that the peptides corresponding to Z and Z' in the formula (II) and the formula (III) are not limited by their lengths or types.

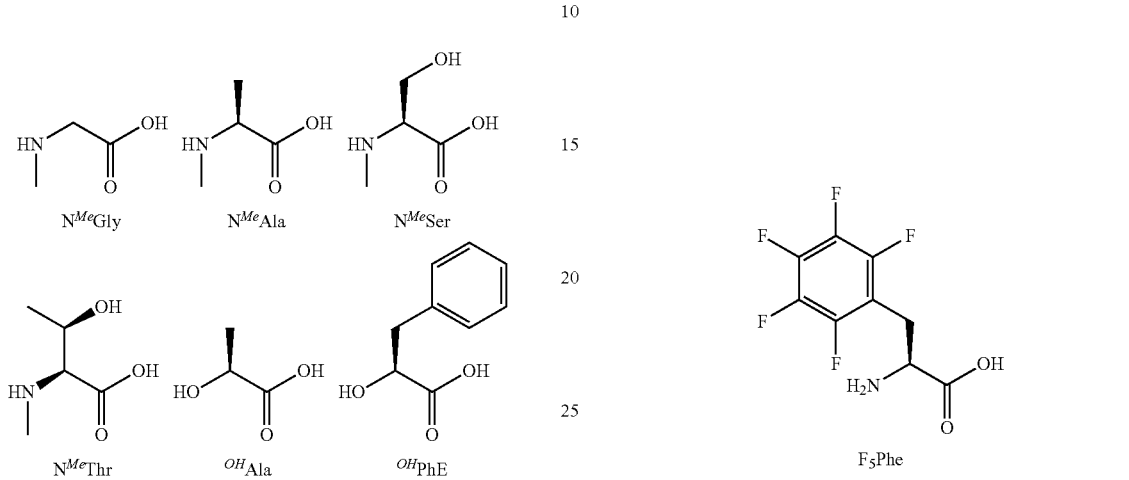

TABLE 42

| DNA template | Codon reprogramming | Amino acid sequence of precursor peptide |
|---|---|---|
| v.061 | tgg = W | MSDITASRVESLDLQDLDLSELTVTSLRDTVALPENGASWGAAAAQASSSCAQP |
| v.061 | tgg = N$^{Me}$Gly | MSDITASRVESLDLQDLDLSELTVISLRDTVALPENGASN$^{Me}$GGAAAAQASSSCAQP |
| v.061 | tgg = N$^{Me}$Ala | MSDITASRVESLDLQDLDLSELTVISLRDTVALPENGASN$^{Me}$AGAAAAQASSSCAQP |
| v.070 | tgg = W | MSDITASRVESLDLQDLDLSELTVTSLRDTVALPENGASAWAAAAQASSSCAQP |
| v.070 | tgg = N$^{Me}$Gly | MSDITASRVESLDLQDLDLSELTVISLRDTVALPENGASAN$^{Me}$GAAAAQASSSCAQP |
| v.070 | tgg = N$^{Me}$Ala | MSDITASRVESLDLQDLDLSELTVISLRDTVALPENGASAN$^{Me}$AAAAAQASSSCAQP |
| v.086 | tgg = W | MSDITASRVESLDLQDLDLSELTVTSLRDTVALPENGASAGWAAAQASSSCAQP |
| v.086 | tgg = N$^{Me}$Gly | MSDITASRVESLDLQDLDLSELTVISLRDTVALPENGASAGN$^{Me}$GAAAQASSSCAQP |
| v.086 | tgg = N$^{Me}$Ala | MSDITASRVESLDLQDLDLSELTVISLRDTVALPENGASAGN$^{Me}$AAAAQASSSCAQP |
| v.087 | tgg = W | MSDITASRVESLDLQDLDLSELTVTSLRDTVALPENGASAGAWAAQASSSCAQP |
| v.087 | tgg = N$^{Me}$Gly | MSDITASRVESLDLQDLDLSELTVISLRDTVALPENGASAGAN$^{Me}$GAAQASSSCAQP |
| v.087 | tgg = N$^{Me}$Ala | MSDITASRVESLDLQDLDLSELTVISLRDTVALPENGASAGAN$^{Me}$AAAQASSSCAQP |
| v.088 | tgg = W | MSDITASRVESLDLQDLDLSELTVTSLRDTVALPENGASAGAAWQASSSCAQP |
| v.088 | tgg = N$^{Me}$Ala | MSDITASRVESLDLQDLDLSELTVISLRDTVALPENGASAGAAN$^{Me}$AQASSSCAQP |
| v.089 | tgg = W | MSDITASRVESLDLQDLDLSELTVTSLRDTVALPENGASAGAAAWQASSSCAQP |
| v.089 | tgg = N$^{Me}$Ala | MSDITASRVESLDLQDLDLSELTVISLRDTVALPENGASAGAAAN$^{Me}$AQASSSCAQP |
| v.074 | tgg = W | MSDITASRVESLDLQDLDLSELTVTSLRDTVALPENGASAGAAAAWASSSCAQP |
| v.074 | tgg = N$^{Me}$Gly | MSDITASRVESLDLQDLDLSELTVISLRDTVALPENGASAGAAAAN$^{Me}$GASSSCAQP |
| v.074 | tgg = N$^{Me}$Ala | MSDITASRVESLDLQDLDLSELTVISLRDTVALPENGASAGAAAAN$^{Me}$AASSSCAQP |
| v.074 | tgg = F$_5$Phe | MSDITASRVESLDLQDLDLSELTVTSLRDTVALPENGASAGAAAA$_{f5}$FASSSCAQP |
| v.074 | tgg = cLeu | MSDITASRVESLDLQDLDLSELTVTSLRDTVALPENGASAGAAAA$_c$LASSSCAQP |
| v.074 | tgg = $^{OH}$Ala | MSDITASRVESLDLQDLDLSELTVTSLRDTVALPENGASAGAAAA$^{OH}$AASSSCAQP |
| v.074 | tgg = $^{OH}$Phe | MSDITASRVESLDLQDLDLSELTVTSLRDTVALPENGASAGAAAA$^{OH}$FASSSCAQP |
| v.074 | tgg = $^D$Ala | MSDITASRVESLDLQDLDLSELTVTSLRDTVALPENGASAGAAAA$^D$ASSSCAQP |
| v.075 | tgg = W | MSDITASRVESLDLQDLDLSELTVTSLRDTVALPENGASAGAAAAAWSSSCAQP |
| v.075 | tgg = N$^{Me}$Gly | MSDITASRVESLDLQDLDLSELTVISLRDTVALPENGASAGAAAAAN$^{Me}$GSSSCAQP |
| v.075 | tgg = N$^{Me}$Ala | MSDITASRVESLDLQDLDLSELTVISLRDTVALPENGASAGAAAAAN$^{Me}$ASSSCAQP |
| v.077 | tgg = A | MSDITASRVESLDLQDLDLSELTVTSLRDTVALPENGASAGAAAAQASSSCAQP |
| v.077 | tgg = M | MSDITASRVESLDLQDLDLSELTVISLRDTVALPENGASAGAAAAQASSSCMQP |

| DNA template | Codon reprogramming | Observation results from LC-MS of precursor peptide after translation | Observation results from LC-MS of thiopeptide derivative formed after Laz enzyme group treatment | Remarks |
|---|---|---|---|---|
| v.061 | tgg = W | m/z = 1424.67 (z = 4) [Cys adduct] | m/z = 682.28 (z = 2) | ~45% Glu misincorporation Partial hydrolysis of precursor |
| v.061 | tgg = N$^{Me}$Gly | m/z = 1395.91 (z = 4) [Cys adduct] | m/z = 624.72 (z = 2) | |
| v.061 | tgg = N$^{Me}$Ala | m/z = 1399.41 (z = 4) [Cys adduct] | m/z = 631.76 (z = 2) | |
| v.070 | tgg = W | m/z = 1428.17 (z = 4) [Cys adduct] | m/z = 682.28 (z = 2) | |

TABLE 42-continued

| | | | | | |
|---|---|---|---|---|---|
| v.070 | tgg = $N^{Me}$Gly | m/z = 1399.40 (z = 4) [Cys adduct] | m/z = 631.77 (z = 2) | peptide |
| v.070 | tgg = $N^{Me}$Ala | m/z = 1402.90 (z = 4) [Cys adduct] | m/z = 638.76 (z = 2) | Partial hydrolysis |
| v.086 | tgg = W | m/z = 1413.91 (z = 4) [βME adduct] | m/z = 682.27 (z = 2) | of precursor |
| v.086 | tgg = $N^{Me}$Gly | m/z = 1385.15 (z = 4) [βME adduct] | m/z = 624.75 (z = 2) | peptide |
| v.086 | tgg = $N^{Me}$Ala | m/z = 1388.66 (z = 4) [βME adduct] | m/z = 631.75 (z = 2) | |
| v.087 | tgg = W | m/z = 1413.92 (z = 4) [βME adduct] | m/z = 682.27 (z = 2) | |
| v.087 | tgg = $N^{Me}$Gly | m/z = 1385.16 (z = 4) [βME adduct] | m/z = 624.74 (z = 2) | |
| v.087 | tgg = $N^{Me}$Ala | m/z = 1388.67 (z = 4) [βME adduct] | m/z = 631.75 (z = 2) | |
| v.088 | tgg = W | m/z = 1413.92 (z = 4) [βME adduct] | m/z = 682.27 (z = 2) | |
| v.088 | tgg = $N^{Me}$Ala | m/z = 1388.66 (z = 4) [βME adduct] | m/z = 631.75 (z = 2) | |
| v.089 | tgg = W | m/z = 1413.92 (z = 4) [βME adduct] | m/z = 682.27 (z = 2) | |
| v.089 | tgg = $N^{Me}$Ala | m/z = 1388.66 (z = 4) [βME adduct] | m/z = 631.75 (z = 2) | |
| v.074 | tgg = W | m/z = 1410.40 (z = 4) [Cys adduct] | m/z = 653.74 (z = 2) | |
| v.074 | tgg = $N^{Me}$Gly | m/z = 1381.65 (z = 4) [Cys adduct] | m/z = 596.24 (z = 2) | |
| v.074 | tgg = $N^{Me}$Ala | m/z = 1385.16 (z = 4) [Cys adduct] | m/z = 603.24 (z = 2) | |
| v.074 | tgg = $F_5$Phe | m/z = 1423.14 (z = 4) [Cys adduct] | m/z = 679.23 (z = 2) | |
| v.074 | tgg = cLeu | m/z = 1391.65 (z = 4) [Cys adduct] | m/z = 616.23 (z = 2) | |
| v.074 | tgg = $^{OH}$Ala | m/z = 1381.91 (z = 4) [Cys adduct] | m/z = 596.72 (z = 2) | |
| v.074 | tgg = $^{OH}$Phe | m/z = 1400.92 (z = 4) [Cys adduct] | m/z = 634.73 (z = 2) | |
| v.074 | tgg = $^{D}$Ala | m/z = 1381.66 (z = 4) [Cys adduct] | m/z = 596.23 (z = 2) | |
| v.075 | tgg = W | m/z = 1410.42 (z = 4) [Cys adduct] | m/z = 653.77 (z = 2) | |
| v.075 | tgg = $N^{Me}$Gly | m/z = 1381.65 (z = 4) [Cys adduct] | m/z = 596.25 (z = 2) | |
| v.075 | tgg = $N^{Me}$Ala | m/z = 1385.15 (z = 4) [Cys adduct] | m/z = 603.25 (z = 2) | |
| v.077 | tgg = A | m/z = 1366.15 (z = 4) | m/z = 624.74 (z = 2) | |
| v.077 | tgg = M | m/z = 1381.15 (z = 4) | m/z = 654.74 (z = 2) | |

From top to bottom, the sequence identifiers are SEQ ID NOs: 108 to 136.

TABLE 43

| DNA template | Codon reprogramming | Amino acid sequence of precursor peptide |
|---|---|---|
| v.080 | tgg = W | MSDITASRVESLDLQDLDLSELTVTSLRDTVALPENGASAGAAAAQASSSCAWP |
| v.080 | tgg = $N^{Me}$Gly | MSDITASRVESLDLQDLDLSELTVISLRDTVALPENGASAGAAAAQASSSCAN$^{Me}$GP |
| v.081 | tgg = W | MSDITASRVESLDLQDLDLSELTVTSLRDTVALPENGASAGAAAAQASSSCAQW |
| v.081 | tgg = $N^{Me}$Gly | MSDITASRVESLDLQDLDLSELTVISLRDTVALPENGASAGAAAAQASSSCAQN$^{Me}$G |
| v.081 | tgg = $N^{Me}$Ala | MSDITASRVESLDLQDLDLSELTVISLRDTVALPENGASAGAAAAQASSSCAQN$^{Me}$A |
| v.071 | tgg = W | MSDITASRVESLDLQDLDLSELTVTSLRDTVALPENGASAWAAAWQASSSCAQP |
| v.071 | tgg = $N^{Me}$Gly | MSDITASRVESLDLQDLDLSELTVISLRDTVALPENGASAN$^{Me}$GAAAN$^{Me}$GQASSSCAQP |
| v.071 | tgg = $N^{Me}$Ala | MSDITASRVESLDLQDLDLSELTVISLRDTVALPENGASAN$^{Me}$AAAAN$^{Me}$AQASSSCAQP |
| v.072 | tgg = W<br>aag = K | MSDITASRVESLDLQDLDLSELTVTSLRDTVALPENGASAWAKAWQASSSCAQP |
| v.072 | tgg = $N^{Me}$Ala<br>aag = K | MSDITASRVESLDLQDLDLSELTVISLRDTVALPENGASAN$^{Me}$AAKAN$^{Me}$AQASSSCAQP |
| v.072 | tgg = W<br>aag = $N^{Me}$Gly | MSDITASRVESLDLQDLDLSELTVISLRDTVALPENGASAWAN$^{Me}$GAWQASSSCAQP |
| v.072 | tgg = $N^{Me}$Ala<br>aag = $N^{Me}$Gly | MSDITASRVESLDLQDLDLSELTVISLRDTVALPENGASAN$^{Me}$AAN$^{Me}$GAN$^{Me}$AQASSSCAQP |
| v.073 | tgg = W<br>aag = K | MSDITASRVESLDLQDLDLSELTVISLRDTVALPENGASWKWKWKQASSSCAQP |
| v.073 | tgg = W<br>aag = $N^{Me}$Gly | MSDITASRVESLDLQDLDLSELTVISLRDTVALPENGASWN$^{Me}$GWN$^{Me}$GWN$^{Me}$GQASSSCAQP |
| v.100 | tgg = W<br>cat = H<br>ttt = F<br>aag = $N^{Me}$Gly | MSDITASRVESLDLQDLDLSELTVISLRDTVALPENGASAWAHAFQASSSCAQN$^{Me}$G |
| v.100 | tgg = $F_5$Phe<br>cat = cLeu<br>ttt = $N^{Me}$Ala<br>aag = $N^{Me}$Gly | MSDITASRVESLDLQDLDLSELTVISLRDTVALPENGASA$_{f5}$FA$_c$LAN$^{Me}$AQASSSCAQN$^{Me}$G |
| v.101 | tgg = $F_5$Phe<br>cat = cLeu<br>ttt = $N^{Me}$Ala<br>aag = $N^{Me}$Gly | MSDITASRVESLDLQDLDLSELTVISLRDTVALPENGASAN$^{Me}$GA$_{f5}$F$_c$CLQASSSCAQN$^{Me}$A |
| v.064 | N. A. | MSDITASRVESLDLQDLDLSELTVTSLRDTVALPENGASWGAAAAAAQASSSCAQPNNLNVG |
| v.082 | N. A. | MSDITASRVESLDLQDLDLSELTVTSLRDTVALPENGASAGAAAAQASSSCAQPGELARP |

| DNA template | Codon reprogramming | Observation results from LC-MS of precursor peptide after translation | Observation results from LC-MS of thiopeptide derivative formed after Laz enzyme group treatment | Remarks |
|---|---|---|---|---|
| v.080 | tgg = W | m/z = 1380.68 (z = 4) | m/z = 653.75 (z = 2) | HPLC tailing |
| v.080 | tgg = $N^{Me}$Gly | m/z = 1351.91 (z = 4) | m/z = 596.24 (z = 2) | of thiopeptide |
| v.081 | tgg = W | m/z = 1388.41 (z = 4) | m/z = 669.27 (z = 2) | |
| v.081 | tgg = $N^{Me}$Gly | m/z = 1359.66 (z = 4) | m/z = 611.74 (z = 2) | |

TABLE 43-continued

| | | | |
|---|---|---|---|
| v.081 | tgg = $N^{Me}$Ala | m/z = 1363.16 (z = 4) | m/z = 618.75 (z = 2) |
| v.071 | tgg = W | m/z = 1456.92 (z = 4) [Cys adduct] | m/z = 746.80 (z = 2) |
| v.071 | tgg = $N^{Me}$Gly | m/z = 1399.40 (z = 4) [Cys adduct] | m/z = 631.76 (z = 2) |
| v.071 | tgg = $N^{Me}$Ala | m/z = 1406.42 (z = 4) [Cys adduct] | m/z = 645.77 (z = 2) |
| v.072 | tgg = W<br>aag = K | m/z = 1471.18 (z = 4) [Cys adduct] | m/z = 775.32 (z = 2) |
| v.072 | tgg = $N^{Me}$Ala<br>aag = K | m/z = 1420.69 (z = 4) [Cys adduct] | m/z = 674.31 (z = 2) |
| v.072 | tgg = W<br>aag = $N^{Me}$Gly | m/z = 1456.94 (z = 4) [Cys adduct] | m/z = 746.80 (z = 2) |
| v.072 | tgg = $N^{Me}$Ala<br>aag = $N^{Me}$Gly | m/z = 1406.43 (z = 4) [Cys adduct] | m/z = 645.78 (z = 2) |
| v.073 | tgg = W<br>aag = K | N. D. | m/z = 593.59 (z = 3) |
| v.073 | tgg = W<br>aag = $N^{Me}$Gly<br>tgg = W | m/z = 1485.68 (z = 4) [Cys adduct] | m/z = 804.32 (z = 2) |
| v.100 | cat = H<br>ttt = F<br>aag = $N^{Me}$Gly<br>tgg = $F_5$Phe | m/z = 1457.18 (z = 4) [Cys adduct] | m/z = 747.30 (z = 2) |
| v.100 | cat = cLeu<br>ttt = $N^{Me}$Ala<br>aag = $N^{Me}$Gly<br>tgg = $F_5$Phe | m/z = 1447.92 (z = 4) [Cys adduct] | m/z = 728.77 (z = 2) |
| v.101 | cat = cLeu<br>ttt = $N^{Me}$Ala<br>aag = $N^{Me}$Gly | m/z = 1447.93 (z = 4) [Cys adduct] | m/z = 728.75 (z = 2) |
| v.064 | N. A. | m/z = 1613.02 (z = 4) [Cys adduct] | m/z = 1058.95 (z = 2) |
| v.082 | N. A. | m/z = 1541.00 (z = 4) [βME adduct] | m/z = 936.42 (z = 2) |

From top to bottom, the sequence identifiers are SEQ ID NOs: 137 to 155.

TABLE 44

| DNA template | Codon reprogramming | Amino acid sequence of precursor peptide |
|---|---|---|
| v.088 | tgg = $N^{Me}$Gly | MSDITASRVESLDLQDLDLSELTVTSLRDTVALPENGASAGAAN**$N^{Me}$G**AQASSSCAQP |
| v.089 | tgg = $N^{Me}$Gly | MSDITASRVESLDLQDLDLSELTVTSLRDTVALPENGASAGAAAN**$N^{Me}$G**QASSSCAQP |
| v.074 | tgg = $^D$Ser | MSDITASRVESLDLQDLDLSELTVTSLRDTVALPENGASAGAAAA**$^D$S**ASSSCAQP |
| v.077 | tgg = F | MSDITASRVESLDLQDLDLSELTVTSLRDTVALPENGASAGAAAAQASSSCFQP |
| v.077 | tgg = R | MSDITASRVESLDLQDLDLSELTVTSLRDTVALPENGASAGAAAAQASSSCRQP |
| v.080 | tgg = $N^{Me}$Ala<br>tgg = W | MSDITASRVESLDLQDLDLSELTVTSLRDTVALPENGASAGAAAAQASSSCA**$N^{Me}$A**P |
| v.100 | cat = H<br>ttt = F<br>aag = K<br>tgg = W | MSDITASRVESLDLQDLDLSELTVTSLRDTVALPENGASAWAHAFQASSSCAQK |
| v.100 | cat = cLeu<br>ttt = F<br>aag = K | MSDITASRVESLDLQDLDLSELTVTSLRDTVALPENGASAWcLAFQASSSCAQK |

| DNA template | Codon reprogramming | Observation results from LC-MS of precursor peptide after translation | Observation results from LC-MS of thiopeptide derivative formed after Laz enzyme group treatment | Remarks |
|---|---|---|---|---|
| v.088 | tgg = $N^{Me}$Gly | m/z = 1385.16 (z = 4) [βmE adduct] | m/z = 624.75 (z = 2) | |
| v.089 | tgg = $N^{Me}$Gly | m/z = 1385.17 (z = 4) [βmE adduct] | m/z = 624.75 (z = 2) | |
| v.074 | tgg = $^D$Ser | m/z = 1385.66 (z = 4) [Cys adduct] | m/z = 604.22 (z = 2) | |
| v.077 | tgg = F | m/z = 1385.17 (z = 4) | m/z = 662.77 (z = 2) | |

TABLE 44-continued

```
v.077    tgg = R         m/z = 1387.42 (z = 4)                    m/z = 667.29 (z = 2)

v.080    tgg = N^MeAla   m/z = 1355.42 (z = 4)                    m/z = 603.24 (z = 2)
         tgg = W v.100    cat = H         m/z = 1177.34 (z = 5)  [Cys adduct]      m/z = 775.83 (z = 2)
         ttt = F
         aag = K
         tgg = W v.100    cat = cLeu      m/z = 1464.95 (z = 4)  [Cys adduct]      m/z = 762.84 (z = 2)
         ttt = F
         aag = K
```

From top to bottom, the sequence identifiers are SEQ ID NOs: 156 to 163.

[Example 14-2] Substrate Tolerance of Macrocyclization to Non-Proteinogenic Amino Acid-Substituted Analog $N^{Me}$Gly As in Example 9-2, W2$N^{Me}$Gly, G3$N^{Me}$Gly, A4$N^{Me}$Gly, AS$N^{Me}$Gly, A6$N^{Me}$Gly, A7$N^{Me}$Gly, Q8$N^{Me}$Gly, A9$N^{Me}$Gly, C13$N^{Me}$Gly, A14$N^{Me}$Gly, Q15$N^{Me}$Gly and P16$N^{Me}$Gly altered precursor peptides (see FIG. 50) were synthesized by replacing the 2nd to 9th and 13th to 16th native amino acids, respectively, with $N^{Me}$Gly. For convenience of reprogramming of genetic codes, the N-terminal residues of the precursor peptides were changed to biotinylated phenylalanine ($^{bio}$F), not formylmethionine (fMet). Subsequently, each altered precursor peptide mentioned above was reacted in accordance with the procedures described in Example 9-2, and the reaction product was analyzed by LC-MS. Modification reaction mediated by the Laz enzyme group and the formation of macrocyclization products were confirmed by broad extracted ion chromatograms (brEIC) in which peaks detected in the range of +400 of the tetravalent m/z value of a precursor peptide were integrated. FIG. 50 shows brEIC of each reaction product.

[Example 14-3] Substrate Tolerance of Macrocyclization to Non-Proteinogenic Amino Acid-Substituted Analog $N^{Me}$Ala As in Example 9-2, W2$N^{Me}$Ala, G3$N^{Me}$Ala, A4$N^{Me}$Ala, AS$N^{Me}$Ala, A6$N^{Me}$Ala, A7$N^{Me}$Ala, Q8$N^{Me}$Ala, A9$N^{Me}$Ala, C13$N^{Me}$Ala, A14$N^{Me}$Ala, Q15$N^{Me}$Ala and P16$N^{Me}$Ala altered precursor peptides (see FIG. 51) were synthesized by replacing the 2nd to 9th and 13th to 16th native amino acids, respectively, with $N^{Me}$Ala. For convenience of reprogramming of genetic codes, the N-terminal residues of the precursor peptides were changed to biotinylated phenylalanine (bioF), not formylmethionine (fMet). Subsequently, each altered precursor peptide mentioned above was reacted in accordance with the procedures described in Example 9-2, and the reaction product was analyzed by LC-MS. Modification reaction mediated by the Laz enzyme group and the formation of macrocyclization products were confirmed by broad extracted ion chromatograms (brEIC) in which peaks detected in the range of +400 of the tetravalent m/z value of a precursor peptide were integrated. FIG. 51 shows brEIC of each reaction product.

[Example 15] Reaction of Precursor Peptide Displayed on mRNA

In order to reveal that a precursor peptide displayed on mRNA would be modified by lactazole biosynthetic enzymes, the experiment outlined in FIG. 52 was conducted. A DNA linker labeled with puromycin was ligated, using T4 RNA ligase, to a 3' region of a mRNA encoding a precursor peptide. A mixture of the precursor peptide and the precursor peptide displayed on the mRNA was obtained by translational synthesis with this mRNA labeled with puromycin used as a template. From this mixture, the precursor peptide displayed on mRNA was isolated by using biotinylated DNA complementary to the mRNA, and streptavidin beads. Modification reaction was carried out by its incubation with the Laz enzyme group, and the products were analyzed by LC-MS. As a result, as shown in FIG. 53, leader peptide fragments formed when the modification reaction proceeded was able to be detected, demonstrating that the precursor peptide displayed on mRNA is modified by the lactazole biosynthetic enzymes.

[Example 16] Study of Influence of Order of Addition of Enzymes on Reaction

By changing the order of addition of enzymes to a reaction system, influence of it on the reaction of a precursor peptide was studied.

The reaction of precursor peptide LazA* in a cell-free translation system was attempted according to the enzyme addition patterns I, II, III and IV shown in FIG. 54. The pattern I involved first adding LazD, LazE and LazF, followed by reaction at 25° C. for 16 hours, next adding LazB, cosubstrate tRNA$^{Glu}$ and aminoacylation enzyme GluRS, followed by reaction at 25° C. for 6 hours, and then adding LazC, followed by reaction at 25° C. for 0.5 hours. The pattern II involved first adding LazD, LazE, LazF, LazB, cosubstrate tRNA$^{Glu}$ and aminoacylation enzyme GluRS, followed by reaction at 25° C. for 16 hours, and then adding LazC, followed by reaction at 25° C. for 0.5 hours. The pattern III involved first adding LazD, LazE, and LazF, followed by reaction at 25° C. for 6 hours, and then adding LazB, cosubstrate tRNA$^{Glu}$, aminoacylation enzyme GluRS and LazC, followed by reaction at 25° C. for 12 hours. The pattern IV involved adding LazD, LazE, LazF, LazB, cosubstrate tRNA$^{Glu}$, aminoacylation enzyme GluRS and LazC, followed by reaction at 25° C. for 16 hours.

The results about I, II, III and IV are shown in FIG. 54. In I and II, Dha4-lactazole A was obtained as a modified form in which unmodified Ser4 in Dha wild-type lactazole A was dehydrated. It was found that the amount of dehydroalanine Dha introduced in the resulting cyclic peptide can be controlled by changing the order of addition of enzymes and other cosubstrates. It was also found that III offers the macrocyclization product more efficiently as compared with I, II and IV.

The invention claimed is:

1. An in vitro method for producing a compound library comprising two or more cyclic compounds represented by the formula (I):

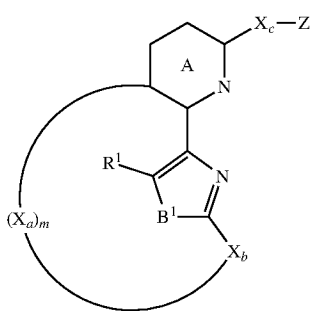

(I)

wherein m number of $X_a$, and $X_b$ and $X_c$ each independently represent an amino acid residue selected from the group consisting of any amino acids and analogs thereof, Z is present or absent and, when present, represents a peptide consisting of 1 to 100 amino acids and/or analogs thereof, m is an integer selected from 2 to 40, ring A is a nitrogen-containing 6-membered ring optionally having a substituent, $B^1$ is an oxygen atom, a sulfur atom, or a NH group, and $R^1$ is a hydrogen atom or a hydrocarbon group, the method comprising allowing a macrocyclase in vitro to act on two or more peptides represented by the formula (II):

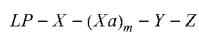

(II)

wherein

X represents a group represented by the formula (1):

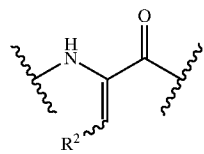

(1)

wherein $R^2$ is a hydrogen atom or a hydrocarbon group,

Y is a peptide residue consisting of four amino acids and/or analogs thereof and contains a group represented by the formula (2):

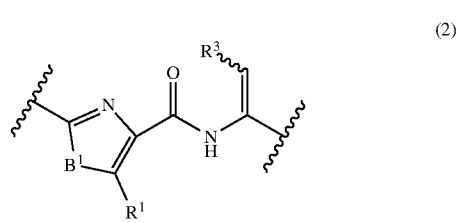

(2)

wherein $R^1$ and $B^1$ are as defined above, and $R^3$ represents a hydrogen or a hydrocarbon group, m number of $X_a$, m and Z are as defined above, and LP is present or absent and, when present, represents a peptide residue consisting of 1 to 100 amino acids and/or analogs thereof, and forming the nitrogen-containing 6-membered ring A while eliminating LP, if present, to form the two or more cyclic compounds represented by the formula (I).

2. The production method according to claim 1, wherein LP is a peptide residue consisting of 11 or more and 100 or less amino acids and/or analogs thereof.

3. The production method according to claim 1, wherein m is an integer selected from 2 to 24.

4. The production method according to claim 1, wherein Y is a group represented by the following formula (3):

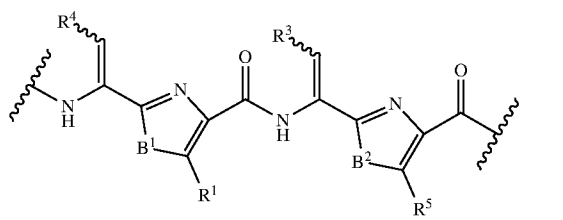

(3)

wherein $R^1$, $R^3$, $R^4$ and $R^5$ each independently represent a hydrogen atom or a hydrocarbon group, and $B^1$ and $B^2$ each independently represent an oxygen atom, a sulfur atom or a NH group.

5. The production method according to claim 1, wherein Y is a group represented by the following formula (3'):

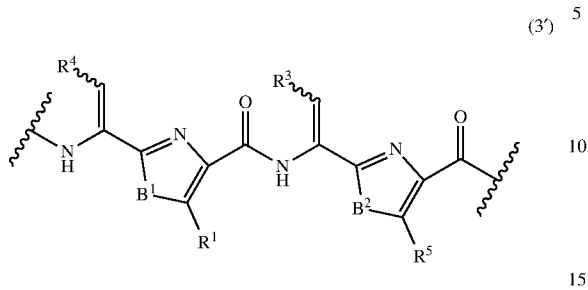

(3')

wherein $R^1$, $R^3$, $R^4$ and $R^5$ each independently represent a hydrogen atom or a methyl group, and $B^1$ and $B^2$ each independently represent an oxygen atom or a sulfur atom, with the proviso that when $B^1$ and/or $B^2$ is a sulfur atom, each of $R^1$ and $R^5$ is a hydrogen.

6. The production method according to claim 1, wherein Y is a group represented by the following formula (3"):

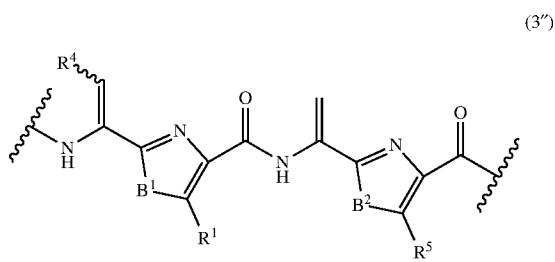

(3")

wherein $R^1$, $R^4$ and $R^5$ each independently represent a hydrogen atom or a methyl group, and $B^1$ and $B^2$ each independently represent an oxygen atom or a sulfur atom, with the proviso that when $B^1$ and/or $B^2$ is a sulfur atom, each of $R^1$ and $R^5$ is a hydrogen.

7. The production method according to claim 1, wherein Y is a group represented by the following formula (3-1):

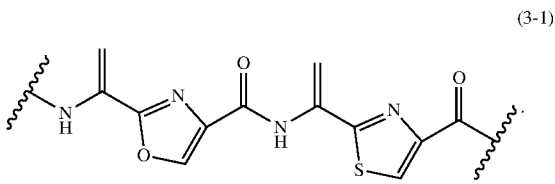 [SMILES: *NC(=C)c1nc(C(=O)NC(=C)c2nc(C(*)=O)cs2)co1]

(3-1)

8. The production method according to claim 1, wherein the macrocyclase comprises LazC and/or an enzyme having homology with LazC.

9. The method for producing a compound library according to claim 1,

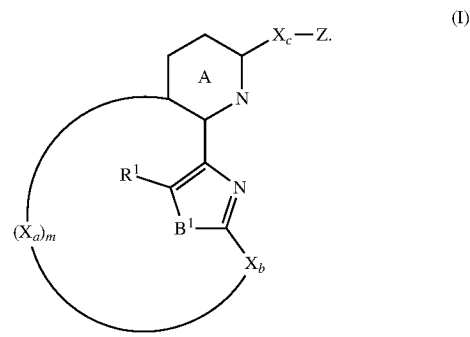

(I)

the method further comprising:

producing a mRNA library encoding precursor peptides represented by the formula (III):

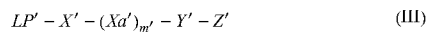

$$LP' - X' - (Xa')_{m'} - Y' - Z' \qquad (III)$$

wherein

X' is serine or threonine, or an analog thereof,

Y' is a peptide consisting of four amino acids represented by -Y'(10)-Y'(11)-Y'(12)-Y'(13)- and/or analogs thereof, wherein Y'(10) is an amino acid residue selected from the group consisting of any amino acids and analogs thereof, Y'(11) is serine, cysteine, threonine or diaminopropionic acid, or an analog thereof, Y'(12) is serine or threonine, or an analog thereof, and Y'(13) is an amino acid residue selected from the group consisting of any amino acids and analogs thereof, m' number of $X_a'$, m' and Z' are the same as defined as m number of $X_a$, m and Z, respectively, in the formula (I), and LP' is present or absent and, when present, represents a peptide consisting of 1 to 100 amino acids and/or analogs thereof;

expressing the precursor peptides by a cell-free translation system with the mRNA library to produce a first peptide library;

forming an azole ring on at least Y'(11) in the precursor peptides with an azole ring-forming enzyme;

converting at least X' and Y'(12) in the precursor peptides to α,β-unsaturated amino acid residues with an α,β-unsaturated amino acid-forming enzyme in the presence of co-substrate $tRNA^{Glu}$ for glutamylation and aminoacylation enzyme GluRS; and forming a nitrogen-containing 6-membered ring with a macrocyclase while eliminating LP', if present.

10. The production method according to claim 9, wherein Y'(10) is serine or threonine, or an analog thereof, and Y'(13) is serine, cysteine, threonine or diaminopropionic acid, or an analog thereof.

11. The production method according to claim 9, wherein Y'(11) is serine, cysteine or threonine, or an analog thereof, and Y'(12) is serine or threonine, or an analog thereof.

12. The production method according to claim 9, wherein
Y'(10) is serine or threonine, or an analog thereof,
Y'(11) is serine, cysteine or threonine, or an analog thereof,
Y'(12) is serine, and
Y'(13) is serine, cysteine or threonine, or an analog thereof.

13. The production method according to claim 9, wherein in ($X_a'$) m' in the formula (III), amino acid residue $X_a'$(1) adjacent to X' is an amino acid other than an acidic amino acid or an analog thereof.

14. The production method according to claim 9, wherein in ($X_a'$) m' in the formula (III), amino acid residue $X_a'$(m') at m'-th position is an amino acid other than an acidic amino acid or an analog thereof.

15. The production method according to claim 9, wherein in ($X_a'$) m' in the formula (III), amino acid residue $X_a'$(m'-1) at (m'-1)-th position is an amino acid other than an acidic amino acid and a basic amino acid or an analog thereof.

16. The production method according to claim 9, wherein the azole ring-forming enzyme comprises LazD, LazE and LazF, and/or an enzyme having homology with any of them.

17. The production method according to claim 9, wherein the α,β-unsaturated amino acid-forming enzyme comprises LazB and LazF, and/or an enzyme having homology with any of them.

18. The production method according to claim 9, wherein the macrocyclase comprises LazC and/or an enzyme having homology with LazC.

19. The production method according to claim 9, wherein the cosubstrate tRNA$^{Glu}$ for glutamylation reaction is actinomycete-derived tRNA$^{Glu}$, and the aminoacylation enzyme GluRS is actinomycete-derived GluRS.

20. The method for producing a compound library according to claim 1,

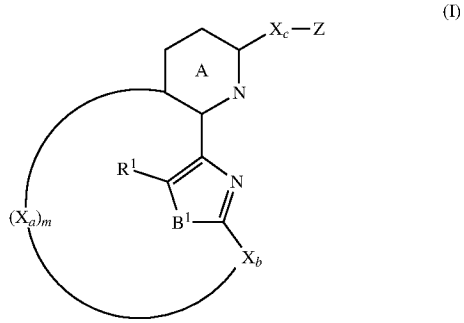

the method further comprising:

producing a mRNA library encoding precursor peptides represented by the formula (III):

$$LP' - X' - (Xa')_{m'} - Y' - Z' \qquad \text{(III)}$$

wherein

X' is serine or threonine, or an analog thereof,

Y' is a peptide consisting of four amino acids represented by -Y'(10)-Y'(11)-Y'(12)-Y'(13)- and/or analogs thereof, wherein Y'(10) is an amino acid residue selected from the group consisting of any amino acids and analogs thereof, Y'(11) is serine, cysteine, threonine or diaminopropionic acid, or an analog thereof, Y'(12) is serine or threonine, or an analog thereof, and Y'(13) is an amino acid residue selected from the group consisting of any amino acids and analogs thereof, m' number of $X_a'$, m' and Z' are the same as defined as m number of $X_a$, m and Z, respectively, in the formula (I), and LP' is present or absent and, when present, represents a peptide consisting of 1 to 100 amino acids and/or analogs thereof;

binding puromycin to the 3' end of each mRNA of the mRNA library to produce a puromycin-bound mRNA library;

expressing the precursor peptides by a cell-free translation system with the puromycin-bound mRNA library to produce a first peptide-mRNA complex library;

forming an azole ring on at least Y'(11) in the precursor peptides with an azole ring-forming enzyme;

converting at least X' and Y'(12) in the precursor peptides to α,β-unsaturated amino acid residues with an α,β-unsaturated amino acid-forming enzyme in the presence of cosubstrate tRNA$^{Glu}$ for glutamylation and aminoacylation enzyme GluRS; and forming a nitrogen-containing 6-membered ring with a macrocyclase while eliminating LP', if present.

* * * * *